(12) United States Patent
Hansen et al.

(10) Patent No.: US 11,434,530 B2
(45) Date of Patent: *Sep. 6, 2022

(54) METHODS FOR ANALYZING GENOMIC VARIATION WITHIN CELLS

(71) Applicant: The University of British Columbia, Vancouver (CA)

(72) Inventors: Carl Lars Genghis Hansen, Vancouver (CA); Hans Zahn, Munich (DE); Jens Huft, Marburg (DE); Marinus Theodorus Johannes Van Loenhout, Vancouver (CA); Kaston Leung, Vancouver (CA); Bill Kengli Lin, Richmond (CA); Anders Klaus, Vancouver (CA); Samuel Alves Jana Rodrigues Aparicio, Vancouver (CA); Sohrab Prakash Shah, Vancouver (CA); Adi Steif, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 13 days.

This patent is subject to a terminal disclaimer.

(21) Appl. No.: 16/850,897

(22) Filed: Apr. 16, 2020

(65) Prior Publication Data
US 2020/0332357 A1 Oct. 22, 2020

Related U.S. Application Data

(63) Continuation of application No. 15/548,292, filed as application No. PCT/CA2016/000031 on Feb. 4, 2016, now Pat. No. 10,760,121.

(60) Provisional application No. 62/237,690, filed on Oct. 6, 2015, provisional application No. 62/162,039, filed on May 15, 2015, provisional application No. 62/111,755, filed on Feb. 4, 2015.

(51) Int. Cl.
| | | |
|---|---|---|
| *C12Q 1/6869* | (2018.01) | |
| *C12Q 1/6806* | (2018.01) | |
| *C12N 15/10* | (2006.01) | |
| *B01L 3/00* | (2006.01) | |
| *C12Q 1/686* | (2018.01) | |

(52) U.S. Cl.
CPC ............ *C12Q 1/6869* (2013.01); *B01L 3/505* (2013.01); *B01L 3/502761* (2013.01); *C12N 15/1093* (2013.01); *C12Q 1/686* (2013.01); *C12Q 1/6806* (2013.01); *B01L 2300/0887* (2013.01); *B01L 2300/123* (2013.01); *B01L 2300/14* (2013.01)

(58) Field of Classification Search
CPC ... C12Q 1/6806; C12Q 1/6869; C12Q 1/6874
See application file for complete search history.

(56) References Cited

U.S. PATENT DOCUMENTS

| | | |
|---|---|---|
| 2010/0120098 A1 | 5/2010 | Grunenwald et al. |
| 2012/0015347 A1 | 1/2012 | Singhal et al. |
| 2015/0376608 A1 | 12/2015 | Kaper et al. |
| 2016/0209319 A1 | 7/2016 | Adalsteinsson et al. |
| 2018/0010179 A1 | 1/2018 | Hansen |

FOREIGN PATENT DOCUMENTS

| | | |
|---|---|---|
| EP | 2660331 | 11/2013 |
| WO | 2003048295 | 6/2003 |
| WO | 2009059430 | 5/2009 |
| WO | 2012054873 | 4/2012 |
| WO | 2016123692 | 8/2016 |

OTHER PUBLICATIONS

USPTO; Non-Final Office Action dated Jul. 9, 2019 in U.S. Appl. No. 15/548,292.
USPTO; Notice of Allowance dated Mar. 17, 2020 in U.S. Appl. No. 15/548,292.
PCT; International Search Report dated May 3, 2016 in International Application No. PCT/CA2016/000031.
PCT; Written Opinion of the International Search Authority dated May 3, 2016 in International Application No. PCT/CA2016/00003 1.
Gole et al., "Massively parallel polymerase cloning and genome sequencing of single cells using nano liter wells," Nature Biotechnology, vol. 31, Abstract, p. 1126 col. 2, pp. 1127-1128 (2013) Abstract Only.
Lutz et al., "Contact-free dispensing of living cells in nano liter droplets," Proceedings of the 11th International Conference on New Actuators, Bremen, Germany, pp. 1-3, ISBN 9783933339102, http://www.imtek.de/data/lehrstuehle/app/dokumente/conferences-2008/lutz-comact-free-dispensmg-of-living-cells.pelf (2008).
Skelley et al., "Microfluidic Control of Cell Pairing and Fusion," Nature Methods, vol. 6(2), pp. 147-152, (2009).
Li et al., "Transport, Retention and Fluorescent Measurement of Single Biological Cells Studied in Microfluidic Chips," Lab on a Chip, vol. 4, pp. 174-180, (Mar. 2004). (Abstract Only).
Li et al., "Microfluidic Selection and Retention of a Single Cardiac Myocyte, On-Chip Dye Loading, Cell Contraction by Chemical Stimulation, and Quantitative Fluorescent Analysis of Intracellular Calcium," Analytical Chemistry, vol. 77(14), pp. 4315-4322, (2005).
Di Carlo et al., "Single-Cell Enzyme Concentration, kinetics, and Inhibition Analysis Using High-Density Hydrodynamic Cell Isolation Arrays," Analytical Chemistry, vol. 78, pp. 4925-4930, (2006).

(Continued)

*Primary Examiner* — Jennifer Dunston
(74) *Attorney, Agent, or Firm* — Potomac Law Group, PLLC

(57) ABSTRACT

Methods, devices and systems for analyzing precious samples of cells, including single cells are provided. The methods, devices, and systems in various embodiments of the invention are used to assess genomic heterogeneity, which has been recognized as a central feature of many cancers and plays a critical role in disease initiation, progression, and response to treatment. The methods devices and systems are also used to analyze embryonic biopsies for preimplantation genetic diagnosis (PGD). In one embodiment, the devices, systems and methods provided herein allow for the construction of genomic and RNA-seq libraries without a pre-amplification step.

24 Claims, 86 Drawing Sheets

(56) References Cited

OTHER PUBLICATIONS

Rowat et al., "Tracking Lineages of Single cells in Lines Using a Microfluidic Device," Proceedings of the National Academy of Sciences, vol. 106(43), pp. 18149-18154, (2009).
Kobel et al., "Optimization of Microfluidic Single Cell Trapping for Long-Term On-Chip Culture," Lab on a Chip, vol. 10, pp. 857-863, (2010).
Warren et al., "Transcription Factor Profiling in Individual Hematopoietic Progenitors by Digital RT-PCR," Proceedings of the National Academy of Sciences USA, vol. 103(47), pp. 17807-17812, (2006).
King et al., "A High-Throughput Microfluidic Real-Time Gene Expression Living Cell Array," Lab on a Chip, vol. 7, pp. 77-85, (2007).
Marcy et al., "Dissecting Biological "Dark Matter" with Single-Cell Genetic Analysis of Rare and Uncultivated TM7 Microbes from the Human Mouth," Proceedings of the National Academy of Sciences USA, vol. 104, pp. 11889-11894, (2007).
Voidman et al., "A Microfabrication-Based Dynamic Array Cytometer," Analytical Chemistry, vol. 74, pp. 3984-3990, (Jul. 2002).
Toriello et al., "Integrated Microfluidic Bioprocessor for Single-Cell Gene Expression Analysis," Proceedings of the National Academy of Sciences USA, vol. 105(51), pp. 20173-20178, (2008).
Braschler et al., "Gentle Cell Trapping and Release on a Microfluidic Chip by in Situ Alginate Hydrogel Formation," Lab on a Chip, vol. 5, pp. 553-559, (Mar. 2005). (Abstract Only).
Neuman et al., "Characterization of Photodamage to *Escherichia coli* in Optical Traps," Biophysical Journal, vol. 77(5), pp. 2856-2863, (1999).
Ma et al., "A Clinical Microchip for Evaluation of Single Immune Cells Reveals High Functional Heterogeneity in Phenotypically Similar T Cells," Nature Medicine, vol. 17(6), pp. 738-743, (2011).
Unger et al., "Monolithic Microfabricated Valves and Pumps by Multilayer Soft Lithography," Science, vol. 80(288), pp. 113-116, (2000).
Fischer et al., "High-Definition Reconstruction of Clonal Composition in Cancer," Cell Reports, vol. 7(5), pp. 1740-1752, (Jun. 2014).
Singhal et al., "Microfluidic Measurement of Antibody-Antigen Binding Kinetics from Low-Abundance Samples and Single Cells," Analytical Chemistry, vol. 82(20), pp. 8671-8679, (Sep. 2010).
Wang et al., "Genome-Wide Single-Cell Analysis of Recombination Activity and De Novo Mutation Rates in Human Sperm," Cell, vol. 150, pp. 402-412, (2012).
Zong et al., "Genome-Wide Detection of Single-Nucleotide and Copy-Number Variations of a Single Human Cell," Science, vol. 338, pp. 1622-1626, (Dec. 2012).
Satyanarayana et al., "Stamp-and-Stick-Room Temperature Bonding Technique for Microdevices," Microelectromechanical Systems, vol. 14(2), pp. 392-399, (2005).
Thorsen et al., "Microfluidic Large-Scale Integration," Science, vol. 298, pp. 580-584, (2002).
Syed et al., "Next-Generation Sequence Library Preparation: Simultaneous Fragmentation and Tagging using In Vitro Transposition," Nature Methods Application Notes, 2 Pages, (Nov. 2009).
White et al., "High-Throughput Microfluidic Single-Cell RT-qPCR," Proceedings of the National Academy of Science USA, vol. 108, pp. 13999-14004, (2011).
Huft et al., "Three-Dimensional Large-Scale Microfluidic Integration by Laser Ablation of Interlayer Connections," Lab on a Chip, vol. 10, pp. 2358-2365, (2010). (Abstract Only).
Adey et al., "Rapid, Low-Input, Low-Bias Construction of Shotgun Fragment Libraries by High-Density In Vitro Transposition," Genome Biology, vol. 11, p. R119, (2010).
Burleigh et al., "A Co-Culture Genome-Wide RNAi Screen with Mammary Epithelial Cells Reveals Transmembrane Signals Required for Growth and Differentiation," Breast Cancer Research, vol. 17(4), 21 Pages, (2015).
Ha et al., "Integrative Analysis of Genome-Wide Loss of Heterozygosity and Monoallelic Expression at Nucleotide Resolution Reveals Disrupted Pathways in Triple-Negative Breast Cancer," Genome Research, vol. 22, pp. 1995-2007, (2012).
Ha et al., "TITAN: Inference of Copy Number Architectures in Clonal Cell Populations from Tumor Whole-Genome Sequence Data," Genome Research, vol. 24, pp. 1881-1893, (2014).
Baslan et al., "Optimizing Sparse Sequencing of Single Cells for Highly Multiplex Copy Number Profiling," Genome Research, vol. 25, pp. 714-724, (2015).
Navin et al., "Tumor Evolution Inferred by Single-Cell Sequencing," Nature, vol. 472, pp. 90-94, (2011).
Peter et al., "Accurate Whole-Genome Sequencing and Haplotyping from 10 to 20 Human Cells," Nature, vol. 487, pp. 190-195, (2012).
Amini et al., "Haplotype-Resolved Whole-Genome Sequencing by Contiguity-Preserving Transposition and Combinatorial Indexing," Nat Genet, vol. 46(12), pp. 1343-1349, (2014).
Eirew et al., "Dynamics of genomic clones in breast cancer patient xenografts at single-cell resolution," Macmillan Publisllers Limited, Nature, vol. 518, pp. 422-426 (2015). Epub Nov. 26, 2014, including pp. 1/5-5/5 of Extended Data Figures, pp. 1/23 of Supplementary Information, and pp. 1/53-53/53 of Supplementary Figures.
Illumina. "An Introduction to Next-Generation Sequencing Technology," www.ihumina.com/NGS, printed as pp. 1/12-12/12 (2012).

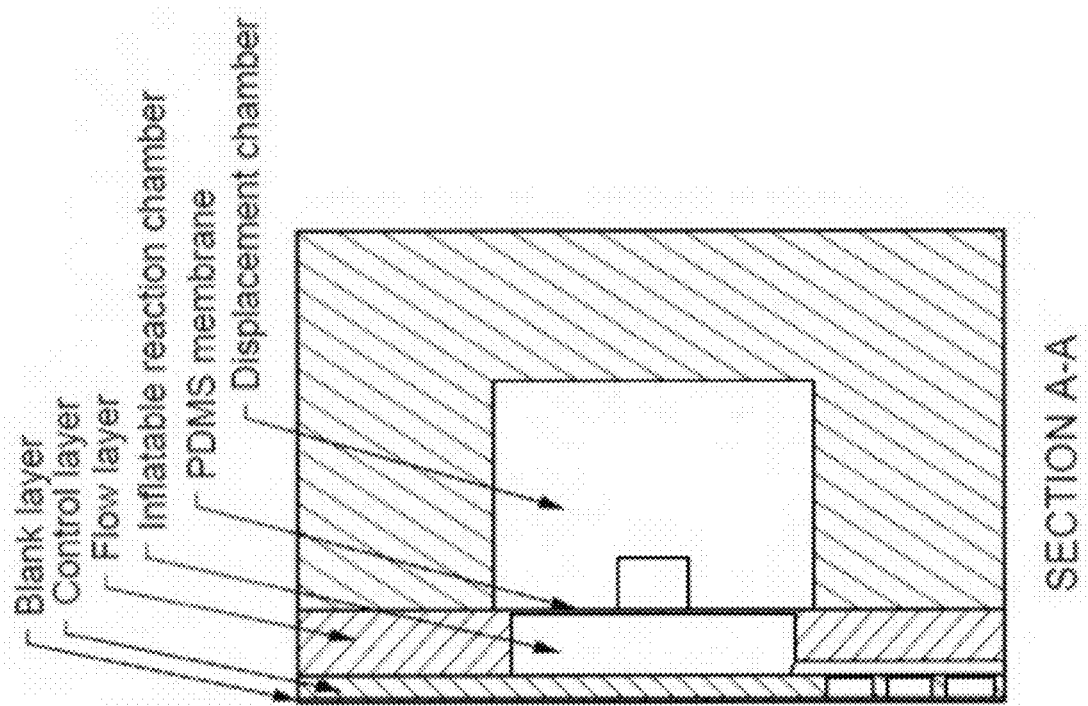

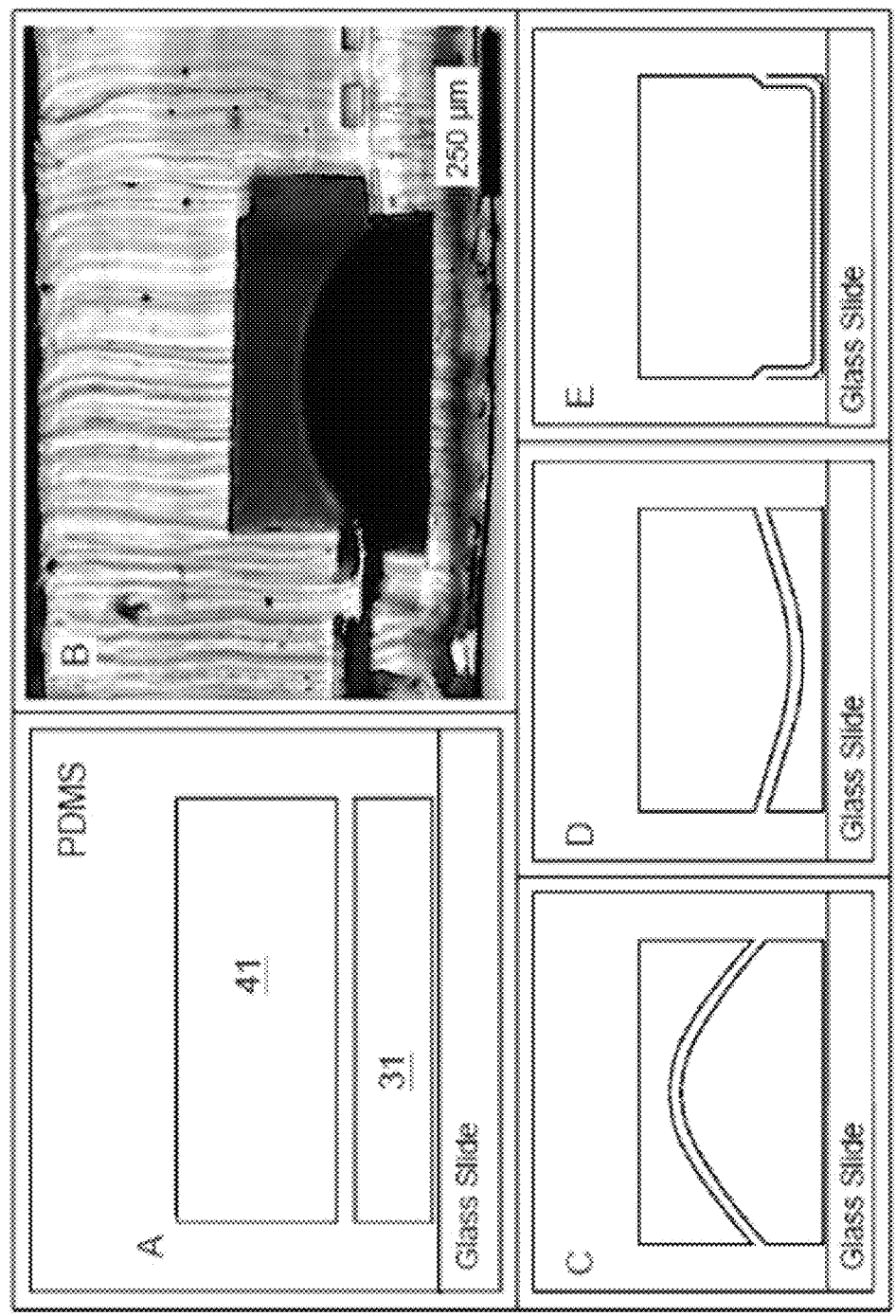
Figs. 3A, B, C, D, E

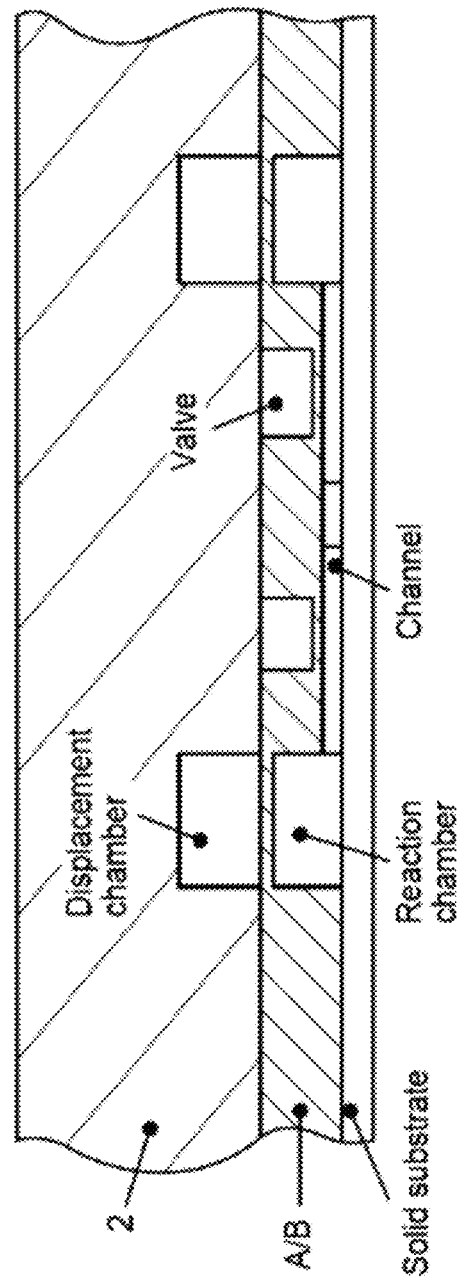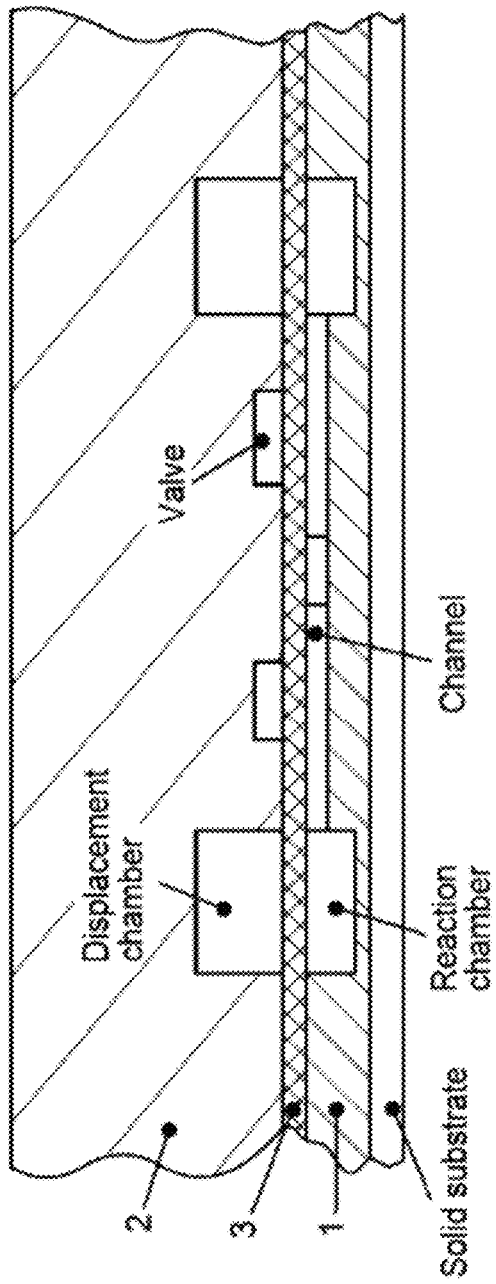

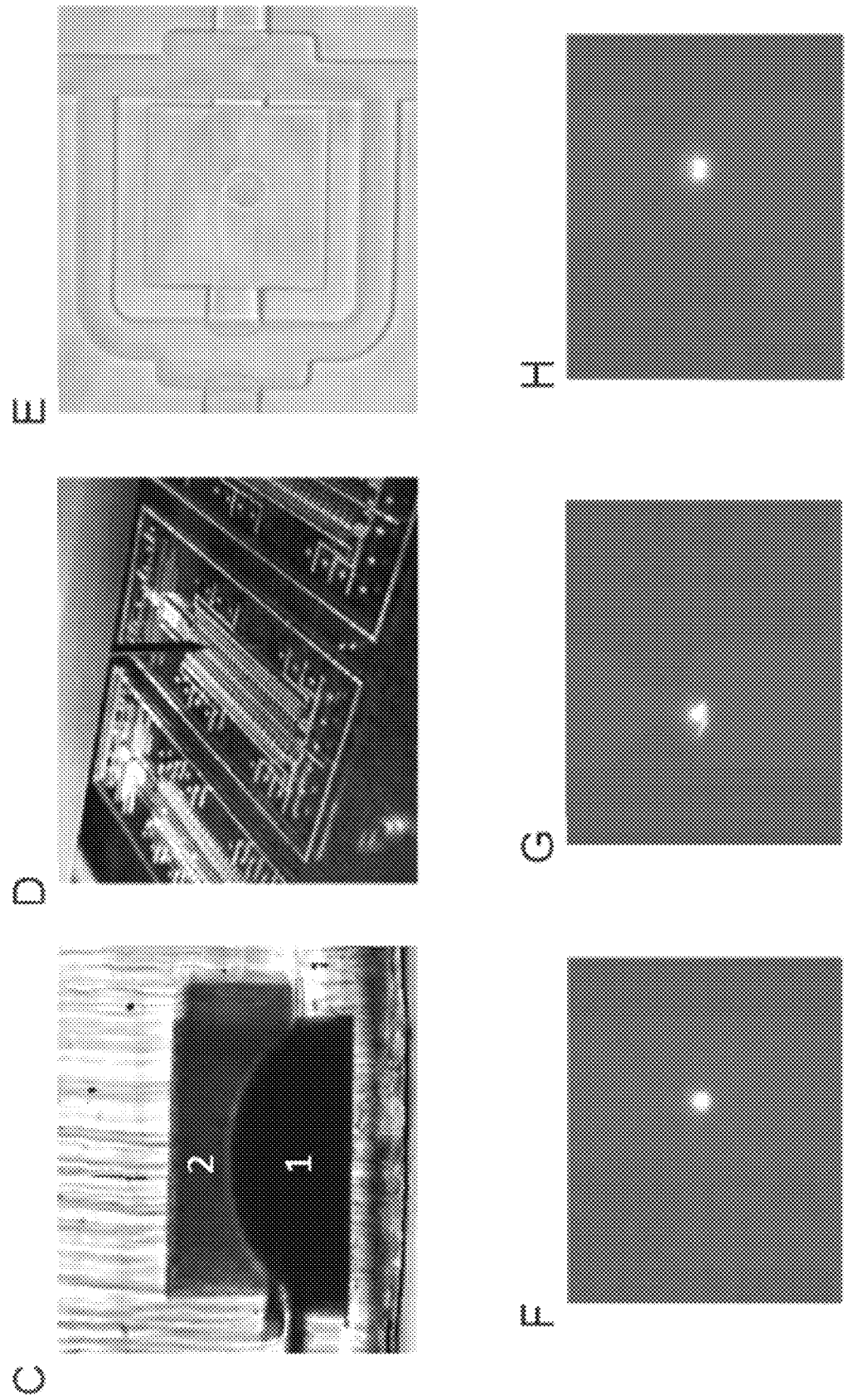
Figs. 46C, D, E, F, G, H

METHODS FOR ANALYZING GENOMIC VARIATION WITHIN CELLS

CROSS REFERENCE TO RELATED APPLICATIONS

This application is a continuation of U.S. application Ser. No. 15/548,292, filed Aug. 2, 2017, which is the national stage entry of PCT/CA2016/000031, filed Feb. 4, 2016, which claims priority from U.S. Provisional Application Nos. 62/111,755, filed Feb. 4, 2015; 62/162,039, filed May 15, 2015 and 62/237,690, filed Oct. 6, 2015, the disclosure of each of which is incorporated by reference in their entireties for all purposes.

GOVERNMENT GRANTS AND FUNDING

Portions of this application were funded by Natural Sciences and Engineering Research Council of Canada (NSERC) grant: RGPIN 386152-10 and Genome BC grant: POC-024.

BACKGROUND OF THE INVENTION

Accurate analysis of nucleic acids having a limited mass is required for many applications. When nucleic acids have an insufficient mass to be sequenced directly, a process of amplification is required. High fidelity amplification is essential so as to ensure an accurate representation of the template, which, in turn, can affect the accuracy of any downstream measurement. This process is required for applications where there are only small numbers of cells (including only one cell) available for analysis.

For example, preimplantation genetic diagnosis (PGD) can be used to determine whether a specific embryo has a genetic abnormality or known aberration that could lead to either failed implantation, subsequent miscarriage or the birth of a child with physical and/or developmental disability. The diagnosis can be used to make decisions on which embryo(s) should be transferred to the uterus for implantation and will with high likelihood result in a normal pregnancy.

PGD can be performed on genomic DNA from cells that are biopsied from embryos. Because the quantity of genomic DNA extracted from this biopsy can be insufficient for current genomic analysis techniques, including DNA sequencing, the DNA is typically amplified. In performing this amplification, a requirement is to accurately represent the state of the embryonic genome in the amplified product. However, amplification methods can result in an over-representation of certain regions of the genome and an under-representation of others, a phenomenon known as "amplification bias". This bias can render the amplification products a distorted version of the original genomic DNA and thus limit the accuracy of PGD.

The present invention addresses this and other needs by providing methods, devices and systems to perform high fidelity amplification of nucleic acids with the goal of accurately analyzing nucleic acids from samples with limited template mass. These methods and devices can be used for numerous applications, including but not limited to PGD.

SUMMARY OF THE INVENTION

In one aspect of the invention, a flexible and scalable microfluidic device is provided, for example, for the is genomic analysis of single-cells is described in more detail. The device comprises a plurality of variable volume chambers that provides a robust and scalable tool for the direct preparation of single-cell libraries.

In one embodiment, a variable volume chamber is provided. The chamber comprises a flow layer defining a reaction chamber and flow channels, wherein at least one wall of the reaction chamber or a portion thereof is an elastomeric membrane, the membrane having: (i) a neutral position; and (ii) a plurality of expanded positions; wherein the expanded positions determine the volume of the reaction chamber, whereby the volume of the reaction chamber is V at the neutral position and the volume of the reaction chamber is greater than V in the plurality of expanded positions, wherein V is less than 1 µl, and wherein the volume at a maximally expanded position is equal to or greater than 2×V; and a blank layer to seal the flow layer.

In another embodiment, a variable volume microfluidic chamber comprising a flow layer and a control layer is provided. The flow layer defines a reaction chamber and flow channels, wherein at least one wall of the reaction chamber or a portion thereof is an elastomeric membrane. The membrane includes a neutral position; a plurality of expanded positions; and a plurality of reduced positions; wherein the expanded and reduced positions determine the volume of the reaction chamber, whereby the volume of the reaction chamber is V at the neutral position, the volume of the reaction chamber is greater than V in the plurality of expanded positions and the volume is less than V in the plurality of reduced positions, such that the volume at a maximally reduced position is essentially zero and wherein V is less than 1 µl. The chamber further comprises a control layer adjacent the flow layer defining control lines; a seal layer adjacent the control, to seal the flow; and a pressure chamber that surrounds the variable volume chamber or chambers, whereby the pressure chamber is operable to produce a positive pressure on the exterior surface of the elastomeric membrane and wherein the displacement chamber is operable to constrain the expansion of the reaction chamber.

In another aspect of the invention, a system for analyzing one or more particles is disclosed, for example a single cell or nucleus, or a plurality thereof. The system includes a transfer device configured to transfer one or more specifically chosen particles to a uniquely specified location on a surface, wherein the transfer device is configured to deposit the one or more particles in a stationary droplet on the surface. The one or more particles may be deposited by contact dispensing. The stationary droplet may comprise a solution of less than about 400 nL. The solution may be 400 nL or less.

In another aspect, methods are provided to analyze polynucleotides from a small number of cells. A small number of cells (e.g., less than 10 cells) can have a limited amount of polynucleotides. Methods provided herein can enhance the accuracy and sensitivity of the analysis of such a limited amount of polynucleotides. The method can enhance the analysis accuracy by performing the analysis in a small volume solution (e.g., less than 400 nL). For example, a sequencing library constructed in a solution of less than 400 nL can yield a greater coverage breadth for a given sequencing depth than that constructed in a solution of larger volume.

One embodiment of the methods described herein is directed to a method for analyzing heterogeneity within a tumor sample. The method comprises isolating a plurality of cells and/or nuclei from the tumor sample. Isolating can also comprise a combination of cell(s) and nuclei. For example, one cell and one nucleus can be isolated by the methods described herein. Alternatively, the plurality of cells and/or nuclei can be obtained, i.e., the plurality of cells and/or nuclei can already have been isolated. Isolating can be carried out e.g., with one of the transfer devices described herein, e.g., a microcapillary or a micropipette or a microdispenser Individual cell(s) and/or nuclei are deposited into individual containers. The individual chambers in some embodiments are individual microwells. In another embodiment, the individual chambers are individual microfluidic chambers. In yet another embodiment, the individual chambers are individual open microwells, droplets on a surface, or droplets in an emulsion. A cell and/or a nucleus in an individual chamber is also referred to herein as a tumor subpopulation. Preparation of sequencing libraries is carried out on nucleic acid from the plurality of individual cells and/or nuclei without prior amplification. In one embodiment, the library preparation method comprises a transposase reaction. In another embodiment, the library preparation comprises DNA fragmentation (e.g. enzymatically or mechanically), end-repair, A-tailing and adapter ligation. In yet another embodiment, libraries can be prepared by targeted PCR. Libraries may also be enriched using capture or pull-down techniques. Methods for generating such libraries are described herein and can be used in the present method for analyzing heterogeneity within a tumor sample. Index sequences are added to the nucleic acid in each individual container such that a unique index sequence is associated with a unique container. Index sequences are added during the transposase reaction, during a ligation step, or during a PCR reaction (or other amplification reaction) or a combination thereof. Individual libraries are then pooled and sequenced to provide sequence information of individual cells and/or nuclei. From this sequence information, the copy number profiles or other genomic structural abnormalities (e.g. translocations, deletions, amplifications, inversions, breakpoints, insertions) of individual cells and/or nuclei is determined. Based on the genomic alterations of each individual cell and/or nuclei, the clonal composition of the tumor is determined.

In another aspect, a method of amplifying polynucleotides from one or more cells is disclosed. The method involves depositing one or more specifically chosen cells in a solution having a volume of less than about 400 nL, wherein the one or more cells contains a polynucleotide; and amplifying the polynucleotides in a solution having a volume less than about 400 nL. The amplification may be carried out by numerous methods including by multiple displacement amplification (MDA) or polymerase chain reaction (PCR). The method described herein may further involve fragmenting the polynucleotide to generate a plurality of polynucleotide fragments prior to amplification. The method may further involve fragmenting the polynucleotide to generate a plurality of polynucleotide fragments wherein the fragmenting occurs in a single solution with the amplification step.

In another aspect, a method of generating a sequencing library with polynucleotides is disclosed. The method involves fragmenting the polynucleotides to generate a plurality of polynucleotide fragments; attaching a first adaptor to a first end and a second adaptor to a second end of each of the polynucleotide fragments; and amplifying the polynucleotide fragments with the first and second adaptors from the aforementioned second step using a primer set, wherein the primer set introduces a third adaptor on the first end and a fourth adaptor on the second end of each of the amplified polynucleotide fragments, wherein the first or second steps are performed in a solution having a volume less than about 400 nL. The polynucleotide fragments from the first (fragmentation) step may not be amplified before the second step. The polynucleotides may be obtained from a single cell. The polynucleotides may be obtained from a specifically chosen single cell or specifically chosen small number of cells placed in a volume less than about 400 nL.

In another embodiment of the methods described herein, a method of analyzing a polynucleotide is disclosed. The method involves depositing one or more cells in a solution having a volume less than about 400 nL to a uniquely specified location on a surface, wherein the one or more cells contains a polynucleotide; amplifying the polynucleotide in the solution; fragmenting the amplified polynucleotide to generate a plurality of polynucleotide fragments; separating the plurality of polynucleotide fragments; amplifying the polynucleotide fragments from the preceding step; and pooling the amplified polynucleotide fragments from the preceding step. The one or more cells may be deposited by contact dispensing. The separating may involve dividing the plurality of polynucleotide fragments into multiple reaction solutions, wherein the multiple reaction solutions are deposited on the surface. Further, the separating may involve depositing the plurality of polynucleotide fragments into an emulsion.

In yet another embodiment of the methods described herein, a method is disclosed comprising dividing the pooled polynucleotide fragments from a preceding and above-mentioned step into multiple pools; amplifying the polynucleotide fragments in the multiple pools; fragmenting the amplified polynucleotide fragments in the multiple pools; generating sequencing libraries in the multiple pools; sequencing the sequencing libraries to obtain sequences of the polynucleotide fragments in the multiple pools; assembling the sequences from a preceding step to obtain an assembled sequence; and comparing the assembled sequence to a reference sequence to determine whether the assembled sequence is inherited from the reference sequence.

In even another embodiment of the methods described herein, a method of determining a haplotype of a polynucleotide is disclosed. The method involves depositing one or more cells in a solution having a volume less than about 400 nL to a uniquely specified location on a surface by contact dispensing, wherein the one or more cells contains a polynucleotide; fragmenting the polynucleotide to generate a sequencing library; sequencing the fragments of the polynucleotide to obtain a plurality of sequence reads; assembling the sequence reads from a preceding step; and comparing the assembled sequence to a reference sequence to determine whether the assembled sequence is inherited from the reference sequence.

In one embodiment of the methods described herein, a method of selecting an embryo to screen for an inheritable disease is disclosed. The method involves depositing one or more cells from the embryo in a solution having a volume less than about 400 nL, wherein the one or more cells comprise a polynucleotide; using a reaction in a volume less than about 400 nL to obtain sequence information from the polynucleotide, thereby obtaining a sequence read of the polynucleotide; and determining whether the polynucleotide carries a genetic variation associated with an inheritable disease using the sequence reads from a preceding step. This method may be further modified by analyzing parental genetic sequences in addition to embryo screening. Sequencing libraries are also generated in embodiments of the methods described herein. Generating a sequencing library may include fragmenting the polynucleotide and tagging the fragmented polynucleotide. Generating a sequencing library may include use of a transposome, wherein the transposome may include a transposase and a custom tagging sequence. The polynucleotide may be fragmented and tagged with the custom tagging sequence by the transposase. The method may further include use of a primer set to introduce adaptors to the sequencing library. The breadth of coverage of the sequencing library may be at least 5%, at least 10%, at least 20%, at least 25%, at least 30%, at least 35%, at least 40%, at least 45%, or at least 50%, wherein the breadth of coverage represents the fraction of the polynucleotide represented by at least one molecule in the sequencing library. The analyzing may include amplifying the polynucleotide. The fidelity of the amplification may be such that for at least about 3.3 Gbp of aligned sequence data, the breadth of coverage is greater than about 35%. The amplifying may be performed by in vitro clone expansion, multiple displacement amplification (MDA), or polymerase chain reaction (PCR). The method may further involve pre-amplifying the polynucleotide before the amplifying. The pre-amplifying may be performed by in vitro clone expansion, MDA, or PCR. The method may further involve determining whether the polynucleotide carries a genetic variation associated with a disease. The genetic variation may include a copy number variation. The polynucleotide fragments may be sequenced to a depth that allow to detect copy number variation of at least 10 kb, at least 20 kb, or at least 50 kb nucleotides in length. The disease may be a genetic disorder. The method may further involve treating the disease, including a heritable disease, by correcting the genetic variation. The genetic variation may be corrected using a nuclease. The nuclease may include a CRISPR-associated protein. The method may further involve fragmenting the polynucleotide, thereby generating a plurality of polynucleotide fragments. The fragmenting may be performed before an amplification step, and the fragmenting and the amplifying may be performed in a single reaction solution. The fragmenting may be performed before an MDA step. The polynucleotide fragments may be distributed into a plurality of reaction solutions. The method may further involve amplifying the polynucleotide fragments in the plurality of reaction solutions. The polynucleotide fragments may be greater than 1000 bp in length. The method may further involve sequencing at least one of the polynucleotide fragments, wherein the fragmentation sites of the sequenced polynucleotide fragments may allow determination of a haplotype of the polynucleotide fragment. The method may further involve determining a haplotype of the polynucleotide. The haplotype determination may include determining haplotype of a region of length in the polynucleotide as described herein. The method may further involve sub-fragmenting the amplified polynucleotide fragments in the plurality of reaction solutions. The method may further involve sequencing the sub-fragmented polynucleotides in the plurality of reaction solutions, thereby obtaining sequence reads of the sub-fragmented polynucleotides. The method may further involve assembling the sequence reads from more than one of the reaction solutions. The assembling may be performed using overlapping heterozygous single nucleotide variant sites. The one or more cells may be circulating cells. The one or more circulating cells may be from a pregnant subject. The one or more cells may be from an embryo, including a mammalian embryo. The method may further include determining whether the embryo is selected for implantation. The polynucleotide may include DNA. The DNA may be genomic DNA. The polynucleotide may be RNA. An above-mentioned method may further involve determining an epigenetic modification in the polynucleotide. The epigenetic modification may include methylation or histone modification. The method may further involve determining expression of a gene in the one or more cells. The expression may be determined using reverse-transcription PCR or whole transcriptome sequencing.

In another embodiment, a method of generating a sequencing library from a polynucleotide from a sample comprising one or more cells is disclosed. The method involves fragmenting the polynucleotide to generate fragmented polynucleotides; and attaching an adaptor to the fragmented polynucleotides to generate a sequencing library of fragmented polynucleotides comprising an adaptor, wherein the above-mentioned steps are performed in a volume less than 400 nL, and wherein the polynucleotide or fragmented polynucleotides of the first step is not amplified before the second step. The steps may be performed in a volume less than 100 nL. The method may further involve sequencing the fragmented polynucleotides comprising an adaptor. The method may further include determining a genetic variation in the fragmented polynucleotides comprising an adaptor. The genetic variation may include a copy number variation. The method may further involve determining a haplotype of the polynucleotide. The haplotype determination may include determining haplotype of a region of length in the polynucleotide as described herein. The method may further involve determining an epigenetic modification in the polynucleotide. The epigenetic modification may include methylation or histone modification. The method may further involve determining expression of a gene in the one or more cells. The expression may be determined using reverse-transcription PCR or whole transcriptome sequencing. The one or more cells may or may not be isolated by fluorescence-activated cell sorting. The fragmenting and attaching may be performed sequentially or simultaneously. The fragmenting and attaching may be performed using a transposase.

In another aspect, a method of analyzing at least one polynucleotide from a sample comprising amplifying the polynucleotides, wherein the fidelity of the amplification is as described herein. In yet another aspect, a method for selecting an embryo with a genetic characteristic is disclosed. The method involves transferring a cluster of cells from the embryo to a uniquely specified location on a surface; and analyzing at least one polynucleotide from the cluster of cells, thereby determining whether the embryo has the genetic characteristic, wherein the cluster of cells is transferred in a solution of no more than 400 nL to the uniquely specified location. The volume of the solution may be less than 100 nL. The cluster of cells may include no more than 30 cells. The cluster of cells may be split into individual cells prior to the analyzing. The analyzing may include analyzing at least one polynucleotide from each of the split cells. The analyzing may involve generating a sequencing library using the polynucleotide. The sequencing library may be generated using a transposase. The analyzing may involve amplifying the polynucleotide. The amplifying may be performed by in vitro clone expansion, MDA, or PCR. The method may further involve pre-amplifying the polynucleotide before the amplifying. The pre-amplifying may be performed by in vitro clone expansion, MDA, or PCR. The analyzing may include determining whether the polynucleotide carries a genetic variation associated with a disease. The disease may be a genetic disorder. The genetic variation may include a copy number variation. The method may further involve treating the disease by correcting the genetic variation. The correcting may be performed using a CRISPR-associated protein. The method may further involve fragmenting the polynucleotide, thereby generating a plurality of polynucleotide fragments. The fragmenting may be performed after an amplification step and the fragmenting and the amplifying may be performed in a single reaction solution. The fragments of the fragmented polynucleotide may be distributed into a plurality of reaction solutions. The method may further involve amplifying the fragmented polynucleotide in the plurality of reaction solutions. The polynucleotide fragments may be greater than 1000 bp in length. The method may further involve sequencing at least one of the polynucleotide fragments. The fragmentation sites of the sequenced polynucleotide fragments may allow determination of a haplotype of the polynucleotide fragment. The polynucleotide fragments may be sequenced to a breadth that allows detection of copy number variation of at least 10 kb, at least 20 kb, or at least 50 kb nucleotides in length. The method may further involve determining a haplotype of the polynucleotide. The haplotype determination may include determining haplotype of a region of length in the polynucleotide. The method may further involve sub-fragmenting the amplified polynucleotide in the plurality of reaction solutions. The method may further involve sequencing the sub-fragmented polynucleotide in the plurality of reaction solutions, thereby obtaining sequence reads of the sub-fragmented polynucleotide. The method may further involve assembling the sequence reads from more than one reaction solution using overlapping heterozygous single nucleotide variant sites. The polynucleotide may be DNA or RNA. The method may further involve determining an epigenetic modification in the polynucleotide. The epigenetic modification may include methylation or histone modification. The method may further involve determining expression of a gene in the one or more cells. The expression may be determined by reverse-transcription PCR or whole transcriptome sequencing. The analyzing may be performed using a microarray.

In yet another embodiment, a method for determining a haplotype is disclosed. The method involves depositing a plurality of polynucleotides into a plurality of first solutions, wherein the first solutions have a volume of less than about 400 nL; contacting each of the plurality of first solutions with one or more transposomes to tag the plurality of polynucleotides, wherein each of the one or more transposomes comprises a transposase and one or more adaptor sequences, thereby generating a plurality of tagged polynucleotides; creating one or more pools of the plurality of tagged polynucleotides; depositing the one or more pools of tagged polynucleotides into a plurality of second solutions, wherein the second solutions have a volume of less than about 400 nL; fragmenting the plurality of tagged polynucleotides in the plurality of second solutions to generate a plurality of fragmented polynucleotides within each of the second solutions, wherein each of the plurality of tagged polynucleotides has the one or more adaptor sequences appended at a first and a second end; sequencing the plurality of fragmented polynucleotides with the one or more adaptor sequences appended at the first and second ends to obtain a plurality of sequence reads; and comparing the sequence reads to a reference sequence to determine the haplotype. Either of the depositing steps, or both of the depositing steps, may include non-contact dispensing. Either of the depositing steps, or both of the depositing steps may include depositing the solutions to a plurality of uniquely specified locations on a surface. The fragmenting may include contacting the plurality of first solutions with a denaturant. The denaturant may be sodium dodecyl sulfate (SDS). The one or more adaptor sequences may be different for each of the plurality of first solutions. The plurality of polynucleotides may be deposited in the plurality of first solutions at a limiting dilution. The plurality of polynucleotides may be deposited in the plurality of first solutions at a dilution such that the probability of two polynucleotides with overlapping sequences is less than 10%, 5%, 2%, 1%, or 0.1%, as determined by the diversity of sequences of the polynucleotides being analyzed. Each of the plurality of polynucleotides in each of the plurality of first solutions may align to a different region of the reference sequence. The diversity and the dilution of polynucleotides may be selected such that the large majority of the plurality of polynucleotides in the majority of each of the plurality of first solutions may align to a different region of the reference sequence. Each of the plurality of first solutions may comprise, on average, one polynucleotide. Each of the plurality of first solutions may comprise, on average, more than one polynucleotide. Determining the haplotype may include constructing a haplotype block. The method may further include, prior to the sequencing, amplifying the plurality of fragmented polynucleotides. The amplifying may include annealing primers containing one or more index sequences to the one or more adaptor sequences appended to the first and second ends of the fragmented polynucleotides. The one or more index sequences may be different for each of the plurality of solutions and may be used to associate the sequence reads with the identity of the first and second solutions from which they were produced. The transposase may be Tn5 transposase. The plurality of polynucleotides may include genomic DNA. The method may further include, prior to the first depositing step, obtaining the plurality of polynucleotides by lysing one or more cells.

In another aspect, a method is provided for determining a haplotype. The method includes fragmenting a plurality of polynucleotides to generate a plurality of fragmented polynucleotides; depositing the plurality of fragmented polynucleotides into a plurality of solutions, wherein the solutions have a volume of less than about 400 nL; contacting each of the plurality of solutions with one or more transposomes to tag the plurality of fragmented polynucleotides, wherein each of the one or more transposomes includes a transposase and one or more adaptor sequences, thereby generating a plurality of tagged polynucleotides with the one or more adaptor sequences appended at a first and a second end; sequencing the plurality of tagged polynucleotides to obtain a plurality of sequence reads; and comparing the sequence reads to a reference sequence to determine the haplotype. The depositing may include non-contact dispensing. The depositing may include depositing the solutions to a plurality of uniquely specified locations on a surface. The method may further include, prior to the fragmenting, obtaining the plurality of polynucleotides by lysing one or more cells. The plurality of fragmented polynucleotides may be deposited in the plurality of solutions at a limiting dilution. Each of the plurality of fragmented polynucleotides in each of the plurality of solutions may align to a different region of the reference sequence. Each of the plurality of solutions may include, on average, one polynucleotide. Determining the haplotype may further include constructing a haplotype block. The method may further include, prior to the sequencing, amplifying the plurality of tagged polynucleotides. The amplifying may include annealing primers containing one or more index sequences to the one or more adaptor sequences appended to the first and second ends of the tagged polynucleotides. The one or more index sequences may be different for each of the plurality of solutions. The transposase may be Tn5 transposase. The plurality of polynucleotides may be genomic DNA. The one or more adapter sequences used in the creation of the tagged polynucleotides during the transposome reaction, and/or the one or more index sequences appended to the first and second ends of the tagged polynucleotides during the amplification, may include one or more unique polynucleotide sequences that may be used to associate the sequenced polynucleotide fragments with the one or more solutions into which the original polynucleotide fragments were deposited.

BRIEF DESCRIPTIONS OF THE DRAWINGS

FIG. 1B shows a cross-sectional view of the variable volume microfluidic chamber of FIG. 1A taken along line A-A.

FIG. 3A shows a simplified cross sectional view of a reaction chamber (31) and displacement chamber (41) separated by a membrane layer. FIG. 3B shows a micrograph of a partially inflated reaction chamber (31) in cross section. FIG. 3C shows a simplified cross sectional view of a reaction chamber (31) and displacement chamber (41) separated by a membrane layer, wherein the reaction chamber is partially inflated. FIG. 3D shows a simplified cross sectional view of a reaction chamber (31) and displacement chamber (41) separated by a membrane layer, wherein the reaction chamber is partially deflated. FIG. 3E shows a simplified cross sectional view of a reaction chamber (31) and displacement chamber (41) separated by a membrane layer, wherein the volume of the reaction chamber is essentially zero in an essentially maximal deflated state.

Figure 4A:
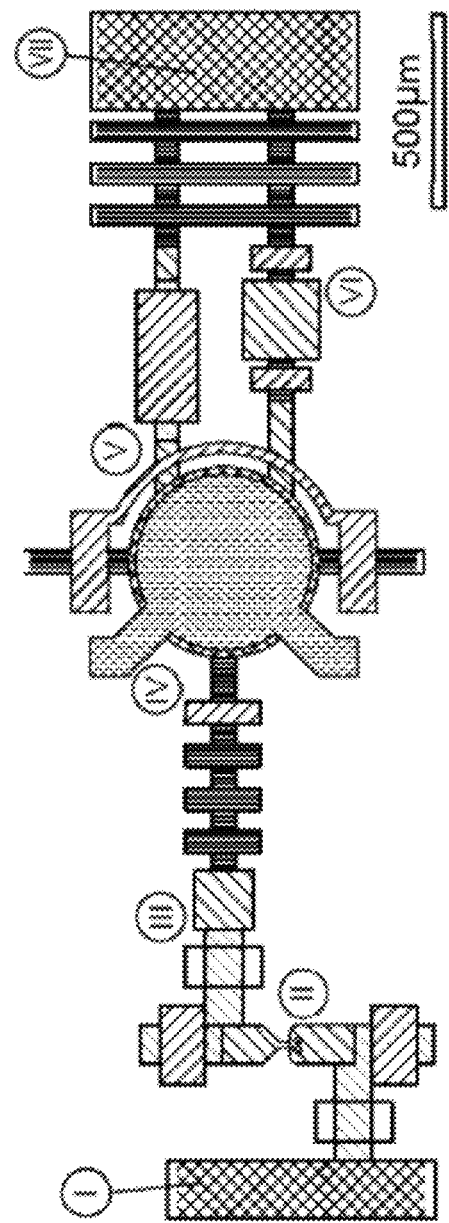
Figure 4B:
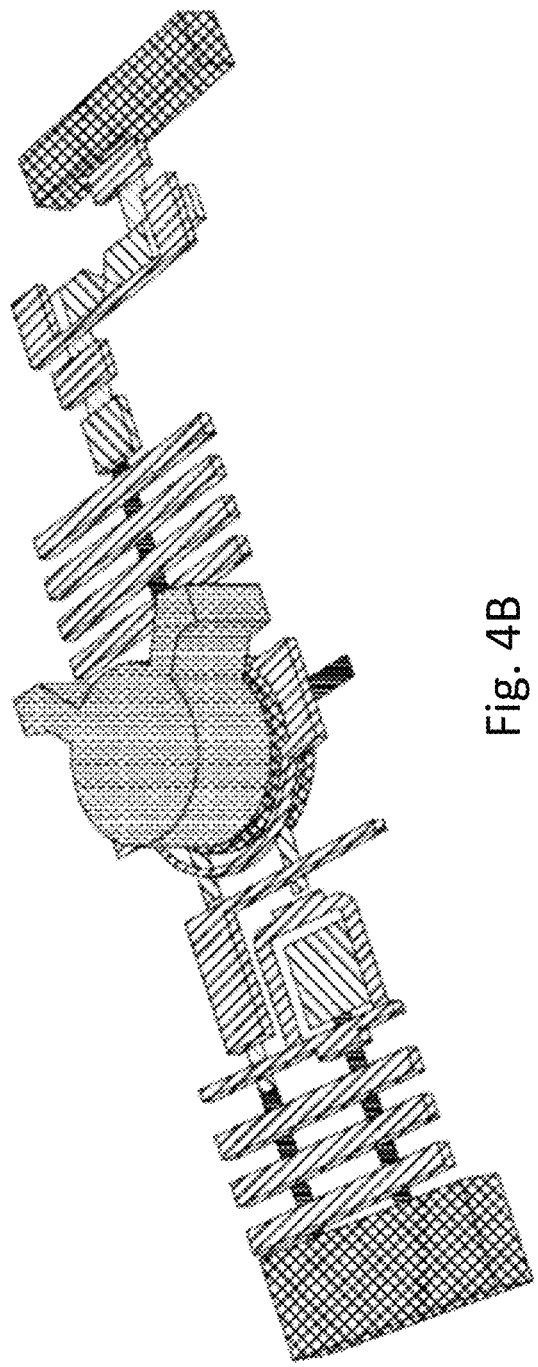
Figure 4C:
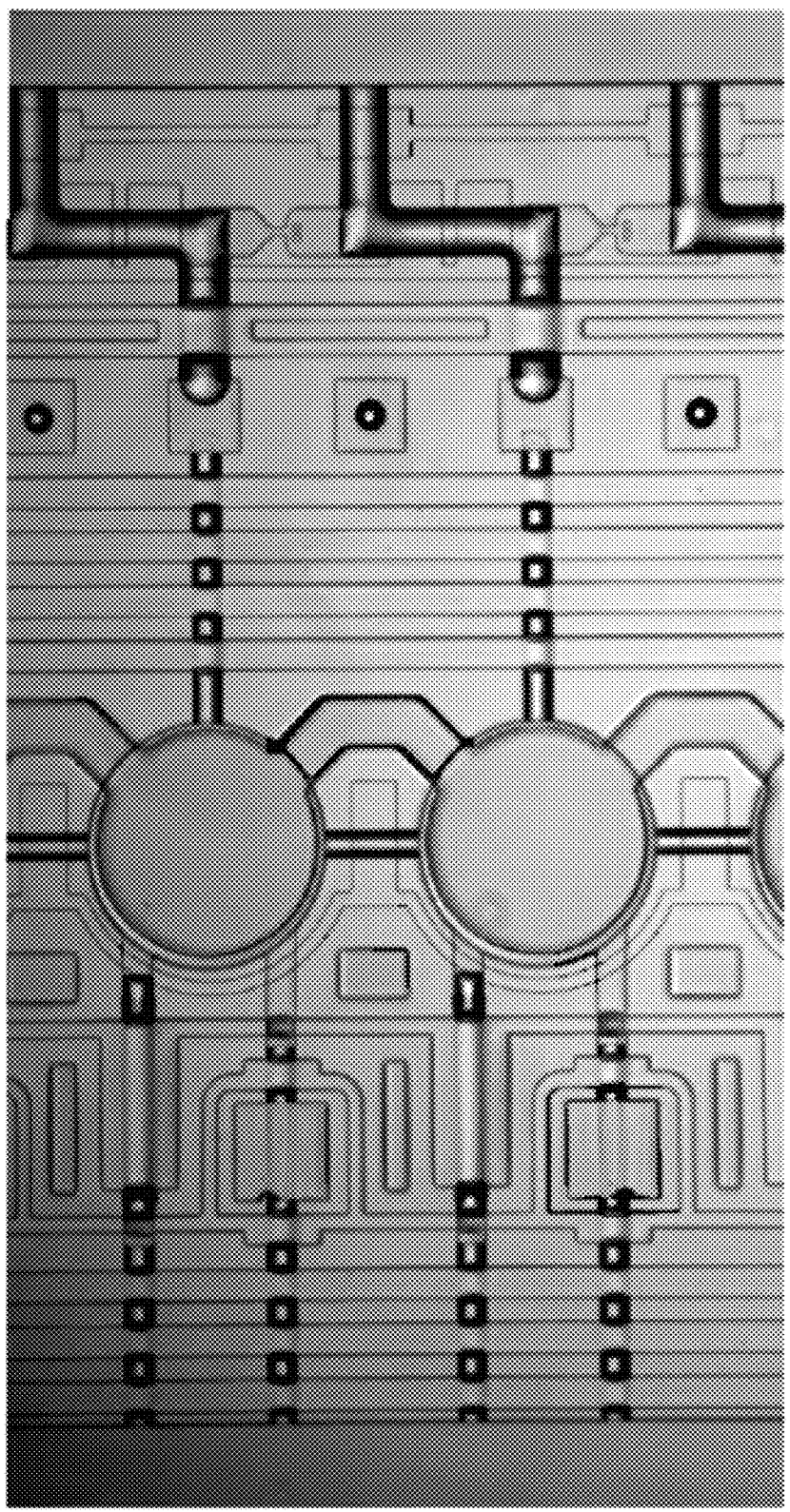
Figure 5:
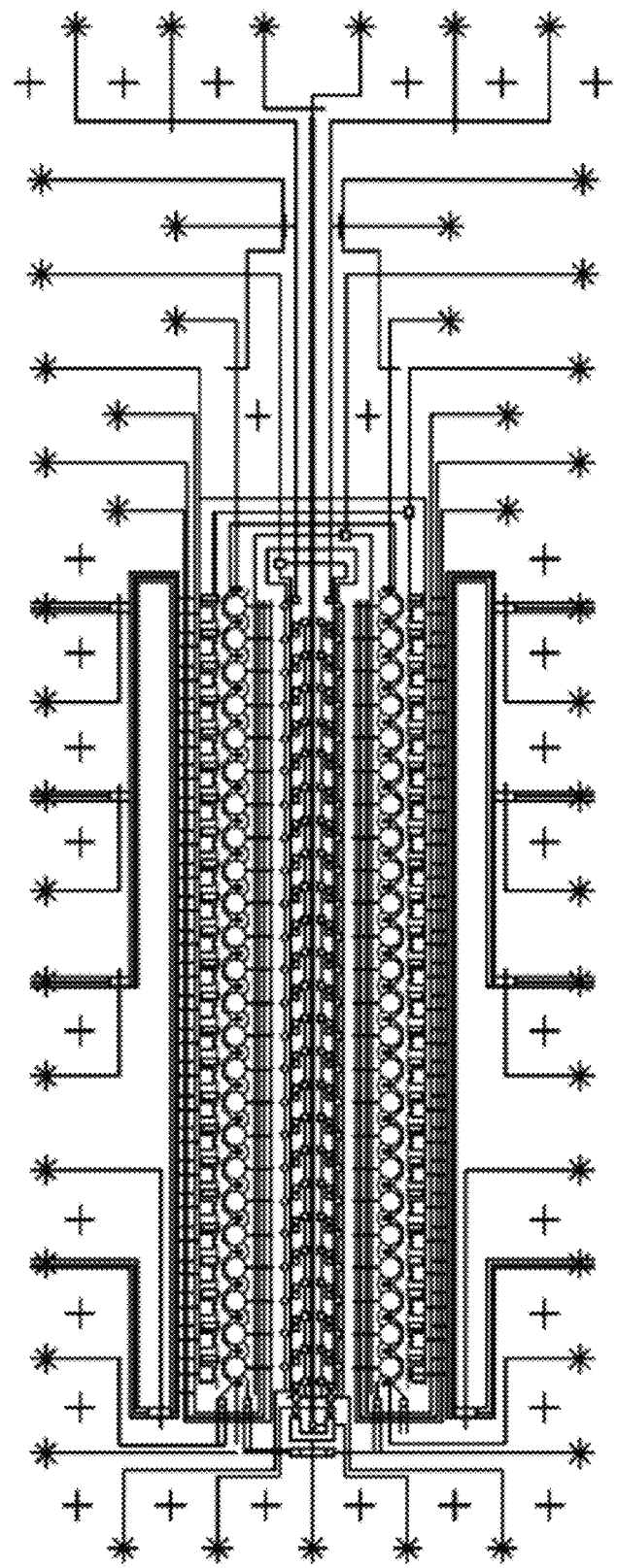

FIG. 4A is a top view of a single cell processing unit of a larger microfluidic device depicted in FIG. 5, showing flow channels (I and VII), a cell trap (II), a stacked variable volume reaction chamber and a displacement chamber (IV), and a variety of pumps and valves. FIG. 4B shows a 3 dimensional perspective view of the single cell processing unit of FIG. 4A. FIG. 4C shows an optical micrograph (top down) of two single cell processing units present on a microfluidic device depicted in FIG. 5.

FIG. 5 shows a plan view of a microfluidic device comprised of 48 single cell processing units as depicted in FIGS. 4A and 4B, the microfluidic device is useful for single cell library preparation.

Figures 6A, 6B:
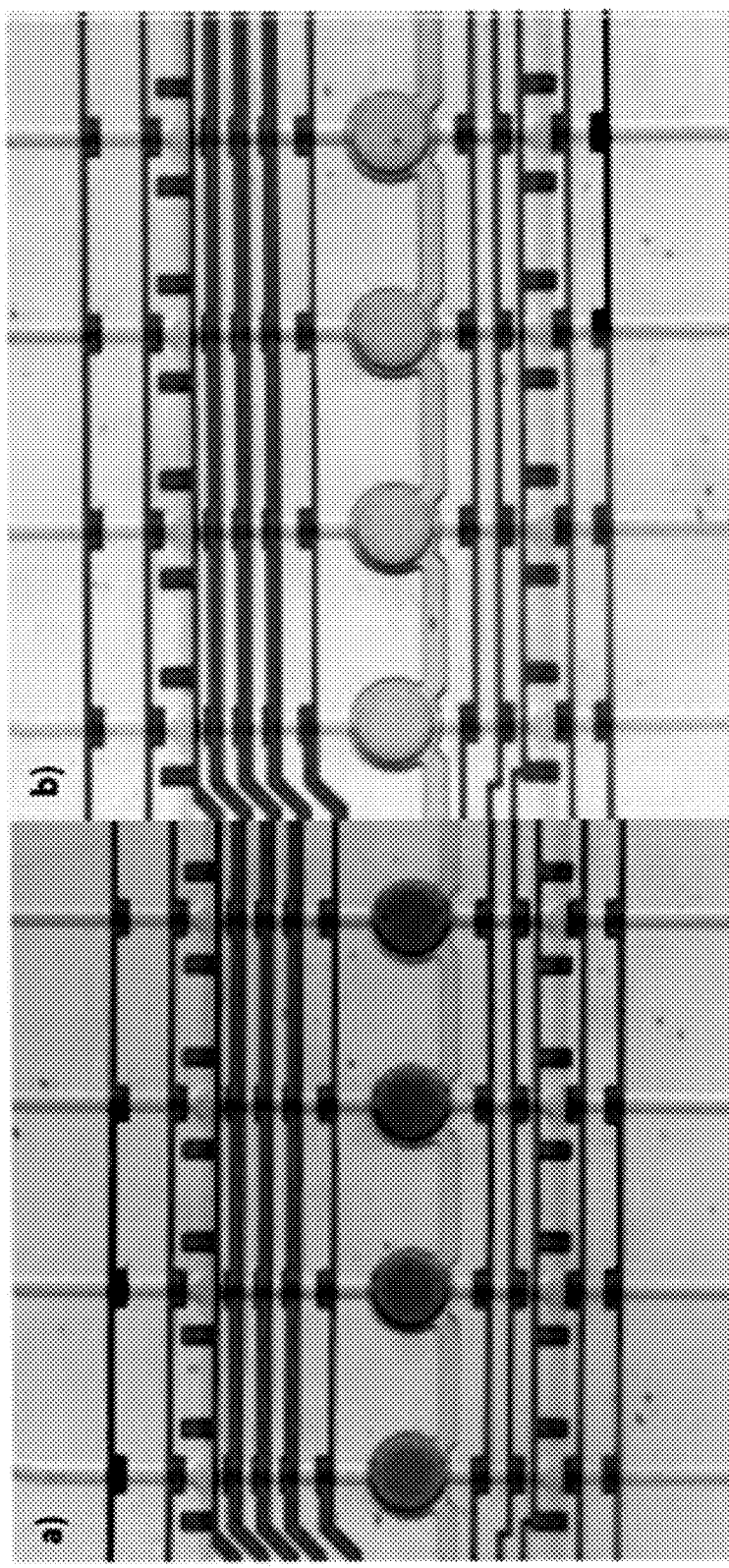

FIG. 6A shows micrograph top view of four variable volume chambers (fully inflated) and associated flow (light lines) and control lines (dark lines), wherein the chamber and flow channels are at 15 psi and the displacement chamber is at 2 psi. FIG. 6B shows micrograph top view of four variable volume chambers (deflated) and associated flow (light lines) and control lines (dark lines), wherein the chamber and flow channels are at 2 psi and the displacement chamber is at 15 psi.

Figure 7:
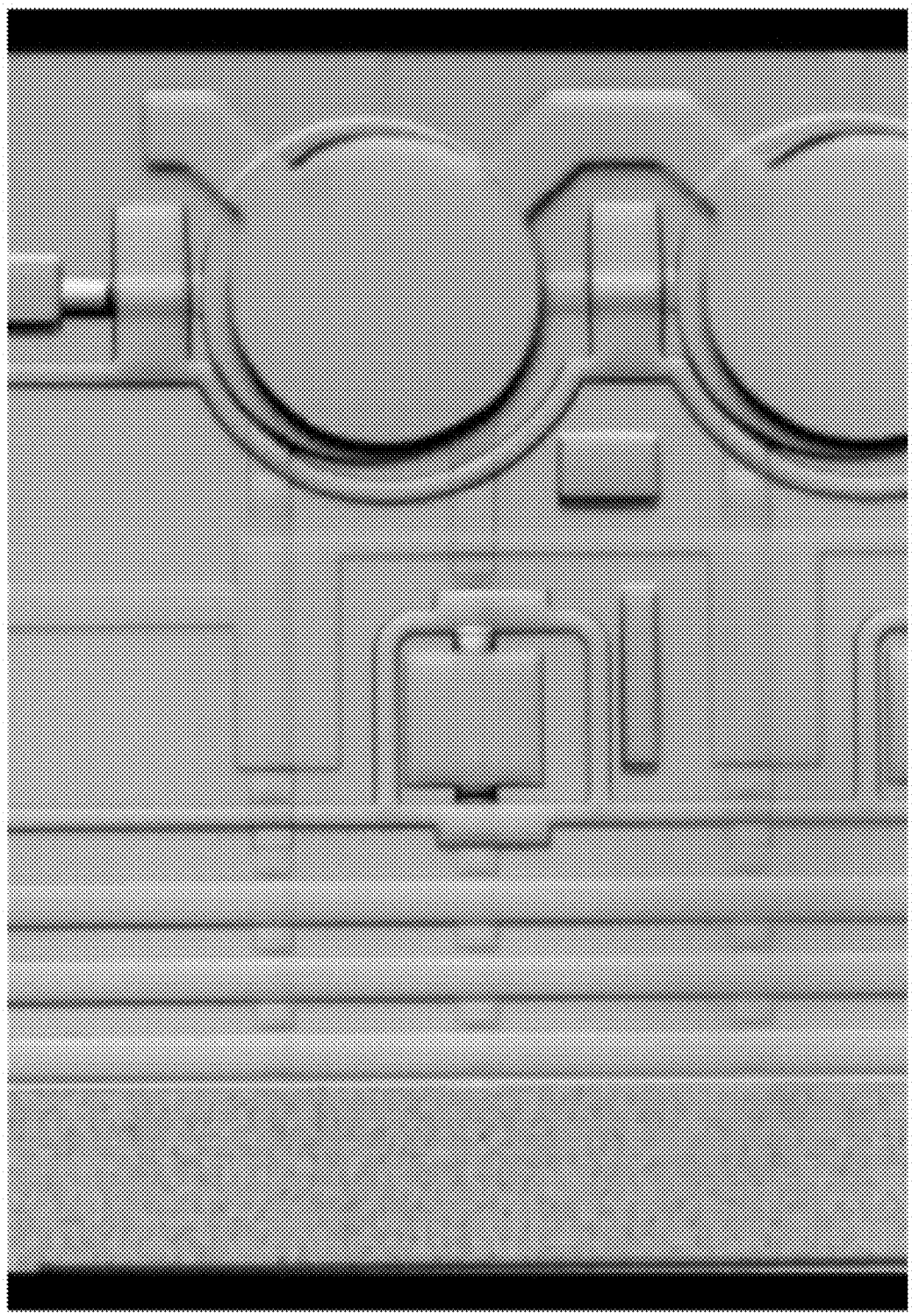

FIG. 7 shows a micrograph top view of four variable volume chambers at higher magnification than those shown in FIGS. 6A-B and without the colored dye in the control lines and flow channels, wherein the vertical speckled area on the far left is a flow channel filled with beads, running parallel to the bead filled flow channel are three control lines that act a peristaltic pump capable of moving bead filled fluid from the flow channel through the smaller flow channels running perpendicular to the bead filled flow channel into the reaction chamber.

Figure 8A:
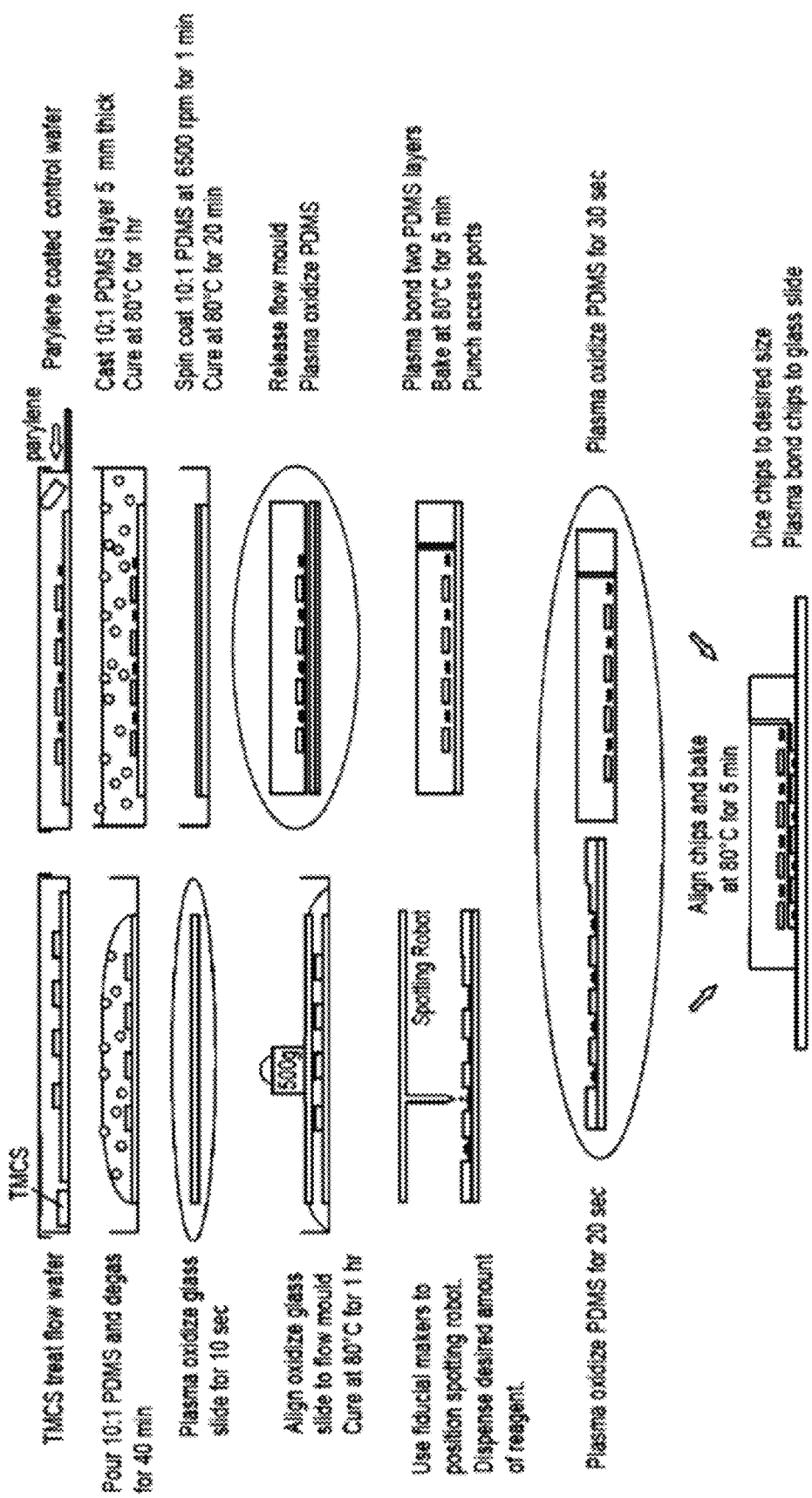
Figure 8B:
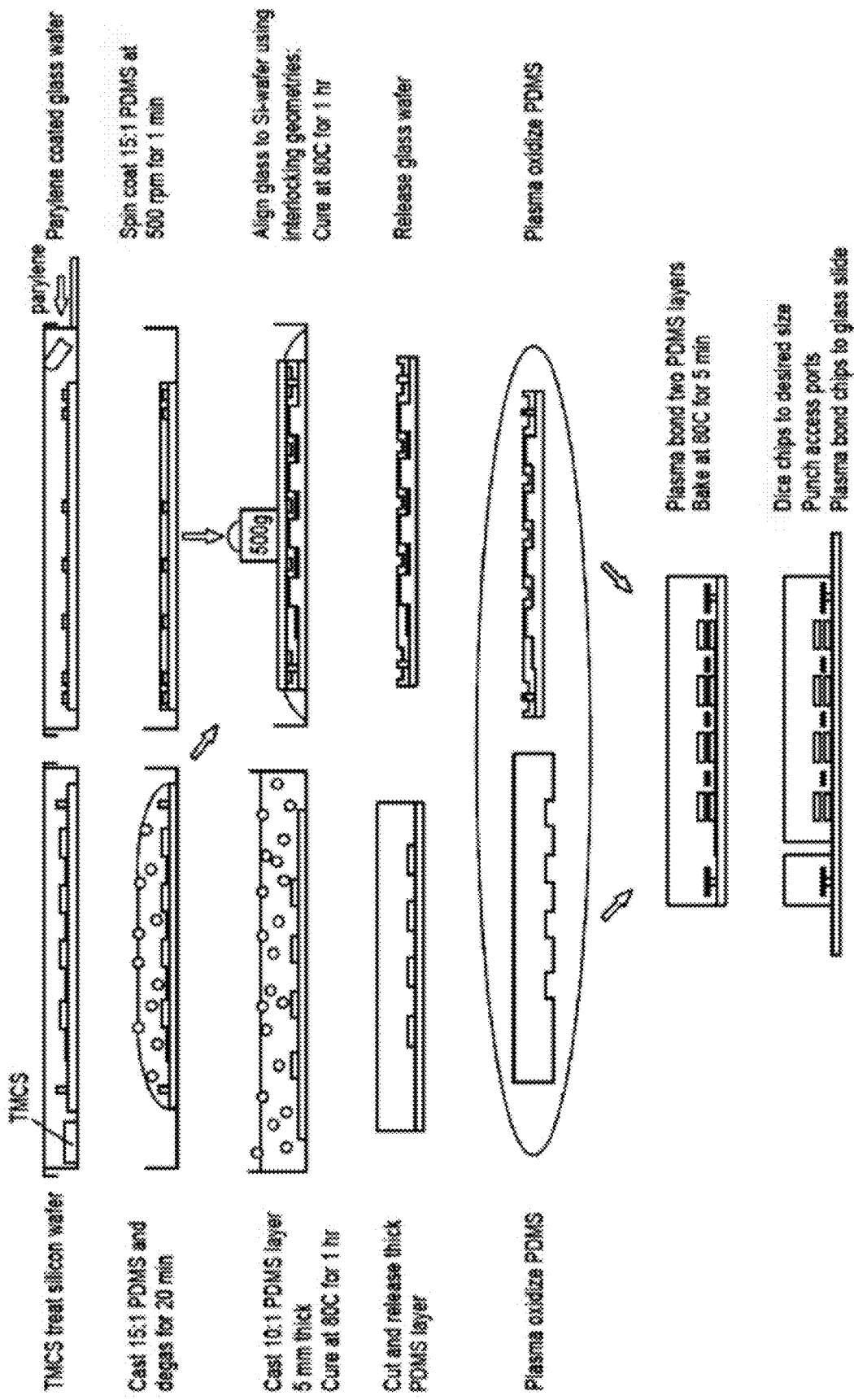
Figure 8E:
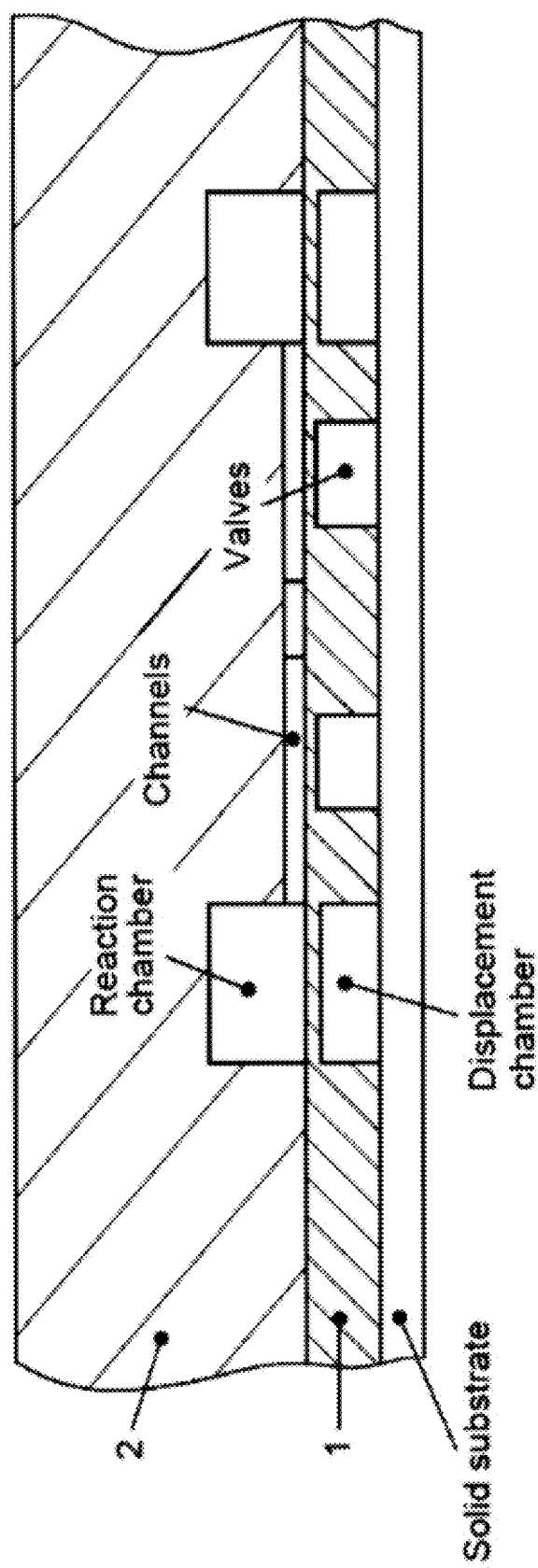

FIG. 8A shows a flow diagram depicting the steps for single sided microfluidic chip fabrication workflow wherein the chip comprises an embodiment of an integrated microfluidic device. FIG. 8B shows a flow diagram depicting the steps for double sided microfluidic chip fabrication workflow wherein the chip comprises an embodiment of an integrated microfluidic device. FIG. 8C shows a microfluidic chip achieved by one embodiment of a fabrication method disclosed herein. FIG. 8D shows a microfluidic chip achieved by one fabrication method disclosed herein. FIG. 8E shows a microfluidic chip achieved by one fabrication method disclosed herein.

Figures 9A, 9B:
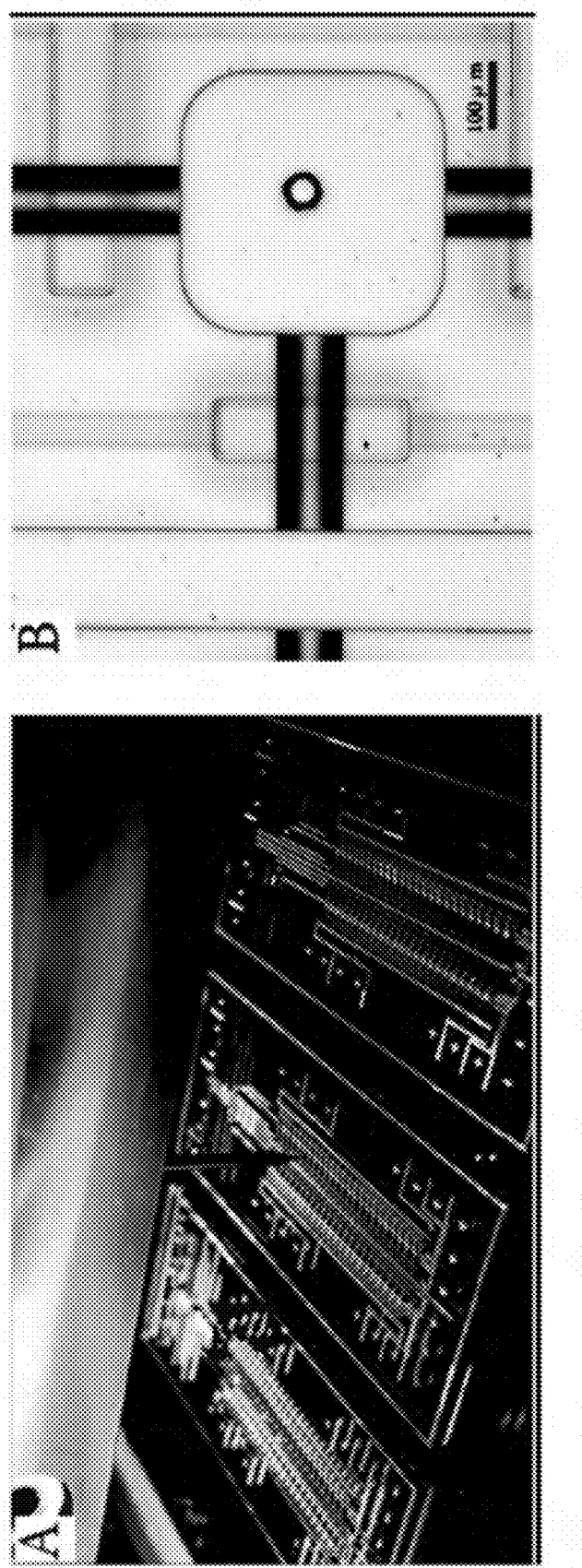
Figure 10A:
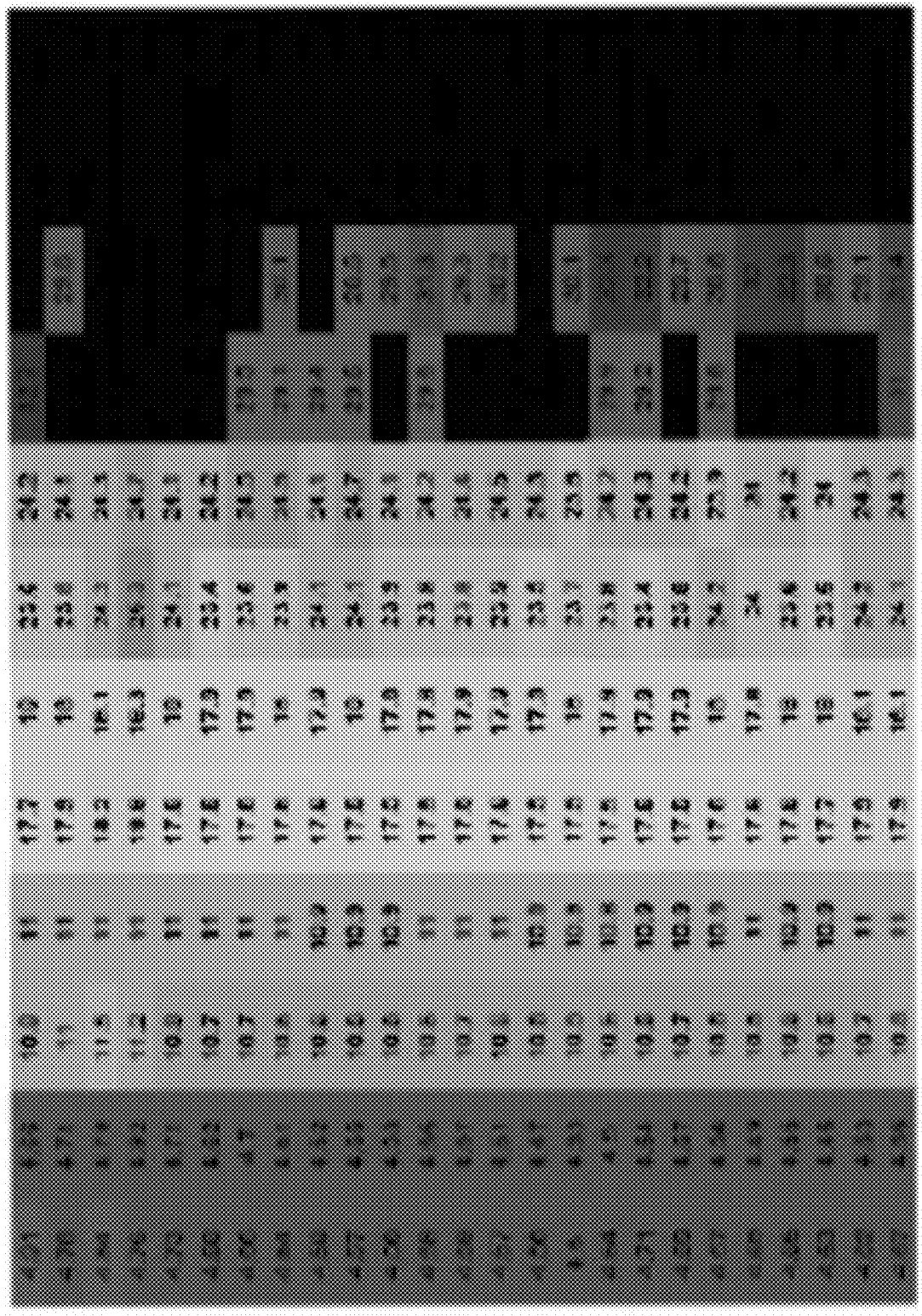
Figure 10B:
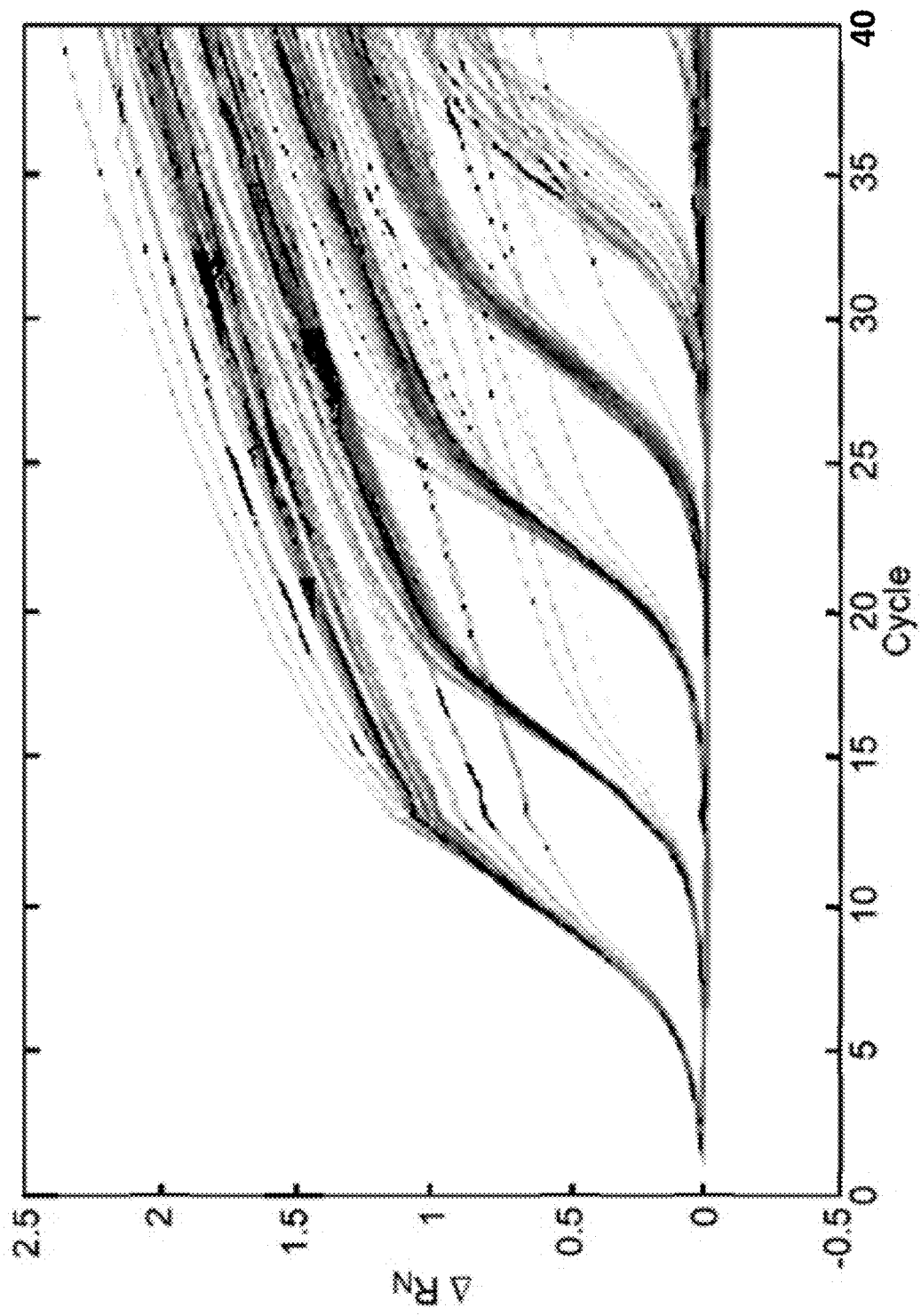
Figure 10C:
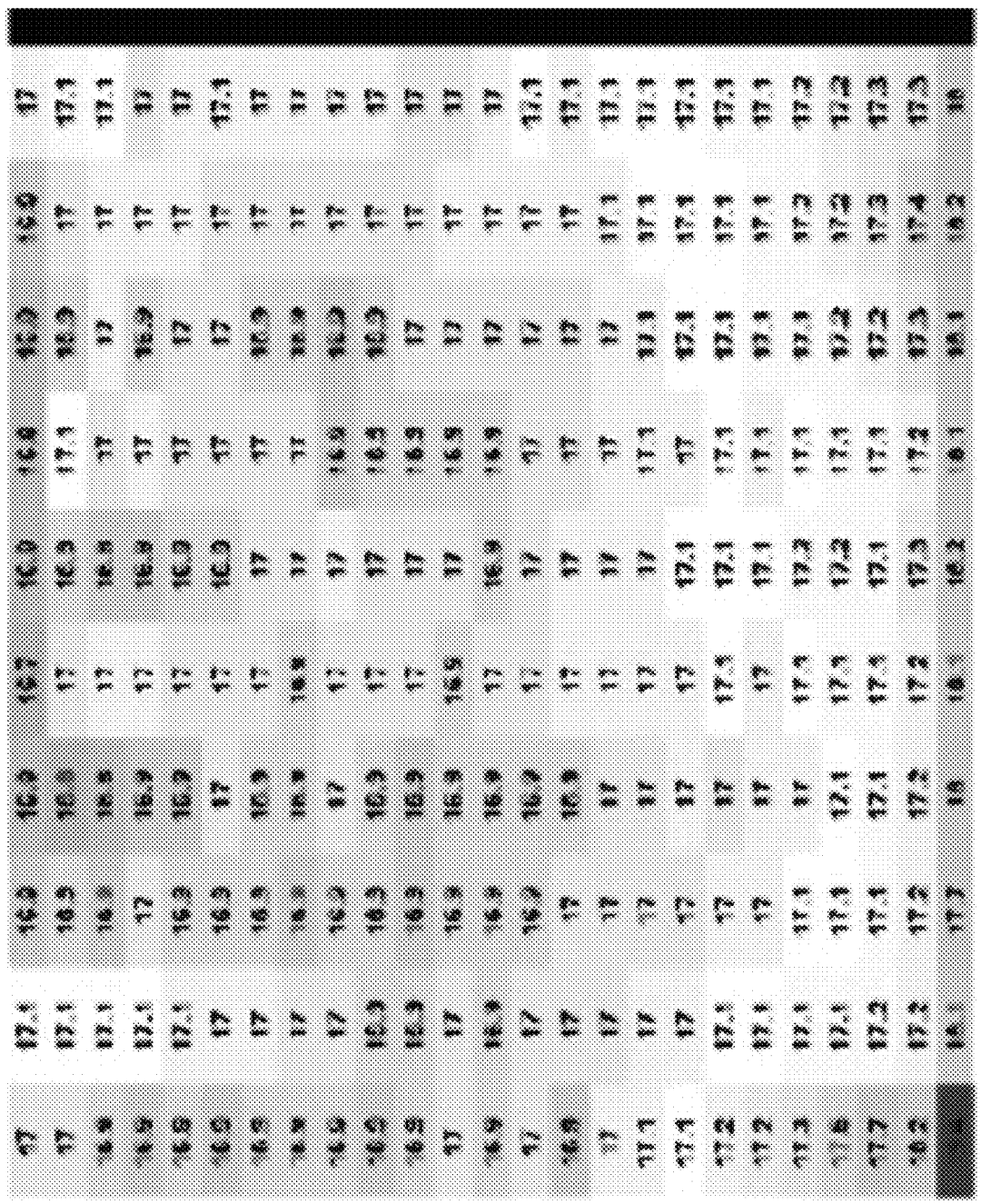
Figure 10D:
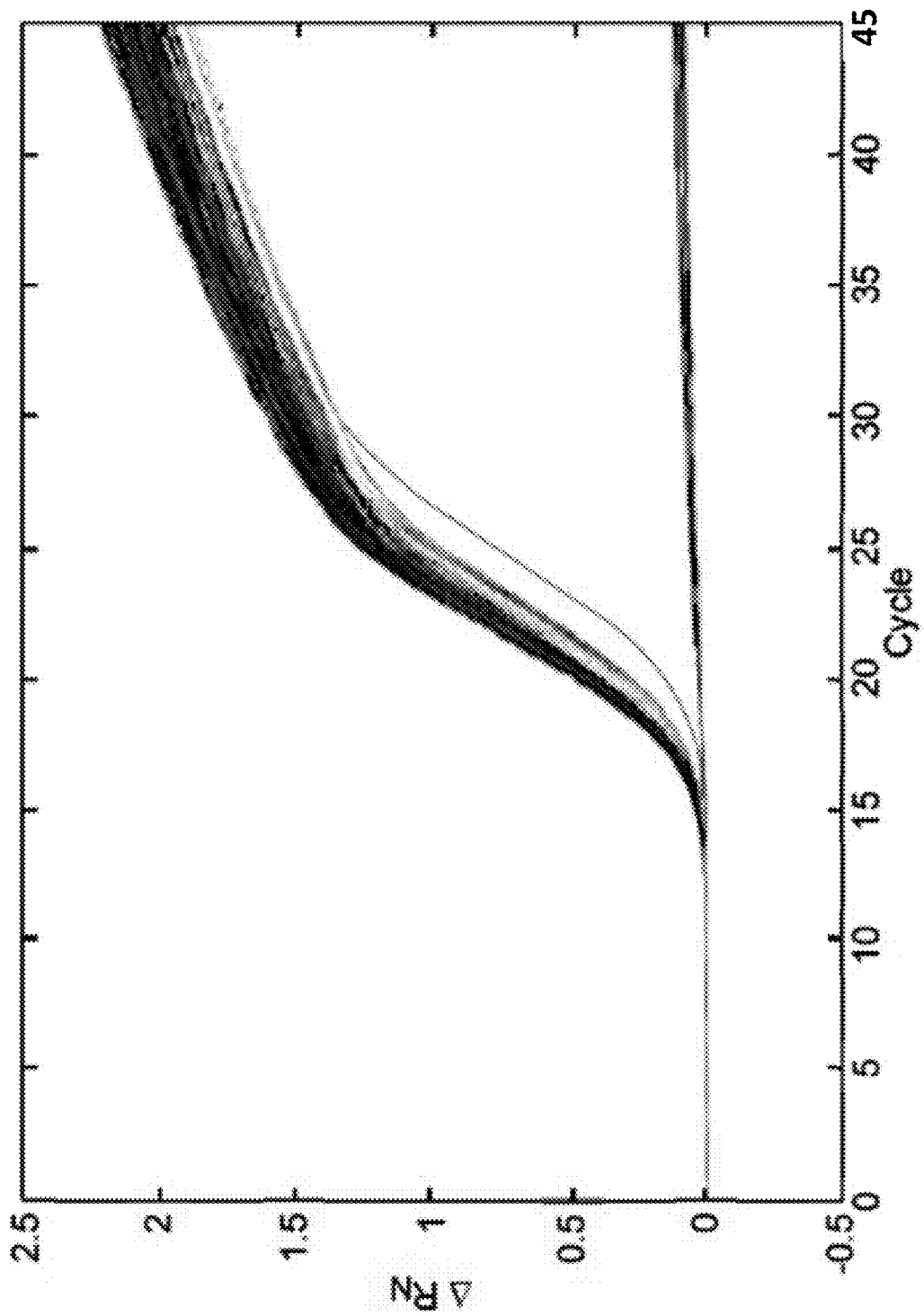
Figure 10E:
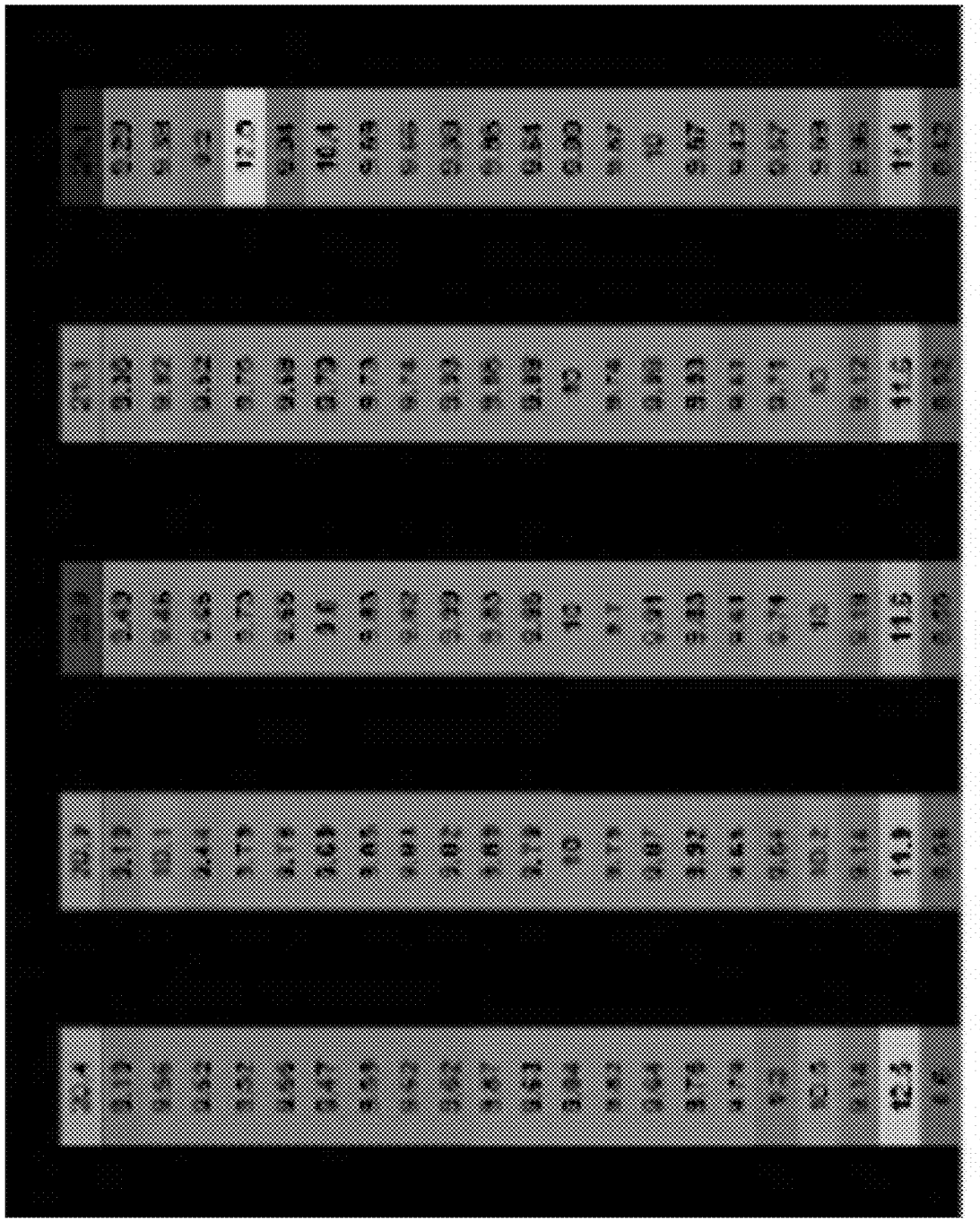
Figure 10F:
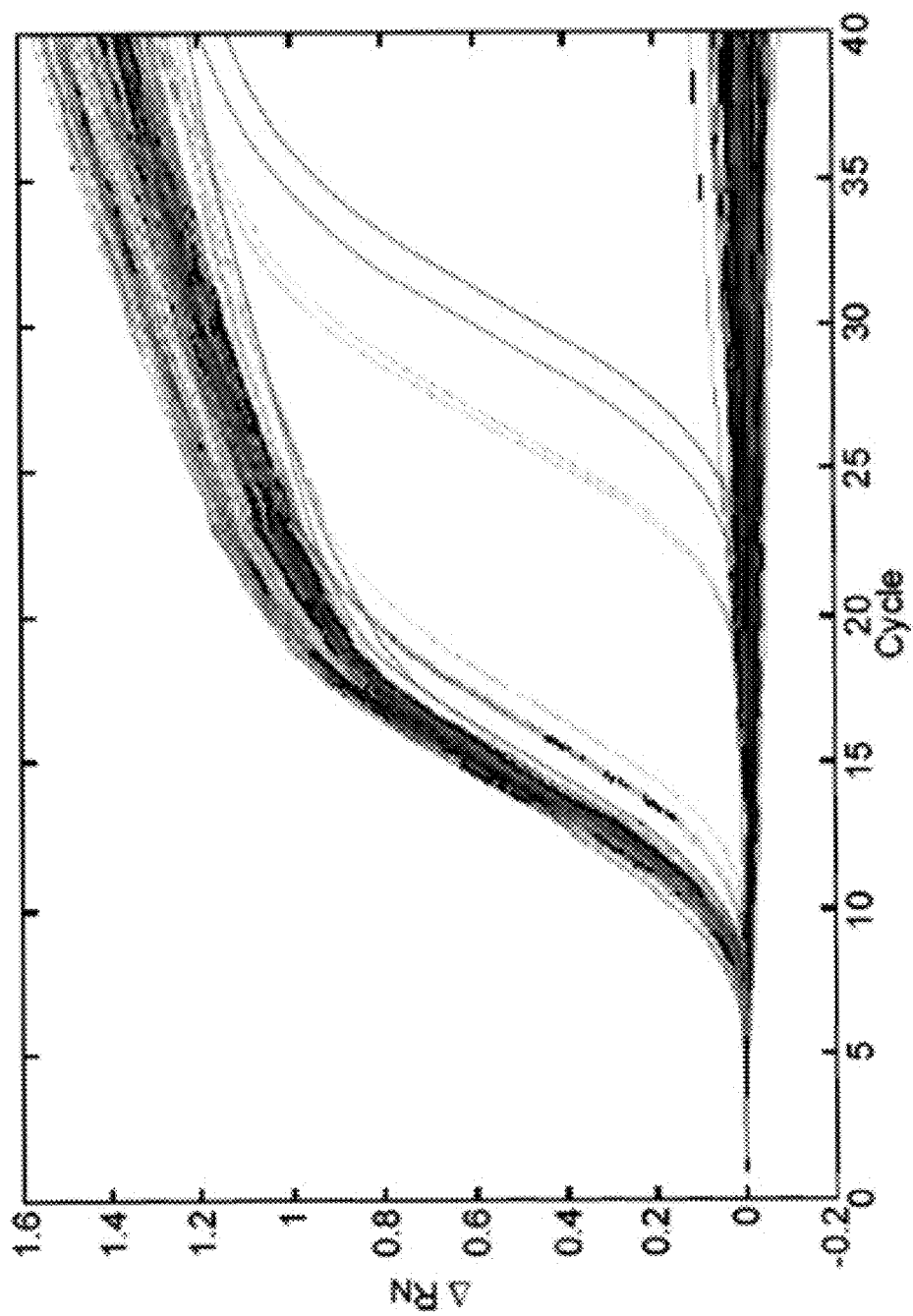

FIGS. 9A-B show a photograph (FIG. 9A) and micrograph (FIG. 9B) of contactless spotting into microfluidic chambers, respectively.

FIGS. 10A-F show primer incorporation performance by a spotting robot dispensing unique indexes with minimal cross-contamination.

Figure 11:
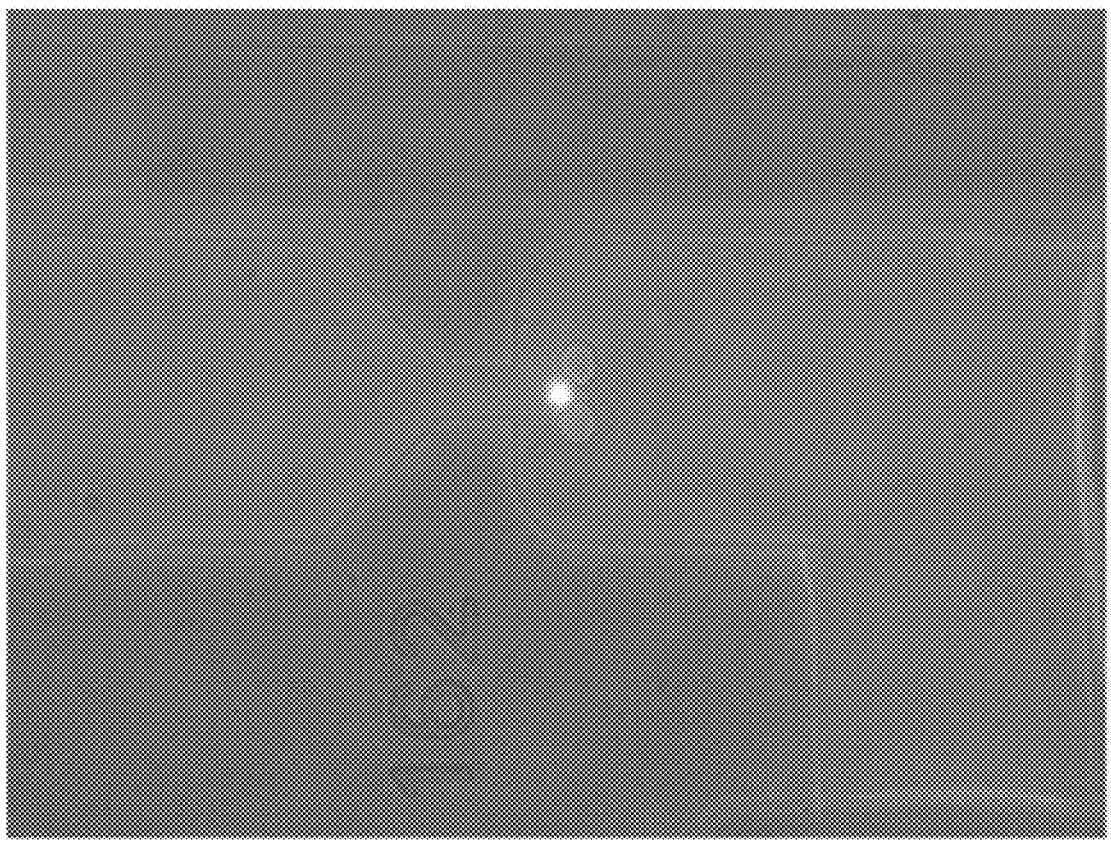

FIG. 11 shows a micrograph of a trapped single nuclei in an embodiment of a cell trap within a chamber.

Figure 12A:
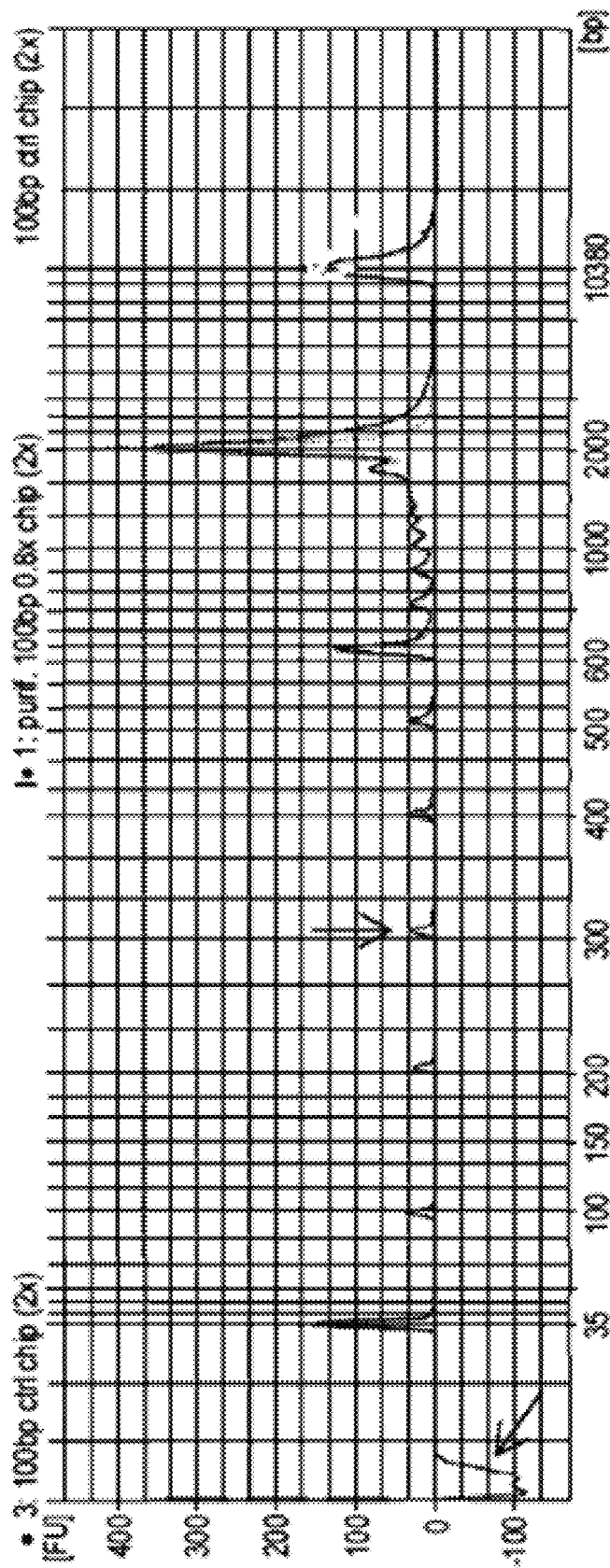
Figure 12B:
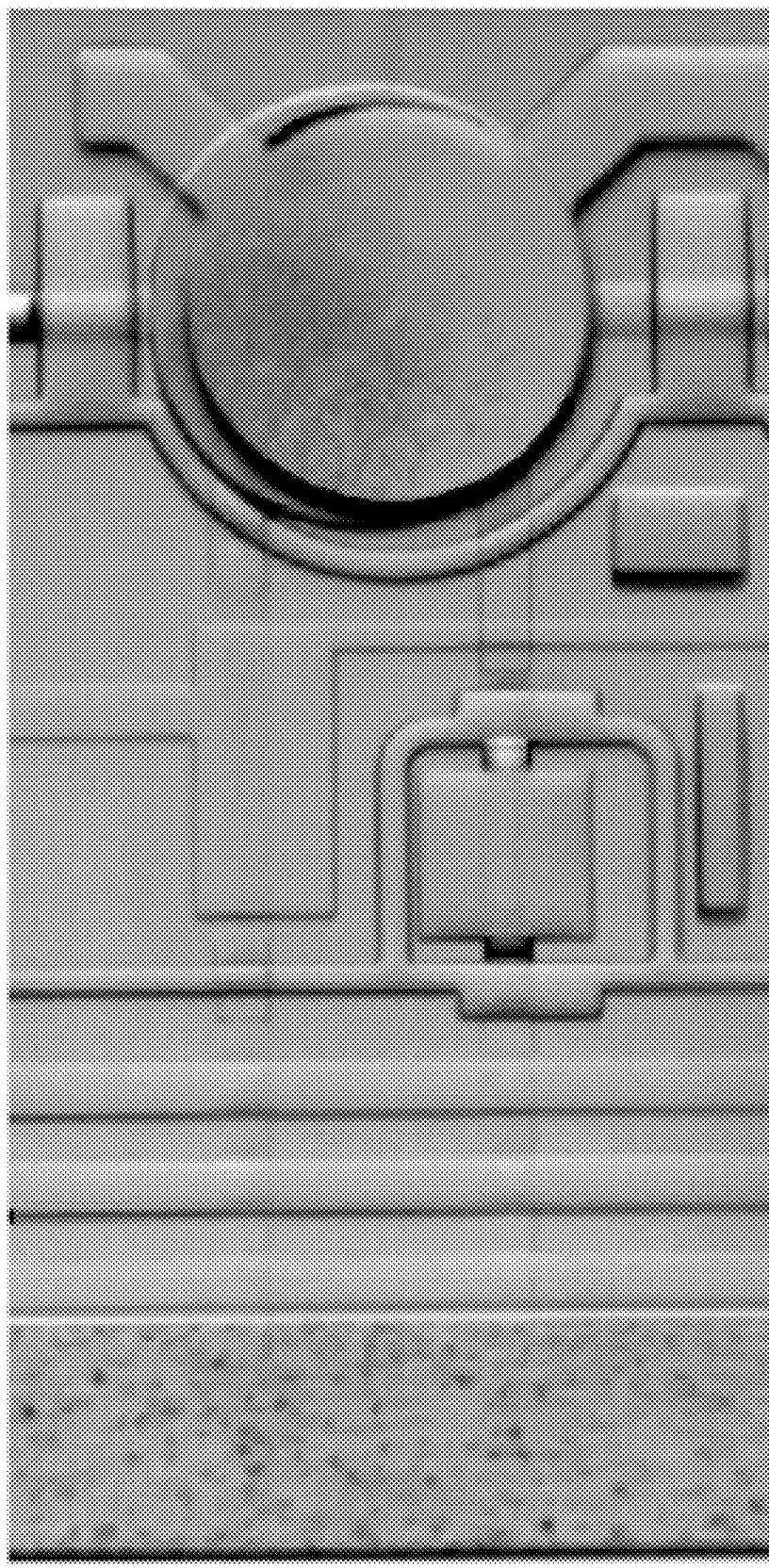

FIG. 12A shows a plot depicting bead purification and size selection on an integrated microfluidic device showing fluorescence units (FU) on the y axis and size of the double stranded DNA purified along the x axis. FIG. 12B shows a micrograph of bead purification and size selection on an integrated microfluidic device.

Figure 13:
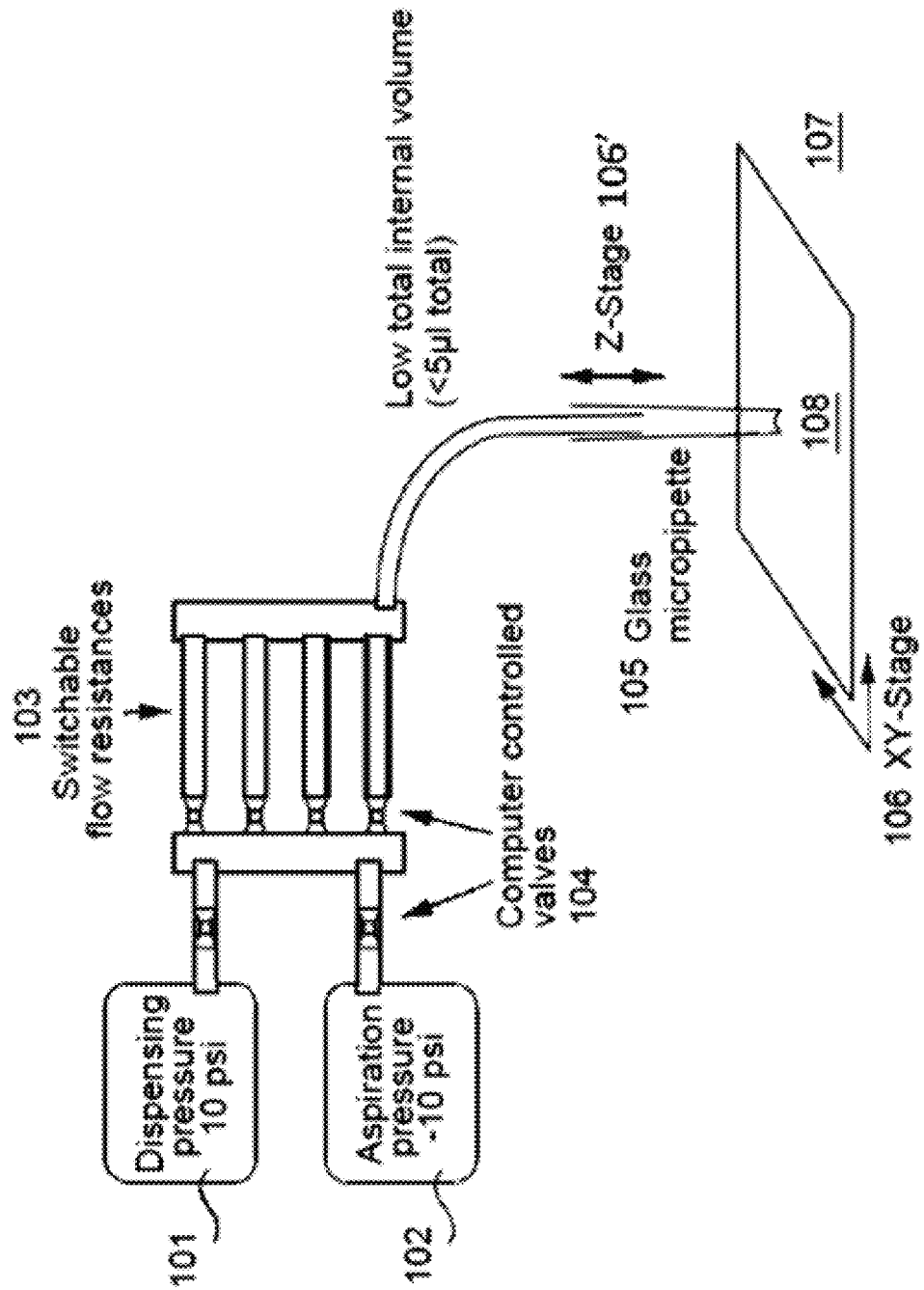

FIG. 13 depicts an automated micropipette coupled to a flow rate controller capable of nanoliter volumetric flows and translation stages for positioning while aspirating and dispensing cells.

Figure 14:
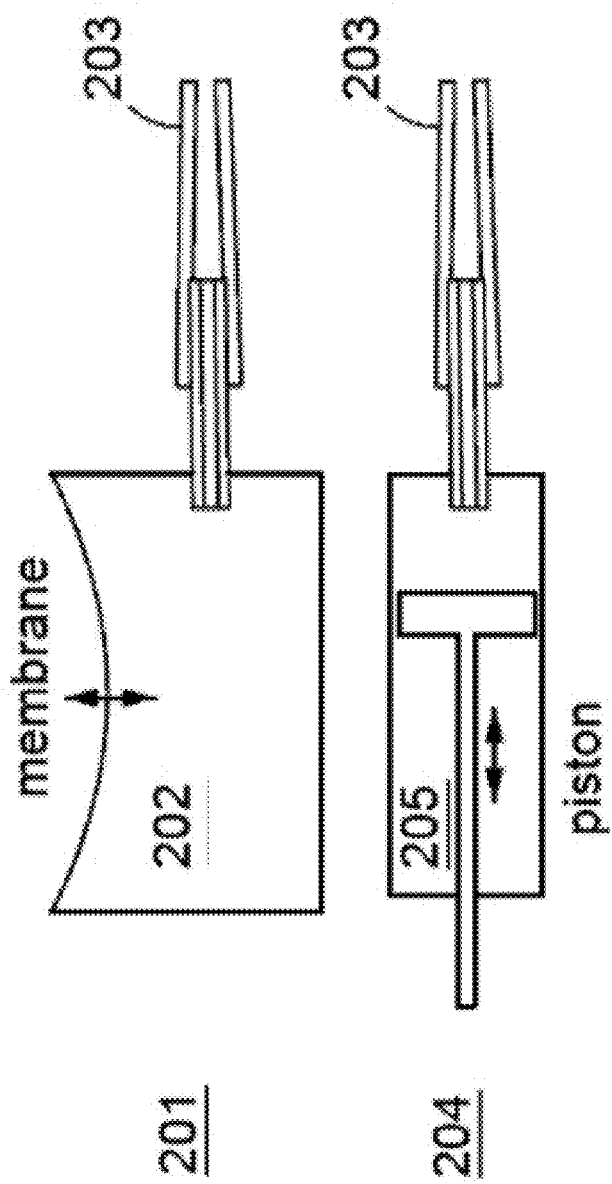

FIG. 14 depicts volume displacement methods of controlling flow.

Figure 15:
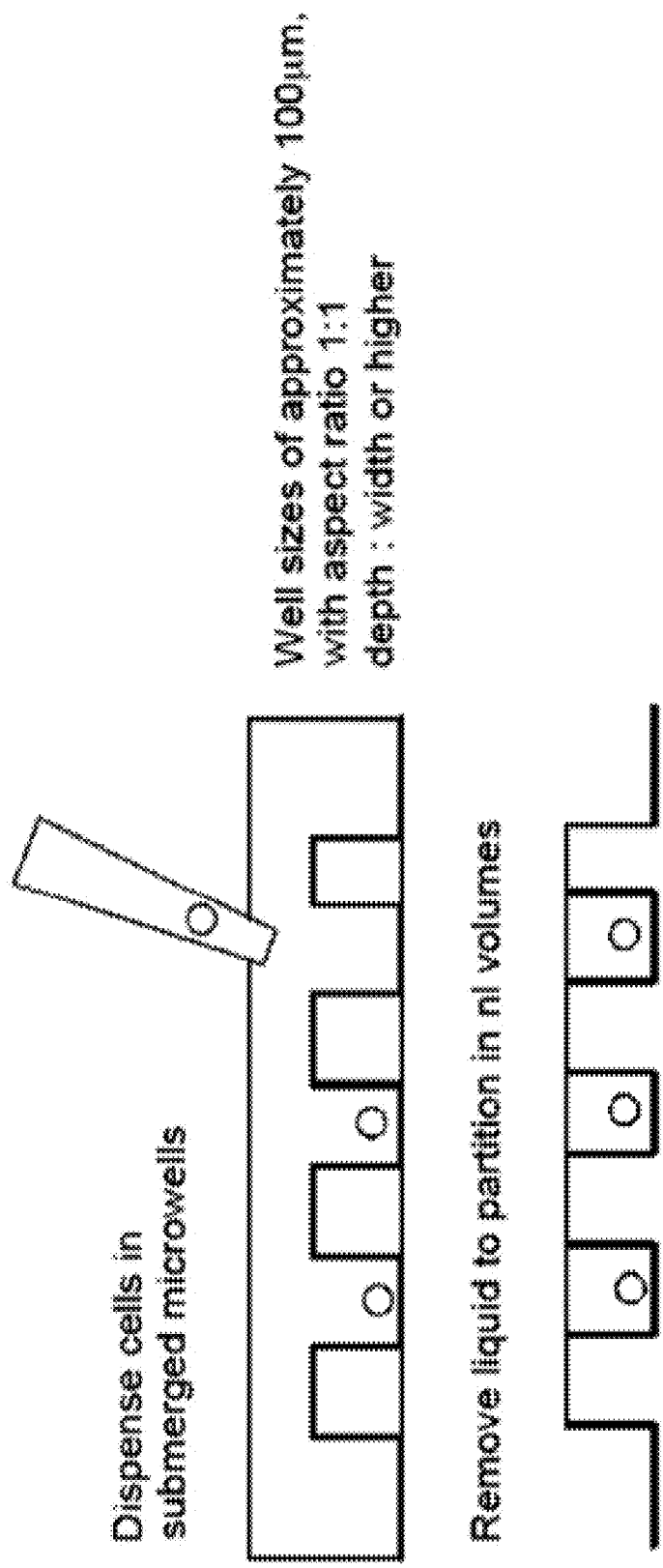

FIG. 15 depicts the use of a microwell array to partition cells into nanoliter-volumes.

Figure 16:
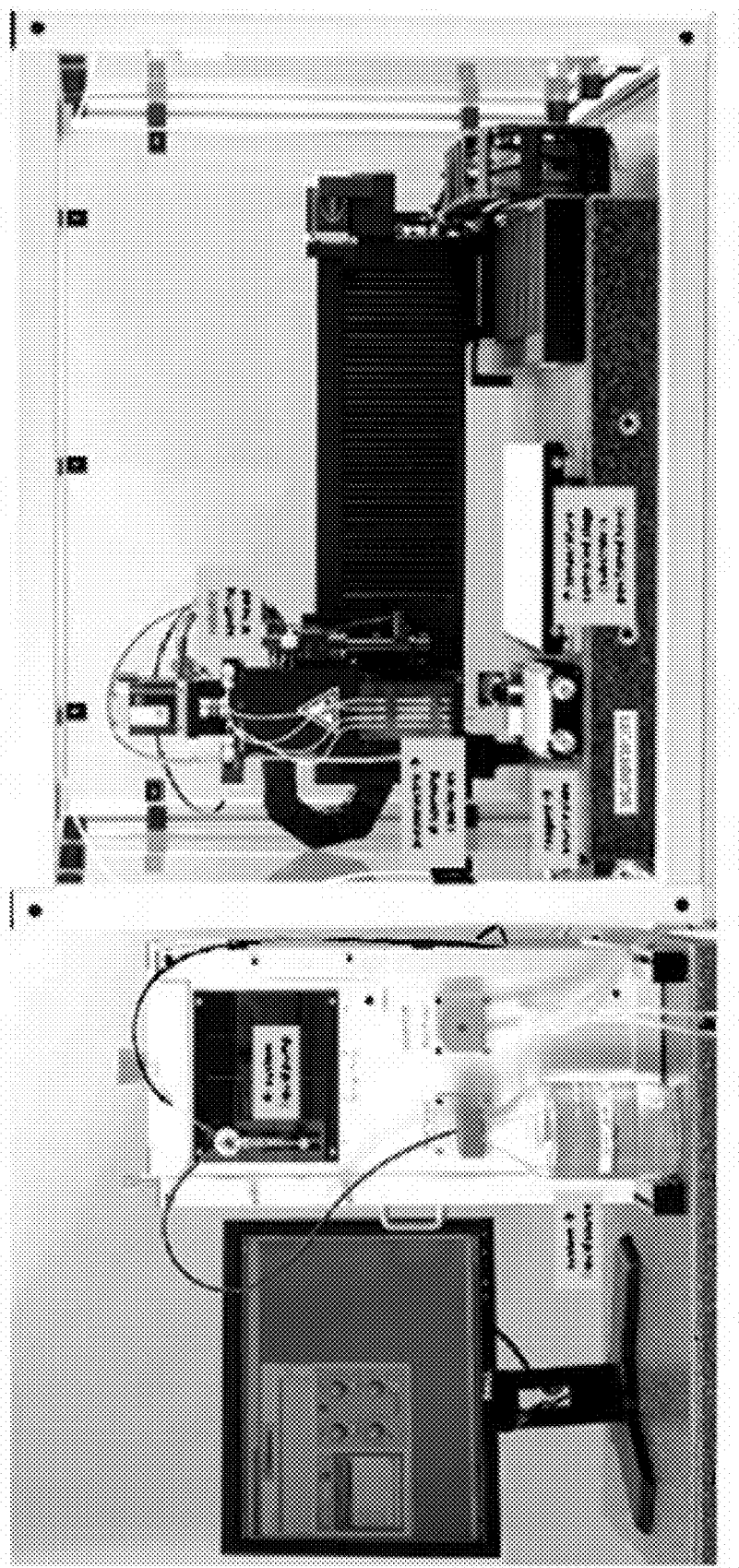

FIG. 16 depicts a piezoelectric spotting robot.

Figure 17:
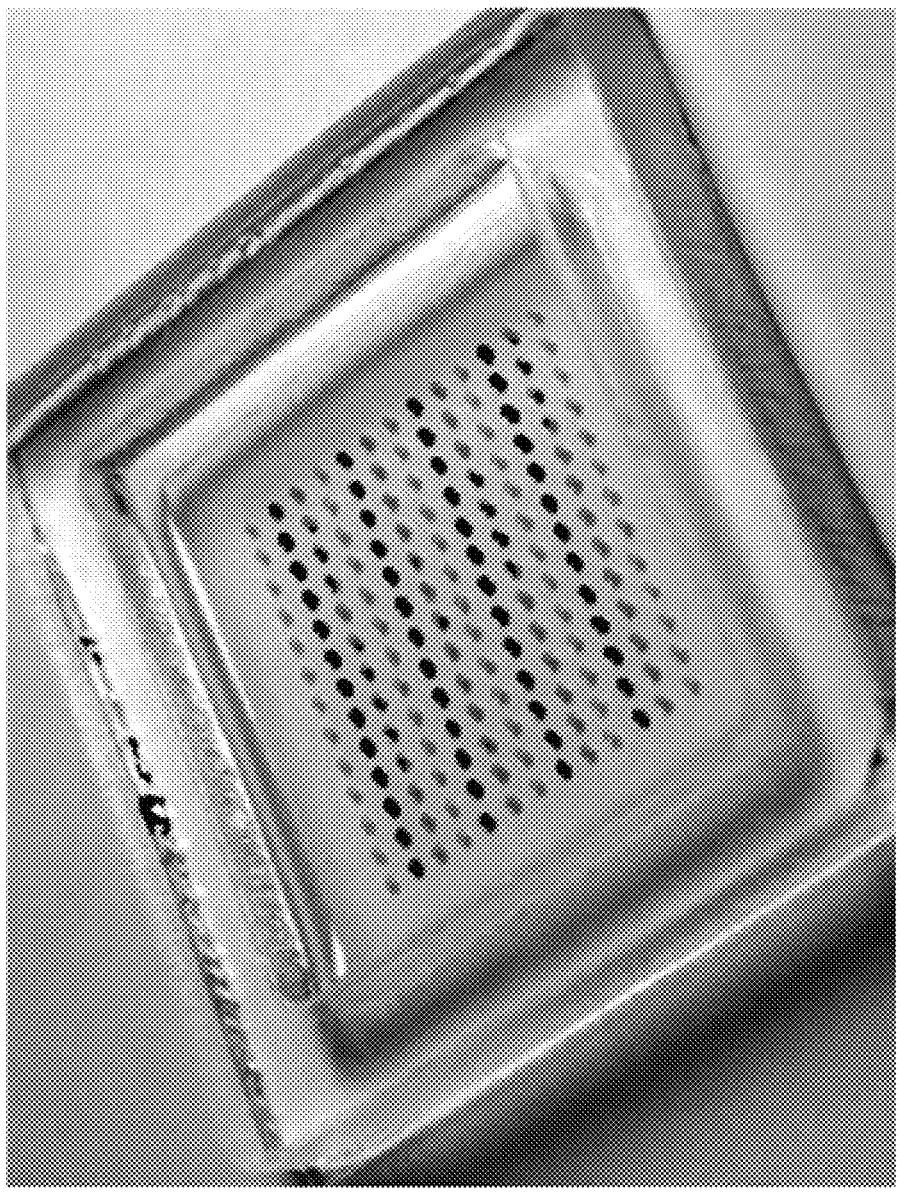

FIG. 17 depicts an engineered surface on which 100 nL droplets of colored dye have been spotted; the droplets are coated with a layer of mineral oil; a barrier surrounds the droplet array to keep the oil on the substrate.

Figure 18:
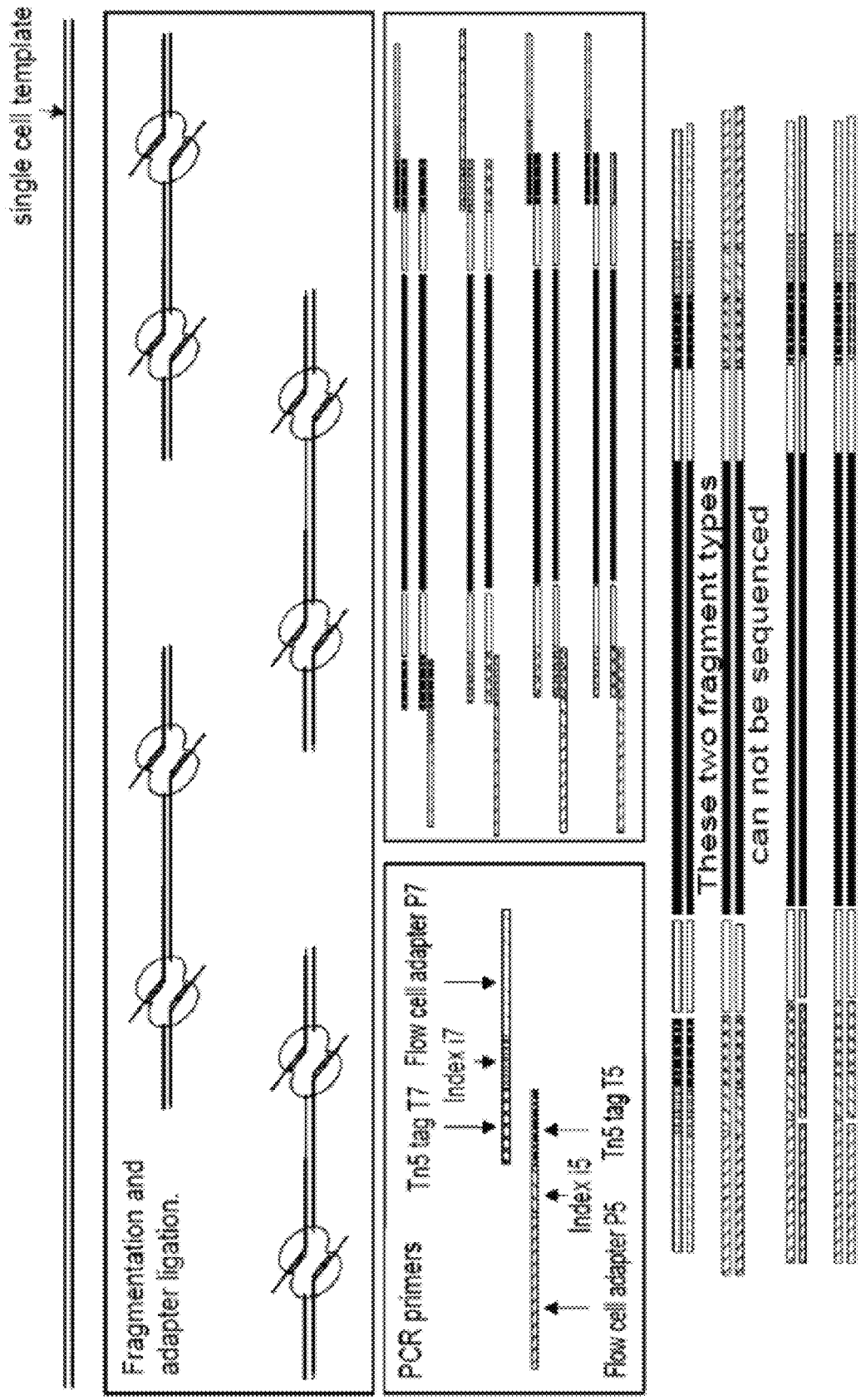

FIG. 18 depicts single-cell direct sequencing library preparation using the Illumina NEXTERA chemistry. As depicted therein, fragments with flow cell adapter P5 on both ends or P7 on both ends cannot be sequenced.

Figure 19:
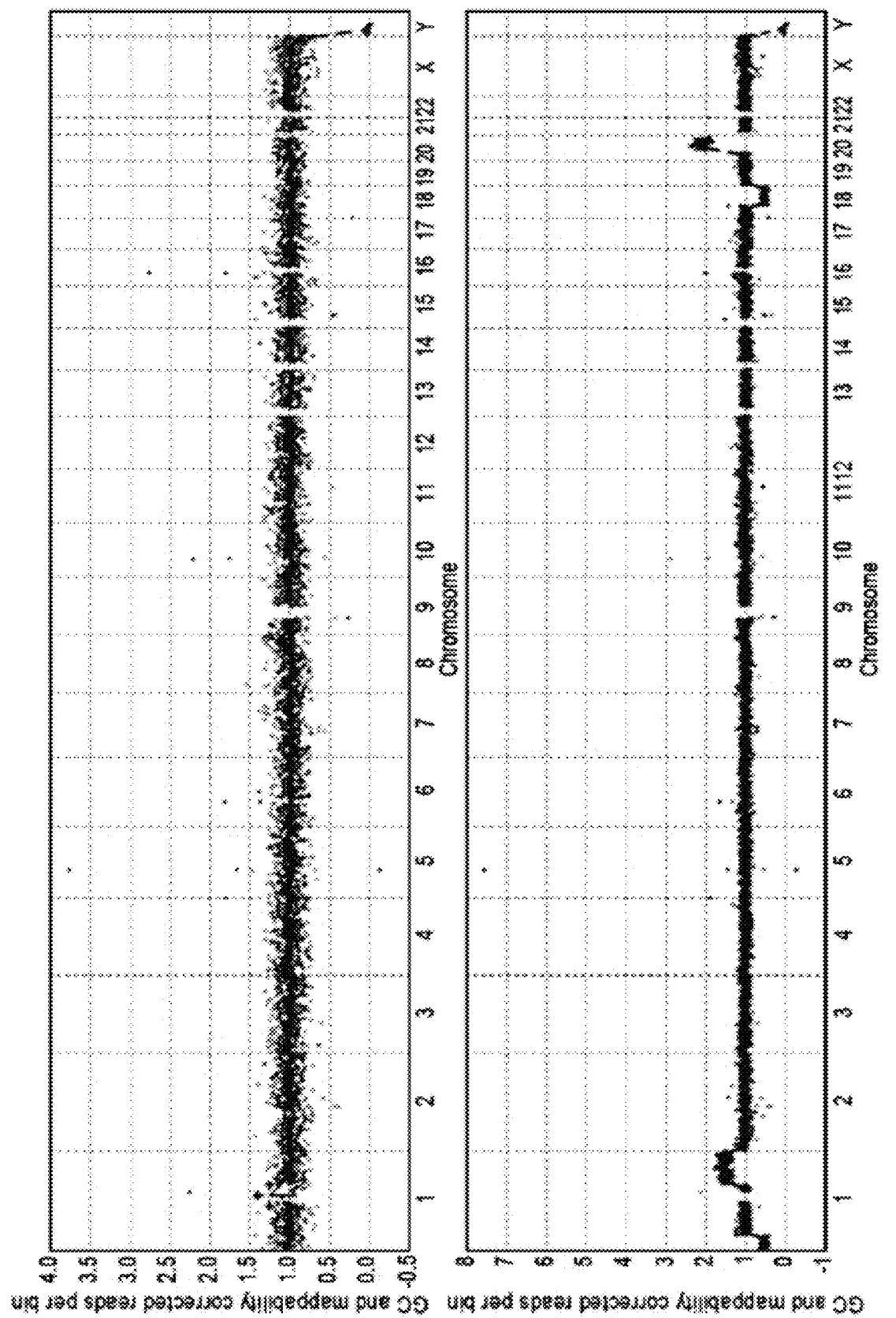

FIG. 19 depicts plots of binned read depth for single-cell amplification reactions using the direct sequencing library preparation method. The top panel shows a plot of a single cell free of CNVs. The bottom panel shows a plot of a single cell with CNVs in chromosomes 1, 18, and 20 (bottom). The cells were derived from a human female and thus lack a Y chromosome.

Figure 20:
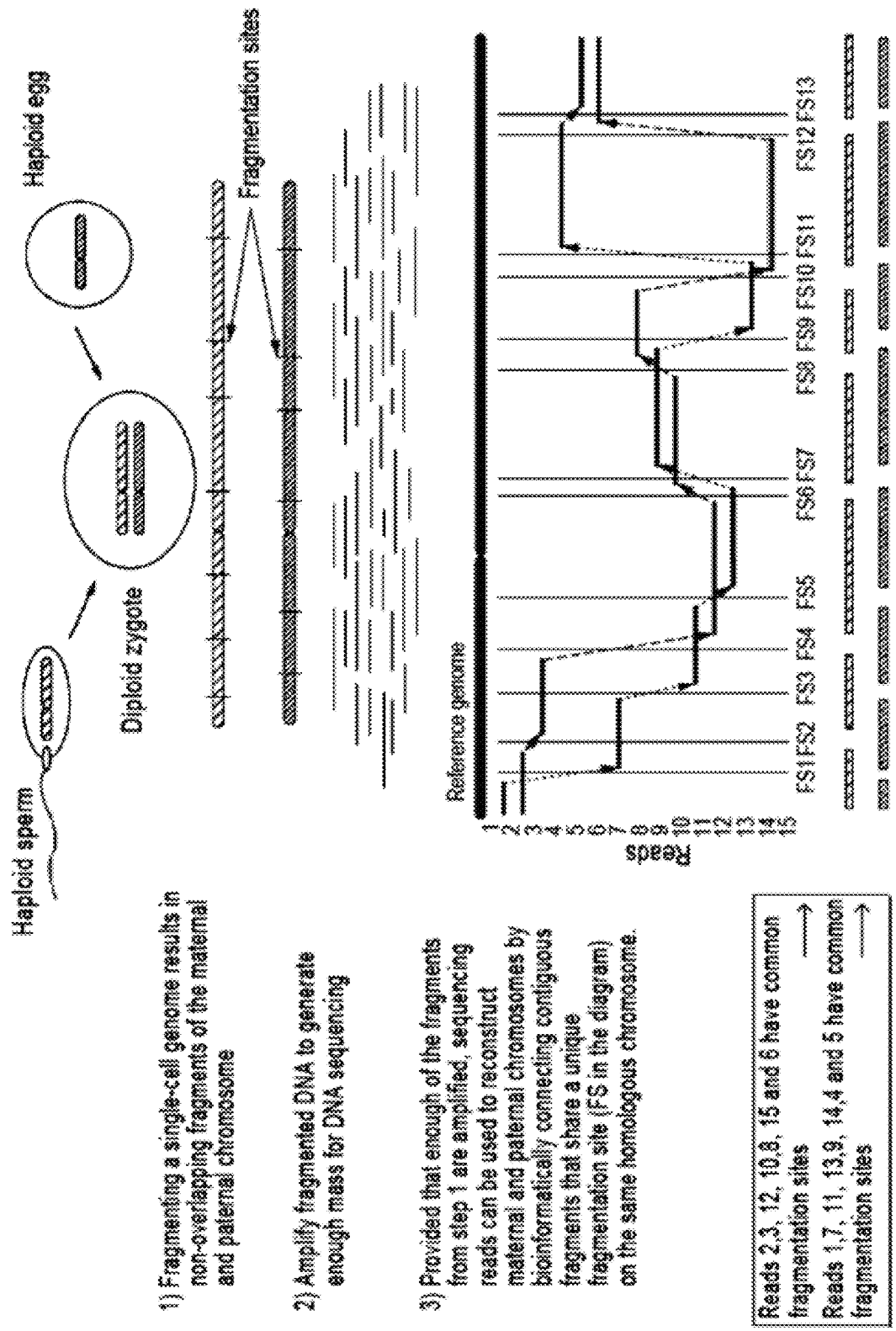

FIG. 20 depicts genome-wide haplotyping using fragmentation sites to reconstruct homologous chromosomes.

Figure 21:
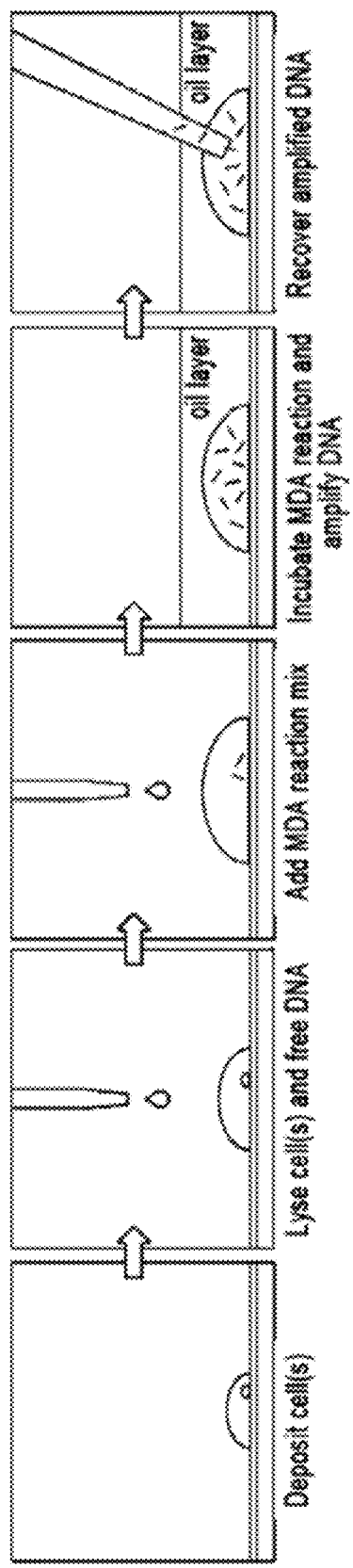

FIG. 21 depicts single-cell nanoliter-volume MDA.

Figure 22:
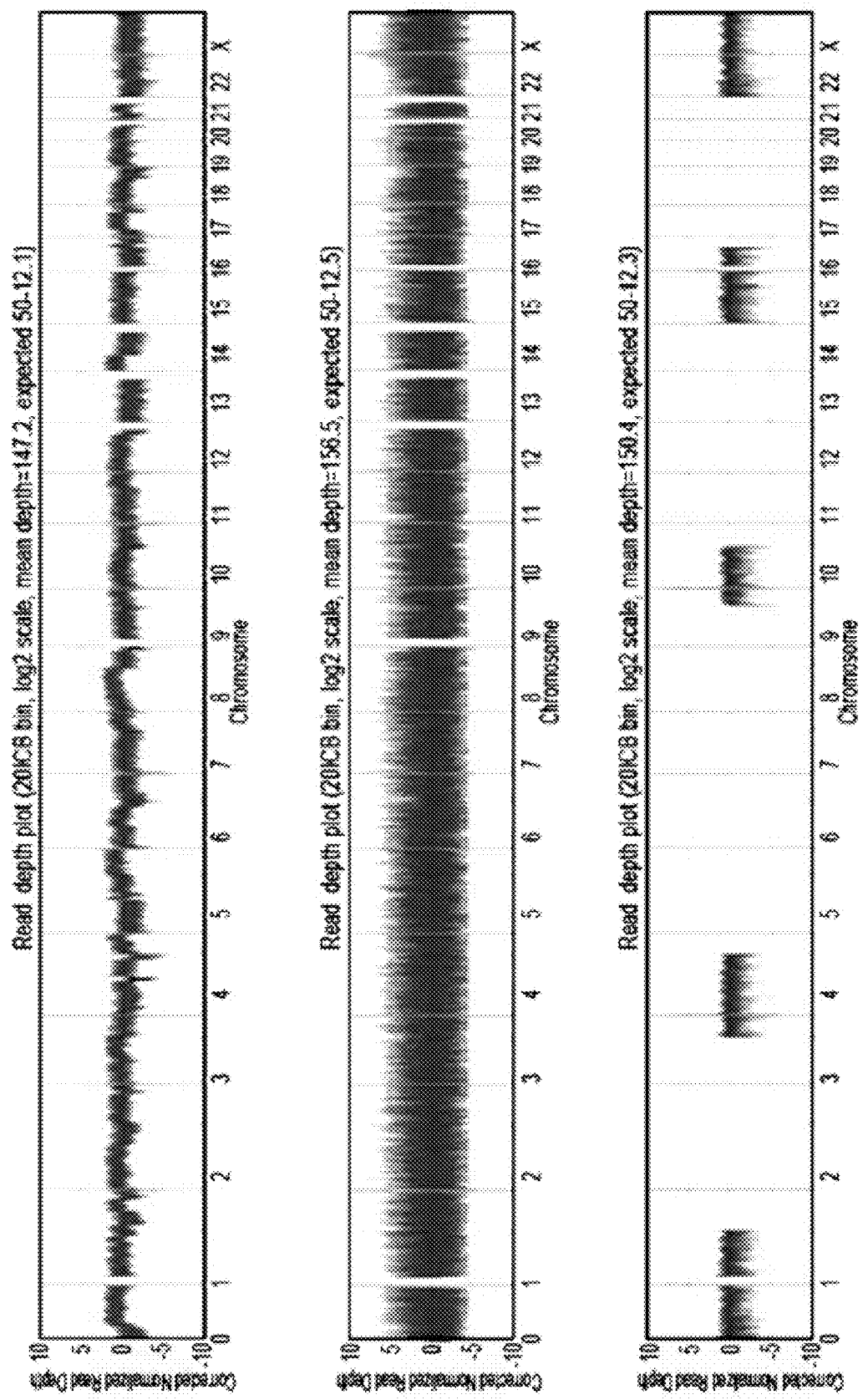

FIG. 22 depicts plots of binned read depth for single-cell amplification reactions using the single-cell nanoliter-volume MDA method (top), microfluidic MDA (middle), and MALBAC (bottom). Genomic regions containing known copy number variations have been omitted.

Figure 23:
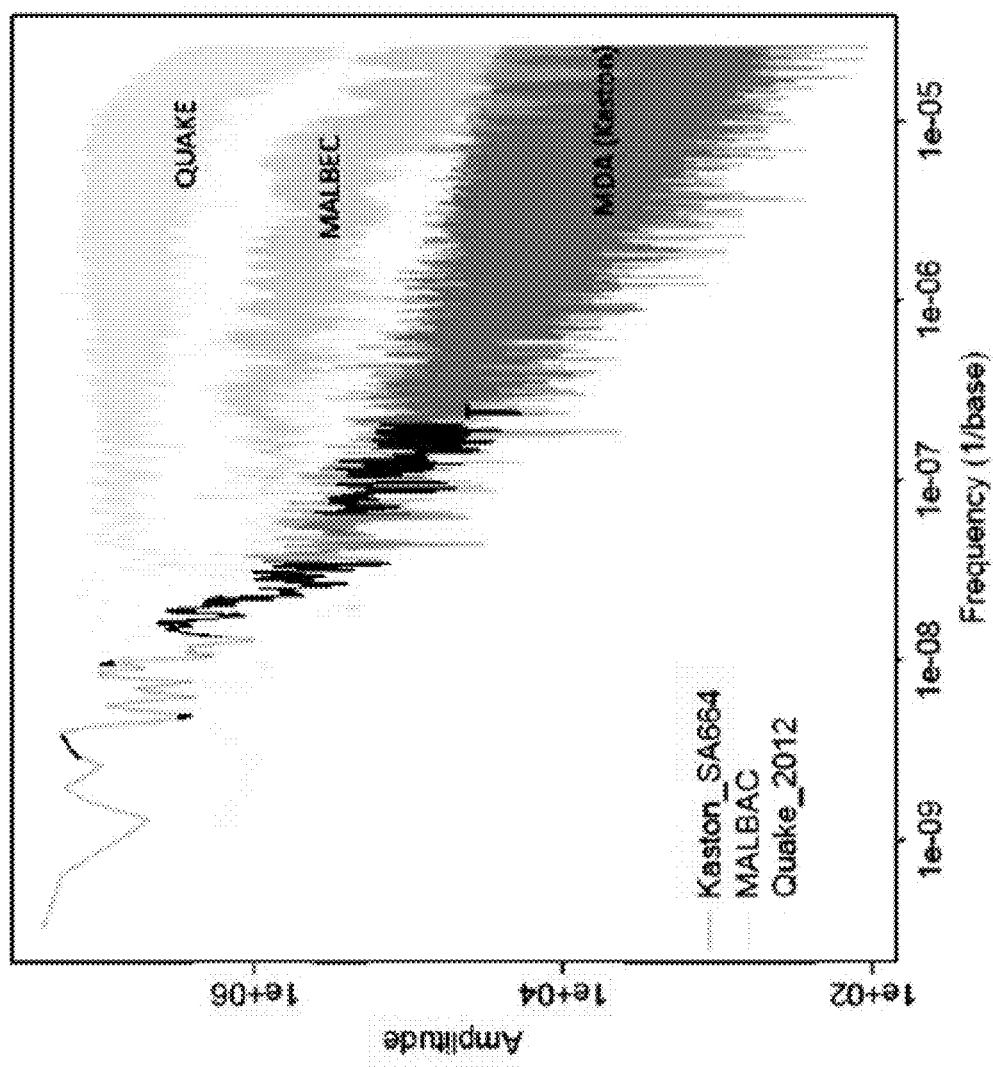

FIG. 23 depicts power spectra of read density variation for single-cell amplification reactions using the single-cell nanoliter-volume MDA method (bottom), microfluidic MDA (top), and MALBAC (middle).

Figure 24:
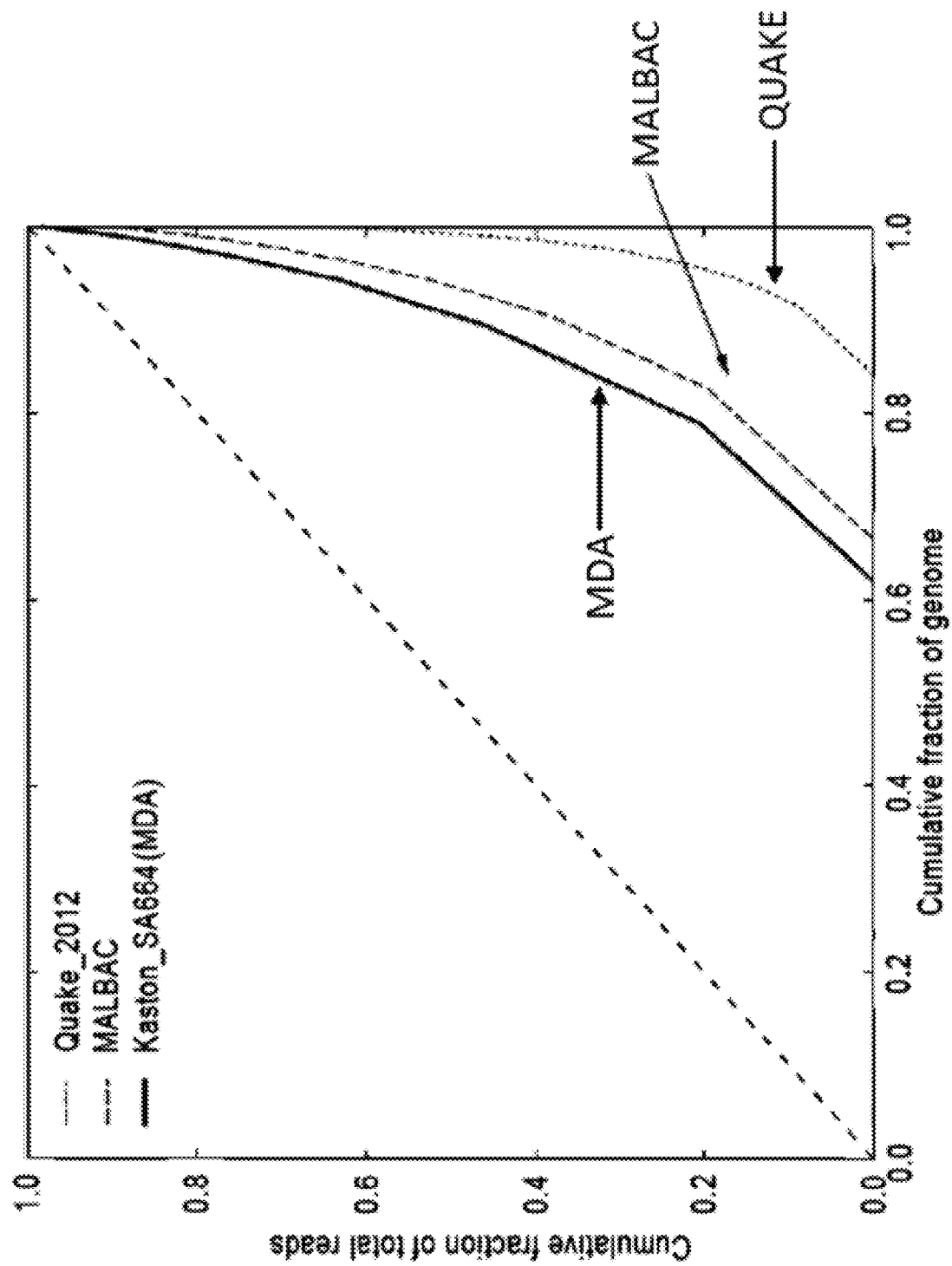

FIG. 24 depicts Lorenz curves for single-cell amplification reactions using the single-cell nanoliter-volume MDA method (left), microfluidic MDA (right), and MALBAC (middle).

Figure 25:
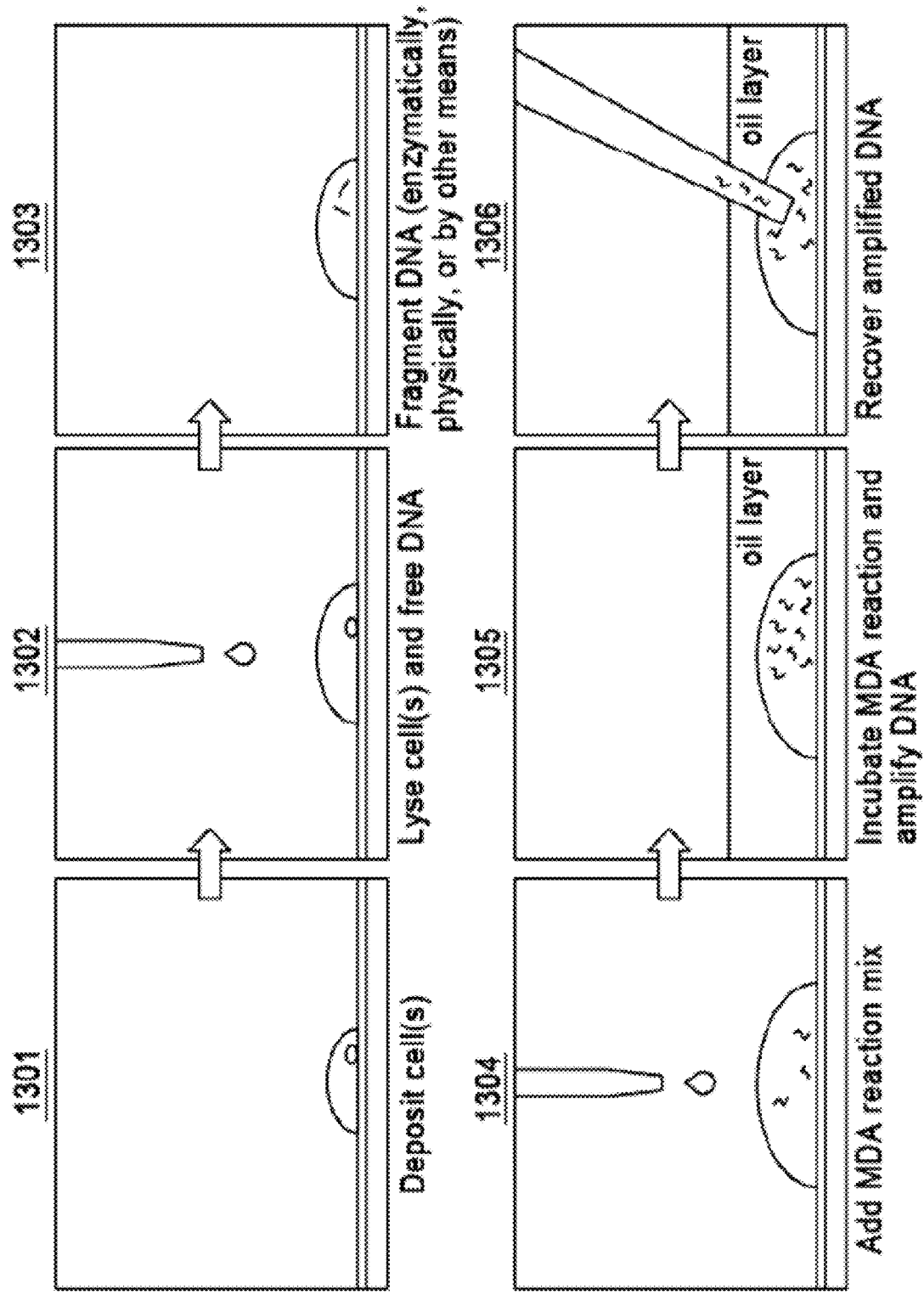

FIG. 25 depicts fragmentation of genomic DNA followed by MDA in a single reaction volume.

Figure 26:
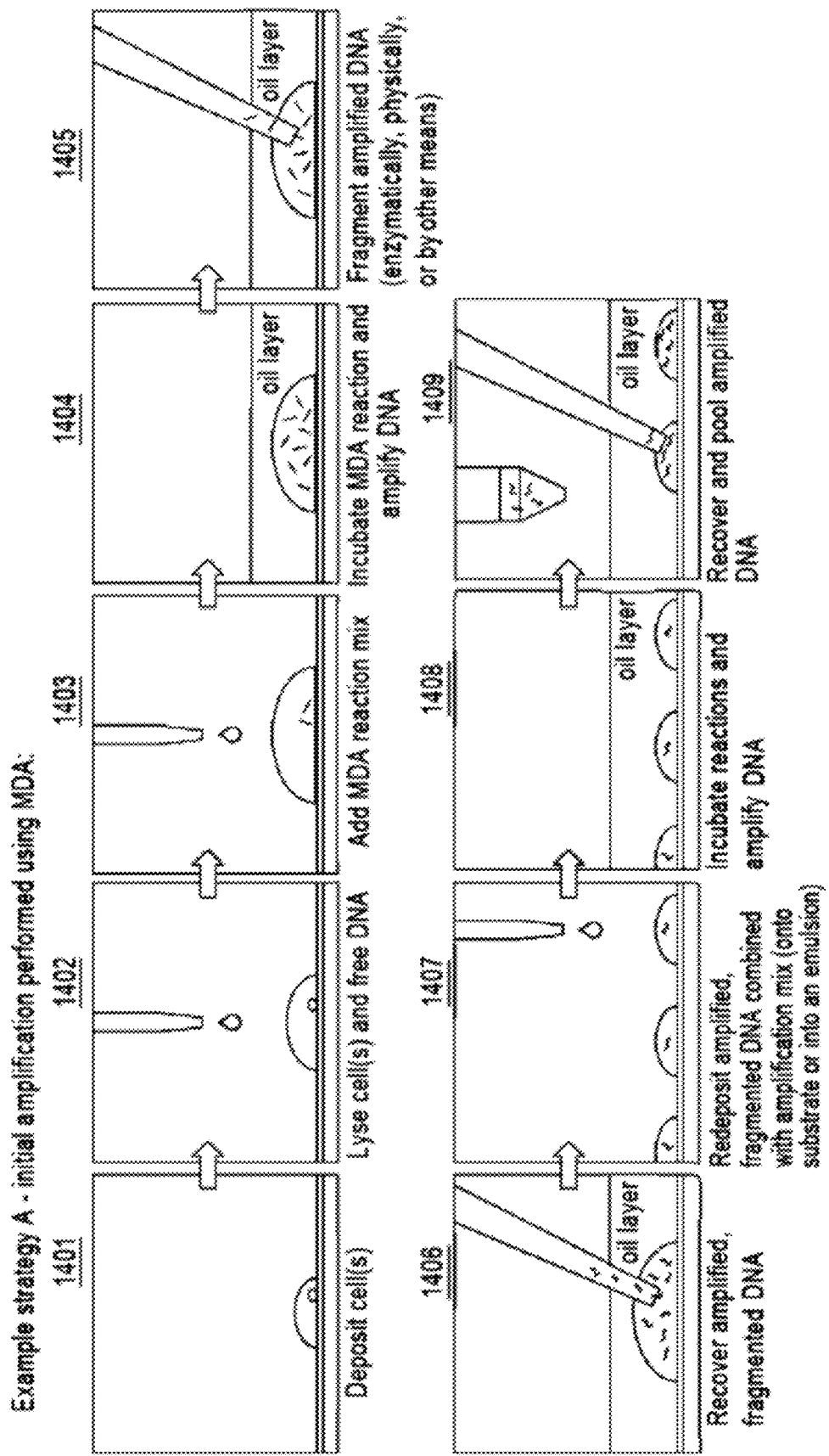

FIG. 26 depicts initial amplification by MDA followed by fragmentation, isolation of fragments into individual reaction solutions, amplification, and pooling.

Figure 27:
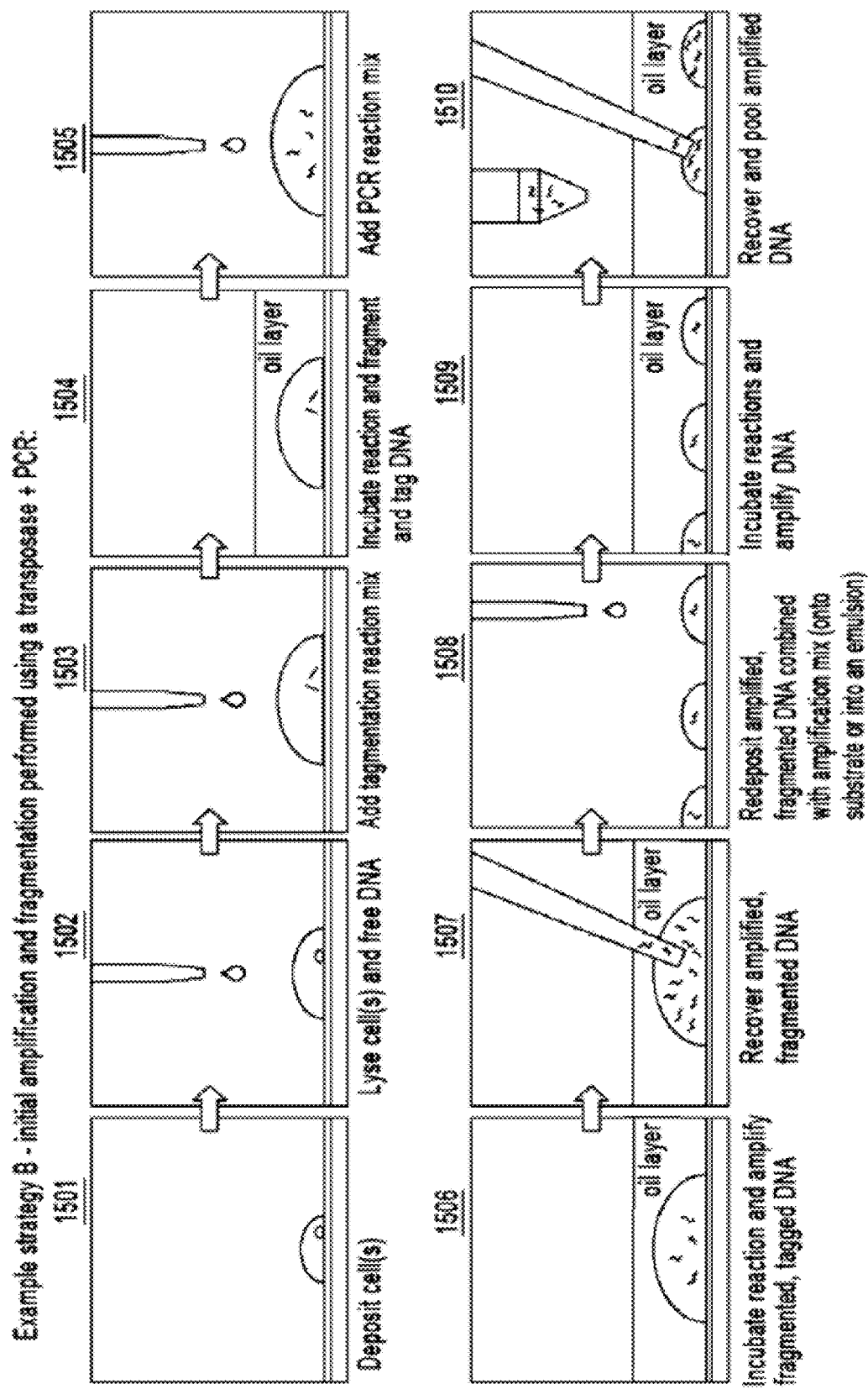

FIG. 27 depicts initial amplification by transposase-based fragmentation and amplification, followed by isolation of amplified fragments into individual reaction solutions, amplification, and pooling.

Figure 28:
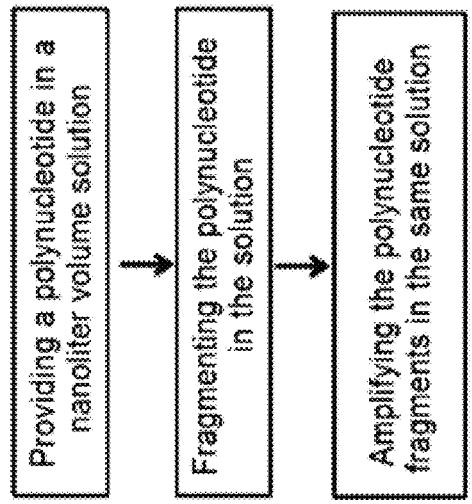

FIG. 28 depicts a flowchart for methods of reducing amplification bias by fragmenting the template polynucleotides before application, where the fragmentation and amplification are performed in a single solution.

Figure 29:
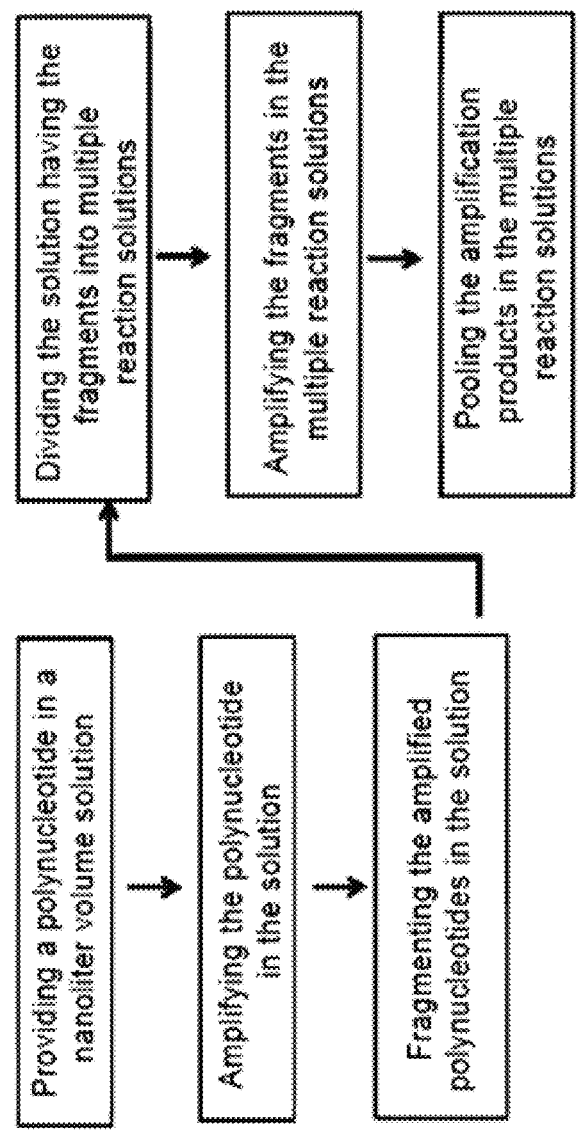

FIG. 29 depicts a flowchart for methods of reducing amplification bias by pre-amplifying and fragmenting a template polynucleotide followed by amplifying the fragments in multiple reaction solutions.

Figure 30:
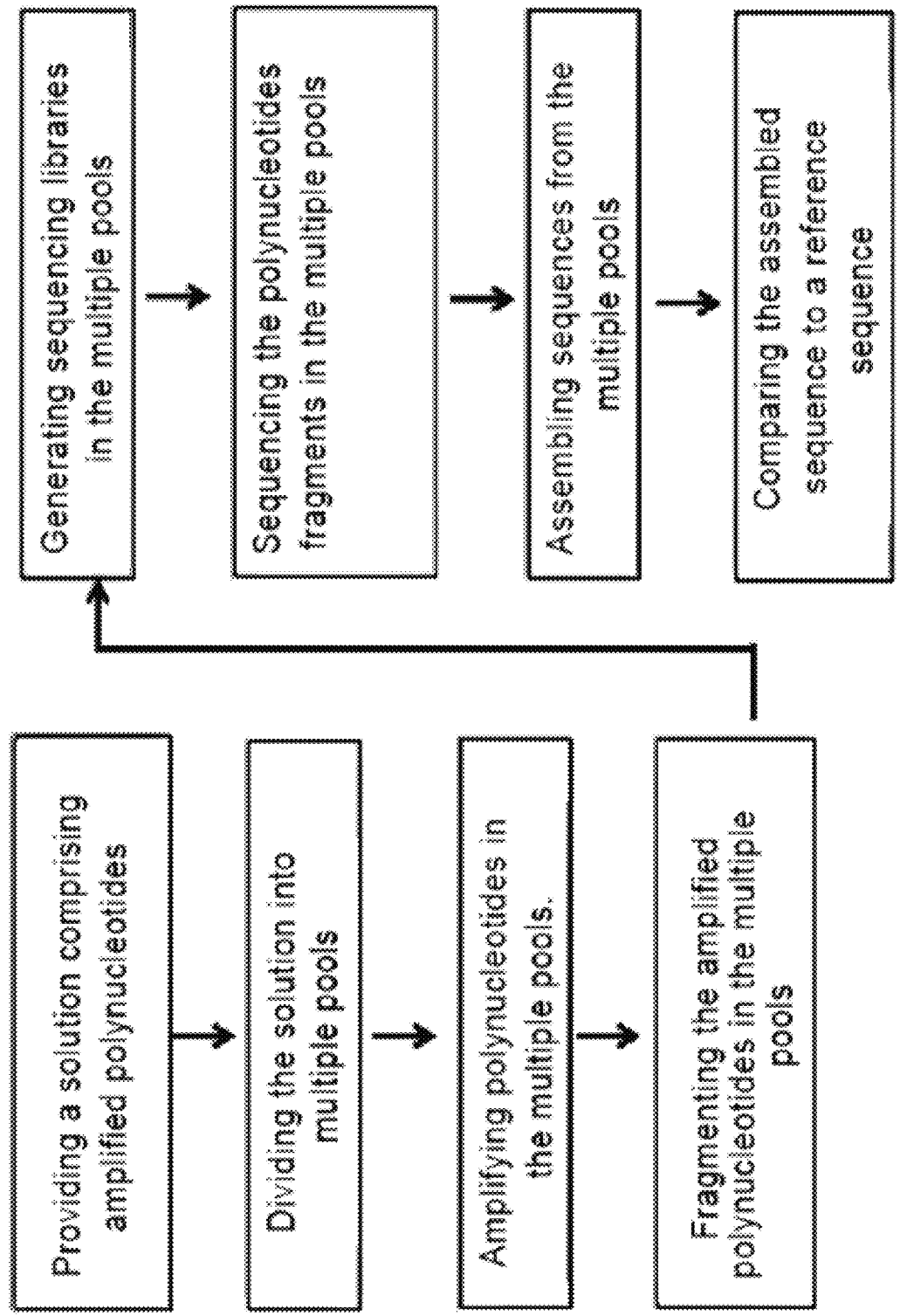

FIG. 30 depicts a flowchart for methods of long range haplotyping of a polynucleotide.

Figure 31:
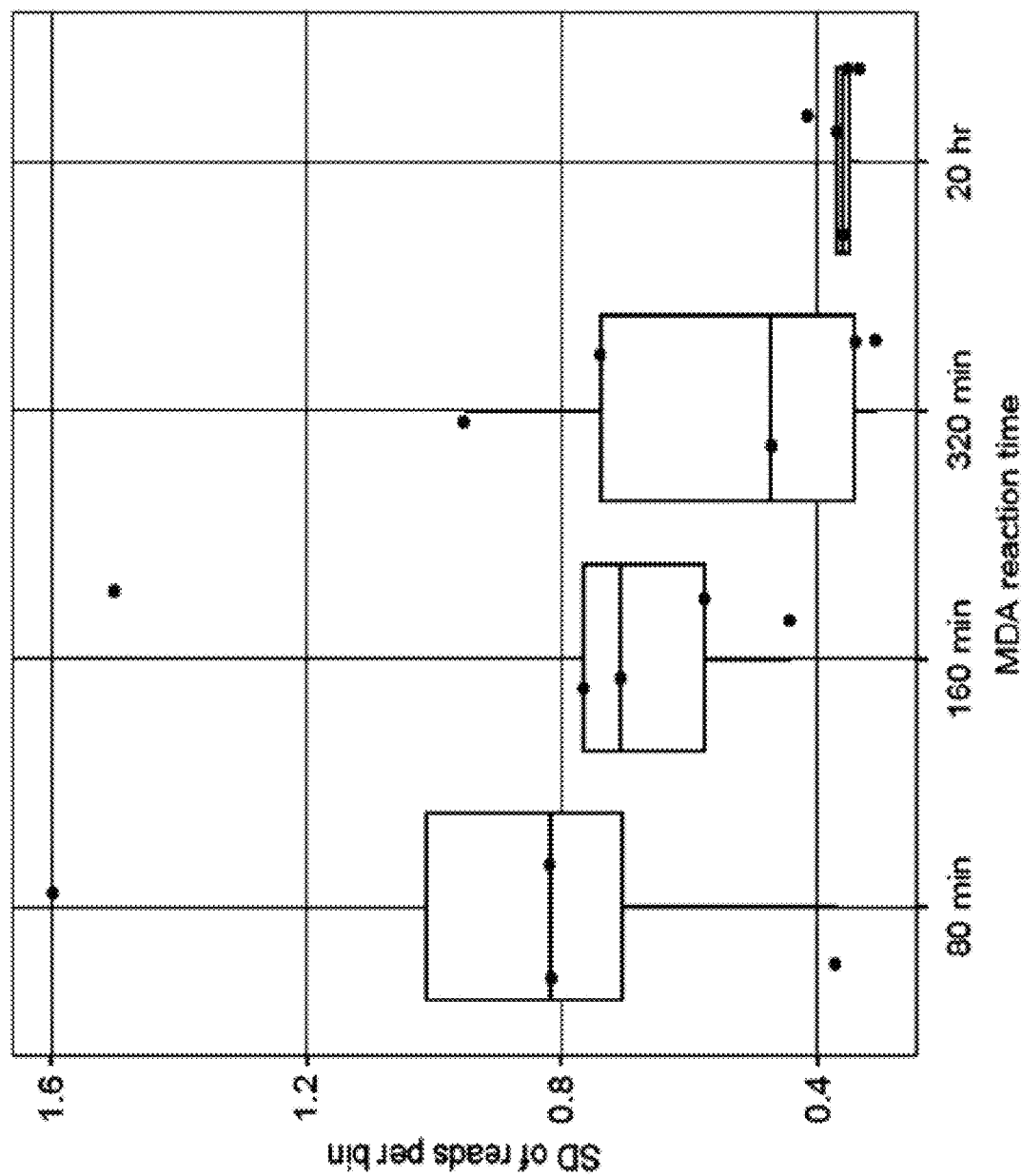

FIG. 31 depicts standard deviation (SD) in reads per 1 Mb bin for different MDA incubation times.

Figure 32:
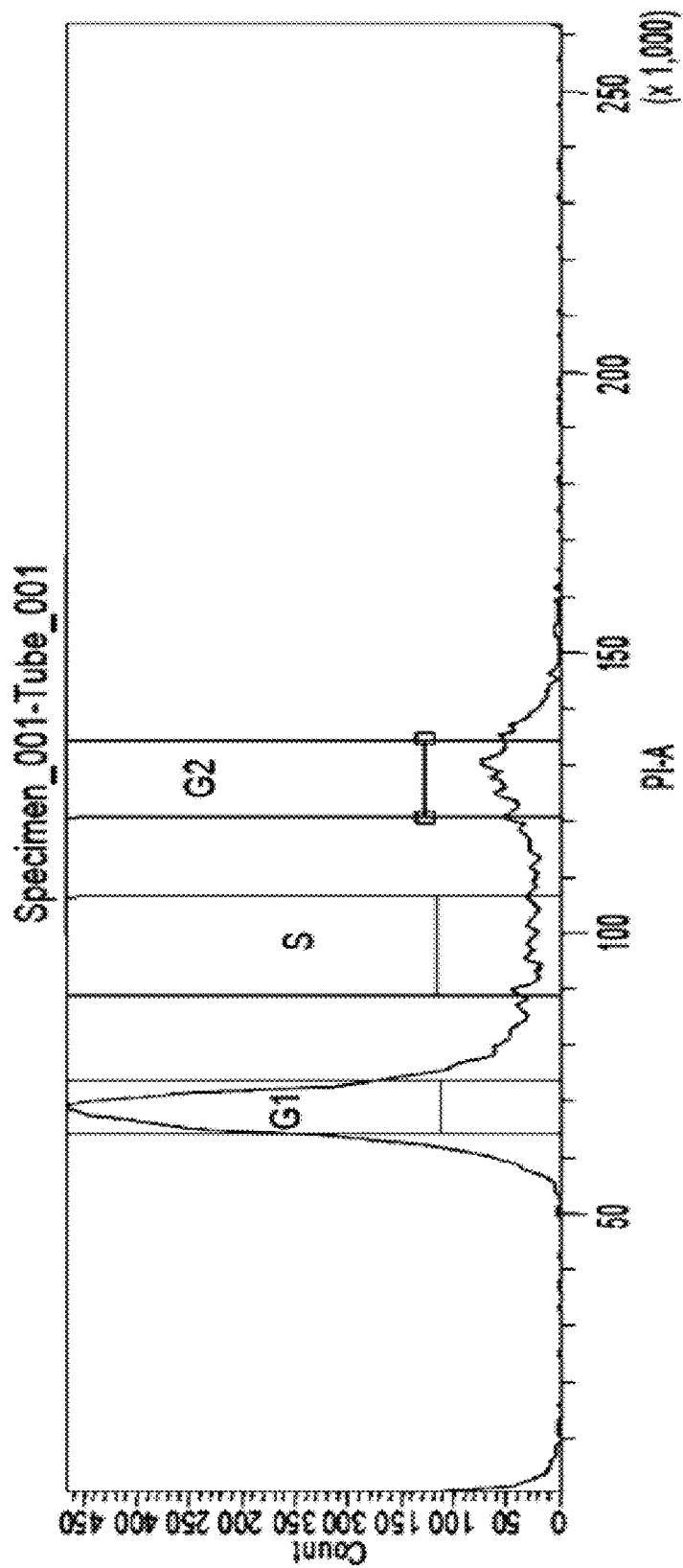

FIG. 32 depicts a histogram of single cells sorted by cell phase using propidium iodide fluorescent intensity.

Figure 33A:
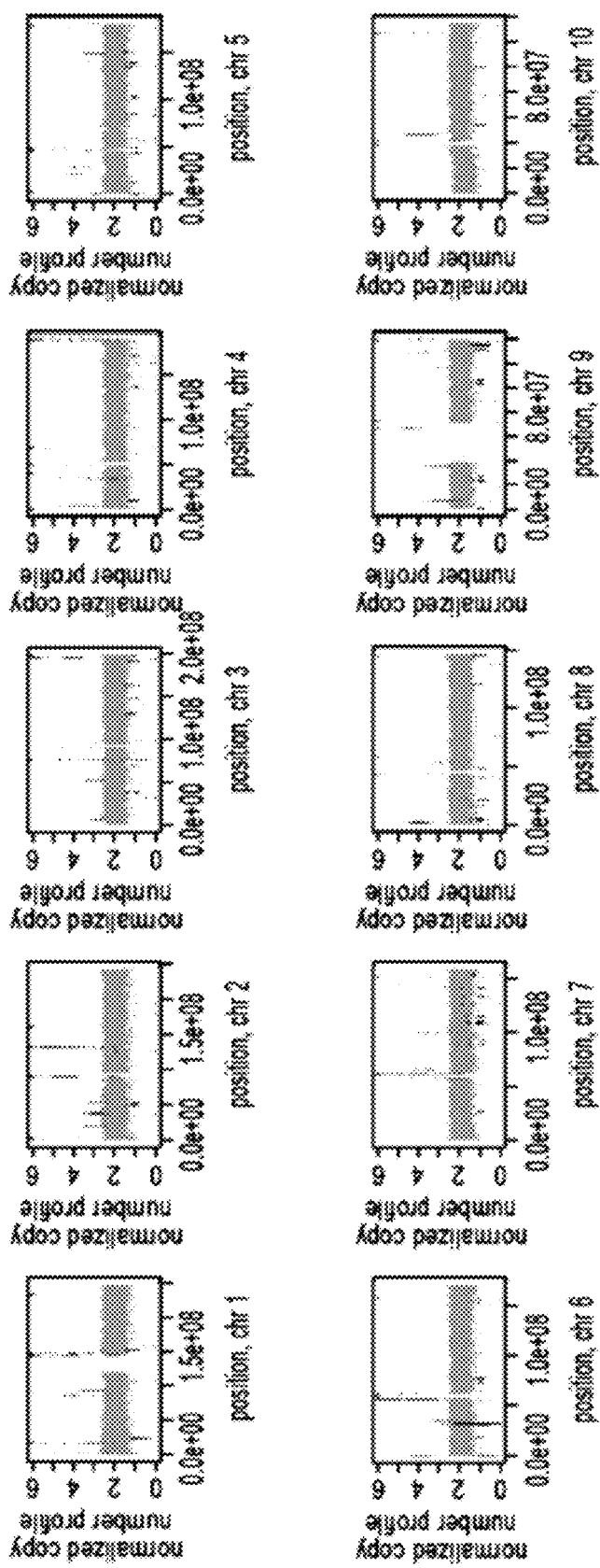
Figure 33A:
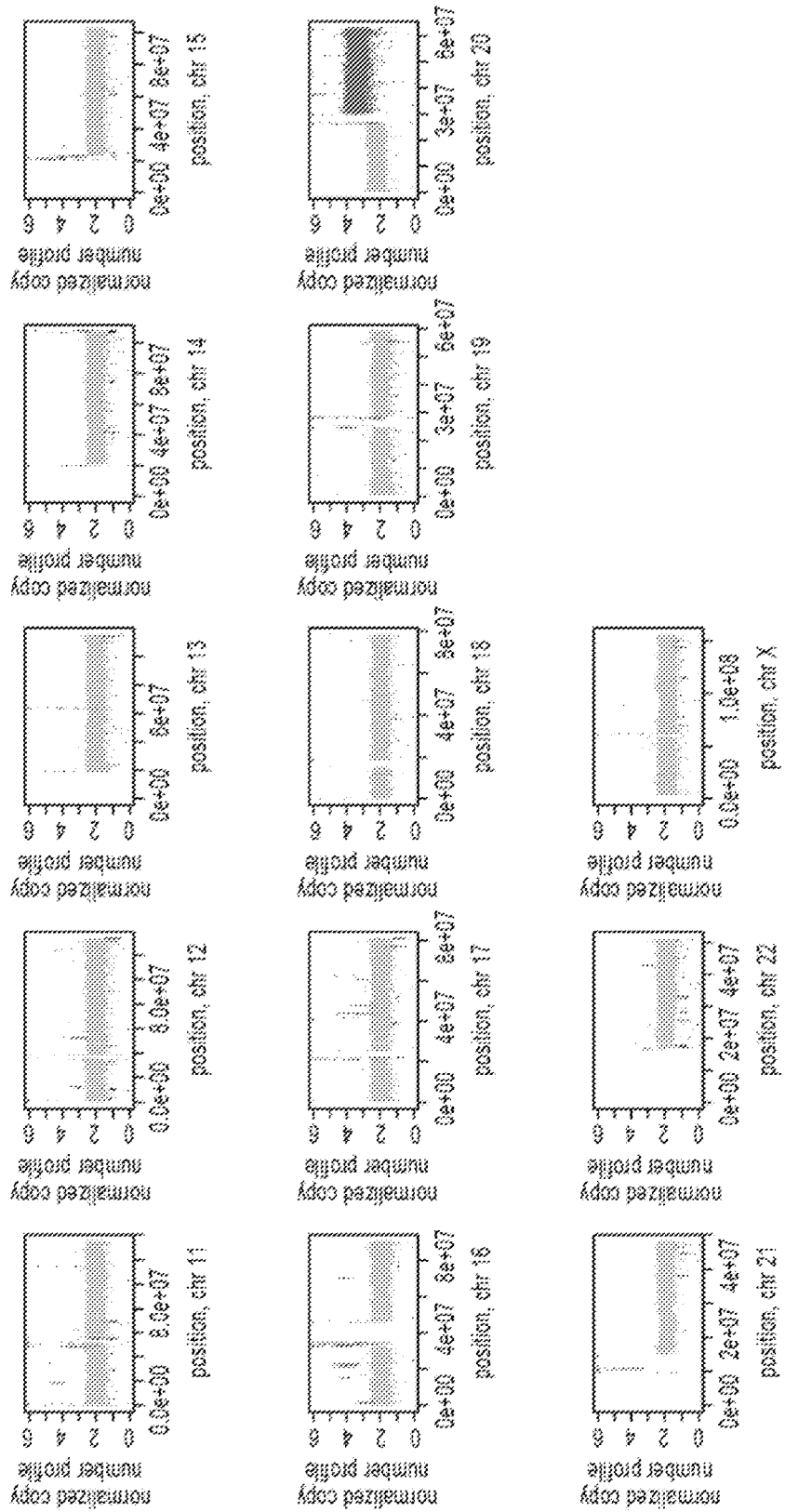
Figure 33B:
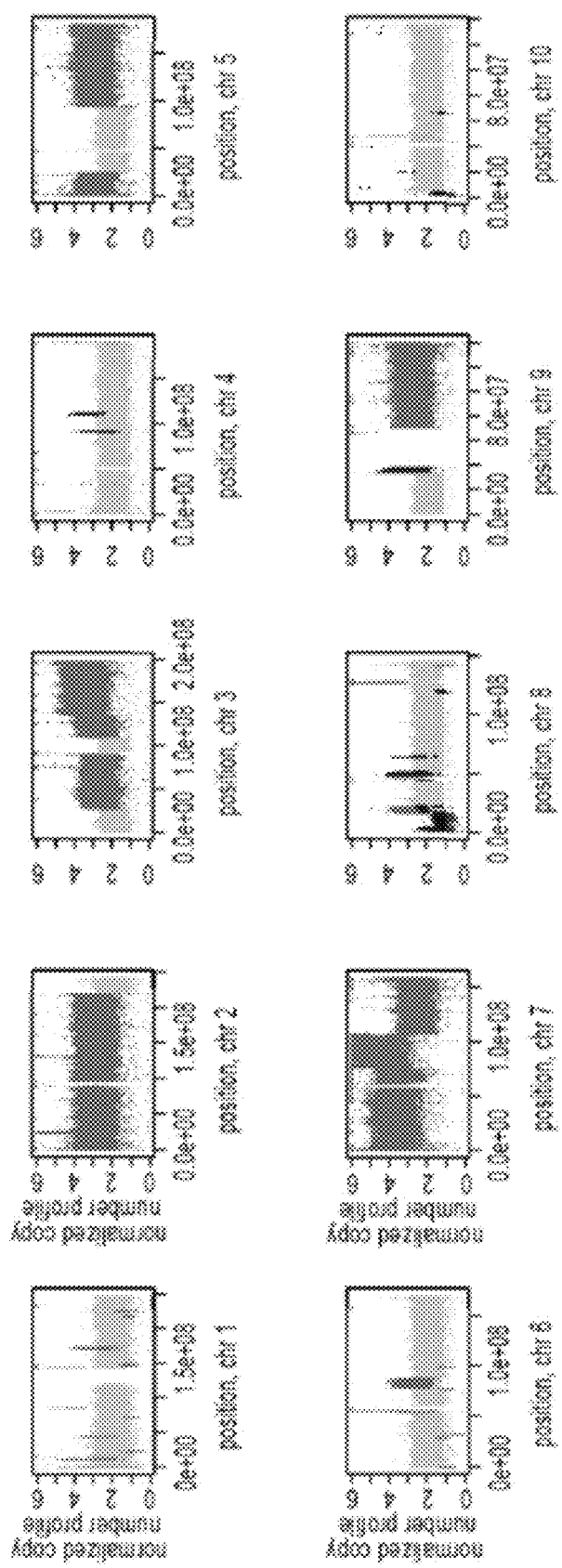
Figure 33B:
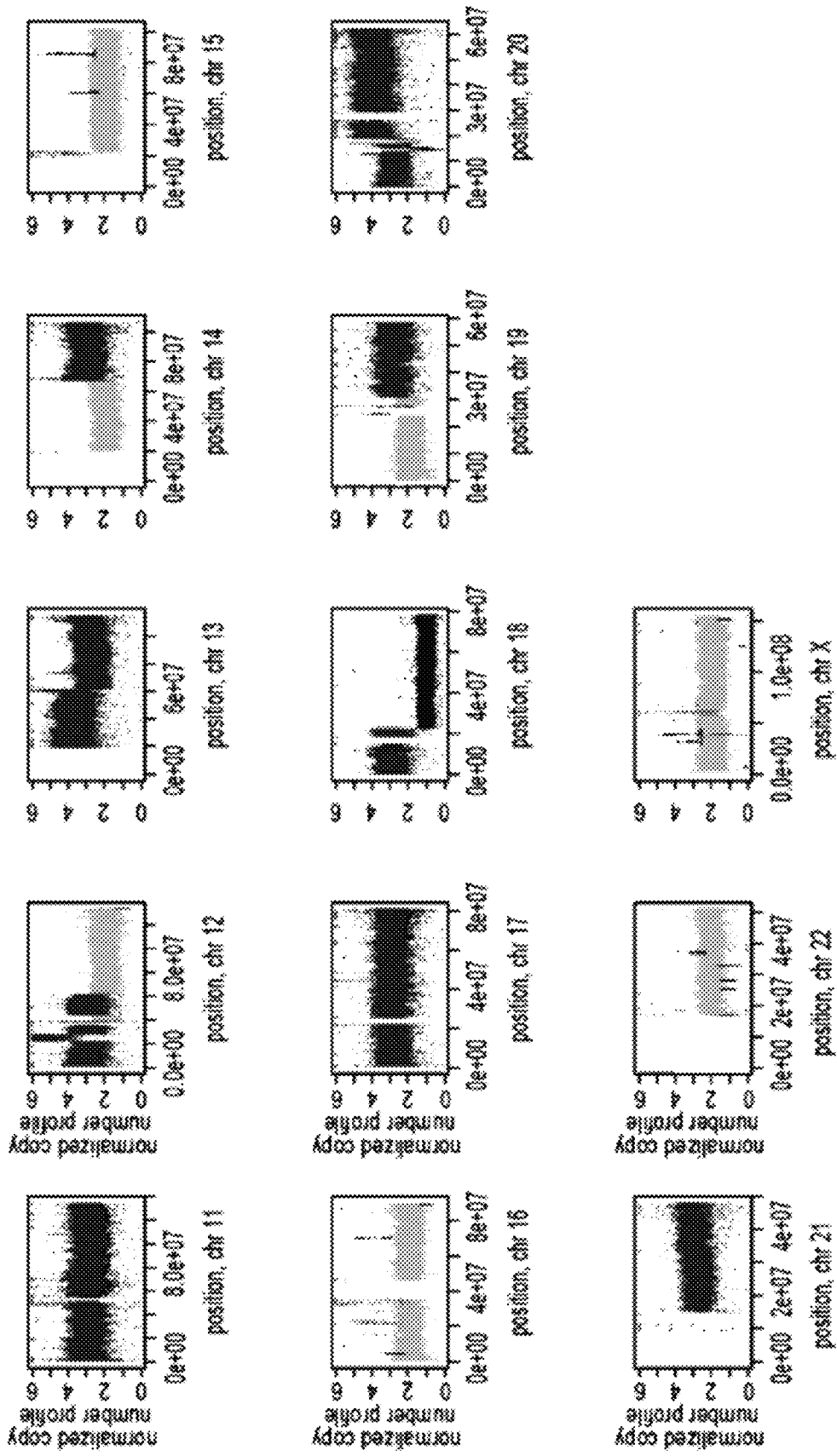
Figure 33C:
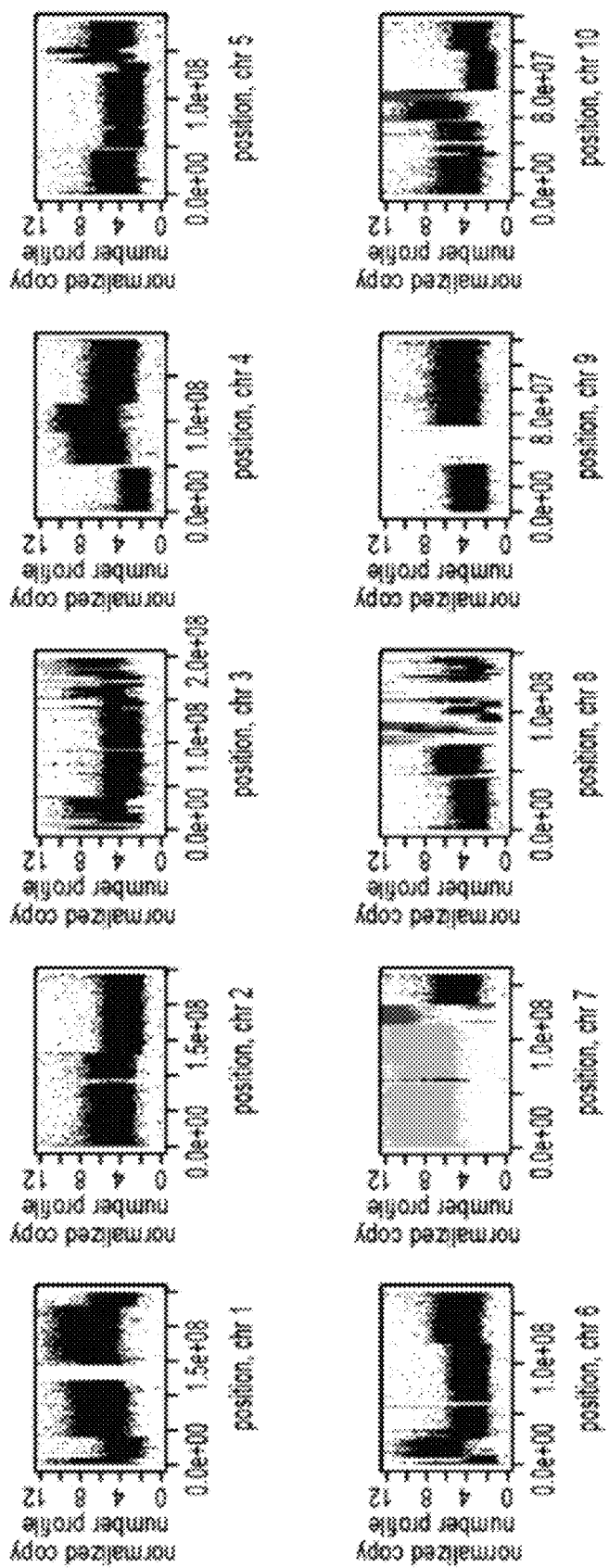
Figure 33C:
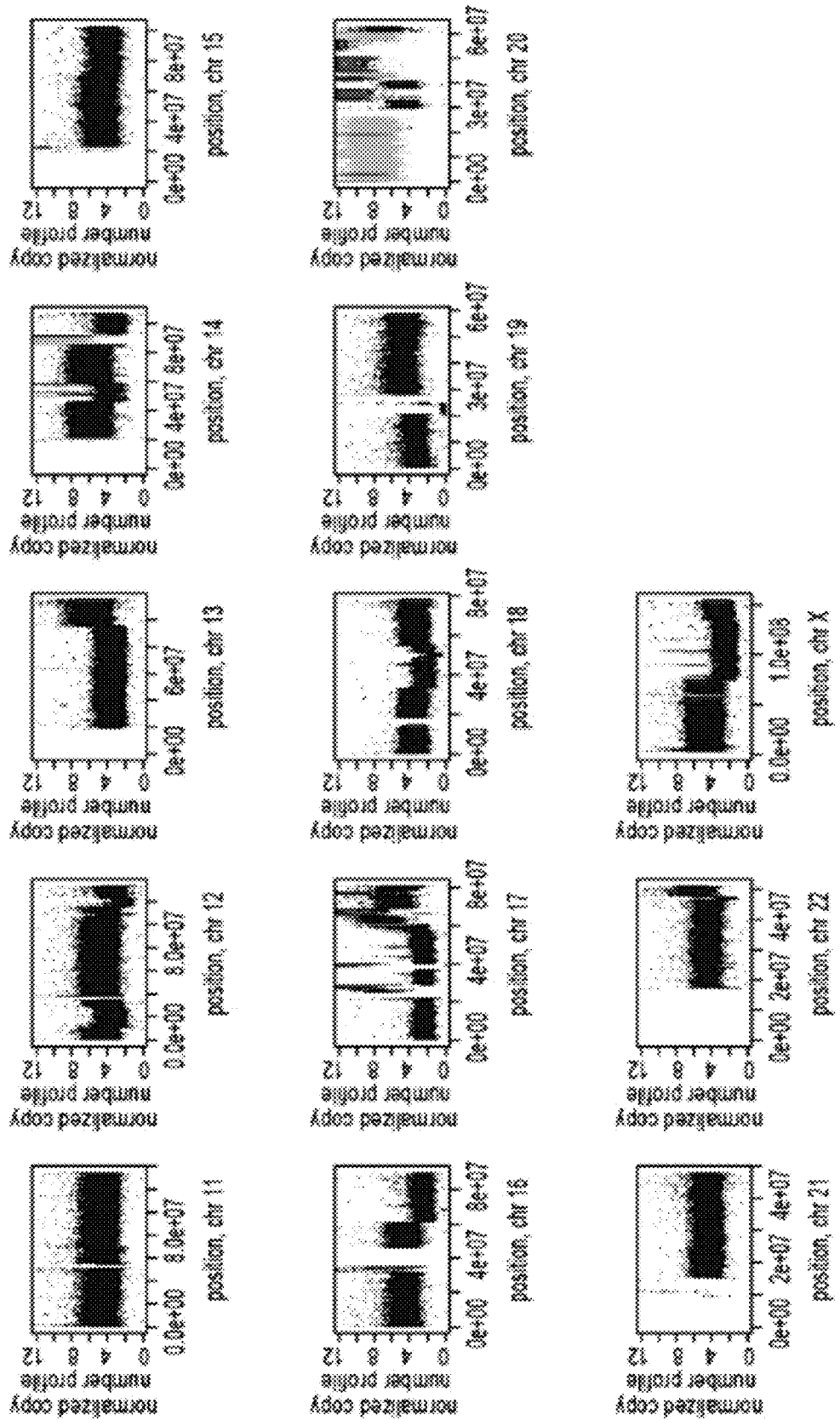

FIGS. 33A-C depict CNVs identified in bulk samples by Control-FREEC. (FIG. 33A) 184-hTERT cell line (droplet MDA), (FIG. 33B) SW480 cancer cell line (MALBAC), and (FIG. 33C) SK-BR-3 breast cancer cell line (nuc-seq).

Figure 34:
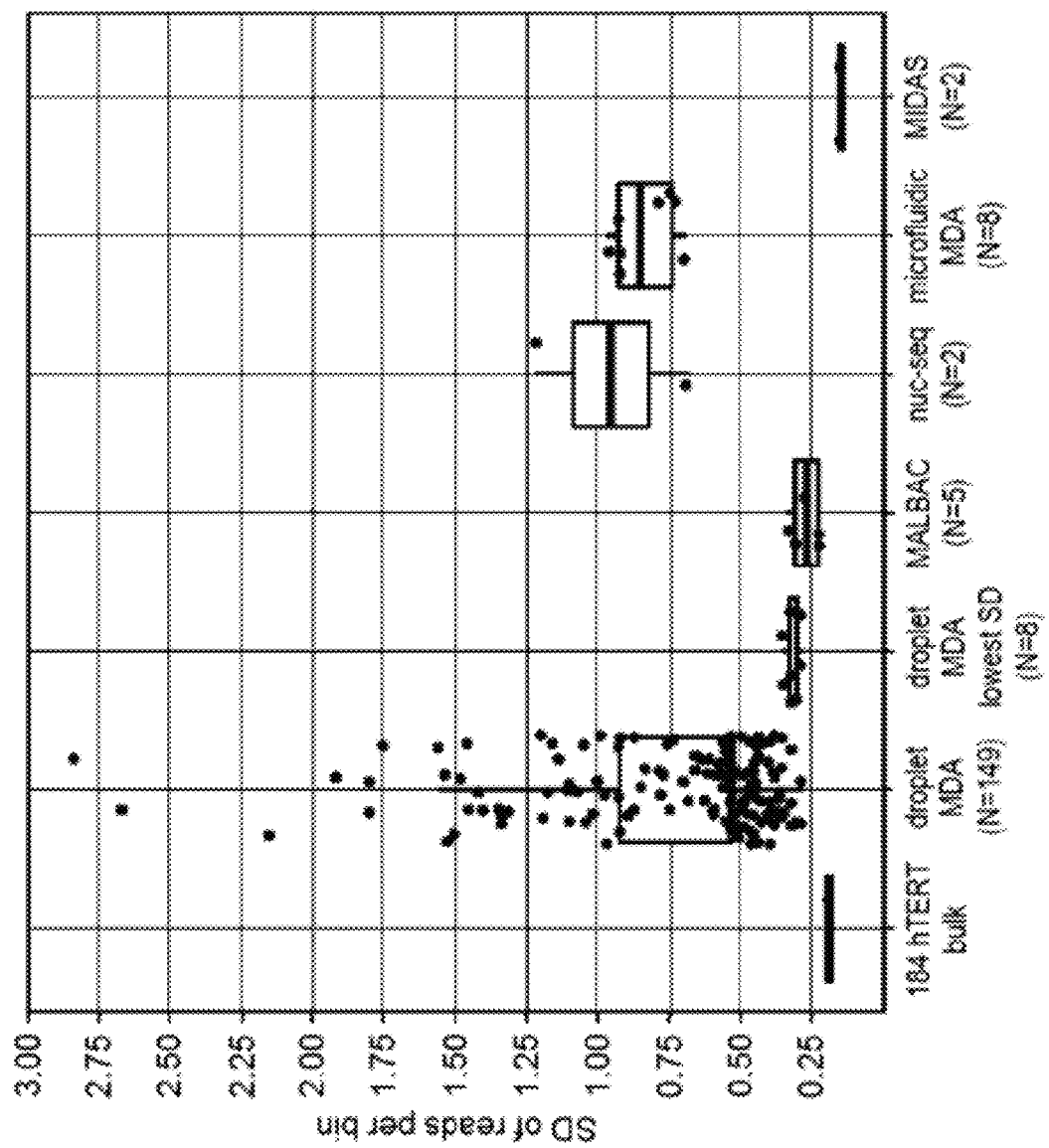

FIG. 34 depicts scatter and box plots of standard deviation in log 2 reads per 1 Mb bin comparing other published methods with all single 184-hTERT cell droplet MDA samples sequenced to low depth and the 8 single 184-hTERT cell droplet MDA samples with the lowest standard deviation in reads per bin.

Figure 35:
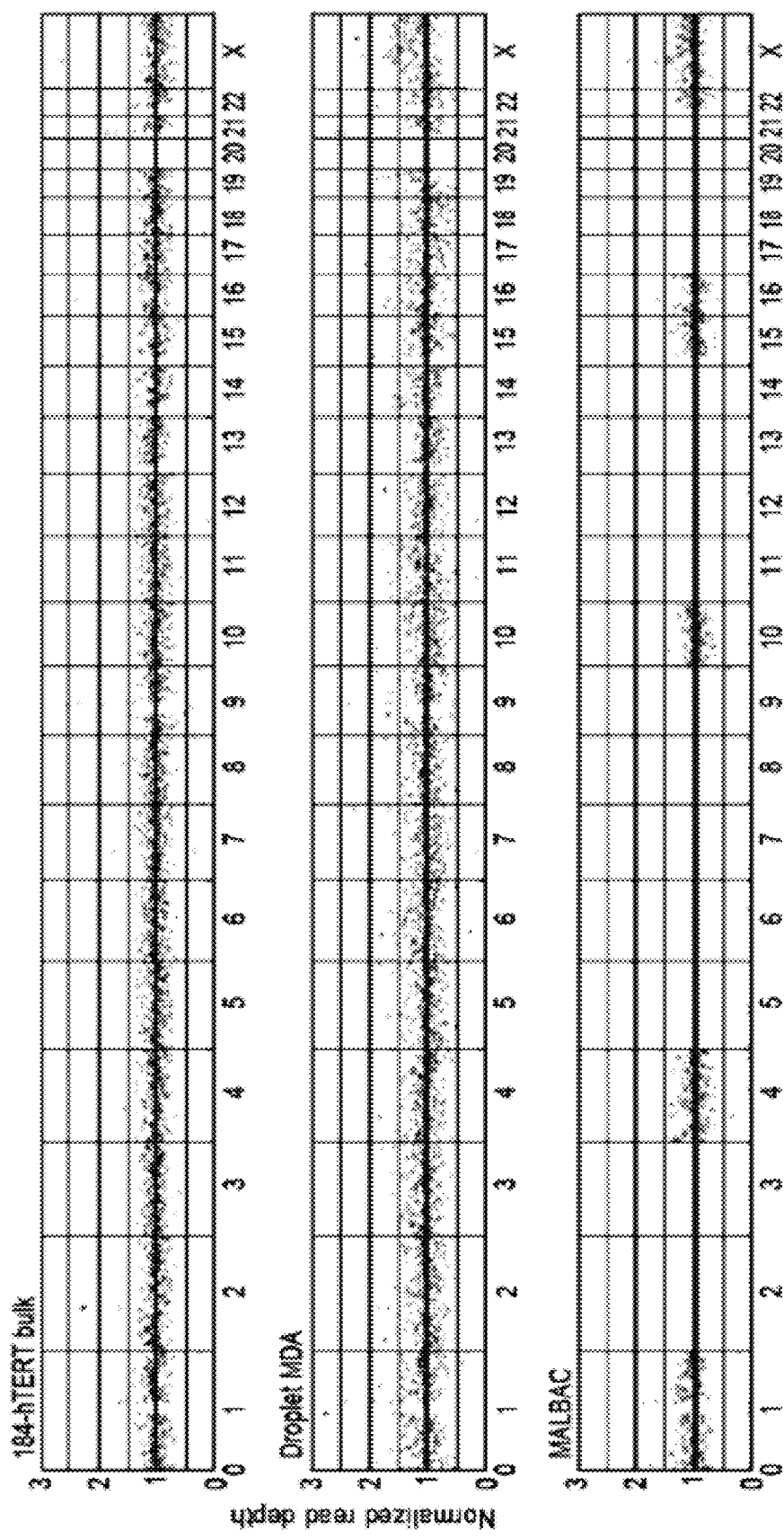
Figure 35:
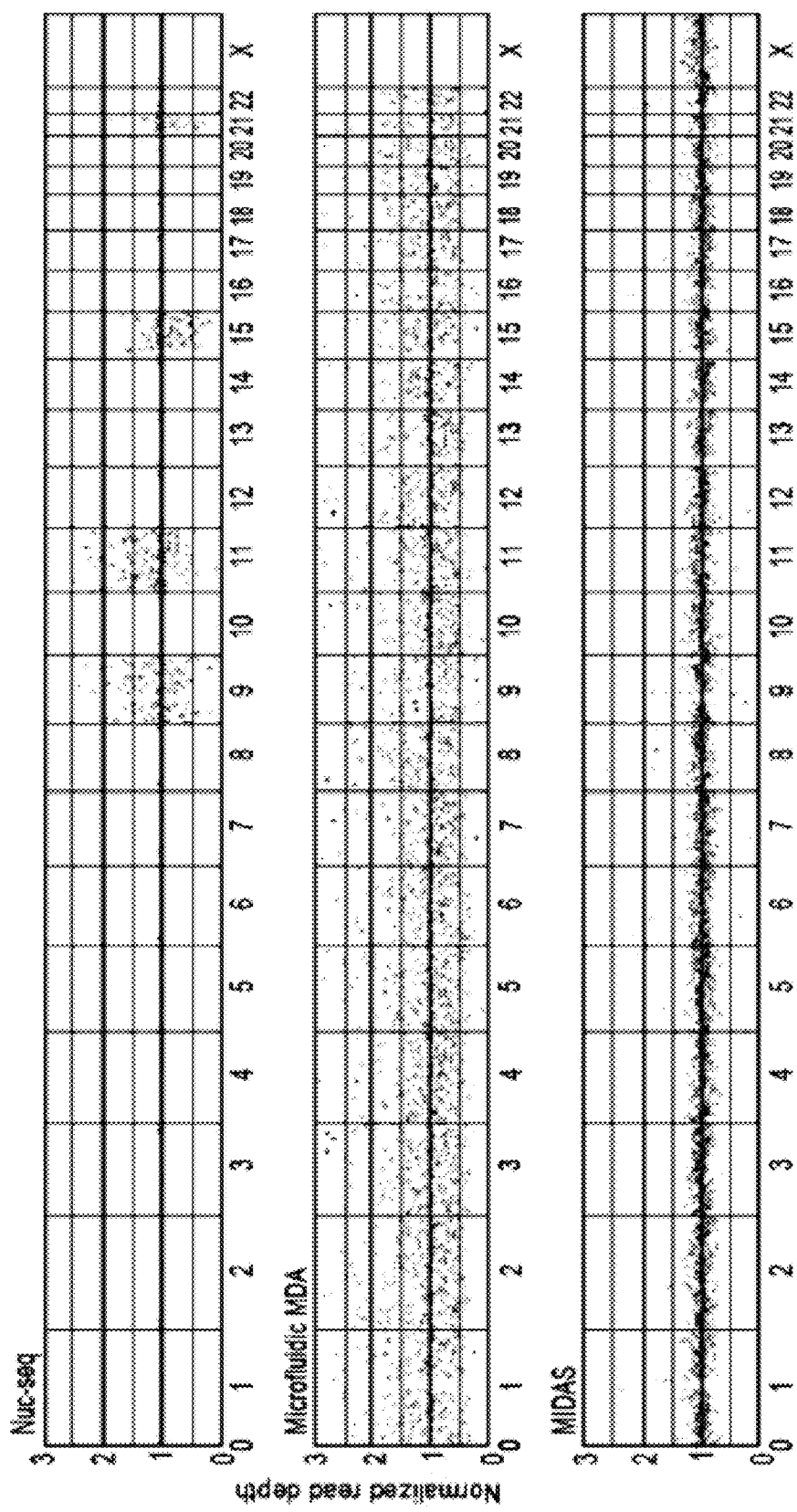

FIG. 35 depicts normalized read depth for 1 Mb bins for the sample from each amplification method with the lowest standard deviation of reads per bin.

Figure 36:
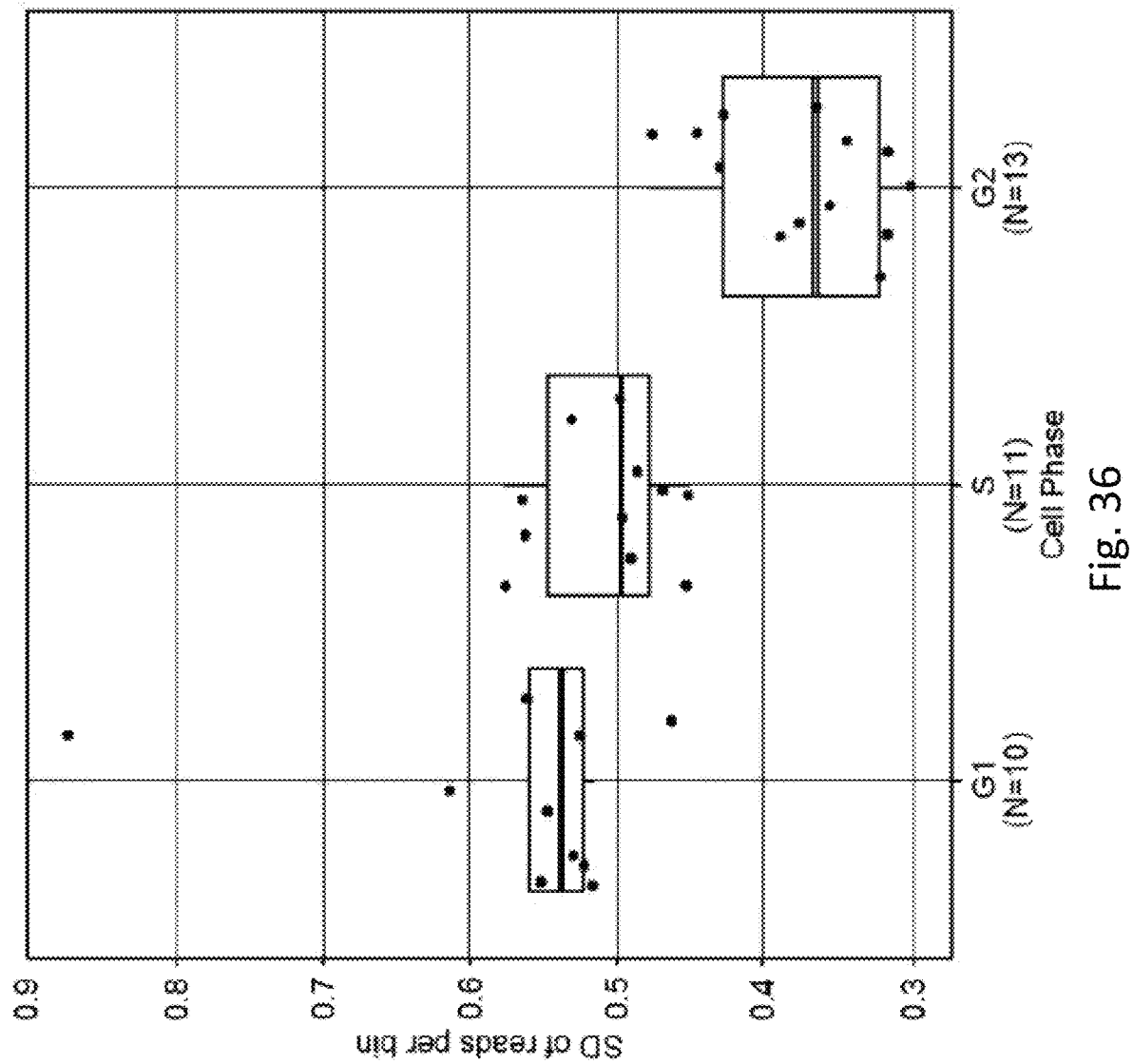

FIG. 36 depicts scatter and box plots of standard deviation in reads per 1 Mb bin comparing droplet MDA on single 184-hTERT cells in G1, S, and G2 phase.

Figure 37A:
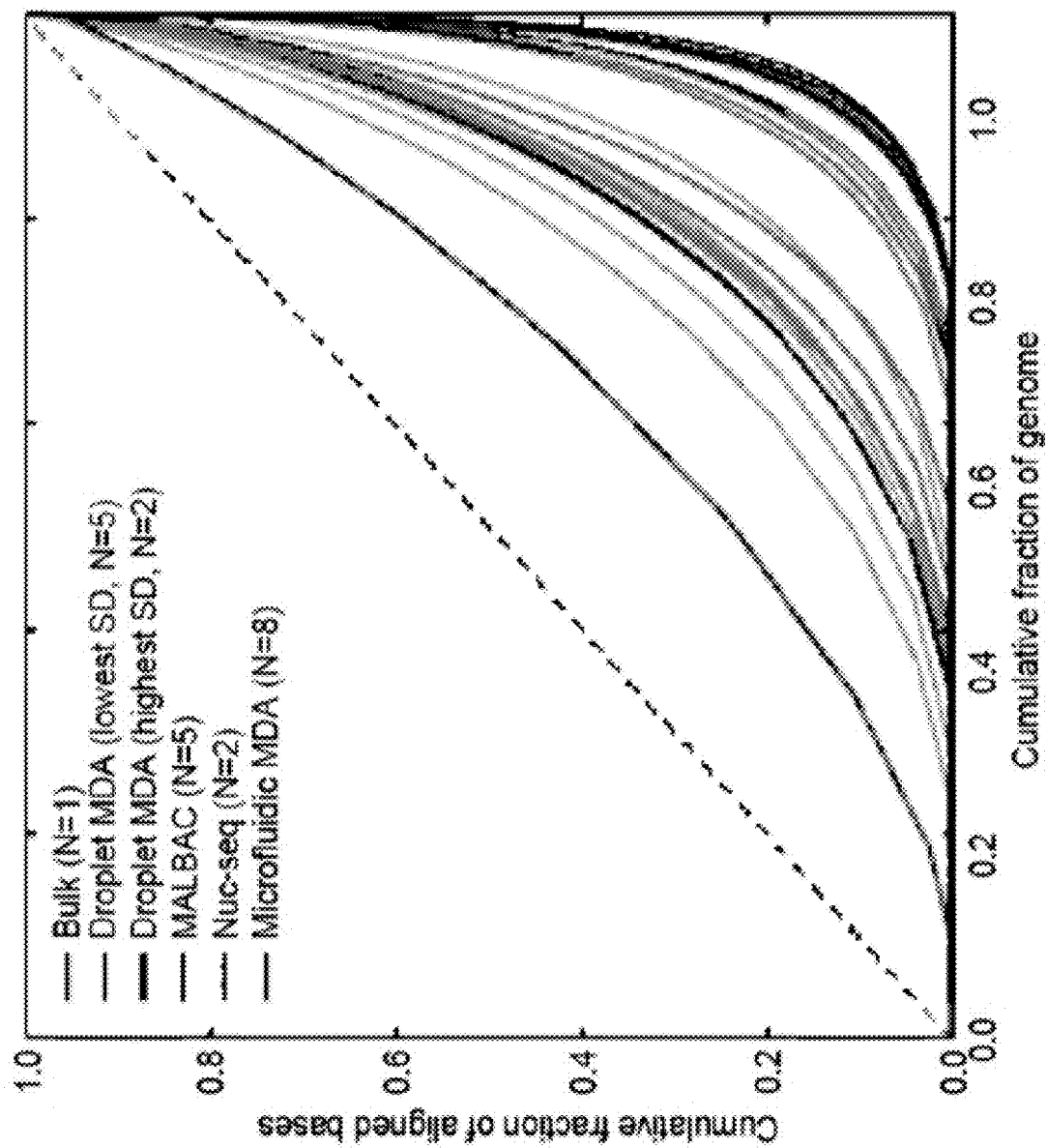

FIGS. 37A-D depict bias analysis from high depth WGS. FIG. 37A depicts Lorenz curves depicting uniformity of coverage for individual samples from each amplification method.

Figure 37B:
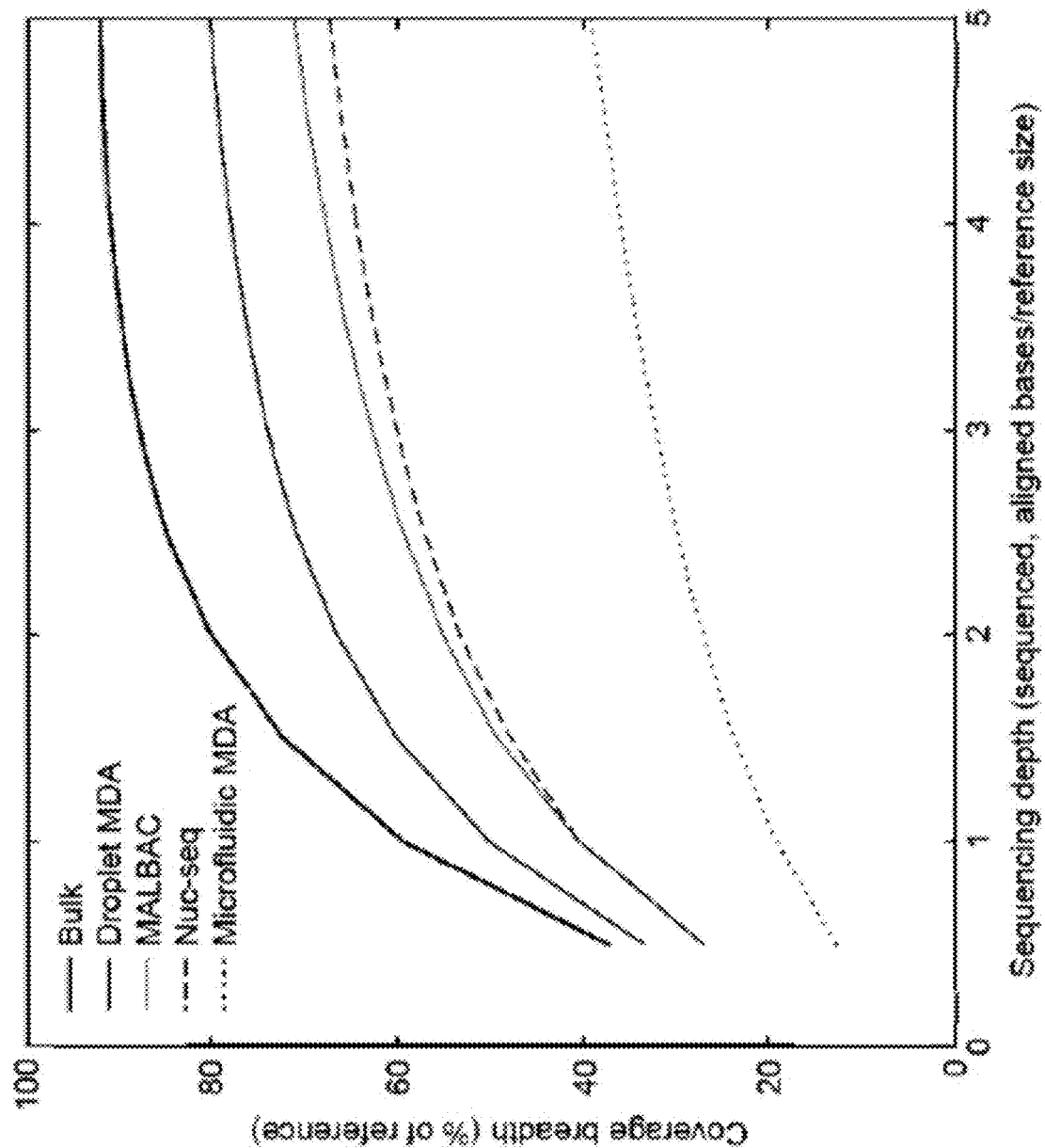
Figure 37C:
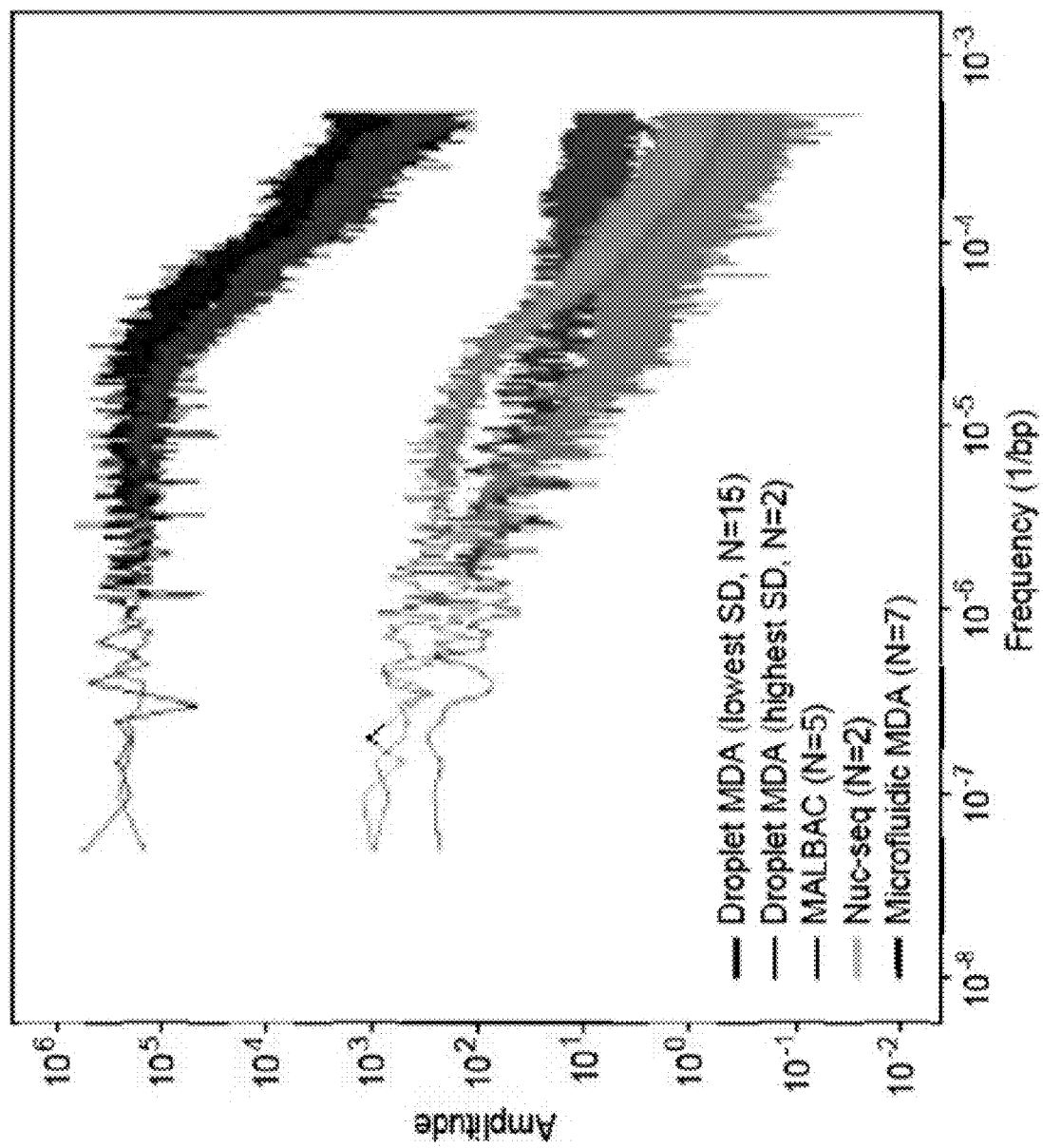
Figure 37D:
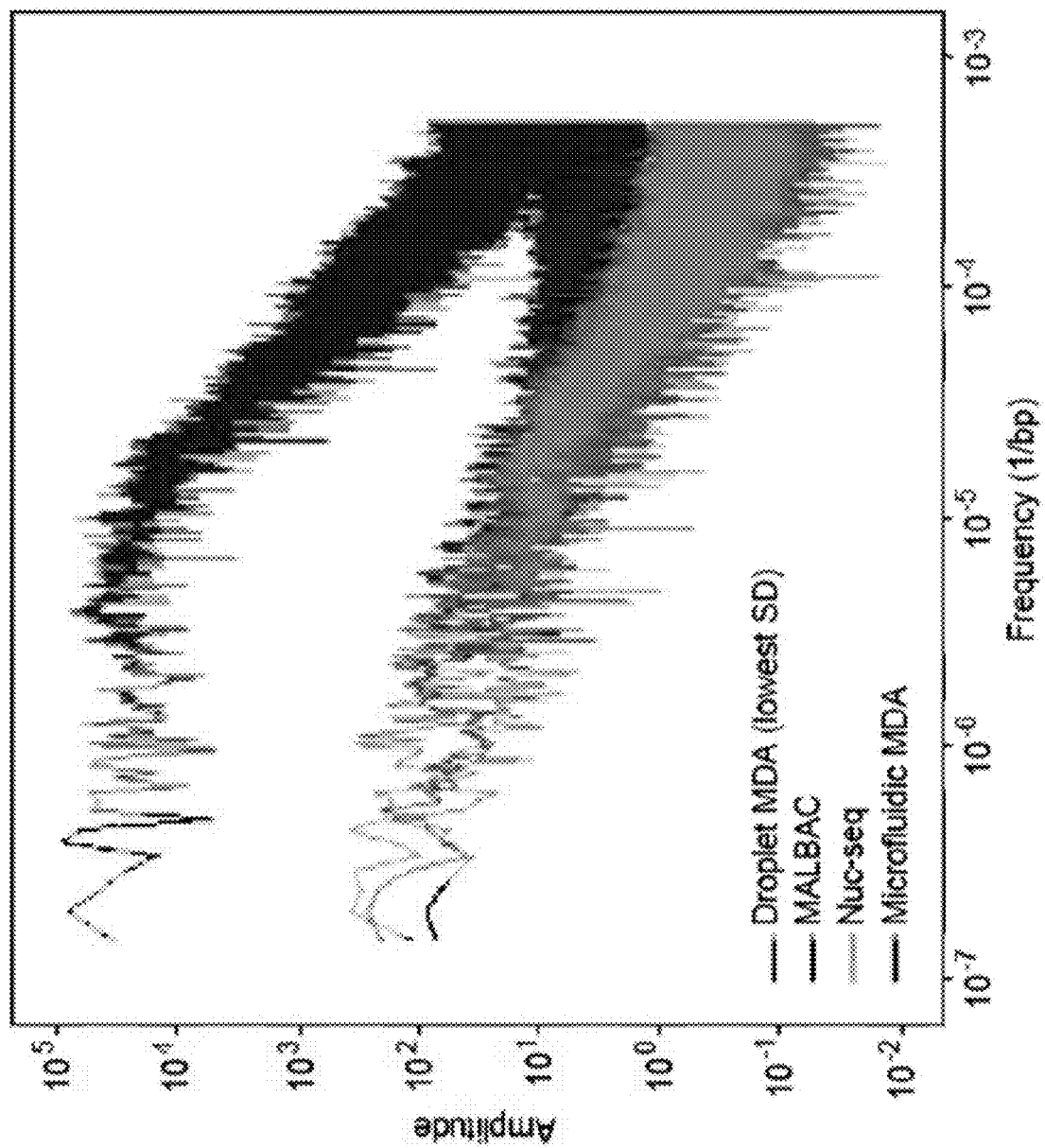

FIG. 37B depicts coverage breadth as a function of sequencing depth for the sample with the lowest standard deviation in reads per 1 kb bin from each method. FIG. 37C depicts frequency-wise mean of power spectra of 1 kb binned read depth for all samples from each amplification method. FIG. 37D depicts power spectra of 1 kb binned read depth for the sample with the lowest standard deviation in reads per bin from each method.

Figure 38:
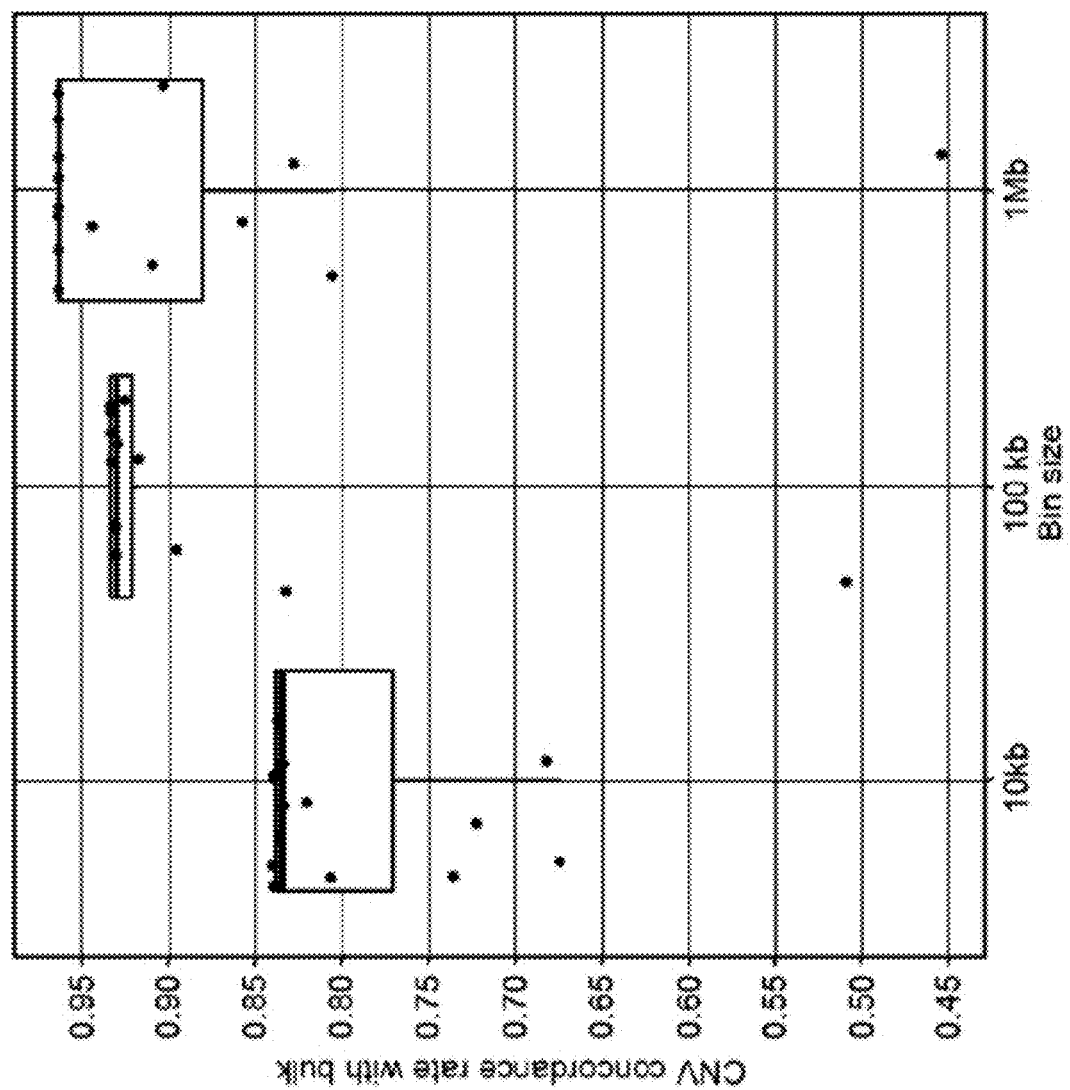

FIG. 38 depicts scatter and box plots of bin-wise copy number concordance between single 184-hTERT cells and bulk when reads are binned into 10 kb, 100 kb, and 1 Mb bins.

Figure 39:
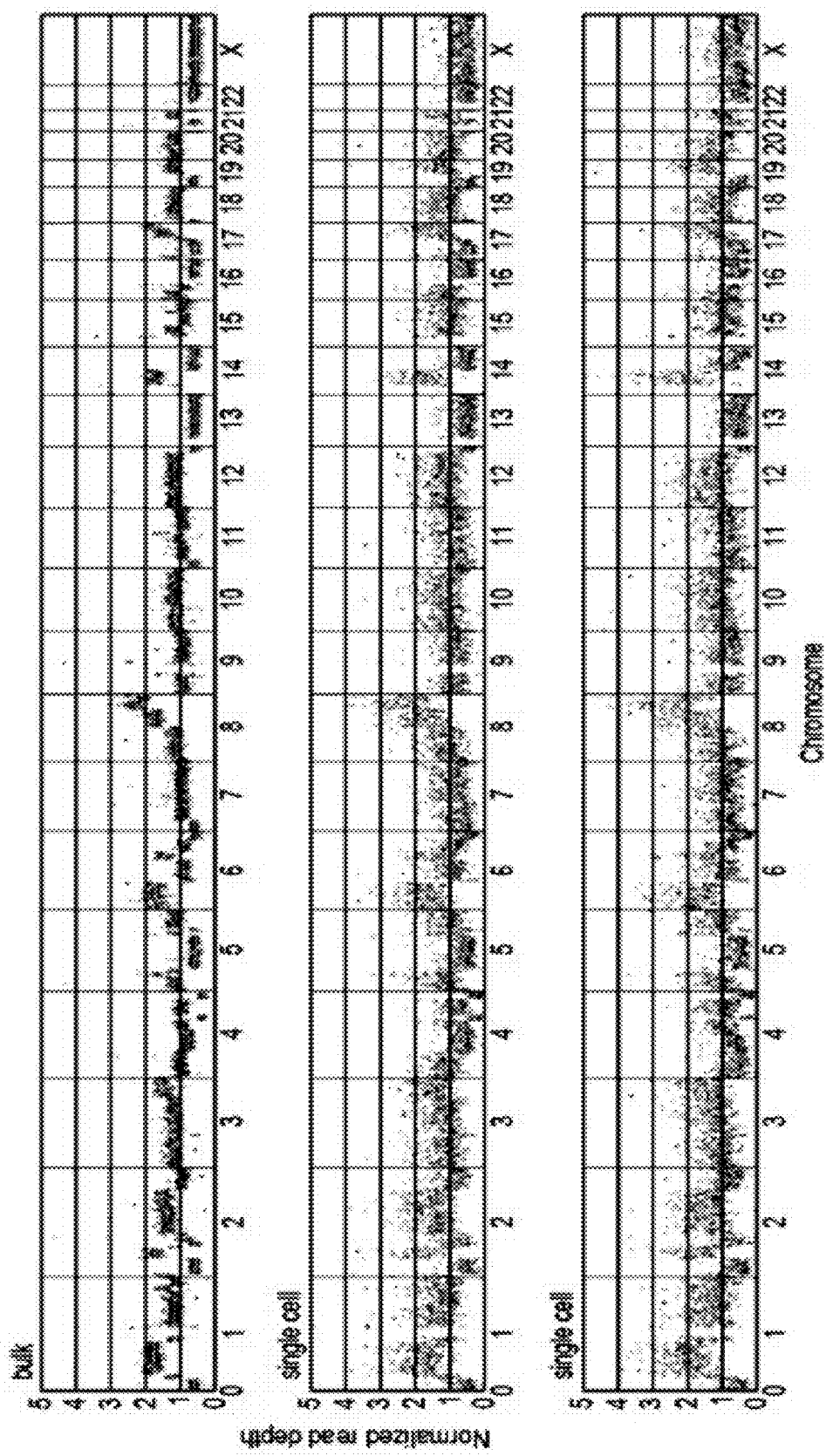
Figure 39:
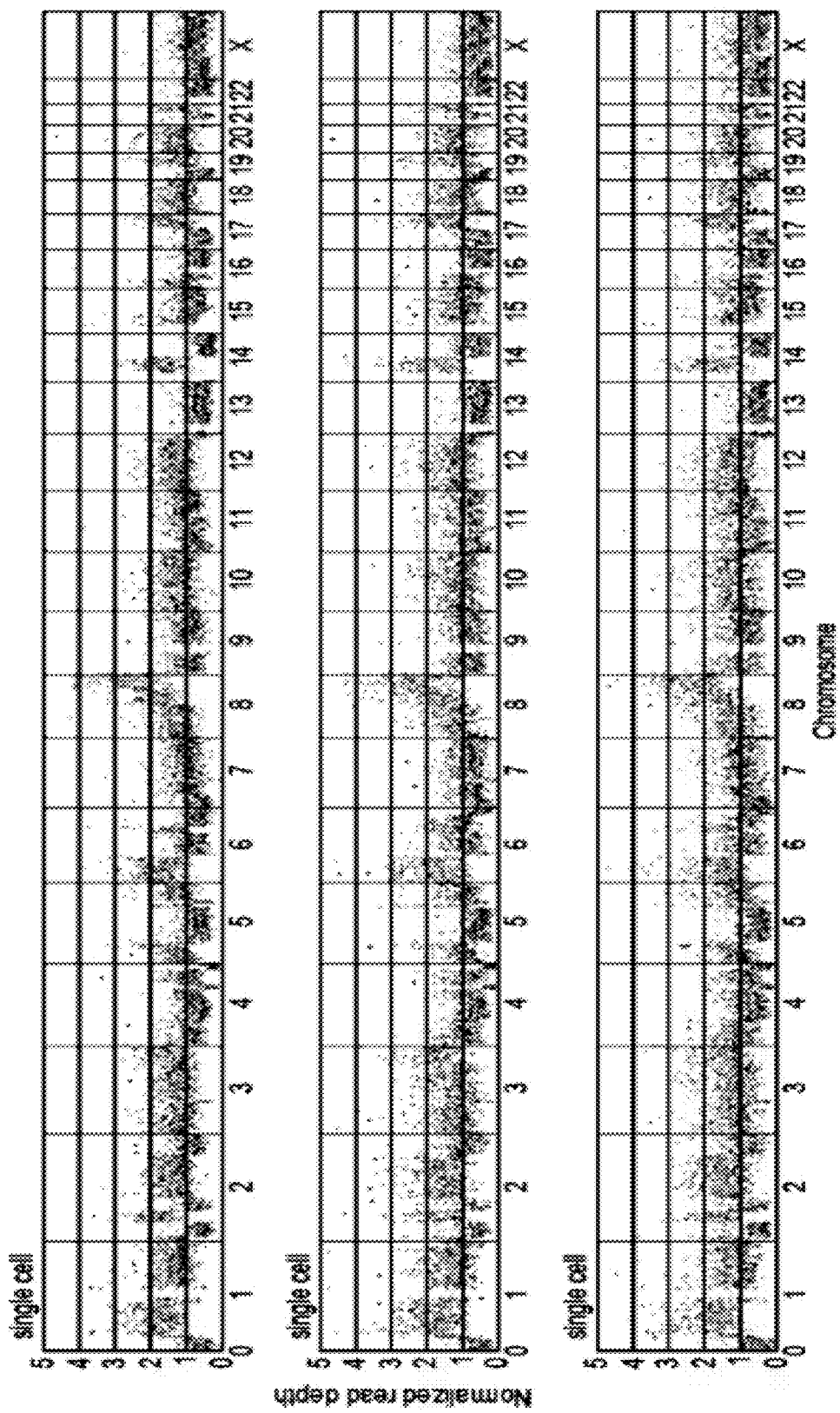

FIG. 39 depicts normalized read depth plots for bulk gDNA and 5 single TOV2295 cells.

Figure 40:
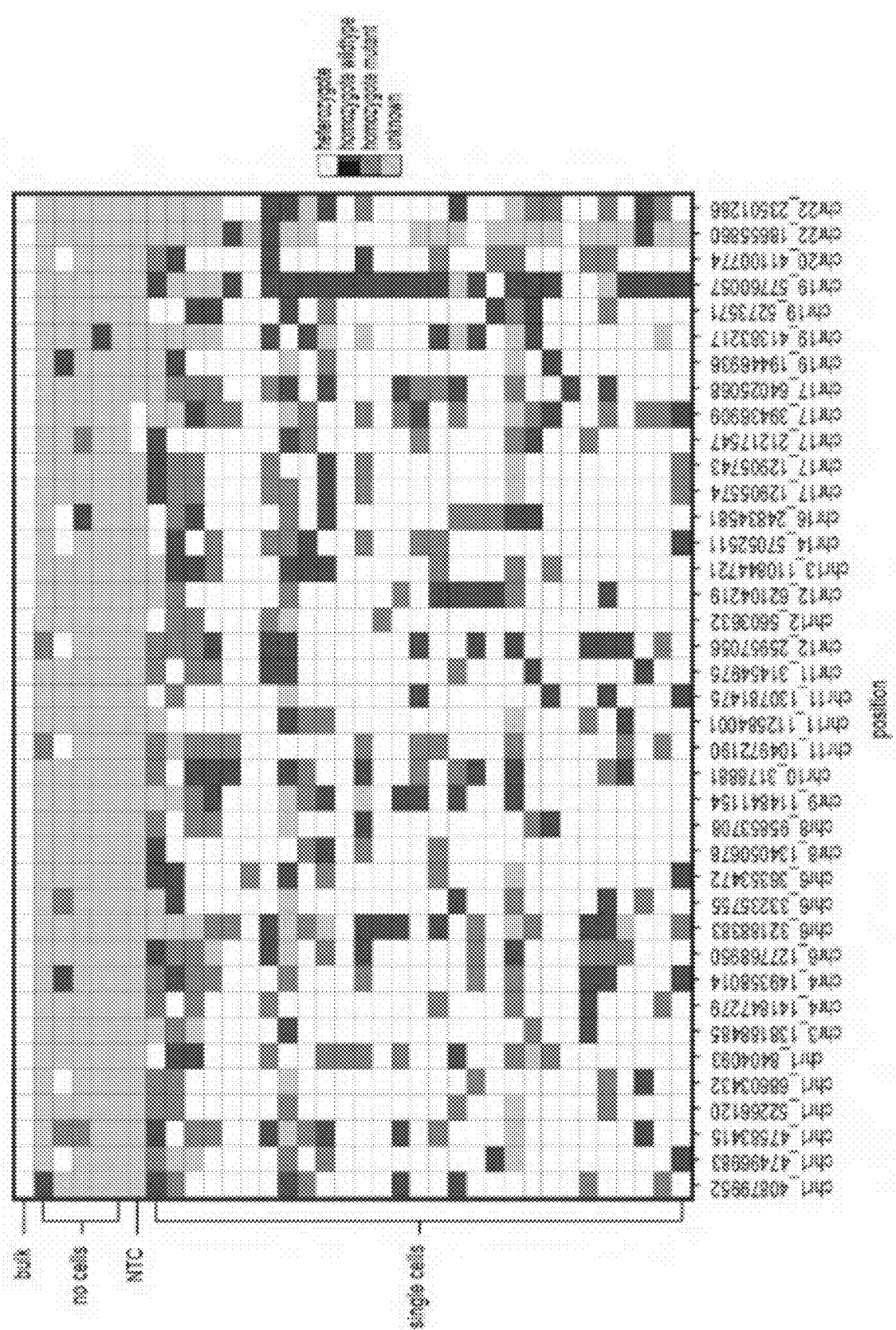

FIG. 40 depicts matrix of called zygosity at 39 heterozygous loci in bulk 184-hTERT gDNA, no-cell controls (cell suspension but no cells as template), no-template control (water as template), and single 184-hTERT cells.

Figure 41:
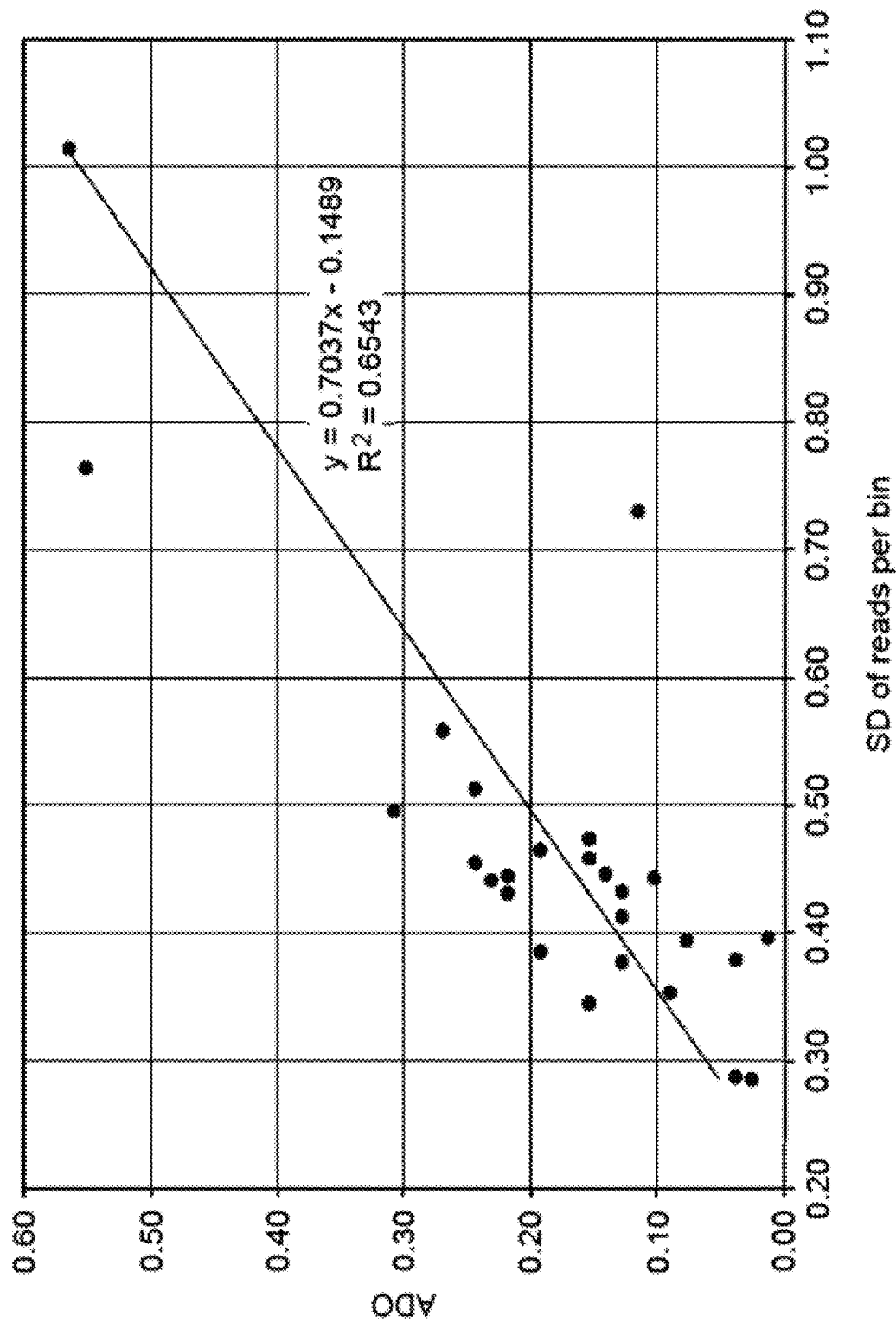

FIG. 41 depicts correlation between standard deviation (SD) of reads per 1 Mb bin (mean reads per bin=100) and allelic dropout (ADO) in single 184-hTERT cells.

Figure 42A:
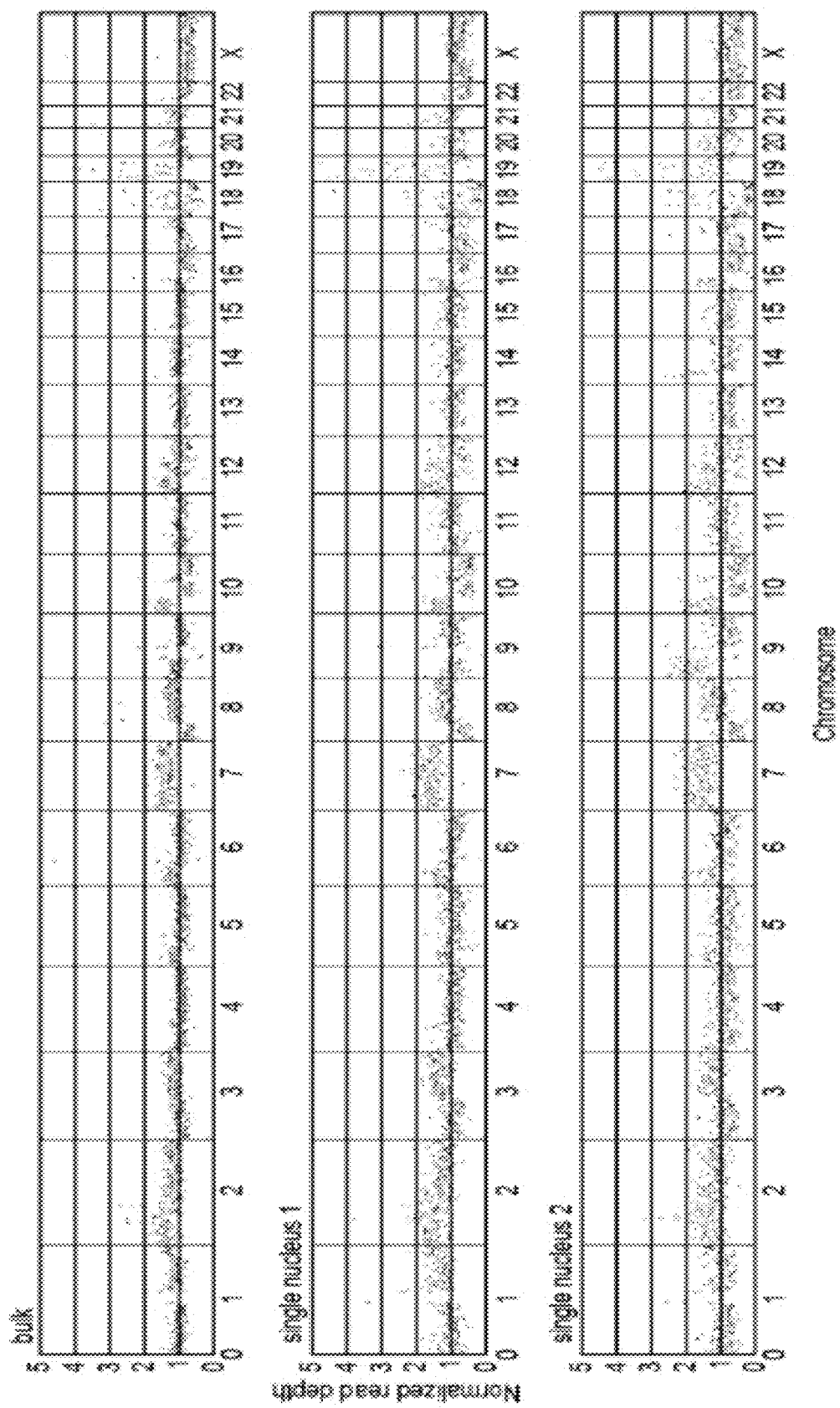
Figure 42A:
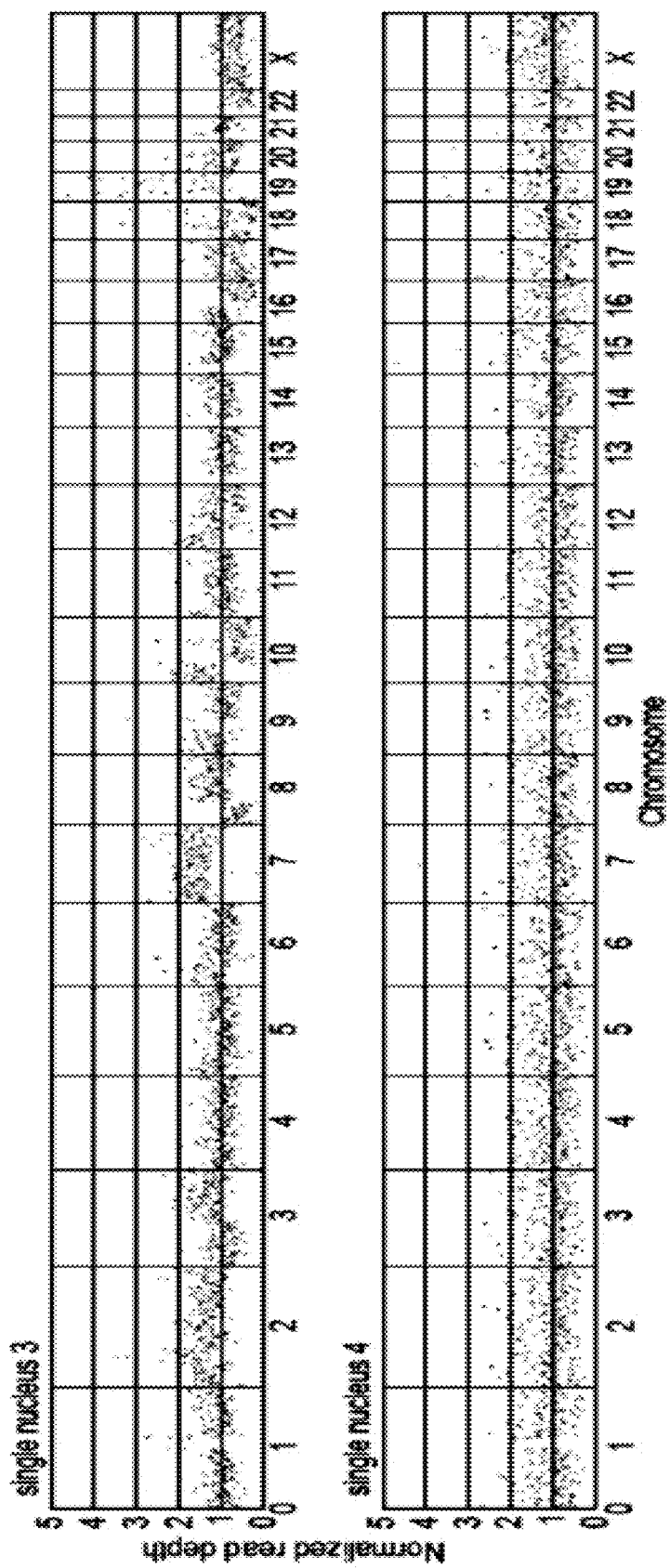
Figure 42B:
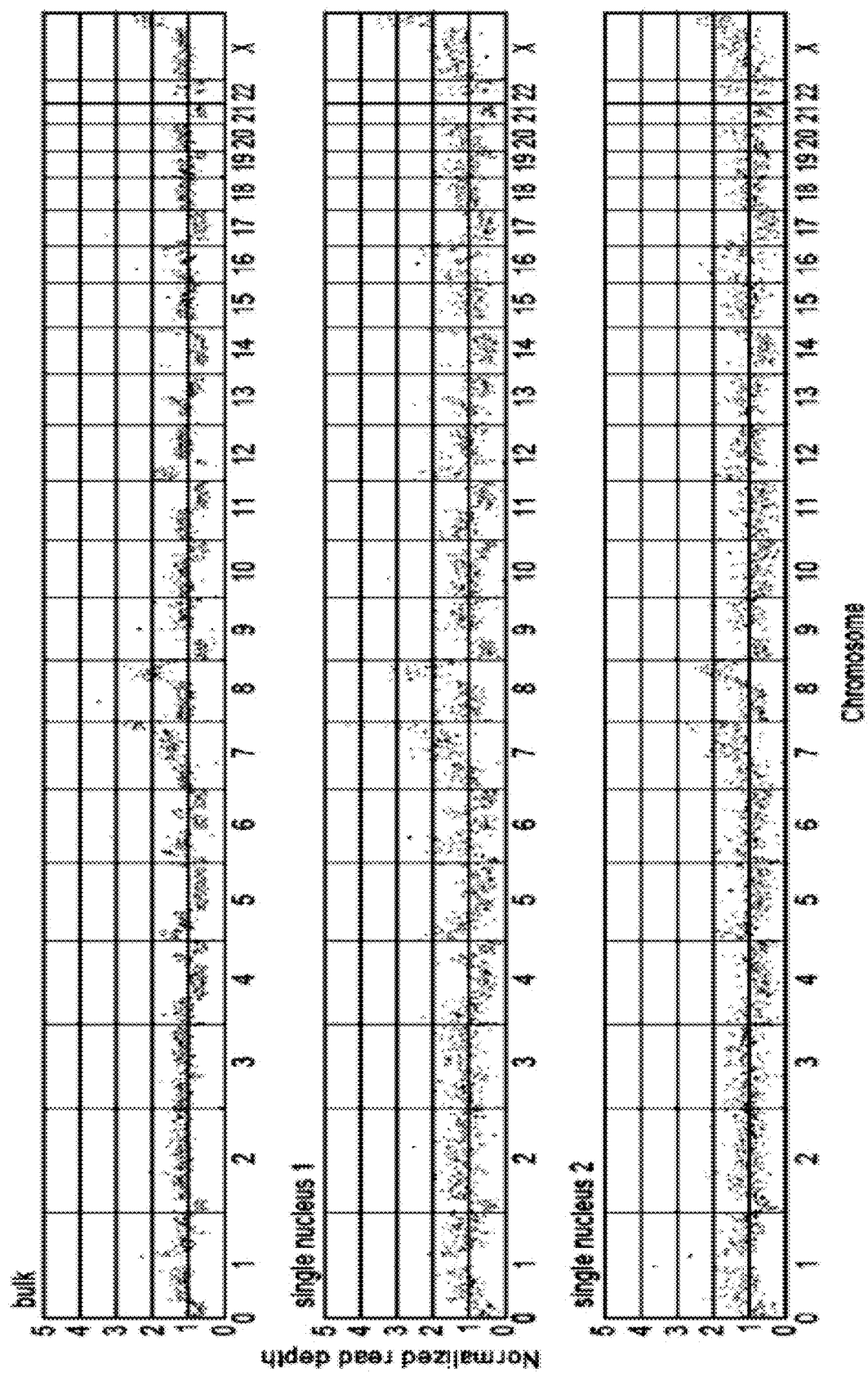
Figure 42B:
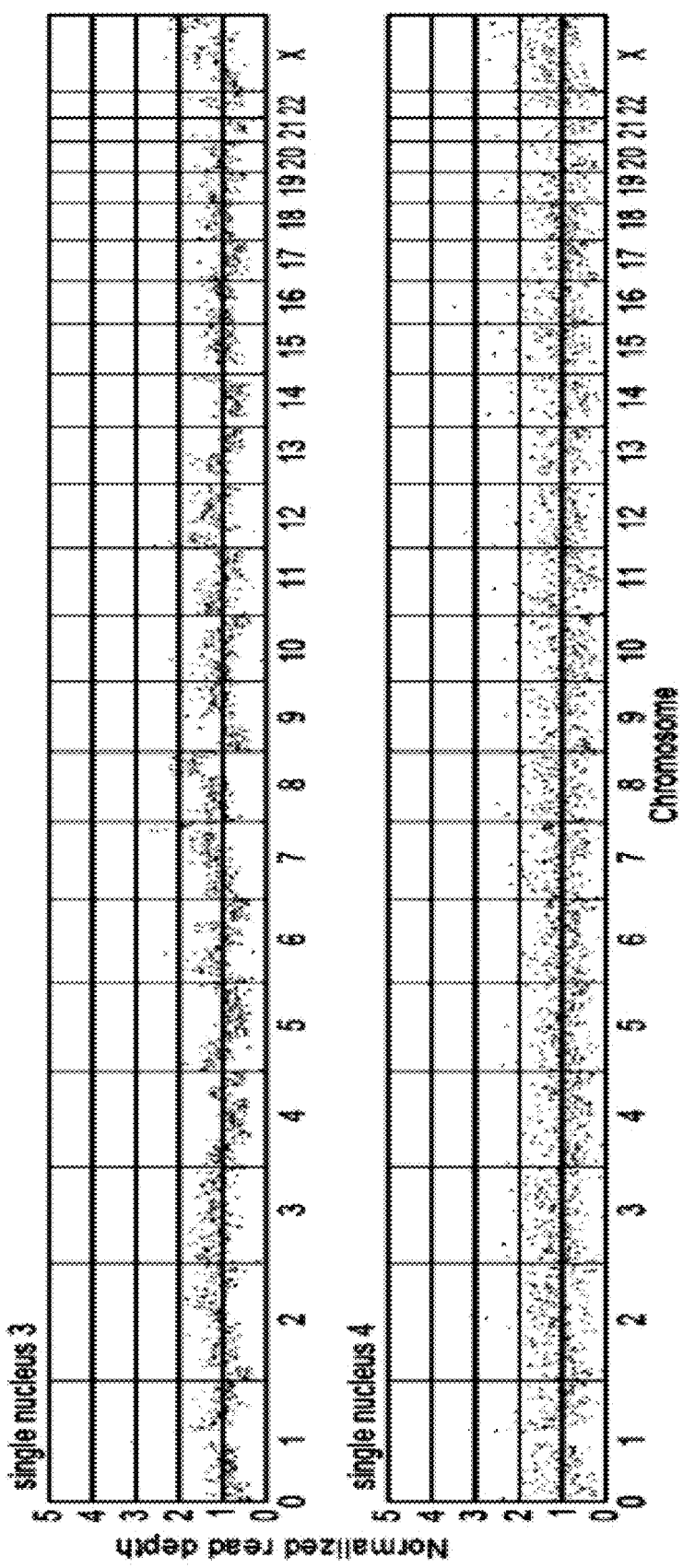

FIGS. 42A-B depict normalized read depth plots from single-cell droplet MDA on 2 high-grade serous ovarian cancer specimens.

Figure 43:
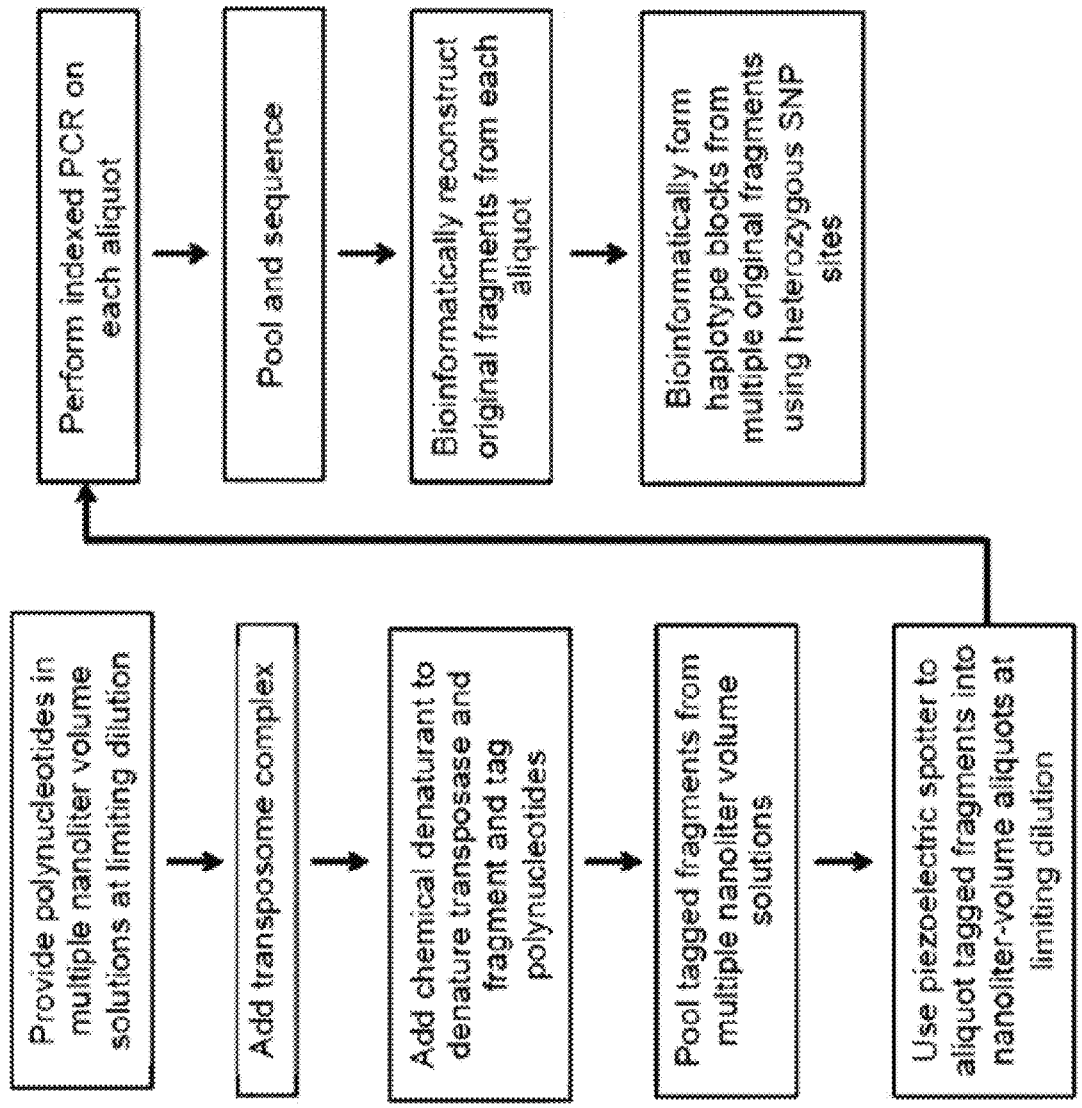

FIG. 43 depicts a flowchart for methods of haplotyping by transposase-based fragmentation.

Figure 44:
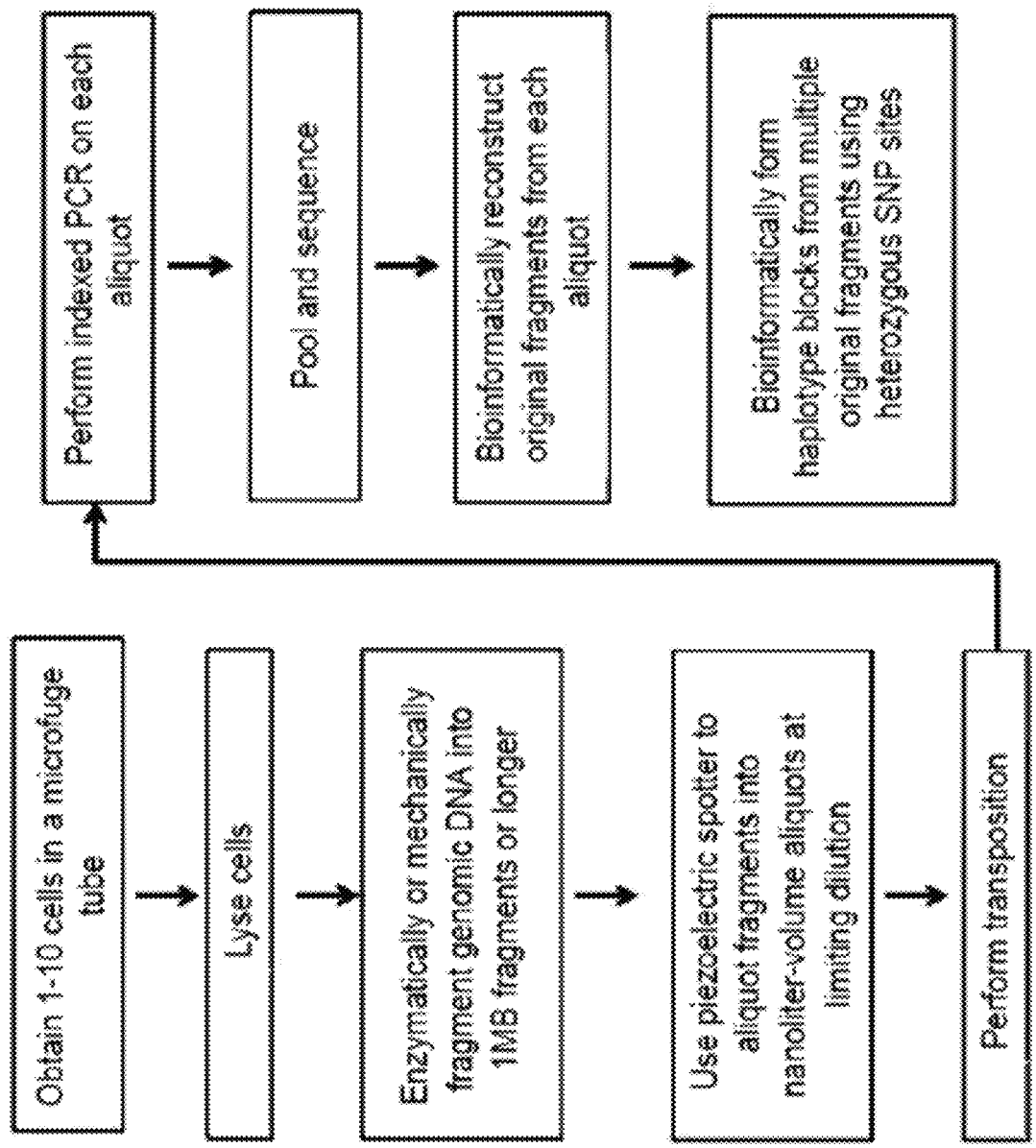

FIG. 44 depicts a flowchart for methods of haplotyping by transposase-based fragmentation.

Figure 45A:
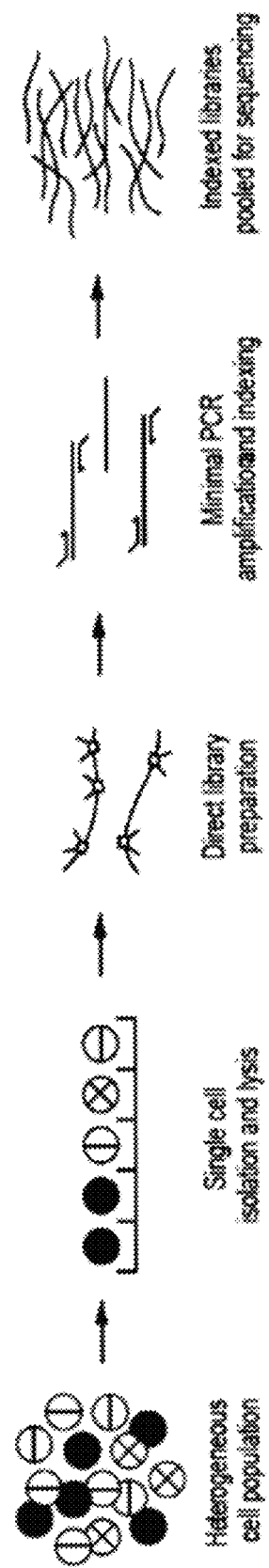
Figure 45B:
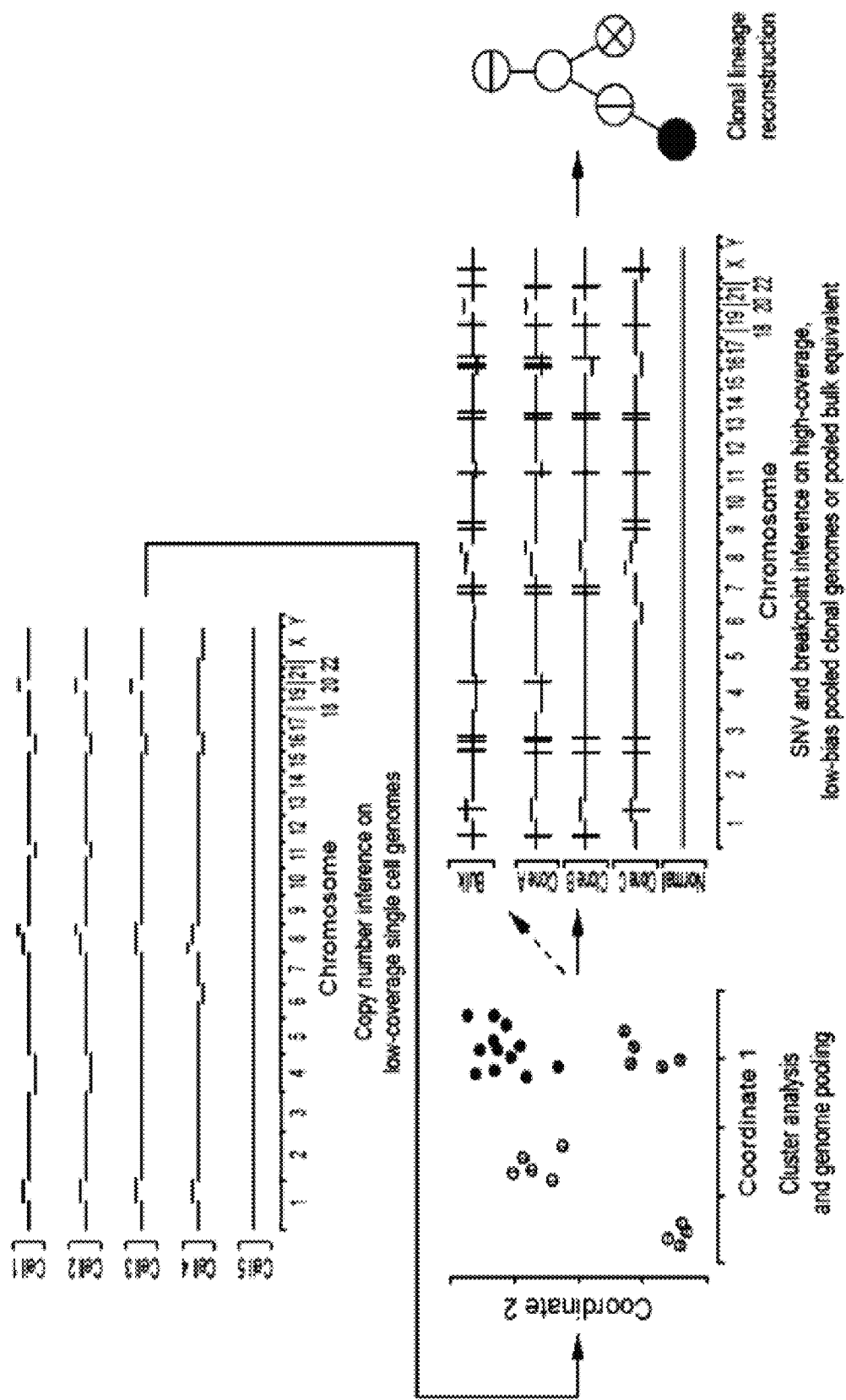

FIGS. 45A-B depict a conceptual schematic. (FIG. 45A) Experimental workflow. Heterogeneous samples are dissociated and single cells (or nuclei) are isolated from a cell suspension in individual reaction chambers; cells are lysed and unamplified single-cell DNA is fragmented and tagged using the NEXTERA chemistry; a minimal number of PCR cycles adds unique single-cell indices and sequencing adaptors to the tagmented DNA; finally, indexed libraries from all cells are pooled for multiplexed sequencing. (FIG. 45B) Analytical workflow. Sequencing reads derived from individual cells are demultiplexed, aligned to the human reference genome, and binned; following GC-content correction, a copy number profile is inferred for each low-coverage single-cell genome; single-cell copy number profiles are clustered, and the sequencing reads of cells with similar profiles are merged to produce higher-depth clonal genomes; sequencing reads from all cells may also be merged to produce a high-depth bulk-equivalent genome; additional variants such as SNVs and breakpoints are inferred on high-coverage merged clonal genomes or the merged bulk-equivalent; finally, phylogenetic inference of the clonal lineage may be derived based on one or more classes of genomic variants.

FIGS. 46A-H depict the microfluidic device design. (FIG. 46A) Device layout, featuring 192 single-cell processing units accessed through four cell loading inlets, to enable case vs. control studies. (FIG. 46B) Expanded view of one cell processing unit, featuring: (I) the cell lysis inlet, (II) a cell trap, (III) an inflatable reaction chamber, (IV) the reagent inlet, (V) an index-spotting chamber, (VI) the reagent supply channel. (FIG. 46C) Micro-photograph of a partially inflated microfluidic reaction chamber (1), and displacement chamber (2). (FIG. 46D) Unique index primers are pre-spotted during device fabrication using contactless spotting technology. (FIG. 46E) Brightfield image of a pre-spotted primer incorporated in the microfluidic device. (FIGS. 46F-H) Fluorescence imaging of cell traps permits the identification and labelling of chambers containing single cells, cells with contaminating debris, and two or more cells, prior to sequencing.

FIGS. 47A-D depict coverage uniformity and sequencing metrics. (FIG. 47A) Bootstrap sampling (n=30) and pooling of diploid single-cell genomes vs. coverage breadth (fraction of the genome covered by at least one read). Direct library preparation of diploid cells sequenced at 0.07× depth (192 cells per HISEQ Sequencing System lane; diagonals) vs. diploid cells sequenced with the C-DOP-L protocol at 0.015CHECKX depth (96 cells per HISEQ Sequencing System lane; crosses). Pooling 64 diploid cells prepared without pre-amplification results in 94.65% genome coverage; while pooling of 64 cells prepared with C-DOP-L results in a median of 44.70% coverage breadth. Downsampling of direct library preparation data to the same mean depth per cell as the C-DOP-L dataset (equivalent to 896 cells per lane, grey) reveals 58.43% coverage breadth upon pooling 64 cells, demonstrating greater coverage uniformity. (FIG. 47B) Lorenz curves, showing uniformity of coverage for pooled single-cell genomes. Each solid grey curve corresponds to the median pooled sample from panel a. A bulk genome for the same sample prepared using the standard NEXTERA protocol (solid black) was sequenced at 3.44× coverage depth. A pooled genome corresponding to 48 single cells prepared using direct library preparation with the same coverage depth (dashed grey) achieves equivalent coverage breadth and uniformity. Dotted black line (line slope=1)_represents perfectly uniform coverage. (FIG. 47C) Comparison of sequencing metrics for single breast cancer tumour cells sequenced following direct library preparation, WGA4, and C-DOP-L. While all multiplexed single-cell libraries featured a median of approximately 2 million reads per cell, WGA4 libraries suffered from low mappability due to WGA adaptor contamination, while C-DOP-L libraries had high duplicate rates. This results in a substantially reduced number of usable reads per cell for these methods relative to direct library preparation without pre-amplification. X3F or SA501X3F, a third passage xenograft tumour sample derived from a primary triple negative breast cancer; X4F or SA501X4F, a fourth passage xenograft tumour sample derived from X3F; Pt41, an estrogen receptor (ER) positive breast cancer tumour sample. (FIG. 47D) Sample copy number profiles for a diploid 184-hTERT-L2 cell (top) and a SA501X4F xenograft tumour cell (bottom), inferred using a hidden Markov model. Colours correspond to the copy number state assignment for a given genomic bin (200 kb bins). Black lines indicate segment medians.

Figure 48A:
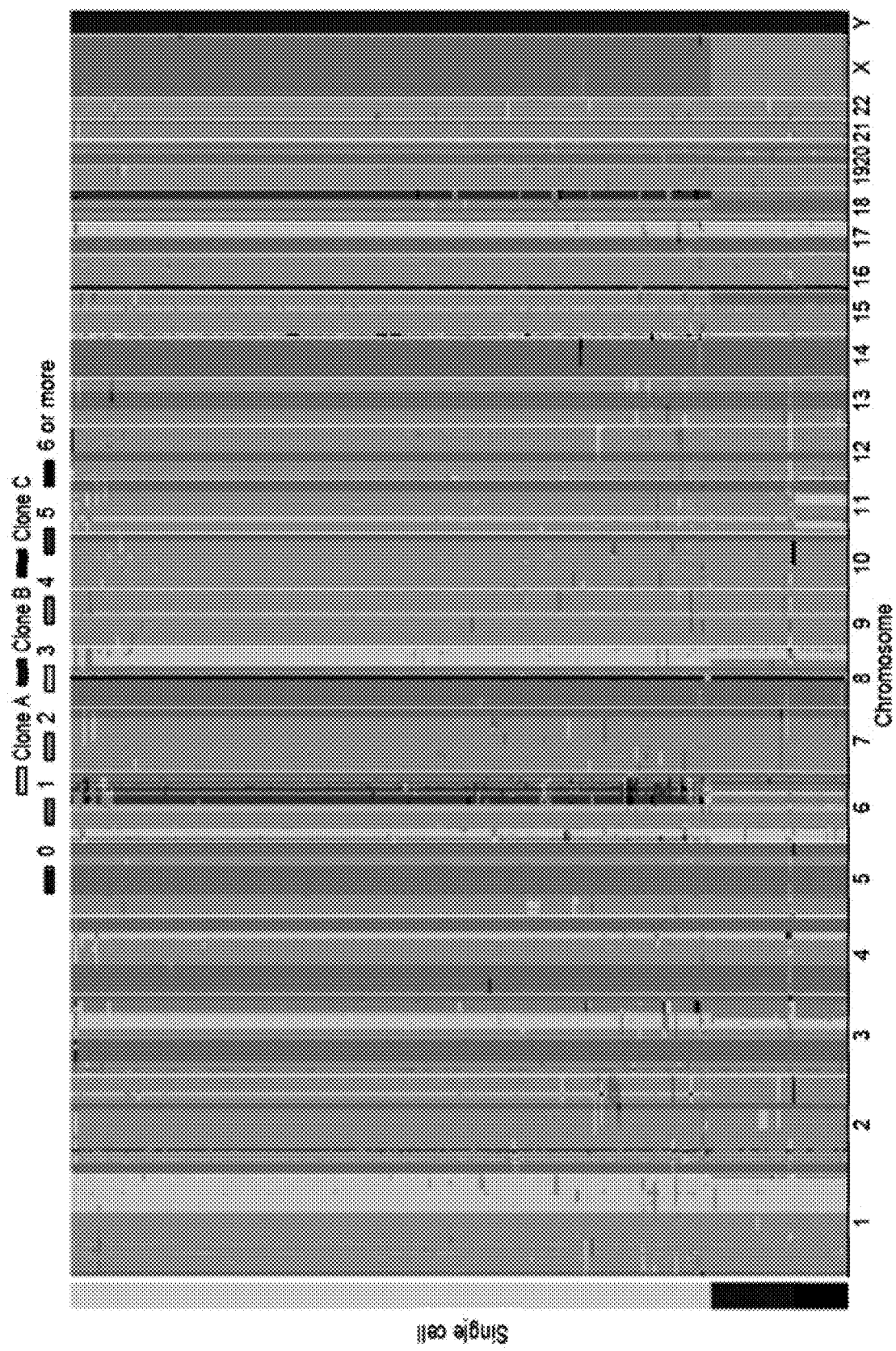
Figure 48B:
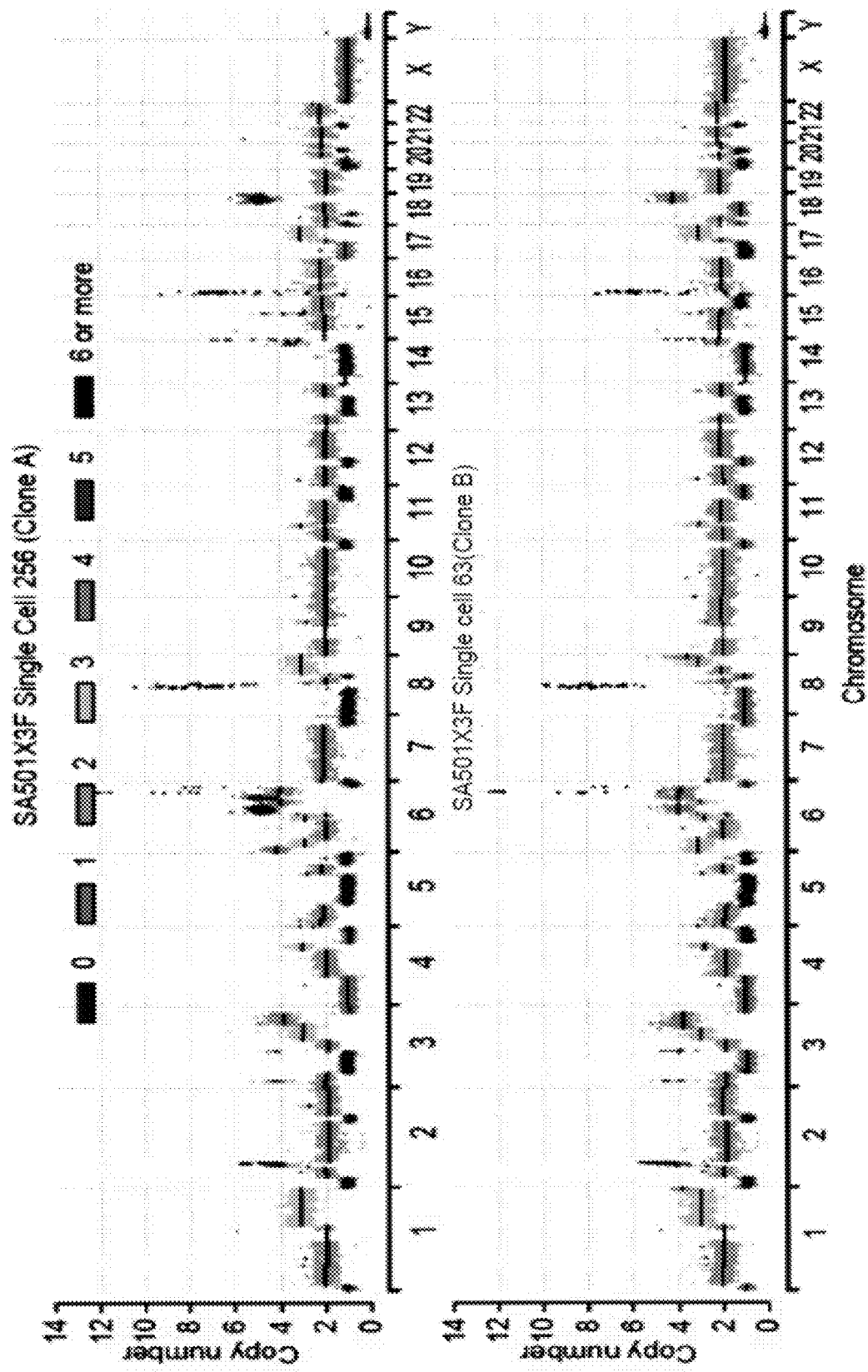
Figure 48B:
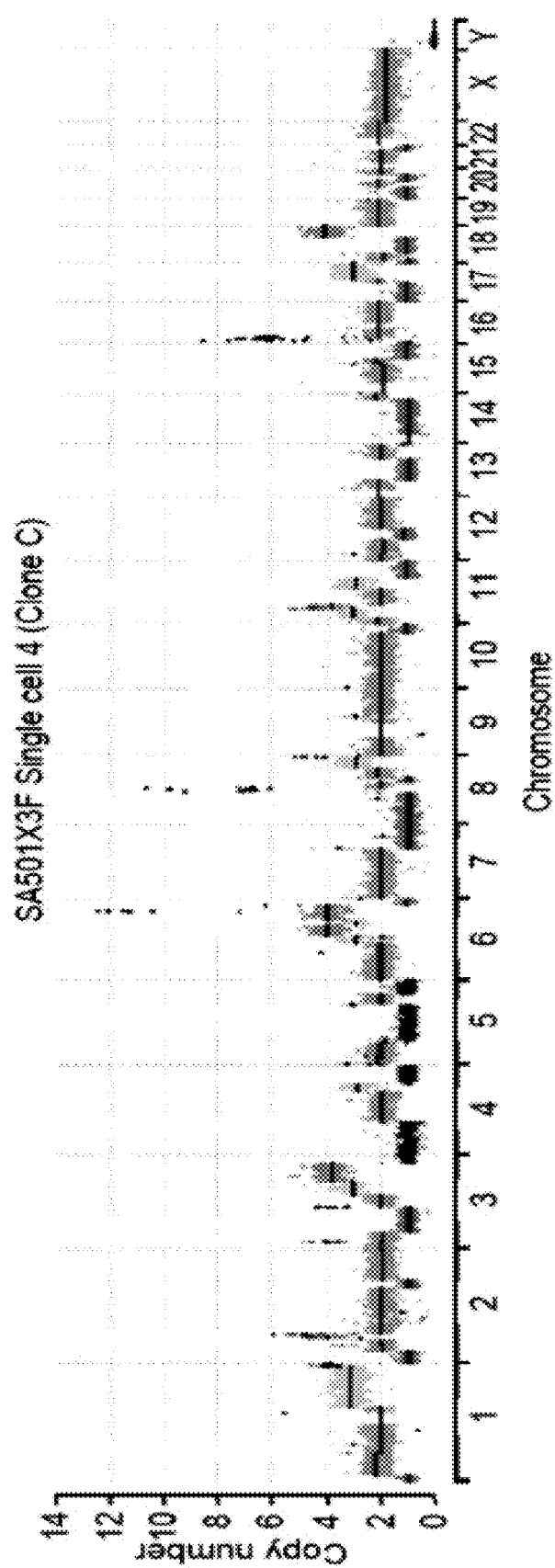
Figure 48C:
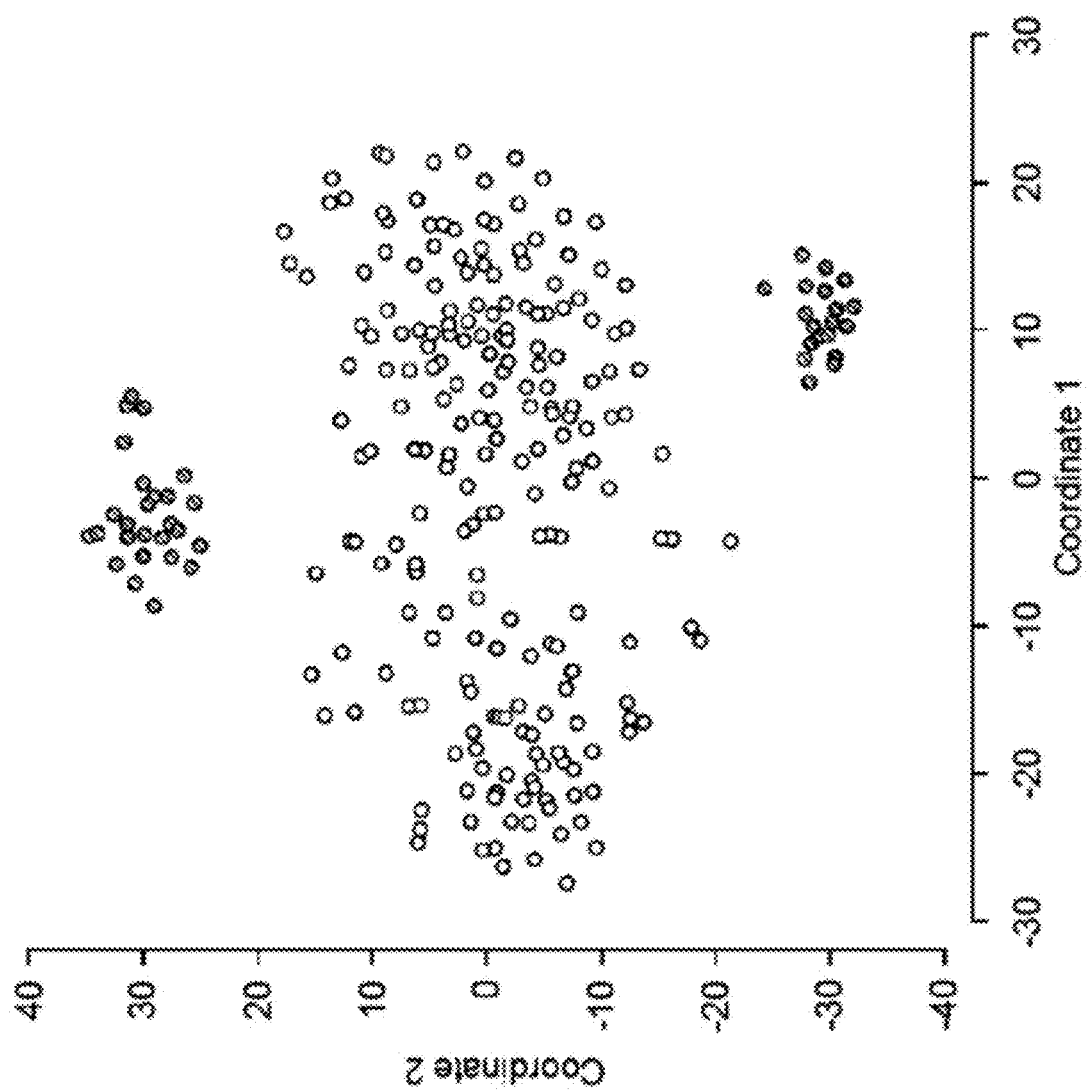

FIGS. 48A-C depict single-cell copy number profiles from sample SA501X3F, a third-passage xenograft derived from a primary triple negative breast cancer tumour. (FIG. 48A) Heatmap showing integer copy number profiles for 259 SA501X3F cells, inferred using a hidden Markov model. Rows correspond to single-cell profiles, columns to genomic bins (200 Kb). Heatmap colours correspond to integer copy number states, while the left-hand bar indicates single-cell clonal cluster assignment. (FIG. 48B) Representative SA501X3F single-cell copy number profiles derived from Clone A (top), Clone B (middle), and Clone C (bottom). Colours correspond to the copy number state assignment for a given genomic bin. Black lines indicate segment medians. (FIG. 48C) Scatter plot of dimensionality-reduced distances between single-cell copy number profiles generated with t-distributed stochastic neighbour embedding (tSNE), and hierarchically clustered to derive clonal group assignment.

FIGS. 49A-E depict a comparison of variant calling for pooled single-cell genomes and a standard bulk genome for sample SA501X3F. (FIG. 49A) Inferred copy number profiles for the pooled genomes of all SA501X3F single cells from Clone A (top, 82.24% of cells), Clone B (top middle, 10.81% of cells), Clone C (lower middle, 6.95% of cells), a bulk-equivalent genome of all cells combined (bottom). Despite clear differences in copy number, little evidence of minor Clones B and C is evident (as shifts in median segment values) in the combined bulk-equivalent copy number profile, underscoring the challenge of identifying subclonal copy number changes from bulk genomes. Profiles were inferred using the same parameters and bin sizes applied to the single-cell genomes (200 kb bins). (FIG. 49B) Simultaneous inference of copy alterations and loss of heterozygosity on the pooled single-cell bulk-equivalent genome with standard 1 Kb bins. (FIG. 49C) Venn diagram demonstrating overlap in high-confidence SNV calls between the pooled single-cell bulk-equivalent genome and a standard bulk genome from xenograft tumour SA501X3F. (FIG. 49D) Scatter plot showing correlation of allelic ratios for high-confidence SNV calls between the pooled single-cell bulk-equivalent genome and a standard bulk genome from xenograft tumour SA501X3F. (FIG. 49E) Scatter plot showing correlation of LOH state calls for heterozygous germline variants between the pooled single-cell bulk-equivalent genome and a standard bulk genome from xenograft tumour SA501X3F.

Figure 50:
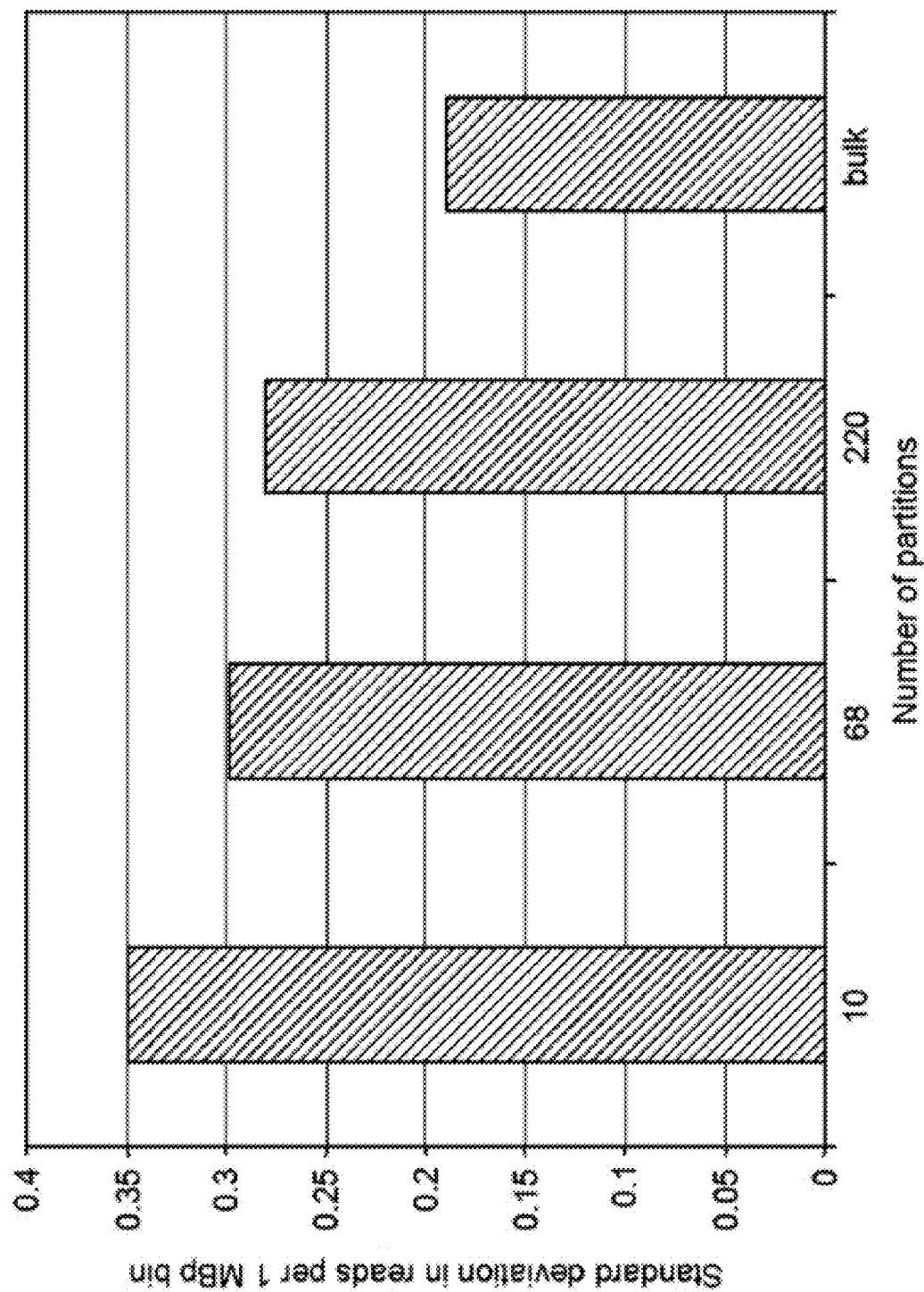

FIG. 50 is a graph showing the representational bias of sequencing libraries as measured by standard deviation (SD) in reads per 1 MBp bins prepared from 10 haploid cell equivalents partitioned into varying numbers of reactions. A standard library prepared from a bulk sample composed of millions of cell equivalents is shown for comparison. Bias decreases with larger numbers of reactions.

DETAILED DESCRIPTION OF THE INVENTION

The term "volumetric flow rate" and its grammatical equivalents as used herein can refer to the volume of fluid that passes a surface per unit time.

The term "aspect ratio" and its grammatical equivalents as used herein can refer to the ratio between the width and the height of an object.

The term "polynucleotide" and its grammatical equivalents as used herein can refer to at least two nucleotides covalently linked together. A polynucleotide can be DNA, including, but not limited to, genomic DNA, mitochondrial DNA, chloroplast DNA, plasmid DNA, oligonucleotide tags, cDNA, or combinations thereof. A polynucleotide can be RNA, including, but not limited to, tRNA, mRNA, rRNA, miRNA, siRNA, mitochondrial RNA, chloroplast RNA or combinations thereof. A polynucleotide can also be hybrid of DNA and RNA.

The term "sequencing depth" and its grammatical equivalents as used herein can refer to an amount of aligned sequencing data produced by a DNA sequencer The term "breadths of coverage" and its grammatical equivalents as used herein can refer to the fraction of a template polynucleotide covered by at least one sequencing read in a sequencing dataset.

The term "haplotype" and its grammatical equivalents as used herein can refer to a collection of specific alleles (e.g., DNA sequences) in a cluster of linked genes on a chromosome that are likely to be inherited together. For example, haplotype can be the group of genes that a progeny inherits from one parent.

The term "assembling" and its grammatical equivalents as used herein can refer to aligning and merging fragments of a much longer DNA sequence in order to reconstruct the original sequence.

The term "adaptor" and its grammatical equivalents can refer to an oligonucleotide. An adaptor can be DNA, RNA or hybrid of DNA and RNA. An adaptor can comprise a known sequence, an unknown sequence, or combinations thereof.

A "microfluidic device", as used herein, refers to any device that allows for the precise control and manipulation of fluids that are geometrically constrained to structures in which at least one dimension (width, length, height) may be less than 1 mm.

A "flow layer" as used herein, refers to a layer of an integrated microfluidic device that contains the flow channels and variable volume reaction chamber or chambers, such that the flow channels are in fluid communication with the variable volume reaction chambers.

A "control layer" as used herein, refers to a layer of an integrated microfluidic device that contains the control lines.

A "control/displacement layer" as used herein, refers to a layer of an integrated microfluidic device that contains the control lines and displacement chamber or chambers, such that the displacement chamber may be aligned with the variable volume reaction chambers and be separated by a thin elastic membrane as described herein.

A "displacement layer" as used herein, refers to a layer of an integrated microfluidic device that contains the displacement chamber or chambers and pressure channels, such that the displacement chamber may be aligned with the variable volume reaction chambers and be separated by a thin elastic membrane as described herein and wherein the displacement chamber or chambers and pressure channels may be in fluid communication such that the pressure of the displacement chamber may be adjusted by a change in the pressure of the pressure channels.

A "membrane layer" as used herein, refers to a thin layer of an integrated microfluidic device that separates the variable volume reaction chambers from the displacement chambers, wherein the membrane is sufficiently elastic to extend into the displacement chamber in an expanded position or into the reaction chamber when in a reduced position or to remain in a neutral position when the pressure is essentially equivalent between the reaction and displacement chambers. Furthermore, the membrane layer may extend out into a void space where there is no displacement chamber and only a pressure chamber.

A "seal layer" as used herein, refers to a layer adjacent the control layer or control/displacement layer, to seal the control layer or control/displacement layer. The seal layer may be a blank wafer or glass slide or other suitable surface.

A "pressure chamber" as used herein, refers to a chamber that surrounds the variable volume chamber or chambers, whereby the pressure chamber is operable to produce a positive pressure on the exterior surface of the elastomeric membrane.

A "reaction chamber" or "variable volume reaction chamber", as used herein, refers to an enclosed space within a microfluidic device in which one or more reactions may be carried out. Each chamber will have at least one inlet for permitting fluid, including fluid containing cells, reagents, buffers, enzymes etc., to enter the chamber, and may also have at least one outlet to permit fluid to exit the chamber. Persons skilled in the art will understand that an inlet or an outlet can vary considerably in terms of structure and dimension, and may be reversibly switched between an open position, to permit fluid to flow into or out of the chamber, and a closed position to seal the chamber and thereby isolate and retain its contents, whereby the aperture may also be intermediate between the open and closed positions to allow some fluid flow. Furthermore, it is also possible to have the same aperture function as both an inlet and outlet. For example, where the pressure within the chamber is less than the pressure surrounding the chamber, the aperture may act as an outlet and where the pressure within the chamber is greater than the pressure surrounding the chamber, then the same aperture may act as an inlet. The variable volume reaction chamber may be used for treatment or assaying of a captured cell, or its isolated contents. Treatment can include cell preparation steps including culture, washing, lysis, and fractionation. Assaying may include DNA and RNA amplification and detection, including mitochondrial PCR; genomic PCR; digital PCR, RT-PCR, RTq-PCR, multiple displacement amplification (DNA), rolling circle amplification sequencing, degenerate PCR, molecular inversion probes, molecular beacons, as well as other DNA/RNA amplification and detection methods, in vitro transcription, ligation, immunochemistry; reporter expression analysis; hybridization studies; and so forth.

A "displacement chamber", as used herein, refers to any that is aligned with a reaction chamber and wherein the reaction chamber and displacement chamber are separated from one another by a thin pliable membrane, such that the volume of the reaction chamber may be expanded or reduced by either expanding the volume of the reaction chamber and thus stretching the membrane into the displacement chamber or reducing the volume of the reaction chamber and thus stretching the membrane into the reaction chamber, respectively. The displacement chamber may also have some mechanism for changing the pressure in the displacement chamber relative to the pressure in the reaction chamber.

A "cell trap" or "nuclei trap", as used herein, refers generally to a means for receiving and retaining cells; or cell nuclei following lysis of a cell; or other cell material following lysis at a pre-determined location over time. A cell trap may comprise localized surface modifications for chemical immobilization of a cell. Alternatively, the cell trap may be a mechanical trap, a hydrodynamic trap (Skelley, A M et al. Nat Methods 6(2):147-152 (2009); Li, P. C. H. et al. Lab on a Chip 4, 174-180 (2004); Li, X. & Li, P. C. H. On-Chip Dye Loading, Cell Contraction by Chemical Stimulation, and Quantitative Fluorescent Analysis of Intracellular Calcium. Anal. Chem. 77, 4315-4322, doi:10.1021/ac048240a (2005); Di Carlo, D. et al. Anal. Chem. 78, 4925-4930, doi:10.1021/ac060541s (2006); each incorporated by reference herein in their entireties), a hydrodynamic balancing trap (Rowat, A. C. et al. Proceedings of the National Academy of Sciences 106, 18149-18154, doi: 10.1073/pnas.0903163106 (2009); and Kobel, S. et al. Lab on a Chip 10, 857-863 (2010), each incorporated by reference herein in their entireties), an active valving trap (Warren L, et al. Proc Natl Acad Sci USA 103(47):17807-17812 (2006); Skelley, A M et al. Nat Methods 6(2):147-152 (2009); Li, P. C. H. et al. Lab on a Chip 4, 174-180 (2004); King, K. R. et al. Lab on a Chip 7, 77-85 (2007); Marcy, Y. et al. Proc. Natl. Acad. Sci. U.S.A. 104, 11889-11894 (2007), each incorporated by reference herein in their entireties), a dielectrophoretic trap (Voldman, J. et al. Anal. Chem. 74, 3984-3990, doi:10.1021/ac0256235 (2002), incorporated by reference herein in its entirety), a DNA immobilization trap (Toriello N M, et al. Proc Natl Acad Sci USA 105(51):20173-20178 (2008), incorporated by reference herein in its entirety), a gel encapsulation trap (Braschler, T. et al. Lab on a Chip 5, 553-559 (2005), incorporated by reference herein in its entirety), a magnetic trap, an acoustic trap or an optical trap (Neuman, K. C. et al. Biophys. J. 77, 2856-2863 (1999), incorporated by reference herein in its entirety). A cell trap may be positioned directly in the path of the smaller cross sectional of cell flow created by the funnel. Where a mechanical funnel is used, a trap may be positioned directly after the downstream opening of the funnel. Furthermore, additional cell trapping and funneling methods may be found in WO 2012/162779, incorporated by reference herein in its entirety.

A "mechanical trap", as used herein, refers to a physical cell trap such as a cage.

A "hydrodynamic trap", as used herein, refers to a cell trap in which the force of the fluid in motion plays a role in retaining a trapped cell in its position. A hydrodynamic trap may be also be comprised of a mechanical trap in which a cell is captured and retained. Exemplary mechanical traps are described in WO 2012/162779, incorporated by reference herein in its entirety. In certain embodiments hydrodynamic traps may be utilized. However, it may be desirable to have three or more inlets to the cell capture chamber so that the flows may be adjusted in order to direct cells to the traps.

A "dielectrophoretic trap", as used herein, refers to a cell trap in which cells, being dielectric objects, are retained by the forces generated by a non-uniform electric field.

A "magnetic trap", as used herein, refers to a cell trap employing magnetic fields to retain cells. Typically, cells will be labeled with magnetic particles, and then positioned and retained by the magnetic fields. However, magnetic traps can also be used to trap-non-magnetic cells in suitable buffers.

An "acoustic trap", as used herein, refers to a cell trap in which ultrasonic standing waves are used to generate stationary pressure gradients that exert forces that position and retain cells.

An "optical trap", as used herein, refers to a cell trap in which a tightly focused laser beam, typically a near-infra red laser beam, is used to draw cells in the direction of the beam.

"Indexing oligonucleotides", as used herein refer to oligonucleotides that are capable of indexing the product of each individual reaction chamber.

"Aspect ratio", as used herein, refers to the ratio (y:x) of the shortest distance between the cell retaining position and the first region (y) to the length of the first region (x). In various embodiments where the inlet and outlet is at the top of the chamber, such that the first region is horizontal and defines an area that is interposed directly between the inlet and outlet positions, the aspect ratio will effectively been the ratio of the height of the chamber (minus the height of the first region) to the width of the chamber.

A "fluid injection channel", as used herein, refers to any conduit through which fluid may be introduced into a chamber of the device. A fluid injection channel can be used to deliver any fluid to a chamber including cell suspensions, cell culture media, wash buffers, reaction mixes, factors, reagents, functionalized beads, etc.

Methods, devices and systems are provided herein to facilitate highly parallel and accurate analysis of biological samples. In particular, the microfluidic devices and systems provided herein find utility in the analysis of single cells and small collections of cells (e.g., from about 1 to about 20 cells, or from about 1 to about 10 cells, or from about 1 to about 5 cells). Analysis of such small samples allow for the preservation of precious samples such as embryonic biopsies that are used for preimplantation genetic diagnosis (PGD). Moreover, cellular heterogeneity can be analyzed because only one to a few cells are necessary.

Genomic heterogeneity is recognized as a central feature of many cancers and plays a critical role in disease initiation, progression, and response to treatment. As a result, the development of robust, scalable and high-fidelity single cell genomics has become critical to advancing our understanding of the structure and dynamics of cellular heterogeneity in cancer. However, to date all existing methods are based on sequencing library construction from pre-amplified samples. These methods generally introduce artifacts and coverage bias, and are also prohibitively expensive for large scale studies of thousands of single cells. The present invention addresses this need by providing methods, devices and systems for the streamlined preparation of single-cell next-generation sequencing libraries without the need for prior amplification, and a workflow that permits the economical high-throughput analysis of a biologically representative number of cells.

As with the analysis of genomic heterogeneity, preimplanatation genetic testing is limited to the analysis of one to a few cells because embryos in the preimplantation stage consist of a very limited number of cells, diagnosis has to be performed by genetic testing of just a single or a few biopsied embryonic cells.

Given that one diploid human cell contains only about 7 pg DNA and that current genomics methodologies require tens to hundreds of nanograms of input DNA, current requirements of whole genome analysis of single or a few cells (e.g., analysis of the genome(s) of a biopsied cell(s)) must first be amplified thousands of times to allow for such genome-wide analysis. However, whole genome amplification methods as applied to single cells and/or a small number of cells are currently lacking.

Previously disclosed whole genome amplification WGA are problematic as they introduce amplification bias into the nucleic acid being amplified. One result of this amplification bias is the introduction of allele dropout (ADO), and a number of chimeric DNA-amplification products that distort the cell's original genomic architecture are created. Moreover, depending on the WGA method chosen, the breadth of genomic coverage, GC bias, chimeric DNA molecules, ADOs, preferential allelic amplifications and nucleotide copy errors will vary significantly.

Previous comparisons of WGA methods suggest that protocols based on degenerate oligonucleotide primed PCR (DOP-PCR) achieve the highest coverage uniformity, with lower dispersion in binned read counts relative to multiple-displacement amplification (MDA) and multiple annealing and looping-based amplification (MALBAC), making these methods most amenable to single-cell copy number inference. However, coverage breadth of DOP-PCR libraries tends to saturate with deeper sequencing, making these methods less suitable for analysis of single-cell single nucleotide variants (SNVs, also known as single nucleotide polymorphisms "SNPs").

MALBAC libraries suffer from a high rate of polymerase base substitutions, while MDA libraries generally exhibit higher dispersion in binned read counts and are therefore susceptible to copy number artifacts. Finally, it should be emphasized that there is a high cost associated with sequencing a biologically meaningful number of cells to high coverage depth and breadth. Past studies examined anywhere from a handful to several hundred single-cell genomes in one or two patient tumors, and some sought to reduce sequencing costs through exome capture or the use of targeted sequencing. Thus far, these studies have been limited in both the ability to detect minor sub-populations, and the ability to infer a range of different variant types.

Accordingly, in aspects described herein, the present invention provides devices, systems and methods as an alternative to both bulk and single-cell WGA approaches, whereby indexed libraries are prepared directly on single-cell nucleic acid template or a small collection of cell nucleic acid template without pre-amplification (FIG. 45A). These libraries are pooled for highly multiplxed sequencing at low depth, producing highly uniform coverage amenable to integer copy number inference, and minimizing the risk of introduced copy number artifacts and polymerase errors. Following sequencing, single-cell copy number profiles are clustered to infer sub-populations clonal in copy number space (FIG. 45B). Sequencing reads from all cells may be pooled to produce a high-depth "bulk-equivalent genome" amenable to SNV, LOH, and breakpoint inference; alternatively, all cells within each copy number clone can be pooled to produce a set of high-depth "clonal genomes" (FIG. 45B).

As described herein, the present invention addresses the problem of amplification bias by providing devices, systems and methods for whole genome analysis without the need for pre-amplification of nucleic acid.

The present invention is based in part on the realization that fabricating and operating microfabricated structures made out of various layers of elastomer is possible such that the volume of a defined structure can be freely adjusted in a range of from about 0 µL to about 10 µL. Furthermore, such a variable volume reaction chamber design supports nearly arbitrary sequences of reagent additions and subtractions from a reaction chamber, making it amenable to an array of biological and chemical applications, for example, the use of a solid substrate to purify molecules and to perform single cell library construction. In another embodiment, the chamber is used for one or more of: PCR amplification; reverse transcription; template switching; RNA amplification using in vitro transcription; in vitro translation; ligation; transposon fragmentation; isothermal amplification; lyses; bisulfite treatment; size selection; antibody binding capture of proteins associated with nucleic acids; selective capture of nucleic acids based on hybridization to nucleic acid oligonucleotide probes; and quantitative PCR assays. In a further embodiment, the variable volume chamber described herein is used to carry out a multistep processes in a single chamber. The chambers described herein can be fabricated on a single device such that hundreds to thousands of chambers are present on a single device.

The use of a variable volume microfluidic chamber provided herein provides a similar flexibility as micro centrifuge tubes, with the added advantage of precise fluid manipulation and reduced risk of contamination. Furthermore, it allows for minimal time for premixing reagents before loading, minimizes handling time and reduces the opportunity for operator error.

In one embodiment, one or more oligonucleotides are deposited in the reaction chamber. The oligonucleotides in one embodiment are indexing oligonucleotides. The reaction chamber as described herein in one communication with an auxiliary chamber. The auxiliary chamber may further include deposited oligonucleotides which may be released into the reaction chamber. The reaction chamber may further include a cell trap. The chamber may further include capture substrate deposited in the reaction chamber. The chamber may further include microparticles deposited in the reaction chamber. The chamber may further include functionalized capture spots in the reaction chamber. The microparticles may be capture beads.

As described herein, reference to a "chamber" includes reference to a device that comprises a plurality of "chambers".

In one aspect, a flexible and scalable microfluidic platform is described herein. In one embodiment, the microfluidic platform is a platform for the genomic analysis of single-cells or from about 1 to about 10 cells per microfluidic chamber. In a further embodiment, genomic analysis includes the integration of an entire genomic library preparation, including single cell sorting, genomic DNA extraction, library synthesis, indexing suitable for multiplexed next generation sequencing analysis, and size selection. As described in more detail herein, the variable volume chambers described herein provide a robust and scalable tool for the direct preparation of single-cell libraries with state of the art performance (e.g., decrease in amplification bias, increase in sequencing depth) and throughput, and significant reduced costs compared to microliter approaches.

In one embodiment, the variable volume chamber comprises (a) a flow layer defining a reaction chamber and flow channels, wherein at least one wall of the reaction chamber or a portion thereof is an elastomeric membrane, the membrane having: (i) a neutral position; and (ii) a plurality of expanded positions; wherein the expanded positions determine the volume of the reaction chamber, whereby the volume of the reaction chamber is V at the neutral position and the volume of the reaction chamber is greater than V in the plurality of expanded positions, wherein V is less than 1 µl, and wherein the volume at a maximally expanded position is equal to or greater than 2×V; and (b) a blank layer to seal the flow layer.

The variable volume chamber of the devices provided herein in one embodiment comprises a control layer adjacent the flow layer or separated from the control layer by a membrane layer, wherein the control layer defines control lines. The elastomeric membrane in one embodiment comprises a plurality of reduced positions whereby the volume is less than V in the plurality of reduced positions, and wherein the reduced volume is equal to or less than 0.5×V. The device in some embodiments comprises a pressure chamber that surrounds the variable volume chamber or chambers, whereby the pressure chamber is operable to produce a variable pressure on the exterior surface of the elastomeric membrane. The device may further include a displacement chamber, whereby the displacement chamber and the reaction chamber (i.e., the variable volume chamber) may be aligned, and whereby the reaction chamber may be operable to expand into the displacement chamber and the displacement chamber may be operable to produce a positive pressure on the exterior surface of the elastomeric membrane of the reaction chamber.

The volume at the expanded position is equal to or greater than: (a) 3×V; (b) 4×V; (c) 5×V; (d) 6×V; (e) 7×V; (f) 8×V; (g) 9×V; (h) 10×V; (i) 11×V; (j) 12×V; (k) 13×V; (l) 14×V; (m) 15×V; (n) 16×V; (o) 17×V; (p); 18×V; (q) 19×V; (r) 20×V; (s) 25×V; (t) 30×V; (u) 35×V; (v) 40×V; (w) 45×V; (x) 50×V; (y) 55×V; (z) 60×V; (aa) 65×V; (bb); 70×V; (cc) 75×V; (dd) 80×V; (ee) 85×V; (ff) 90×V; (gg) 95×V; (hh) or is equal to 100×V. The volume at the reduced position may be equal to or less than: (a) 0.4×V; (b) 0.3×V; (c) 0.2×V; (d) 0.1×V; (e) 0.09×V; (f) 0.08×V; (g) 0.07×V; (h) 0.06×V; (i) 0.05×V; (j) 0.04×V; (k) 0.03×V; (l) 0.02×V; (m) 0.01×V; or is essentially zero×V. The expanded position may be equal to or greater than 5×V and the reduced position may be equal to or less than 0.5×V. The expanded position may be equal to or greater than 3×V and the reduced position may be equal to or less than 0.4× V. The expanded position may be equal to or greater than 10×V and the reduced position may be equal to or less than 0.5×V.

In another embodiment, a variable volume chamber of the device provided herein comprises (a) a flow layer defining a reaction chamber and flow channels, wherein at least one wall of the reaction chamber or a portion thereof is an elastomeric membrane, the membrane having: (i) a neutral position; and (ii) a plurality of expanded positions; wherein the expanded positions determine the volume of the reaction chamber, whereby the volume of the reaction chamber is V at the neutral position and the volume of the reaction chamber is greater than V in the plurality of expanded positions, wherein V is less than 1 µL, and wherein the volume at a maximally expanded position is equal to or greater than 2×V; and (b) a blank layer to seal the flow layer;

and (c) a displacement chamber that surrounds the reaction chamber, whereby the displacement chamber and the reaction chamber are aligned, such that the reaction chamber is operable to expand into the displacement chamber and wherein the displacement chamber is operable to constrain the expansion of the reaction chamber.

The variable volume chamber in a further embodiment comprises a control layer adjacent the flow layer or separated from the control layer by a membrane layer, wherein the control layer defines control lines. The elastomeric membrane in one embodiment comprises a plurality of reduced positions whereby the volume may be less than V in the plurality of reduced positions, and wherein the reduced volume may be equal to or less than $0.5 \times V$. In some embodiments, the chamber comprises a pressure chamber that surrounds the variable volume chamber or chambers, whereby the pressure chamber is operable to produce a variable pressure on the exterior surface of the elastomeric membrane. The volume at the expanded position in one embodiment, is equal to or greater than: (a) $3 \times V$; (b) $4 \times V$; (c) $5 \times V$; (d) $6 \times V$; (e) $7 \times V$; (f) $8 \times V$; (g) $9 \times V$; (h) $10 \times V$; (i) $11 \times V$; (j) $12 \times V$; (k) $13 \times V$; (l) $14 \times V$; (m) $15 \times V$; (n) $16 \times V$; (o) $17 \times V$; (p); $18 \times V$; (q) $19 \times V$; (r) $20 \times V$; (s) $25 \times V$; (t) $30 \times V$; (u) $35 \times V$; (v) $40 \times V$; (w) $45 \times V$; (x) $50 \times V$; (y) $55 \times V$; (z) $60 \times V$; (aa) $65 \times V$; (bb); $70 \times V$; (cc) $75 \times V$; (dd) $80 \times V$; (ee) $85 \times V$; (ff) $90 \times V$; (gg) $95 \times V$; (hh) or is equal to $100 \times V$. The volume at the reduced position may be equal to or less than: (a) $0.4 \times V$; (b) $0.3 \times V$; (c) $0.2 \times V$; (d) $0.1 \times V$; (e) $0.09 \times V$; (f) $0.08 \times V$; (g) $0.07 \times V$; (h) $0.06 \times V$; (i) $0.05 \times V$; (j) $0.04 \times V$; (k) $0.03 \times V$; (l) $0.02 \times V$; (m) $0.01 \times V$; or is essentially zero$\times V$. The expanded position in one embodiment is greater than $5 \times V$ and the reduced position y is equal to or less than $0.5 \times V$. The expanded position in another embodiment is equal to or greater than $3 \times V$ and the reduced position is equal to or less than $0.4 \times V$. The expanded position in yet another embodiment is equal to or greater than $10 \times V$ and the reduced position is be equal to or less than $0.5 \times V$.

In yet another embodiment, a variable volume chamber comprises (a) a flow layer defining a reaction chamber and flow channels, wherein at least one wall of the reaction chamber or a portion thereof is an elastomeric membrane, the membrane comprising: (i) a neutral position; (ii) a plurality of expanded positions; and (iii) a plurality of reduced positions; wherein the expanded and reduced positions determine the volume of the reaction chamber, whereby the volume of the reaction chamber is V at the neutral position, the volume of the reaction chamber is greater than V in the plurality of expanded positions and the volume is less than V in the plurality of reduced positions, such that the volume at a maximally reduced position is essentially zero and wherein V is less than 1 µL; (b) a control layer adjacent the flow layer defining control lines; (c) a seal layer adjacent the control, to seal the flow; and (d) a pressure chamber that surrounds the variable volume chamber or chambers, whereby the pressure chamber is operable to produce a positive pressure on the exterior surface of the elastomeric membrane and wherein the displacement chamber is operable to constrain the expansion of the reaction chamber.

The flow layer in one embodiment is a polymeric organosilicon. In a further embodiment, the flow layer is comprised of polydimethylsiloxane (PDMS). The reaction chamber may further include oligonucleotides deposited in the reaction chamber. The oligonucleotides may be indexing oligonucleotides. The reaction chamber may be in fluid communication with an auxiliary chamber. The auxiliary chamber may further include deposited oligonucleotides which may be released into the reaction chamber. The reaction chamber may further include a cell trap. The chamber may further include capture substrate deposited in the reaction chamber. The chamber may further include microparticles deposited in the reaction chamber. The chamber may further include functionalized capture spots in the reaction chamber. The microparticles may be capture beads.

In one embodiment, the variable volume reaction chamber is employed to trap a cell or a lysed cell, or a plurality of cells or a plurality of lysed cells. The entire cell/nuclei or the material of a lysed cell in one embodiment is initially trapped within the variable volume reaction chamber. Alternatively, the entire cell/nuclei or the material of a lysed cell is trapped elsewhere and then be transferred to the variable volume reaction chamber for processing. Furthermore, a trap may allow for the concentration of secreted products and the detection of these on a capture substrate. A trapped cell in one embodiment is a biopsied cell, for example from a tumor or embryo.

The variable volume chambers described herein in one embodiment comprise a "capture substrate". A "capture substrate", as used herein, is meant to encompass a wide range of substrates capable of capturing a protein or biomolecule (e.g., nucleic acid) of interest or proteins or biomolecules of interest or the entire contents of a lysed cell. These substrates may be modified to alter their surface (internal and external) properties depending on the desired use. For example, a substrate may be bound to antibodies or antigens to capture an antibody of interest. A capture substrate is, for example, a microsphere or a nanosphere or other microparticles including, but not limited to a polystyrene bead or a silica bead (for example, antibody capture beads and oligo(dT) mRNA capture beads). In another embodiment, instead of modifying the beads with oligo(dT), specific primers could be utilized instead. In one embodiment, the microsphere is a carboxylic acid (COOH) functionalized bead. Beads which make use of alternate chemical interactions can fall within this definition. See: for e.g., G. T. Hermanson (2008), *Bioconjugate Techniques, 2nd Edition*, Published by Academic Press, Inc., incorporated by reference herein in its entirety for all purposes. For example, an alternate scheme for preparing these beads is to use streptavidin coated beads and to mix these beads with biotinylized rabbit anti-mouse pAbs and biotinylated oligo(dT). A capture substrate in another embodiment, is an anti-Ig bead which binds an antibody to the capture substrate. A capture substrate can be modified such that it binds multiple biomolecules of interest, for example both mRNA and protein. Alternately, each capture substrate could be limited to a particular biomolecule, for example, one capture substrate being limited to binding mRNA and a second capture substrate being limited to binding a protein. Capture substrates are commercially available or may be made de novo and/or modified as needed for the particular application. Capture substrates may be removable, as in the case of beads. However, capture substrates may also be fixed (and thus, non-removable). Capture substrates, such as microparticles are described, for example, in US Patent Publication No. 2012-0015347 and Singhal et al., Anal Chem, 82:8671-8679 (2010) and functionalized capture spots are described, for example, Ma et al., Nat Med, 10:1088-1092 (2011); the disclosure of each of which is incorporated herein in its entirety for all purposes.

In devices that include a variable volume chamber that comprises a cell trap, the cell trap may be varied according to the size, type, mechanical properties, or number of cells that the operator of the device would like to trap. A microfluidic device according to various embodiments may further include a combination of trap designs for the capture of a range of cell types. Furthermore, each chamber can include multiple traps or each chamber or a subset of chambers may be optimized to capture a particular cell type, i.e., in some embodiments, different trap dimensions/features are associated with unique chambers.

Additionally or alternatively, a variable diameter chamber provided herein in one embodiment comprises a cell funnel. A "cell funnel" as used herein, refers to an apparatus which is designed to focus the flow of cells from a first location, where the cells are dispersed, to one or more desired second or more locations within the chamber wherein the cell funnel has a smaller cross sectional area of cell flow. The cell funnel may exert a force to direct cells towards the one or more desired locations within the cell capture chamber. For the purposes of clarity, "force" is defined herein as any influence that causes a free body (e.g. a cell) to undergo a change in velocity. Funnels may either span the entire height and/or width of the cell capture chamber, or partially span the height and/or width. Exemplary cell funnels are described in WO 2012/162779, the disclosure of which is incorporated by reference herein in its entirety for all purposes.

A multilayer soft lithography process is used to build microfabricated elastomeric microfluidic devices with variable volumes (Unger, M. A. et al. Monolithic Microfabricated Valves and Pumps by Multilayer Soft Lithography. *Science* (2000) (80)288:113-116, the disclosure of which is incorporated by reference herein in its entirety). Micromachined molds are used to form recesses in elastomeric membranes. The recesses can extend along various layers as described in the below fabrication methods, but they always form a structure or structures that comprises:

I. A layer defining a chamber or a plurality of chambers
II. An elastomeric membrane forming at least one wall of a chamber, or a portion thereof.

The microfluidic device in one embodiment comprises an adjacent structure that surrounds the variable volume chamber or chambers, or which is located in juxtaposition with the membrane wall of the chamber, and which is operated to produce a pressure gradient across the elastomeric membrane. The elastomeric membrane in one embodiment is deflected to increase or decrease the volume of the variable volume chamber.

The membrane at minimal elongation corresponds to a neutral volume. A deflection into the reaction chamber reduces the volume, whereas a membrane deflection in the opposite direction increases the volume. The deflection can be altered by controlling the pressure gradient across the membrane or by controlling the volume in the chamber or the adjacent structure. By careful design of the membrane, the volume of the chamber volume is varied over a large range of volumes, ranging from substantially zero volume to the maximum volume as is determined by the mechanical properties of the membrane and the geometry of the chamber and membrane.

The different layers/membranes can be fabricated and bonded in various ways to form a microfluidic device. Three exemplary fabrication workflows are described below using silicon rubber materials or elastomers such as RTV615 (General Electric) to fabricate the desired structure. Additional protocols are provided in the Example section herein.

Workflow 1: An elastomer in its liquid state is sandwiched between a micro-machined mold and a planar substrate, with recesses being formed between the mold and the surface of the planar substrate. Surfaces are modified so that the cured PDMS can create a stronger adhesion to the planar substrate. Surface modification can involve plasma oxidation, silane treatments, or surface coatings. The stronger adhesion towards the planar surface allows the opposing mold to be lifted off, while the casted membrane remains attached to the planar surface (1). In a separate molding step, a second elastomeric structure (2) is fabricated on top of a micro-machined mold such that recesses are formed along the bottom surface. A third membrane is fabricated on top of a planar surface (3). The elastomeric structure (2) is bonded to the top of the planar membrane (3) with the recesses extending along the top surface of the planar membrane. The composite is removed from the planar surface (2) and then aligned and sealed to the remaining micro-machined membrane (1). In this arrangement, the recesses from the two micro-machined structures are facing each other and may be separated by an elastomeric membrane (see workflow shown in FIG. 8A and cross-section of final structure shown in FIG. 8C).

Workflow 2: An elastomer in its liquid state is sandwiched between two micro-machined moulds (A, B), with recesses being formed on both sides of the membrane. Interlocking geometries (alignment features) can be used to align the two molds (A, B). The molds are treated with two different surface treatments, allowing the solidified PDMS to create a stronger adhesion to one mold (A). Surface modification can involve plasma oxidation, silane treatments, surface coatings or a combination thereof. The stronger adhesion towards one mold (A) allows the opposing mold (B) to be lifted off, while the micro-machined membrane remains attached the second mold (A). In a separate molding step, a second elastomeric structure is fabricated on top of a micro-machined mold such that recesses are formed along the bottom surface. The elastomeric structure is aligned and bonded to the micro-machined membrane. The composite is removed from the mold and the recesses (from mold A) are sealed. (workflow show in FIG. 8B and cross-section of final structure shown in FIG. 8D)

Workflow 3: Two elastomeric structures are fabricated on top of a micro-machined mold such that recesses are formed along the bottom surface. The casted membranes/layers are aligned and bonded together, such that the recesses from one membrane are sealed to the top surface of the second membrane. (cross-section of final structure shown in FIG. 8E)

The use of the variable volume chambers provided herein provides a more compact process unit footprint, compared to commercial devices that use a series of chambers for multistep protocols. The variable volume chamber design allows the addition of new solutions without altering the footprint of the unit. By deflecting the membrane, the volume is adjusted as desired and is only restricted by the total volume of the adjacent chamber or the maximum elongation of the PDMS membrane. Thus, many different reactions can be assembled on a single device architecture, simply by changing the order and timing of volume addition. Furthermore, the complexity of the microfluidic device remains independent of the protocol used.

Figure 1A:
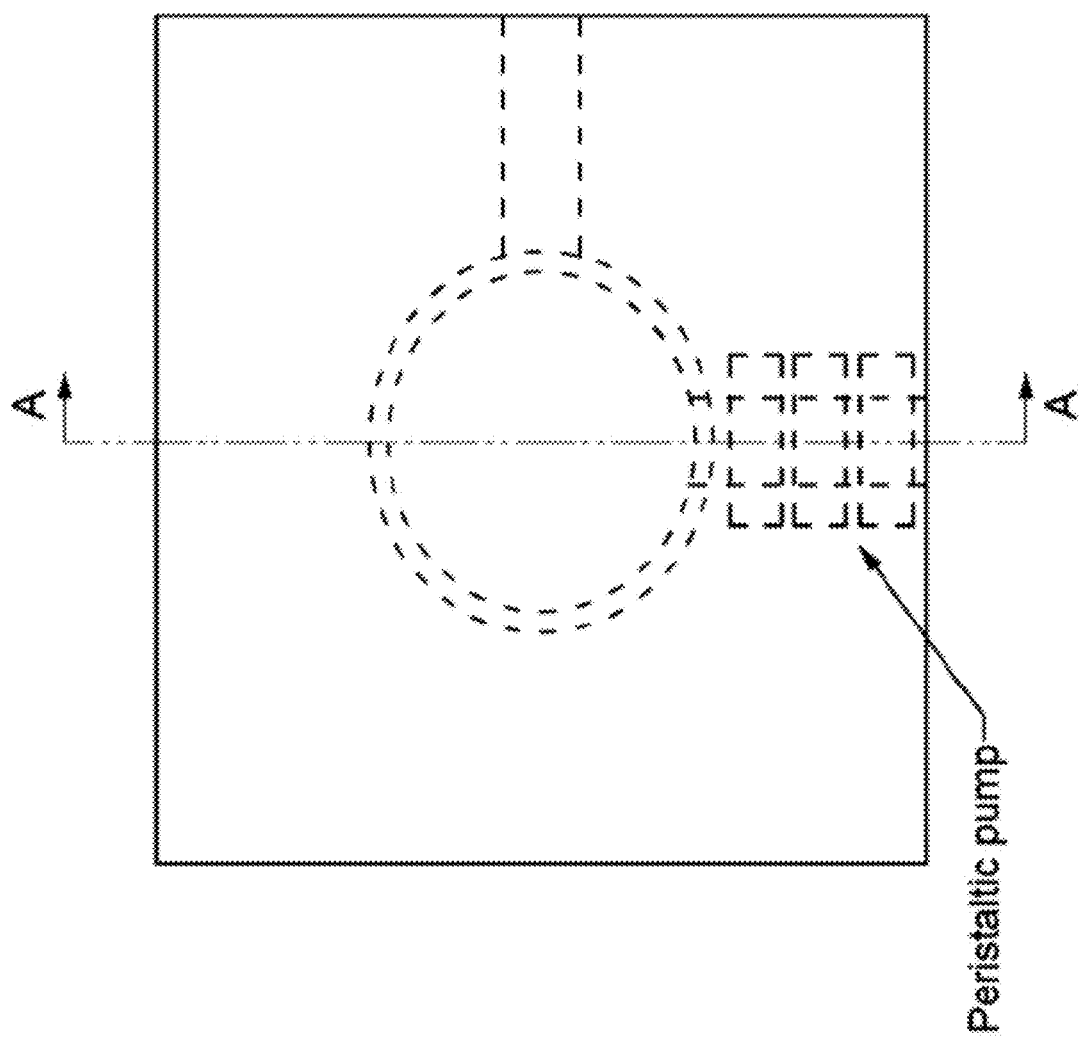
FIG. 1A shows a top schematic view of a variable volume microfluidic chamber with associated flow line and peristaltic pump.

The structures shown in FIGS. 1A-B represent one embodiment of the variable volume reaction chamber, showing a blank or seal layer, control layer, flow layer and displacement layer, such that the variable volume reaction chamber is aligned adjacent to the displacement chamber.

Figure 2B:
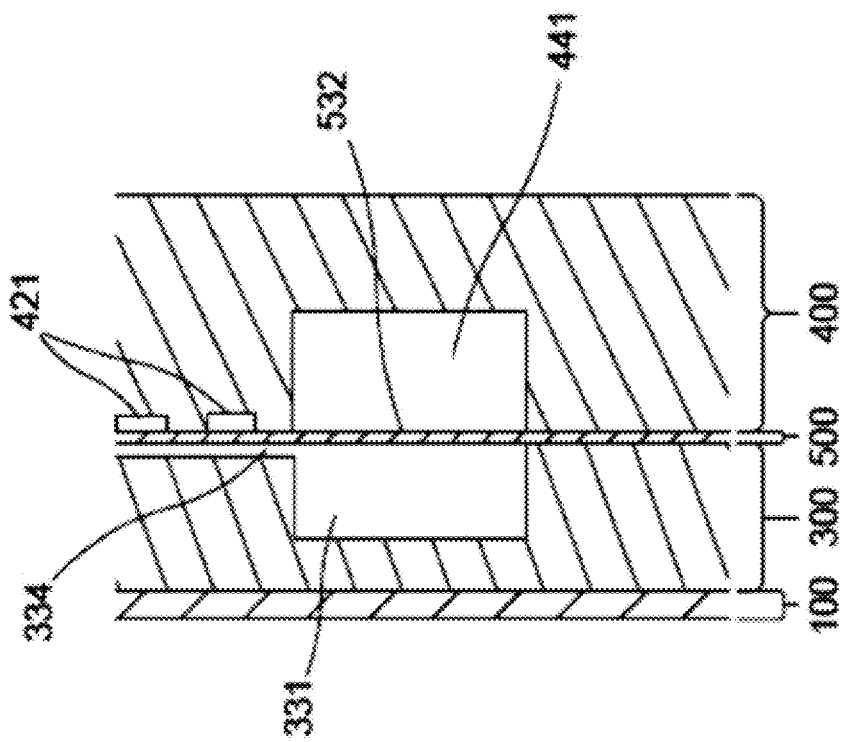
FIG. 2B shows an alternative embodiment of the variable volume microfluidic chamber with a discrete membrane layer in cross-sectional view.
Figure 2A:
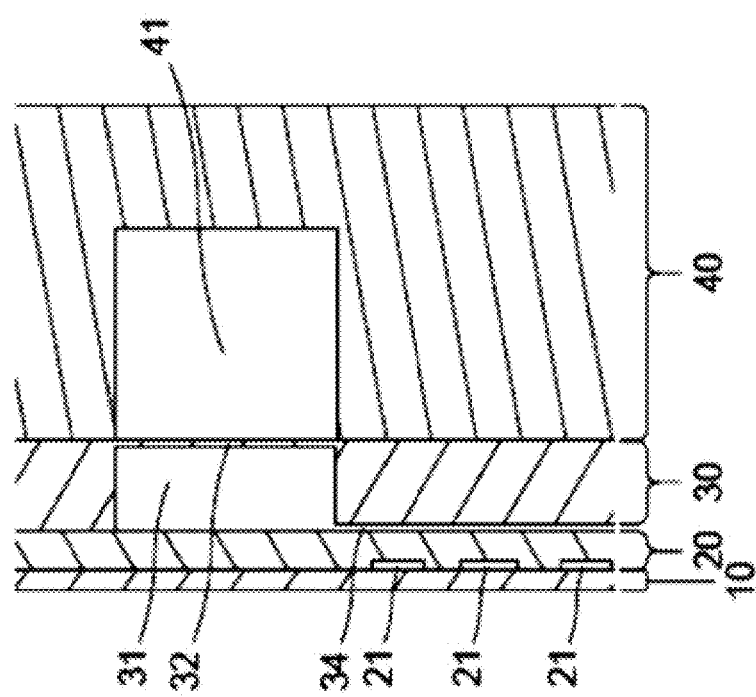
FIG. 2A shows an alternative cross-sectional view of the variable volume microfluidic chamber similar to FIG. 1B.

FIG. 2A represents a cross section of a similar embodiment to the one shown in FIG. 1B, with a seal layer (10), control layer (20), flow layer (30) and displacement layer (40), but does not show the pressure channel of FIG. 1B. FIG. 2A also shows that the variable volume reaction chamber (31) is aligned adjacent to the displacement chamber (41) and is separated by the membrane (32). Also, shown in FIG. 2A are the flow channel (34) and the control layer peristaltic pump (21).

Similarly, FIG. 2B shows a cross section of an alternative embodiment, with a seal layer (100), control/displacement layer (400), flow layer (300) and membrane layer (500). FIG. 2B also shows that the variable volume reaction chamber (331) is aligned adjacent to the displacement chamber (441) and is separated by the membrane (532). Also, shown in FIG. 2B are the flow channel (334) and the control layer peristaltic pump (421).

Figure 2C:
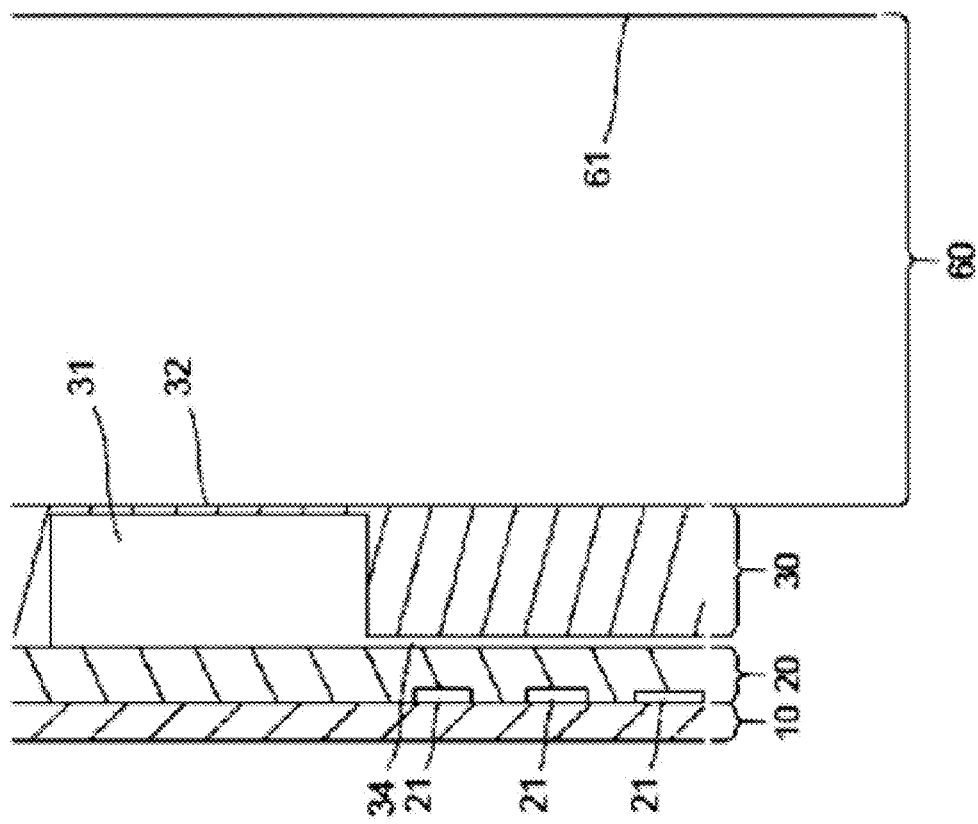
FIG. 2C shows an alternative embodiment of the variable volume microfluidic chamber without the displacement chamber but within a pressure chamber in cross-sectional view.

FIG. 2C represents a cross section of a similar embodiment to the one shown in FIGS. 1B and 2A, with a seal layer (10), control layer (20), flow layer (30) but no displacement layer. Instead, FIG. 2C shows a pressure chamber (60) and pressure chamber wall (61). FIG. 2C also shows that the variable volume reaction chamber (31) and the membrane (32). Also, shown in FIG. 2C are the flow channel (34) and the control layer peristaltic pump (21).

FIGS. 3A-3E show an embodiment of the variable volume reaction chamber in operation whereby the FIG. 3A shows a simplified cross sectional view of a reaction chamber (31) and displacement chamber (41) separated by a membrane layer in a neutral position. FIG. 3B shows a micrograph of a partially inflated reaction chamber (31) in cross section. FIG. 3C shows a simplified cross sectional view of a reaction chamber (31) and displacement chamber (41) separated by a membrane layer, wherein the reaction chamber is partially inflated in an expanded position. FIG. 3D shows a simplified cross sectional view of a reaction chamber (31) and displacement chamber (41) separated by a membrane layer, wherein the reaction chamber is partially deflated in a reduced position. FIG. 3E shows a simplified cross sectional view of a reaction chamber (31) and displacement chamber (41) separated by a membrane layer, wherein the volume of the reaction chamber is essentially zero in an essentially maximal deflated state.

FIG. 4A shows a top view of a single cell processing unit of a larger microfluidic device depicted in FIG. 5, showing flow channels (I and VII), a cell trap (II), a stacked variable volume reaction chamber and a displacement chamber (IV), and a variety of pumps and valves. Each single cell processing unit shows 2 cell inlets and has a size of 700×2920 µm, with a 20 nl reaction chamber and 35 nl displacement chamber both in the neutral position. Also the unit depicted has a 32 pl pump volume. FIG. 4B shows a 3 dimensional perspective view of the single cell processing unit of FIG. 4A. FIG. 4C shows an optical micrograph (top down) of two single cell processing units present on a microfluidic device depicted in FIG. 5.

FIG. 5 shows a plan view of a microfluidic device comprised of 48 single cell processing units as depicted in FIGS. 4A and 4B, the microfluidic device is useful for single cell library preparation.

FIG. 6A shows micrograph top view of four variable volume chambers (fully inflated) and associated flow (light lines) and control lines (dark lines), wherein the chamber and flow channels are at 15 psi and the displacement chamber is at 2 psi.

FIG. 6B shows micrograph top view of four variable volume chambers (deflated) and associated flow (light lines) and control lines (dark lines), wherein the chamber and flow channels are at 2 psi and the displacement chamber is at 15 psi.

FIG. 7 shows micrograph top view of four variable volume chambers at higher magnification than those shown in FIGS. 6A-B and without the colored dye in the control lines and flow channels, wherein the vertical speckled area on the far left is a flow channel filled with beads, running parallel to the bead filled flow channel are three control lines that act a peristaltic pump capable of moving bead filled fluid from the flow channel through the smaller flow channels running perpendicular to the bead filled flow channel into the reaction chamber.

The variable volume chambers and devices comprising the same are fully compatible with the use of particles, e.g., magnetic beads, or other micro-particles, for the purification of molecules or cells. Specifically, the chamber may be operated in a ways so as to mix beads with a solution under binding conditions, separation of the beads to the side of the chamber using a magnetic field gradient (thereby moving them substantially out of the flow), washing the beads by the addition of a wash buffer, removing the wash solution by reducing the chamber volume, optionally repeating additional wash and buffer removal steps, and then adding a subsequent reagent to the next biochemical step.

The variable volume chamber is a structure that is compatible with real-time volume control. For example, a marker fluid in the variable volume chamber or in the adjacent displacement chamber in one embodiment allows for real time monitoring of the filling, recovery or purification or other assay carried out in the chamber.

In addition, the fabrication methods provided herein facilitate the inclusion of oligonucleotides (such as primers) or other biomolecules such as an antigen or antibody into the device during the fabrication process (shown in FIG. 8A). In one embodiment, these molecules are deposited into defined chambers of the device prior to device assembly. In one embodiment, the method for depositing biomolecules (e.g., primers) into the chambers is a contactless spotting technology (FIGS. 9A and 9B). The process for depositing biomolecules such as primers may be automated using fiducial markers and image recognition software, which allow for highly accurate deposition directly into micromachined recesses even when the array is distorted or misplaced on the target holder. As such, oligonucleotides can be routinely incorporated in the chip fabrication workflow for PCR reactions, dispensed spots can be resolved reliably during an experiment, and a transfer mechanism/device (e.g., spotting robot) provides a dependable routine to dispense unique indexes with minimal cross-contamination (FIGS. 10A-F).

The ability to incorporate oligonucleotides into a variable volume chamber or a plurality thereof during fabrication provides an important advantage in many applications, including that of using microfluidic devices for single cell genomic analysis. For example, unique molecular index sequences that are associated with the primers can be used to decipher which chamber the primers were deposited, and therefore to differentiate genomic information from cell(s) in individual chambers.

In one embodiment, and described in more detail below, molecular index sequences, also referred to as barcodes, are added to each reaction product separately. This allowed for the pooling of samples for recovery while maintaining the ability to ascertain the identity of the cell from which each resulting molecule in the final pool was derived. In this way, it is possible to create devices having hundreds or even thousands of different cell processing chambers, to generate nucleic acid products from each of these chambers, and to maintain the identity of the source of each product, without having to include a large number of input ports or output ports on the device. Therefore, the inclusion of unique oligonucleotides during the assembly of the device can be used to solve the device-to-world interface problem, and to remove the need for large numbers of ports and complex channel routing.

The present in one aspect, is directed to a system for analyzing a small number of particles, such as cells. Embodiments of the systems can include one or more of the following elements: a surface in which such surface has a hydrophobicity that has been adjusted, a transfer device, a volume control device, a liquid dispenser, a humidity controller, a temperature control module, one or more reagent reservoirs, and an imaging device. This system in one embodiment, is used to deposit single/small numbers of particles into a sub 400 nL volume.

The particles in one embodiment are transferred from e.g., a microtube to a location on a surface by a transfer device. A transfer device in one embodiment is configured to transfer one or more particles to a uniquely specified location on a surface. The transfer device is configured in another embodiment to transfer one or more particles to a uniquely specified location on a surface. The transfer device, in yet another embodiment, is configured to transfer one or more particles to a uniquely specified location in a container (e.g., a microtube, a test tube, a cell culture dish, or a cell plate).

A transfer device can be made of materials to prevent adhesion of particles on a surface. For example, the transfer device can be made of glass, metal, silica, a polymer, or mixtures thereof. The transfer device comprises a component that aspires and dispenses a solution. For example, the transfer device in one embodiment, comprises a micropipette (e.g., a glass micropipette).

The system provided herein, in one embodiment, is configured to move the transfer device. In one embodiment, the system is configured to move the transfer device to one or more specified locations. In some embodiments, the system is configured to move the transfer device in 1 dimension, 2 dimensions, or 3 dimensions. Movement of the transfer device can be automated. For example, the transfer device can be controlled by an automated stage. The automated stage can be a stage of at least 1-axis, 2-axis, 3-axis, 4-axis, 5-axis, or 6-axis. For example, the transfer device can be controlled by an automated 3-axis stage.

An example of one embodiment of the transfer device is shown in FIG. 13. The transfer device can apply a dispensing pressure (e.g., of about 10 psi) using pressure source 101 and an aspiration pressure of 10 psi using pressure source 102. The pressure can initiate flow in the system. The pressure is directed through a network of channels of varying cross-section and thus varying flow resistance 103. Computer controlled valves 104 are used to direct flow through a selection of one or more of these channels in order to control the flow resistance of the network and thus the flow rate through the system. The transfer device also includes a glass micropipette 105 to transfer particles, e.g., a biological sample comprising a cell or a plurality of cells. To avoid the effect of temperature change on the flow rate in the system, a low total internal volume between the opening of the micropipette and the flow rate controller can be maintained to less 5 µL. In one embodiment disclosed herein, the system temperature is maintained at approximately 4° C. The micropipette can be moved using a 3 axis automated stage 107 that includes an XY-stage 106 and a Z-Stage 106'. The stage can move the micropipette in 3 dimensions. This configuration can be used to transfer particles to a unique specified location on the surface, as represented by 108.

Depositing the particles in certain ways can cause damage (e.g., by shear stress) to the particles. Therefore, systems provided herein are configured to deposit the particles in ways with reduced or no damage to the particles caused by dispensing. For example, in one embodiment, the system can deposit the particles in a solution by contact dispensing. When deposited by contact dispensing, a droplet of the solution can form at the exit of the transfer device. The droplet can be deposited by contacting the droplet with a target area (e.g., a surface), while the droplet is still on the transfer device. Contact dispensing can reduce the pressure required to dispense the solution by the transfer device, and thus reduce or prevent the damage caused by high pressure to the particles. For example, contact dispensing can reduce or eliminate shear stress to the particles.

When a transfer device deposits a solution less than about 400 nL by contact dispensing, capillary force (e.g., a Laplace pressure) can occur. A Laplace pressure occurs wherever there is an interface between two fluids (i.e., water-air or water-oil) and the magnitude of the pressure is dependent on the radius of curvature of the interface (i.e., smaller radius=larger pressure). In the case of contact dispensing, when the tip of the micropipette or other transfer means is submerged in an aqueous liquid and the contents of the micropipette or other transfer means is aqueous, there is no interface between the tip and the liquid. Thus, there is no dependence on the tip opening diameter. If the tip is being immersed into a small droplet (e.g., nL volume) which is exposed to air, the curvature of the air-water interface between the droplet and the air becomes the interface that determines the Laplace pressure. This will likely still be a significant pressure since such a small droplet will have a small radius of curvature.

The system, in one embodiment, includes a volume control device that can overcome the capillary force to dispense a solution of less than or equal to about 400 nL in volume (e.g., from about 1 nL to about 400 nL) by contact dispensing. A volume control device in one embodiment comprises a pressure source and a flow rate controller. A pressure source, as provided for herein, overcomes the capillary force to initiate flow in the system. A flow rate controller, as provided for herein, controls the flow rate after initiation of the flow. For example, the flow rate controller can prevent the flow rate from being too high to damage the particles. A constant flow rate, e.g., a constant volumetric flow rate can also be achieved.

A pressure source in one embodiment is in communication with one or more components in the system. In one embodiment, the pressure source is in fluid communication with one or more components in the system. In some embodiments, the pressure source can be in communication (e.g., fluid communication) with a transfer device. In another embodiment, the pressure source is in communication (e.g., fluid communication) with a valve. For example, the pressure source is in communication (e.g., fluid communication) with a computer-controlled valve. The pressure source in yet another embodiment is in communication with a transfer device and a valve.

A pressure source, as provided for herein, can be configured to apply a pressure to one or more components in the system disclosed herein. In one embodiment, a pressure source is configured to apply a pressure to the transfer device of the system. In a further embodiment, the pressure source is configured to apply a dispensing pressure to the transfer device. In some embodiments, the dispensing pressure applied by the pressure source is about 0.1 psi, 0.5 psi, 1 psi, 2 psi, 3 psi, 4 psi, 5 psi, 6 psi, 7 psi, 8 psi, 9 psi, 10 psi or greater. For example, a pressure source in one embodiment is configured to apply a dispensing pressure of about 1 psi or greater to the transfer device. In some cases, the dispensing pressure applied by the pressure source is not greater than about 1 psi, 2 psi, 3 psi, 4 psi, 5 psi, 6 psi, 7 psi, 8 psi, 9 psi, or 10 psi.

In yet another embodiment, the pressure source is configured to apply an aspirating pressure to the transfer device. In some embodiments, the aspirating pressure applied by the pressure source is about 0.1 psi, 0.5 psi, 1 psi, 2 psi, 3 psi, 4 psi, 5 psi, 6 psi, 7 psi, 8 psi, 9 psi, 10 psi or greater. In some embodiments, the aspirating pressure applied by the pressure source can be no more than about 1 psi, 2 psi, 3 psi, 4 psi, 5 psi, 6 psi, 7 psi, 8 psi, 9 psi, or 10 psi. For example, the pressure source can be configured to apply an aspirating pressure of about 1 psi or greater to the transfer device.

A pressure source, as provided for herein, can be configured to initiate flow in the system disclosed herein. For example, the pressure source can be configured to initiate flow in the transfer device of the system. A pressure source can be configured to apply a pressure greater than a threshold pressure. The threshold pressure can be a characteristic of a device, and flow can be initiated in the device if a pressure in the device is greater than the threshold pressure. In some cases, the threshold pressure is a Laplace pressure. A Laplace pressure is determined by the radius of curvature of the relevant fluid interface. For example, the Laplace pressure of the transfer device can be determined by the formula $\Delta p = 2\gamma/R$, wherein $\Delta p$ is the Laplace pressure, R is the radius of curvature of the interface, and $\gamma$ is the surface tension.

A pressure source in one embodiment is used with a flow rate controller to obtain a constant or substantially constant flow rate. A flow rate controller in one embodiment controls a flow rate in one or more components of the system. For example, the flow rate controller can control a flow rate in the transfer device. A flow rate in a device can be controlled by controlling the flow resistance or pressure in the device. In some embodiments, the flow rate controller is configured to control pressure within the transfer device thereby controlling the flow rate in the transfer device. In some embodiments, the flow rate controller can be configured to control flow resistance in the transfer device thereby controlling a flow rate in the transfer device. The flow rate controlled by the flow rate controller can be a volumetric flow rate. The volumetric flow rate controlled by the flow rate controller can be a constant or variable volumetric flow rate.

Temperature changes can alter the internal volume in the system, and thus affect the flow rate in the system. Keeping a small internal volume in the system can reduce the effect of temperature on the flow rate in the system. In some cases, the total internal volume between the opening of the transfer device and the flow rate controller is ≤100 µL, ≤99 µL, ≤98 µL, ≤97 µL, ≤96 µL, ≤95 µL, ≤94 µL, ≤93 µL, ≤92 µL, ≤91 µL, ≤90 µL, ≤89 µL, ≤88 µL, ≤87 µL, ≤86 µL, ≤85 µL, ≤84 µL, ≤83 µL, ≤82 µL, ≤81 µL, ≤80 µL, ≤79 µL, ≤78 µL, ≤77 µL, ≤76 µL, ≤75 µL, ≤74 µL, ≤73 µL, ≤72 µL, ≤71 µL, ≤70 µL, ≤69 µL, ≤68 µL, ≤67 µL, ≤66 µL, ≤65 µL, ≤64 µL, ≤63 µL, ≤62 µL, ≤61 µL, ≤60 µL, ≤59 µL, ≤58 µL, ≤57 µL, ≤56 µL, ≤55 µL, ≤54 µL, ≤53 µL, ≤52 µL, ≤51 µL, ≤50 µL, ≤49 µL, ≤48 µL, ≤47 µL, ≤46 µL, ≤45 µL, ≤44 µL, ≤43 µL, ≤42 µL, ≤41 µL, ≤40 µL, ≤39 µL, ≤38 µL, ≤37 µL, ≤36 µL, ≤35 µL, ≤34 µL, ≤33 µL, ≤32 µL, ≤31 µL, ≤30 µL, ≤29 µL, ≤28 µL, ≤27 µL, ≤26 µL, ≤25 µL, ≤24 µL, ≤23 µL, ≤22 µL, ≤21 µL, ≤20 µL, ≤19 µL, ≤18 µL, ≤17 µL, ≤16 µL, ≤15 µL, ≤14 µL, ≤13 µL, ≤12 µL, ≤11 µL, ≤10 µL, ≤9 µL, ≤8 µL, ≤7 µL, 6 µL, ≤5 µL, ≤4 µL, ≤3 µL, ≤2 µL, or ≤1 µL. In some embodiments, the total internal volume between the opening of the transfer device and the flow rate controller is ≤100 µL. In some embodiments, the total internal volume between the opening of the transfer device and the flow rate controller is ≤5 µL.

A volume displacement control device in one embodiment is used to overcome the capillary force to dispense a solution less than 400 nL by contact dispensing. In one embodiment, a volume displacement control device is used to dispense a solution by displacing the volume of the dispensed solution in the device by an object. Any object can be used to displace the volume of a dispensed solution. In some embodiments, a volume displacement control device comprises a membrane. In some embodiments, a volume displacement control device comprises a piston. For example, the piston can be part of a syringe pump. In one embodiment, a volume displacement control device is configured to control volume displacement in one or more components in the system. For example, the volume displacement control device is configured to control volume displacement in the transfer device. FIG. 14 shows an example of a membrane volume displacement control device (201). 201 can be connected to a micropipette 203. Movement of the membrane towards inside or outside of the chamber 202 can control the volume dispensed or aspirated from the micropipette 203. FIG. 14 also shows an example of a piston volume displacement control device (204). 204 can be connected to a micropipette 203. Movement of the piston can control the volume 205 dispensed or aspirated from the micropipette 203.

A device that can regulate liquid expansion in the transfer device can also be used to overcome the capillary force to dispense a solution less than 400 nL by contact dispensing. In one embodiment, the transfer device comprises a capillary filled with liquid and a temperature control. The capillary can be in communication (e.g., fluid communication) with other components in the system. A device can dispense a solution less than 400 nL from the capillary by controlling liquid expansion in the capillary. Liquid expansion in the capillary can occur in response to a change in temperature. In one embodiment, liquid expansion in the capillary is controlled by a temperature control apparatus. Therefore, in one embodiment, the system comprises a temperature control apparatus.

A temperature control apparatus can be configured to control a temperature of the capillary. In some cases, the temperature of capillary can affect the temperature of the liquid in the capillary. Thus, the temperature control apparatus can control the temperature of the liquid in the capillary. Liquid expansion in the capillary can occur when the temperature control apparatus changes the temperature of the capillary tube. The temperature of the capillary can be controlled by any temperature control apparatus disclosed herein or known in the art. In some embodiments, a temperature control apparatus comprises a heater element. A heater element in one embodiment, is a metal heating element, a ceramic heating element, a composite heating element, or a combination thereof.

In some embodiments, a heater element comprises a nichrome element (e.g., a nichrome wire, a nichrome ribbon or a nichrome strip), a resistance wire element, an etched foil element, radiative heating element (e.g., a heating lamp), a molybdenum disilicide element, a positive temperature coefficient (PTC) ceramic element, a tubular heating element, a screen-printed metal-ceramic element, or combinations thereof. In some cases, a temperature control apparatus comprises a laser. The laser can be gas laser, chemical laser, dye laser, metal-vapor laser, solid-state laser, semiconductor laser, free electron laser, gas dynamic laser, Raman laser, nickel-like Samarium laser, or any type of laser known in the art.

In one embodiment, the volume control device comprises a pressure source, a flow rate controller, a volume displacement device, a capillary filled with liquid, a liquid expansion regulator (e.g., a temperature controller) or any combinations thereof. The volume control device can also be used in combination with one or more components in the system (e.g., the transfer device). For example, the volume control device in one embodiment comprises a micropipette and a flow rate controller. The micropipette in one embodiment is connected to the flow rate controller setting flow rates and is positioned to uniquely specified locations while aspirating and dispensing solutions.

In one embodiment, dispensing a solution less than 400 nL is achieved without a volume control device. In one example, particle(s) (e.g., cell(s)) are deposited in a chamber or vessel (e.g., an open microwell) at the uniquely specified location on the surface. In the case of a microfluidic chamber, depositing can occur during assembly of the device or after assembly (e.g., through flow channels). In one embodiment, the chamber or vessel is one of the inflatable microfluidic chambers described herein. As used herein, an "inflatable microfluidic chamber" is interchangeable with "variable volume microfluidic chamber".

In some embodiments, a vessel comprises a microwell in a microwell array, as shown in FIG. 15. The microwell array in one embodiment is covered by liquid. In some embodiments, the microwell is covered by liquid before a particle is transferred to the microwell or microfluidic chamber. The system disclosed herein, in one embodiment, is configured to deposit one or more particles in the microwell or microfluidic chamber covered by liquid. When the liquid covering the microwell or microfluidic chamber is removed (e.g., by aspiration), the particle(s) in the microwell or microfluidic chamber can be in a solution of a volume equal to or less than the volume of the microwell or microfluidic chamber. The volume of the vessel (e.g., microfluidic chamber or microwell), in one embodiment, is less than 1 µL. For example, the volume in the vessel is less than about 500 nL, less than about 200 nL, less than about 100 nL, less than about 50 nL, less than about 20 nL, or less than about 10 nL. Thus, in one embodiment, particles are deposited into nanoliter-volume without the need of dispensing a nanoliter-volume solution. In some embodiments, the system is configured to remove the liquid that covers the vessel (container) after the one or more particles are transferred to the microwell, thereby rendering the vessel isolated from other vessels in the vessel array.

In some embodiments, the vessel is a microwell. In a further embodiment, the microwell has a minimum dimension of from about 1 µm to about 200 µm. For example, the microwell in one embodiment, has a minimum dimension of about 50 µm, about 51 µm, about 52 µm, about 53 µm, about 54 µm, about 55 µm, about 56 µm, about 57 µm, about 58 µm, about 59 µm, about 60 µm, about 61 µm, about 62 µm, about 63 µm, about 64 µm, about 65 µm, about 66 µm, about 67 µm, about 68 µm, about 69 µm, about 70 µm, about 71 µm, about 72 µm, about 73 µm, about 74 µm, about 75 µm, about 76 µm, about 77 µm, about 78 µm, about 79 µm, about 80 µm, about 81 µm, about 82 µm, about 83 µm, about 84 µm, about 85 µm, about 86 µm, about 87 µm, about 88 µm, about 89 µm, about 90 µm, about 91 µm, about 92 µm, about 93 µm, about 94 µm, about 95 µm, about 96 µm, about 97 µm, about 98 µm, about 99 µm, about 100 µm, about 101 µm, about 102 µm, about 103 µm, about 104 µm, about 105 µm, about 106 µm, about 107 µm, about 108 µm, about 109 µm, about 110 µm, about 111 µm, about 112 µm, about 113 µm, about 114 µm, about 115 µm, about 116 µm, about 117 µm, about 118 µm, about 119 µm, about 120 µm, about 121 µm, about 122 µm, about 123 µm, about 124 µm, about 125 µm, about 126 µm, about 127 µm, about 128 µm, about 129 µm, about 130 µm, about 131 µm, about 132 µm, about 133 µm, about 134 µm, about 135 µm, about 136 µm, about 137 µm, about 138 µm, 139 µm, about 140 µm, about 141 µm, about 142 µm, about 143 µm, about 144 µm, about 145 µm, about 146 µm, about 147 µm, about 148 µm, about 149 µm, or about 150 µm.

In some embodiments a microwell has an aspect ratio of from about 10:1 to about 1:10. For example, in one embodiment, the microwell has an aspect ratio of about 1:1, about 1:2, about 1:3, about 1:4, about 1:5, about 2:1, about 3:1, about 4:1, or about 5:1. In one embodiment, the microwell has an aspect ratio of about 1:1.

It is noted that a solution of less than 400 nL in volume can evaporate faster on a surface than a larger volume solution. Analyzing of one or more particles in a solution of less than 400 nL can include in one embodiment, heating the solution on a surface of the vessel. The heating can further facilitate evaporation of the solution.

The system disclosed herein can be configured to reduce or prevent evaporation of the solution. As such, the solution of less than 400 nL can include one or more substances that reduce or prevent evaporation of the solution. For example, the solution can include glycerol. In some cases, the solution is an aqueous solution or suspension. Covering the aqueous solution with a water-immiscible substance can reduce or prevent evaporation of the solution. The system can be configured to cover a solution at the uniquely specified location with a water-immiscible substance. A water-immiscible substance can be castor oil, corn oil, mineral oil, miglyol, benzyl benzoate, polycaprolactone, poly(caprolactone) triol, ethyl oleate, derivatives thereof, or combinations thereof. In one embodiment, the system is configured to cover a solution with mineral oil. The water-immiscible substance in one embodiment is removed during or after analysis of the particles in the solution or suspension. Moreover, the system can be configured to remove the water-immiscible substance. In some cases, the water-immiscible substance can be removed in a way that does not disturb the covered solution. The water-immiscible substance can be removed by any transfer device described herein or known in the art.

The surface of the vessel can be configured to allow the solution to remain immobilized on the surface when covered by a water-immiscible substance and when the water-immiscible substance is removed. A high degree of hydrophobicity of a surface can cause an aqueous solution to lift off the surface when the water-immiscible substance is applied. The hydrophobicity of the surface in one embodiment, is adjusted to allow the solution to stay immobilized. In one embodiment, the hydrophobicity of the vessel surface is adjusted such that droplets on such surface are immobilized when oil is added or removed.

Hydrophobicity of a surface can be adjusted by coating the surface with a substance. The surface can be coated by other materials, including polydimethylsiloxane (PDMS), perfluorodecylcarboxylic acid, perfluorooctylamine, perfluorooctylcarboxylic acid, perfluorinated polyethylenoxide, polyhydridomethylsilane (PHMS), perfluorinated alkyl silanes, siloxanes, or any derivatives thereof. Hydrophobicity of the coated materials can be adjusted by treatments such as baking, plasma bonding, or combinations thereof. In one example, the surface can be coated with polydimethylsiloxane (PDMS). Hydrophobicity of the PDMS coating can be adjusted by baking and plasma bonding of the PDMS. Such a surface can be made of any material known in the art. In some cases, the surface can be made of glass, plastic, fused silica, silicon, ceramic, metal, or a combination thereof. For example, the surface can comprise a PDMS-coated glass slide.

In one embodiment, analysis of particles in a solution or suspension comprises regulating the temperature of the solution or suspension. Temperature of solutions or suspensions on a surface can be controlled by adjusting the temperature of the surface. As such, the system described herein, in one embodiment, comprises a temperature modulation device configured to alter the temperature of the surface. The temperature modulation device can comprise any temperature control apparatus disclosed herein or known in the art. In some cases, the temperature modulation device can comprise a thermocycler, e.g., a flatbed thermocycler.

A humidity control device, as provided for herein, is used in some embodiments to reduce or prevent evaporation of a solution. Therefore, the system disclosed herein in one embodiment, comprises a humidity control device. The humidity control device is used to reduce or prevent evaporation of solution in the system. A humidity control device, in one embodiment, is a humidifier, such as an evaporative humidifier, a natural humidifier, a vaporizer, an impeller humidifier, a ultrasonic humidifier, a forced-air humidifier, or combinations thereof. In one example, the system can be configured to analyze the particles in the solution in a chamber with a humidity control device.

Individual particles or a small group of particles can be transferred to a uniquely specified location on a surface of the system for analysis. When transferring particles, the system can be configured to deposit the particles in a solution of less than about 400 nL. Analysis performed in such a small volume solution can have enhanced accuracy and sensitivity compared to that performed in a solution of greater volume. The system can be configured to deposit a single particle or small group of particles in a volume of ≤400 nL, ≤350 nL, ≤300 nL, ≤250 nL, ≤200 nL, ≤250 nL, ≤100 nL, ≤90 nL, ≤100 nL, ≤99 nL, ≤98 nL, ≤97 nL, ≤96 nL, ≤95 nL, ≤94 nL, ≤93 nL, ≤92 nL, ≤91 nL, ≤90 nL, ≤89 nL, ≤88 nL, ≤87 nL, ≤86 nL, ≤85 nL, ≤84 nL, ≤83 nL, ≤82 nL, ≤81 nL, ≤80 nL, ≤79 nL, ≤78 nL, ≤77 nL, ≤76 nL, ≤75 nL, ≤74 nL, ≤73 nL, ≤72 nL, ≤71 nL, ≤70 nL, ≤69 nL, ≤68 nL, ≤67 nL, ≤66 nL, ≤65 nL, ≤64 nL, ≤63 nL, ≤62 nL, ≤61 nL, ≤60 nL, ≤59 nL, ≤58 nL, ≤57 nL, ≤56 nL, ≤55 nL, ≤54 nL, ≤53 nL, ≤52 nL, ≤51 nL, ≤50 nL, ≤49 nL, ≤48 nL, ≤47 nL, ≤46 nL, ≤45 nL, ≤44 nL, ≤43 nL, ≤42 nL, ≤41 nL, ≤40 nL, ≤39 nL, ≤38 nL, ≤37 nL, ≤36 nL, ≤35 nL, ≤34 nL, ≤33 nL, ≤32 nL, ≤31 nL, ≤30 nL, ≤29 nL, ≤28 nL, ≤27 nL, ≤26 nL, ≤25 nL, ≤24 nL, ≤23 nL, ≤22 nL, ≤21 nL, ≤20 nL, ≤19 nL, ≤18 nL, ≤17 nL, ≤16 nL, ≤15 nL, ≤14 nL, ≤13 nL, ≤12 nL, ≤11 nL, ≤10 nL, ≤9 nL, ≤8 nL, ≤7 nL, ≤6 nL, ≤5 nL, ≤4 nL, ≤3 nL, ≤2 nL, ≤1 nL, ≤0.9 nL, ≤0.8 nL, 0.7 nL, 0.6 nL, 0.5 nL, 0.4 nL, 0.3 nL, 0.2 nL, or 0.1 nL.

In one embodiment, the system is configured to deposit the particles in a volume of less than about 100 nL. A small number of particles can be analyzed by the system in a small volume. For example, the system can be used to analyze no more than 10, 20, 30, 40, 50, 60, 70, 80, 90, or 100 particles. In one example, the system can be used to analyze 1, 2, 3, 4, 5, 6, 7, 8, 9, or 10 particles (e.g., cells).

The systems herein can be used to analyze any type of particle. For example, the particle can be a cell, virus, or a prion. In one embodiment the particle is a cell. In a further embodiment, the particle comprises a prokaryotic cell (e.g. a bacterial cell), or a eukaryotic cell (e.g., animal cell, fungi cell, or plant cell). The particle in one embodiment is a plurality of particles, e.g., a plurality of cells. The plurality of cells, in one embodiment, comprises one or more of the following cell types: trichocytes, keratinocytes, gonadotropes, corticotropes, thyrotropes, somatotropes, lactotrophs, chromaffin cells, parafollicular cells, *glomus* cells melanocytes, nevus cells, merkel cells, odontoblasts, cementoblasts corneal keratocytes, retina muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic ε cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, or pericyte mural cells.

The cells can be from any source. In one embodiment, the cells are from blood, saliva, urine, stool, amniotic fluid, a tumor, or a biopsy. In one case, the one or more cells comprises one or more circulating cells.

In one embodiment, the particle comprises a plurality of particles and the plurality of particles comprises one or more cells. In a further embodiment, the one or more cells are circulating cells from a pregnant subject (e.g., a pregnant woman). In one embodiment, the one or more cells are from an embryo, i.e., one or more embryonic cells. In another embodiment, the one or more cells can be from a blastocyte. The one or more cells, in one embodiment, are from a blastocyte, including, but not limited to, embryoblast or trophoblast (e.g., cytotrophoblast, or syncytiotrophoblast). In some embodiments, the one or more cells are one or more human cells. In some embodiments, the one or more particles disclosed herein comprises one or more organelles of a cell, including, but not limited to, mitochondria, chloroplasts, endoplasmic reticulum, flagella, Golgi apparatuses, vacuoles nuclei, lysosomes, proteasomes, ribosomes, cell membrane, or a combination thereof.

In one embodiment, the system disclosed herein comprises a dispenser. The dispenser can be used to add one or more reagents into the solution during the analysis. A dispenser in one embodiment is a piezoelectric dispenser, a solenoid dispenser, an acoustic dispenser, an ink-jet dispenser, a pump-action dispenser, a pin dispenser, or combinations thereof. In one example, the system comprises a S3 piezoelectric spotter made by Scienion (FIG. 16).

The dispenser dispenses a reagent in discrete increments. A dispenser in one embodiment is configured to dispense a reagent in a discrete increment of a volume between from about 1 pL to about 500 nL. For example, a dispenser in one embodiment is configured to dispense a reagent in a discrete increment of about 1 pL, about 10 pL, about 50 pL, about 100 pL, about 200 pL, about 300 pL, about 400 pL, about 500 pL, about 600 pL, about 700 pL, about 800 pL, about 900 pL, about 1 nL, about 50 nL, about 100 nL, about 200 nL, about 300 nL, about 400 nL, or about 500 nL.

The volume of liquid deposited by the dispenser in one embodiment comprises a reagent. In some embodiment, a reagent can be used in an amplification reaction, a sequencing reaction, a polynucleotide fragmentation reaction, a polynucleotide tagmentation reaction, a polynucleotide ligation reaction, a polynucleotide digestion reaction, or a combination thereof.

The dispenser in one embodiment deposits the volume of liquid to any location, e.g., on a surface or in a container (e.g., a vessel such as a microtube, a test tube, microwell, microfluidic chamber, or a cell culture dish or plate). In some cases, the system disclosed herein can be configured to move the dispenser to one or more specified locations. For example, the system can comprise a dispenser configured to deposit a volume of liquid comprising a reagent at the uniquely specified location on the surface. In some cases, the system can be configured to move the dispenser in 1 dimension, 2 dimensions, or 3 dimensions. The dispenser can be automated. In some cases, the dispenser can be controlled by an automated stage. The automated stage can be a stage of at least 1-axis, 2-axis, 3-axis, 4-axis, 5-axis, or 6-axis.

The system disclosed herein can be capable of depositing particles to a plurality of uniquely specified locations on a surface. The system can be capable of depositing particles to a plurality of uniquely specified locations on a surface with a success rate of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

After analysis, the solution comprising the particles can be extracted from the system. Extraction can be performed using the transfer device disclosed herein or any device known in the art, e.g., a pipette. Reagents (e.g., water or buffer solution) can be added to the solution to make extraction easier. Reagents of any volume can be added to the solution to make extraction easier. In one example, reagents can be added to bring the volume of solution up to 300 nL to make extraction easier.

The systems disclosed herein in one embodiment comprises an imaging device to monitor the particles during the analysis. In some cases, the system disclosed herein can comprise an imaging device configured to image a uniquely specified location. In some cases, the system can be configured to deposit a solution comprising particles to a location (e.g., a surface) as one or more droplets. An imaging device can be used to detect the presence of particles in an individual droplet. An imaging device can also be used to detect the number of particles in an individual droplet. An imaging device in one embodiment comprises a microscope. The microscope can be a fluorescence microscope, a phase contrast microscope, a digital microscope, a bright field microscope, a confocal microscope, an epifluorescence microscope, a multifocal plane microscope, a dark field microscope, a fluorescence interference contrast microscope, an X-ray microscope, a microspectrosope, an ultraviolet microscope, a near-infrared microscope, a multiple transmission microscope, an electron microscope, a scanning probe microscope, or a combination thereof.

In yet another aspect of the invention, methods for analyzing a small number of particles, e.g., cells are provided. The methods and devices can place a specific group of cells (e.g., 1-10 cells) into a small volume solution (e.g., less than 100 nL). In one embodiment, the small volume solution is in one of the variable diameter microfluidic chamber apparatuses described herein. However, the methods described herein are not limited to such devices. For example, open well devices and microcentrifuge tubes can be used in the methods described herein. The methods finds utility in the analysis of single cells that are present in a heterogeneous population of cells, e.g., a single cell in a tumor or a stem cell. In another embodiment, the sample is an embryo biopsy and is used in a preimplantation genetic analysis.

Thus, the methods and devices, including the microfluidic devices described herein, in one embodiment, are used to analyze a sample comprising a small number of cells, e.g., a biopsy from an embryo, circulating fetal cells isolated from maternal blood, circulating tumor cells in a blood sample, or cells harvested from a particular tissue or organ.

In one embodiment, the method comprises depositing an individual cell or a small number of cells (e.g., that are specifically chosen by the user of the method) in a small volume solution by contact dispensing. The device therefore in one embodiment, comprises means for the depositing of a single cell or the small number of cells. Without wishing to be bound by theory, it is thought that contact dispensing reduces or prevents damage (e.g., shear stress) to the cell(s) compared to non-contact dispensing methods. In a further embodiment, the single cell or small number of cells are deposited to a uniquely specified location on a surface by an automated transfer device, e.g., a surface of an open microwell or a surface of a microfluidic chamber (e.g., one of the microfluidic chambers described herein).

In one embodiment, the methods and devices are used to generate a sequencing library in a small volume solution (e.g., a nanoliter-volume solution), e.g., from a single cell or a small number of cells (e.g., from about 1 to about 10 cells). For example, the sequencing library can be a genomic DNA library or an RNA-seq library. When generated in such a small volume solution, in one embodiment, the sequencing library yields greater coverage breadth for a given sequencing depth compared to that generated in a larger volume solution (e.g., a microliter-volume solution).

In another embodiment, the methods and devices are used to amplify polynucleotides in a small volume solution (e.g., a nanoliter-volume solution). Such amplification can have higher fidelity as described herein as compared to that performed in a larger volume solution (e.g., a microliter volume solution). By enhancing the accuracy and sensitivity of analyses, methods and devices provided herein allow a small amount of polynucleotides, e.g., genomic DNA from a single cell, to be analyzed.

With the capacity of performing amplification and generating sequencing libraries with high fidelity, the methods and devices are used to perform molecular biology analysis on a small number of cells.

For example, in one embodiment, the methods and devices provided herein are used to determine the haplotype of the DNA, detect a genetic variation, evaluate epigenetic modification of the genome, or examine gene expression profiles in a single cell or a small group of cells (e.g., from about 1 cell to about 10 cells).

Such capacity can allow the methods and devices be used to perform diagnosis on a sample containing a small number of cells, e.g., an embryo biopsy, or a blood sample containing rare circulating tumor cells.

In one aspect, methods are provided herein for analyzing a small number of cells (which can be a single cell). The method in one embodiment comprises analyzing one or more molecules (e.g., polynucleotides, proteins, carbohydrates, lipids, subunits thereof, or combinations thereof) from one or more cells. A small number of cells (e.g., less than 10 cells) can have a limited amount of molecules, which may require amplification to be analyzed. This amplification is typically prone to bias which can reduce fidelity and limit the accuracy of downstream analysis. The fidelity of amplification can be improved by performing the amplification and analysis in a small volume solution (e.g., less than 400 nL), e.g., in one of the microwells and/or microfluidic chambers described herein. Moreover, the present methods allow for sequencing libraries to be generated without pre-amplification, which greatly reduces such amplification bias.

Methods disclosed herein include in one embodiment, transferring a specific group of a small number of cells or a single cell to a solution having a volume less than 400 nL. The solution can be deposited to a uniquely specified location. The uniquely specified location can be in a container (also referred to as a "vessel" herein) (e.g., a microtube, microwell, microfluidic chamber (e.g., one of the variable volume chambers described herein), test tube, a cell culture dish or plate or a combination thereof). The uniquely specified location can also be on a surface. The solution of less than 400 nL in one embodiment is deposited on a surface by contact dispensing.

Analysis performed in such a solution of less than 400 nL in one embodiment, has an enhanced accuracy compared to that performed in a solution of greater volume. The methods provided herein in one embodiment are carried out in a volume of ≤400 nL, e.g., from about 400 nL to about 0.1 nL, or from about 400 nL to about 0.5 nL, or about 350 nL, about 300 nL, about 250 nL, about 200 nL, about 250 nL, about 100 nL, about 90 nL, about 100 nL, about 99 nL, about 98 nL, about 97 nL, about 96 nL, about 95 nL, about 94 nL, about 93 nL, about 92 nL, about 91 nL, about 90 nL, about 89 nL, about 88 nL, about 87 nL, about 86 nL, about 85 nL, about 84 nL, about 83 nL, about 82 nL, about 81 nL, about 80 nL, about 79 nL, about 78 nL, about 77 nL, about 76 nL, about 75 nL, about 74 nL, about 73 nL, about 72 nL, about 71 nL, about 70 nL, about 69 nL, about 68 nL, about 67 nL, about 66 nL, about 65 nL, about 64 nL, about 63 nL, about 62 nL, about 61 nL, about 60 nL, about 59 nL, about 58 nL, about 57 nL, about 56 nL, about 55 nL, about 54 nL, about 53 nL, about 52 nL, about 51 nL, about 50 nL, about 49 nL, about 48 nL, about 47 nL, about 46 nL, about 45 nL, about 44 nL, about 43 nL, about 42 nL, 41 nL, 40 nL, 39 nL, 38 nL, 37 nL, 36 nL, about 35 nL, about 34 nL, about 33 nL, about 32 nL, about 31 nL, about 30 nL, about 29 nL, about 28 nL, about 27 nL, about 26 nL, about 25 nL, about 24 nL, about 23 nL, about 22 nL, 2 about 1 nL, about 20 nL, about 19 nL, about 18 nL, about 17 nL, about 16 nL, about 15 nL, about 14 nL, about 13 nL, about 12 nL, about 11 nL, about 10 nL, about 9 nL, about 8 nL, about 7 nL, about 6 nL, about 5 nL, about 4 nL, about 3 nL, about 2 nL, about 1 nL, about 0.9 nL, about 0.8 nL, about 0.7 nL, about 0.6 nL, about 0.5 nL, about 0.4 nL, about 0.3 nL, about 0.2 nL, or about 0.1 nL. In one example, the method can be used to analyze a small number of cells in a volume of less than 100 nL.

By providing the benefits of analyzing the particle(s) in a small volume solution, the methods disclosed herein can be used to analyze a small number of cells. Analysis in a small volume solution disclosed herein can have the accuracy required for analyzing a small number of cells. In one embodiment, the methods provided herein are employed on a cell sample comprising no more than 10, 20, 30, 40, or 50 cells. In one example, the methods can be used to analyze no more than 1, 2, 3, 4, 5, 6, 7, 8, 9, or 10 cells, e.g., from about 1 to about 10 cells in a single container or vessel. It should be noted that the methods described herein can be carried out in a parallel fashion, for example, in a plurality of wells of an open well array, or a plurality of chambers of a microfluidic device.

In one embodiment, the methods provided herein are used to analyze polynucleotides from the cells. A small number of cells (e.g., less than 10 cells) can have a limited amount of polynucleotides. Methods provided herein can enhance the accuracy and sensitivity of the analysis of such a limited amount of polynucleotides. The method can enhance the analysis accuracy by performing the analysis in a small volume solution (e.g., less than 400 nL). For example, a sequencing library constructed in a solution of less than 400 nL can yield a greater coverage breadth for a given sequencing depth than that constructed in a solution of larger volume.

Exemplary applications of the methods provided are described below. In one embodiment, the method is used to amplify a polynucleotide, wherein the fidelity of the amplification for a normal diploid human cell yields sequencing data wherein for at least about 3.3 Gbp of aligned sequence data, the breadth of coverage is greater than about 35%.

In another embodiment, the method described herein is used to generate a sequencing library with polynucleotides from one or more cells. The method comprises, in one embodiment, fragmenting the polynucleotides to generate a plurality of polynucleotide fragments; attaching a first adaptor to one end and a second adaptor to the other end of each of the polynucleotide fragments, thereby generating polynucleotide fragments with the first adaptor on one end and the second adaptor on the other end; and amplifying the polynucleotide fragments with the first and second adaptors using a primer set, wherein the primer set introduces a third adaptor on one end and a fourth adaptor on the other end of each of the amplified polynucleotide fragments. In one embodiment, amplification of the polynucleotides or polynucleotide fragments from the first step is carried out, prior to the second step of attaching a first adaptor.

In another embodiment, the method comprises determining the haplotype of a polynucleotide, for example, the haplotype of the genomic DNA of a single cell or a small number of cells (e.g., from about 1 to about 10 cells). In a further embodiment, the method comprises depositing one or more cells in a solution having a volume less than 400 nL to a uniquely specified location on a surface by contact dispensing, wherein the one or more cells comprise a polynucleotide. The surface can be one of the vessels described herein, for example one of the microwells or variable volume (inflatable) microfluidic chambers described herein.

In one embodiment, the method of determining the haplotype of the polynucleotide comprises generating a sequencing library comprising fragments of the polynucleotide; sequencing the fragments of the polynucleotide, thereby obtaining a plurality of sequence reads; and assembling the sequence reads; and comparing the assembled sequence to a reference sequence, thereby determining whether the assembled sequence is inherited from the reference sequence.

The sequence reads can be assembled into a contiguous aligned fragment of an approximate pre-determined number of nucleotides in length. Without wishing to be bound by theory, the haplotyping methods described herein allow for long range haplotyping due to the uniqueness of the fragmentation sites inherent to each homologous chromosome.

In another embodiment, the method comprises amplifying the polynucleotides in a solution having a volume less than 400 nL, wherein the amplification is multiple displacement amplification (MDA).

In another embodiment, the method comprises fragmenting the polynucleotide, thereby generating a plurality of polynucleotide fragments; and amplifying the plurality of polynucleotide fragments, wherein the fragmenting and amplifying are performed in a single solution. In yet another embodiment, the method is used to detect an epigenetic modification of the polynucleotide by amplifying the polynucleotide in the solution; and detecting an epigenetic modification on the polynucleotide.

In even another embodiment, the method is used to detect expression of a gene, or to detect a genetic variant in a sample (e.g., a copy number variant or a single nucleotide polymorphism) in one or more cells by depositing one or more cells in a solution having a volume less than 400 nL to a uniquely specified location on a surface by contact dispensing, wherein the one or more cells comprise a gene; and amplifying the gene in the solution; and detecting expression of the gene, for example, via a PCR or sequencing based approach.

In another embodiment, the method is used to analyze a polynucleotide from one or more cells that are transferred to a uniquely specified location on a surface by contact dispensing, in a solution having a volume less than 400 nL, wherein the one or more cells comprise a polynucleotide; optionally pre-amplifying the polynucleotide; fragmenting the amplified polynucleotide, thereby generating a plurality of polynucleotide fragments; dividing the plurality of polynucleotide fragments into multiple reaction solutions, wherein the multiple reaction solutions are deposited on the surface; amplifying polynucleotide fragments in each reaction solution; and pooling the amplified polynucleotide fragments for further analysis. The multiple reaction solutions can also be deposited into an emulsion or a series of microchambers or any other suitable implementation which keeps the multiple reaction solutions separated from each other. In some embodiments, the pooled polynucleotides are used for determining haplotype of the polynucleotide.

The haplotype determination in one embodiment comprises dividing the amplified polynucleotide fragments into multiple pools, wherein the multiple pools are deposited on the surface and whereby the concentration of fragments per pool is adjusted such that the number of overlapping fragments in each pool is minimized; amplifying the polynucleotide fragments in the multiple pools; fragmenting the amplified polynucleotide fragments in the multiple pools; generating sequencing libraries in the multiple pools; sequencing the sequencing libraries, thereby obtaining sequences of the polynucleotide fragments in the multiple pools; assembling the sequences, thereby obtaining an assembled sequence; and comparing the assembled sequence to a reference sequence, thereby determining whether the assembled sequence is inherited from the reference sequence.

In another embodiment, the method is used to select an embryo (e.g., for PGD). The method comprises, in one embodiment, depositing one or more cells from the embryo in a solution having a volume less than 400 nL to a uniquely specified location on a surface by contact dispensing (e.g., a vessel surface such as a microwell or microfluidic chamber surface), wherein the one or more cells comprise a polynucleotide; sequencing the polynucleotide, thereby obtaining a sequence read of the polynucleotide; and determining whether the polynucleotide carries a genetic variation associated with a disease using the sequence reads. From this determination, the user is able to select the embryo (or not select) for PGD.

In another embodiment of the methods described herein, a method for correcting a genetic variation in one or more cells is provided. The method in one embodiment comprises, depositing one or more cells from the embryo in a solution having a volume less than 400 nL to a uniquely specified location on a surface by contact dispensing, wherein the one or more cells comprise a polynucleotide; sequencing the polynucleotide, thereby obtaining a sequence read of the polynucleotide; and detecting a genetic variation on the polynucleotide; and correcting the genetic variation by gene editing. Notably, the methods can also be used to perform any combinations of the applications disclosed herein.

Generation of High-Fidelity Sequencing Libraries

Methods for analyzing one or more cells comprise in some embodiments, generating a sequencing library using polynucleotides from a small number of cells (e.g., a single cell or from about 1 cell to about 20 cells). The method can be used to generate a sequencing library that yields a high breadth of coverage by performing the sequencing reaction in a solution less than 400 nL. The method disclosed herein can generate a sequencing library with a maximum breadth of coverage of at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%. Methods of sequencing library generation herein can also be performed after any amplification methods disclosed herein. With the benefit of high fidelity, the methods disclosed herein can be used to generate a sequencing library without amplification of the small amount of polynucleotides before generating the library. In some cases, the methods can be used to generate a sequencing library from a limited amount of polynucleotides, e.g., genomic DNA from a small number of cells (e.g., a single cell).

Generating a sequencing library from polynucleotides from a small amount of cells in one embodiment, comprises fragmenting the polynucleotides and attaching a first adaptor to one end and a second adaptor to the other end of each of the fragments, or a subportion thereof. The fragments with the first set of adaptors can then be amplified using a primer set that introduces a third adaptor to one end and a fourth adaptor the other end to each of the fragments attached with the first and second adaptors. Sequencing of an individual fragment can require the third and fourth adaptors on the fragment have different sequences. Generating a sequencing library from polynucleotides can include fragmenting the polynucleotide. Fragmenting can be performed by any method disclosed herein or known in the art. Generating a sequencing library from polynucleotides can comprise fragmenting the polynucleotide into fragments of any length. The fragments can be at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, 165, 170, 175, 180, 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, at least about 270, at least about 275, at least about 280, at least about 285, at least about 290, at least about 295, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3500, at least about 4000, at least about 4500, at least about 5000, at least about 6000, at least about 7000, at least about 8000, at least about 9000, or at least about 10,000 nucleotides in length.

Generating a sequencing library from at least one polynucleotide can further include attaching the fragmented polynucleotides with one or more adaptors. Adaptors can be attached to a polynucleotide by primer extension, reverse transcription, or hybridization. In some cases, an adaptor can be tagged to a polynucleotide by ligation. For example, an adaptor can be attached to a polynucleotide by sticky-end ligation or blunt end ligation. In some cases, an adaptor can be attached to a polynucleotide by a transposase. A polynucleotide can be attached an adaptor at only one end, or both ends. In some cases, a polynucleotide can be attached the same adaptor or different adaptors at both ends. In some cases, a polynucleotide can be attached one or more adaptors on one end. In one example, each end of a polynucleotide can comprise an adaptor with a sequencing primer binding site and an adaptor with a flowcell primer sequence (e.g., used in next generation sequencing such as an Illumina Platform).

Methods disclosed herein can be used to generate a sequencing library by performing fragmenting and adaptor attaching simultaneously. Such simultaneous fragmenting and adaptor attaching can be performed using one or more transposomes. In some cases, the transposome used in generating a sequencing library can comprise a custom tagging sequence. A custom tagging sequence can comprise one or more adaptors disclosed herein. A custom tagging sequence can comprise any adaptor disclosed herein. Generating a sequencing library from at least one polynucleotide can be performed using any number of transposomes. Different transposomes can comprise different custom sequences, thereby tagging the polynucleotide fragments with different adaptors.

Generating a sequencing library from at least one polynucleotide can be performed using a transposome comprising any types of transposase known in the art. In some embodiments, the transposase is a transposase recognizing transposable element TN3, TN5, TN10, TN917, ISS1, TN5990, Ty1, Ty2, Ty3, or mariner. In one embodiment, the transposase can be a NEXTERA transposase (Illumina).

Methods provided herein can also be used to generate a sequencing library by performing fragmenting and adaptor attaching sequentially. Fragmenting and adaptor attaching can be performed in separated step using any methods disclosed herein or known in the art.

Generating a sequencing library can further comprise adding additional adaptors to the attached polynucleotide fragments. The additional adaptors can be the same as or different from the adaptors attached to the polynucleotide fragments. In one example, generating a sequencing library further comprises use of a primer set to introduce additional adaptors to the attached polynucleotide fragments.

With the sequencing libraries generated with the polynucleotides from the small number of cells, sequences of the polynucleotides are determined. The sequence information can be used for further analysis such as genetic variation detection in the cells. Methods for analyzing a small number of cells can include sequencing at least one polynucleotide from the cells. In some cases, a sequencing step comprises determining the sequence of at least one polynucleotide from one or more cells, or polynucleotide products of any amplification step, fragmentation step, or attaching step.

In one embodiment, sequencing is performed by basic sequencing methods, including but not limited to Maxam-Gilbert sequencing, chain-termination sequencing, shotgun sequencing or Bridge PCR. In one embodiment, sequencing is performed by massively parallel sequencing methods, including high-throughput sequencing, pyro-sequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS)(Helicos), massively-parallel sequencing, Clonal Single Molecule Array (Solexa), shotgun sequencing, Maxam-Gilbert or Sanger sequencing, primer walking, sequencing using Illumina, PacBio, SOLiD, Ion Torrent, 454, or nanopore platforms.

As described throughout, analyzing a limited amount of polynucleotides from a small amount of cells (e.g., less than 10 cells) in some embodiments comprises amplifying the polynucleotides. When analyzing a limited amount of polynucleotides from a small number of cells, methods provided herein can amplify the polynucleotides with reduced amplification bias. High fidelity amplification can be used in analyzing a limited amount of polynucleotide with enhanced accuracy. The enhanced accuracy can improve the effectiveness of clinical applications such as PGD, or other purposes.

Also provided herein are methods for reducing amplification bias. In one example, the method includes amplifying polynucleotides in a small volume solution (e.g., less than 100 nL). In another example, a polynucleotide can be fragmented first and then amplified in a single solution. Fragmentation can allow fragments comprising different regions of the polynucleotide to distribute more evenly in the solution, thus giving each region a similar chance of being amplified.

Amplification bias can be reduced by performing the amplification in a small volume solution. Methods provided herein can be used to amplify polynucleotides from one or more cells in a solution having a volume less than 400 nL. For example, the volume of solution can be ≤100 nL, ≤99 nL, ≤98 nL, ≤97 nL, ≤96 nL, ≤95 nL, ≤94 nL, ≤93 nL, ≤92 nL, ≤91 nL, ≤90 nL, ≤89 nL, ≤88 nL, ≤87 nL, ≤86 nL, ≤85 nL, ≤84 nL, ≤83 nL, ≤82 nL, ≤81 nL, ≤80 nL, ≤79 nL, ≤78 nL, ≤77 nL, ≤76 nL, ≤75 nL, ≤74 nL, ≤73 nL, ≤72 nL, ≤71 nL, ≤70 nL, ≤69 nL, ≤68 nL, ≤67 nL, ≤66 nL, ≤65 nL, ≤64 nL, ≤63 nL, ≤62 nL, ≤61 nL, ≤60 nL, 59 nL, 58 nL, ≤57 nL, ≤56 nL, ≤55 nL, ≤54 nL, ≤53 nL, ≤52 nL, 51 nL, ≤50 nL, ≤49 nL, ≤48 nL, ≤47 nL, ≤46 nL, ≤45 nL, ≤44 nL, ≤43 nL, ≤42 nL, ≤41 nL, ≤40 nL, ≤39 nL, ≤38 nL, ≤37 nL, ≤36 nL, ≤35 nL, ≤34 nL, ≤33 nL, ≤32 nL, ≤31 nL, ≤30 nL, ≤29 nL, ≤28 nL, ≤27 nL, ≤26 nL, ≤25 nL, ≤24 nL, ≤23 nL, ≤22 nL, ≤21 nL, ≤20 nL, ≤19 nL, ≤18 nL, ≤17 nL, ≤16 nL, ≤15 nL, ≤14 nL, ≤13 nL, ≤12 nL, ≤11 nL, or ≤10 nL.

Amplifying steps described herein can be performed using a method known in the art. These methods can depend on the catalyzed formation of multiple copies of a nucleic acid or polynucleotide molecule or its complement. One such method for the enzymatic amplification of specific double stranded sequences of DNA is polymerase chain reaction (PCR; and including any known implementation of PCR such as digital PCR, droplet digital PCR, or single cell PCR), including AFLP (amplified fragment length polymorphism) PCR, allele-specific PCR, Alu PCR, assembly, asymmetric PCR, colony PCR, helicase dependent PCR, hot start PCR, inverse PCR, in situ PCR, intersequence-specific PCR or IS SR PCR, linear-after-the-exponential-PCR or Late PCR, long PCR, nested PCR, real-time PCR, duplex PCR, multiplex PCR, or quantitative PCR.

Amplification can also be performed using multiple displacement amplification (MDA). In some cases, MDA can be used to amplify minute amounts of polynucleotides (e.g., DNA) to a sufficient quantity for analysis. The reaction can start by annealing random hexamer primers to a template polynucleotide (e.g., DNA). Polynucleotide (e.g., DNA) synthesis can be carried out by a high fidelity enzyme, e.g., Φ29 DNA polymerase, at a constant temperature. In some cases, MDA can be used in whole genome amplification (WGA), single cell genome sequencing, or sequencing-based genetic studies. In one example, methods provided herein can provide amplifying polynucleotide from a small number of cells (e.g., less than 10 cells) by MDA.

Other amplification methods can also be used, including in vitro clone expansion, ligase chain reaction (LCR), nucleic acid sequence based amplification (NASBA), linear amplification, isothermal linear amplification, Q-beta-replicase method, 3SR, Transcription Mediated Amplification (TMA), Strand Displacement Amplification (SDA), bridge amplification (e.g., using an Illumina flow cell), or Rolling Circle Amplification (RCA).

A sequencing library generated using amplified polynucleotides can yield low breadth of coverage due to amplification bias. To reduce the effect of amplification bias, provided herein includes a method of generating a sequencing library without amplification of template polynucleotides prior to the sequencing library generation. Methods provided herein can comprise (a) fragmenting the polynucleotide to generate a plurality of polynucleotide fragments; (b) attaching a first adaptor to one end and a second adaptor to the other end of each of the fragmented polynucleotides, thereby generating polynucleotide fragments with adaptors on each end; and (c) amplifying the polynucleotide fragments from step (b) using a primer set, wherein the primer set introduces a second adaptor on each end of the amplified polynucleotide fragments, wherein steps (a) and (b) are performed in a volume less than 400 nL, and wherein the polynucleotide or fragmented polynucleotides of step (a) is not amplified before step (b).

Generation of a sequencing library in a small reaction volume can enhance the concentration of the template polynucleotides, thus improving the reaction efficiency. Generating a sequencing library without prior amplification of the template polynucleotides can be performed in a solution of a small volume (e.g., less than 400 nL). In some cases, steps (a) and (b) (as detailed in the preceding paragraph) are performed in a volume ≤400 nL, ≤350 nL, ≤300 nL, ≤250 nL, ≤200 nL, ≤250 nL, ≤100 nL, ≤90 nL, ≤100 nL, ≤99 nL, ≤98 nL, ≤97 nL, ≤96 nL, ≤95 nL, ≤94 nL, ≤93 nL, ≤92 nL, ≤91 nL, ≤90 nL, ≤89 nL, ≤88 nL, ≤87 nL, ≤86 nL, ≤85 nL, ≤84 nL, ≤83 nL, ≤82 nL, ≤81 nL, ≤80 nL, ≤79 nL, ≤78 nL, ≤77 nL, ≤76 nL, ≤75 nL, ≤74 nL, ≤73 nL, ≤72 nL, ≤71 nL, 70 nL, 69 nL, 68 nL, ≤67 nL, 66 nL, 65 nL, 64 nL, 63 nL, ≤62 nL, ≤61 nL, ≤60 nL, ≤59 nL, ≤58 nL, ≤57 nL, ≤56 nL, ≤55 nL, ≤54 nL, 53 nL, 52 nL, 51 nL, 50 nL, ≤49 nL, ≤48 nL, ≤47 nL, ≤46 nL, ≤45 nL, ≤44 nL, ≤43 nL, ≤42 nL, ≤41 nL, ≤40 nL, ≤39 nL, ≤38 nL, ≤37 nL, ≤36 nL, ≤35 nL, ≤34 nL, ≤33 nL, ≤32 nL, ≤31 nL, ≤30 nL, ≤29 nL, ≤28 nL, ≤27 nL, ≤26 nL, ≤25 nL, ≤24 nL, ≤23 nL, ≤22 nL, ≤21 nL, ≤20 nL, ≤19 nL, ≤18 nL, ≤17 nL, ≤16 nL, ≤15 nL, ≤14 nL, ≤13 nL, ≤12 nL, ≤11 nL, ≤10 nL, ≤9 nL, ≤8 nL, ≤7 nL, ≤6 nL, ≤5 nL, ≤4 nL, ≤3 nL, ≤2 nL, ≤1 nL, ≤0.9 nL, ≤0.8 nL, ≤0.7 nL, ≤0.6 nL, ≤0.5 nL, ≤0.4 nL, ≤0.3 nL, ≤0.2 nL, or ≤0.1 nL.

Generating a sequencing library without amplification prior to the sequencing library generation can comprise fragmentation performed using any methods disclosed herein or known in the art. Generating a sequencing library without amplification prior to the sequencing library generation can comprise attaching performed using any tagging methods disclosed herein or known in the art. In some cases, fragmenting and attaching can be performed sequentially. For example, polynucleotides can be fragmented and ligated with one or more adaptors in separate enzymatic steps.

Fragmenting and attaching in one embodiment, are performed simultaneously. For example, fragmenting and attaching can be performed simultaneously using a transposase. The transposase can be any transposase disclosed herein and known in the art. In one example, generating a sequencing library can further comprise use of a primer set to introduce additional adaptors to the attached polynucleotide fragments.

The breadth of coverage yielded by a sequencing library generated without prior amplification can be enhanced by any methods provided herein. Breadth of coverage can be enhanced by increasing the number of adaptor variants attached to both ends of polynucleotides. In one example, the number of the adaptor variants can be increased by using transposomes with one or more different custom tagging sequences. In one example, the number of the adaptor variants can be increased by using primer sets to introduce different combinations of primers that are necessary for sequencing.

The method of generating a sequencing library without amplification prior to the sequencing library generation can be used in any combination with any other methods disclosed herein. In some embodiments, the method of generating a sequencing library comprises sequencing the fragmented polynucleotides comprising an adaptor. In some embodiments, the method comprises determining a genetic variation in the fragmented polynucleotides comprising an adaptor.

In addition to the fragmenting steps in sequencing library generation, methods provided herein can also include fragmenting polynucleotides from the cells to be analyzed for other purposes. Fragmentation methods provided herein can be used with any amplification methods to reduce amplification bias. Methods for analyzing at least one polynucleotide from one or more cells can comprise fragmenting the polynucleotide, thereby generating a plurality of polynucleotide fragments. In some embodiments, fragmenting of polynucleotides can be performed by mechanical shearing, e.g., passing the sample through a syringe, sonication, or heat treatment (e.g., 30 minutes at 90° C.). In some other embodiments, fragmenting of polynucleotides is performed using an enzyme, including a nuclease, or a transposase. Nucleases used for fragmenting in one embodiment, comprise restriction endonucleases, homing endonucleases, nicking endonucleases, or high fidelity (HF) restriction enzymes. Methods for analyzing at least one polynucleotide from one or more cells can comprise fragmenting the polynucleotide into fragments of any length. The fragments can be at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, 165, 170, 175, 180, 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, at least about 270, at least about 275, at least about 280, at least about 285, at least about 290, at least about 295, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3500, at least about 4000, at least about 4500, at least about 5000, at least about 6000, at least about 7000, at least about 8000, at least about 9000, or at least about 10,000 nucleotides in length.

Fragmentation of polynucleotides before amplification of the polynucleotides can reduce amplification bias. Amplification bias can be increased due to certain template polynucleotides being exposed to higher local concentrations of reagents, and thus being amplified more than other template polynucleotides. Fragmentation of template polynucleotides before amplification can allow template polynucleotides to distribute throughout the reaction solution and prevent some template polynucleotides from being preferentially amplified over others. Thus, in some embodiments, amplification bias can be reduced or prevented by fragmenting a polynucleotide before amplifying the polynucleotides. In some embodiments, fragmenting is performed before an amplification step, and the fragmenting and the amplifying can be performed in a single reaction solution. In one embodiment, fragmenting is performed before an amplification step, and the fragmenting and the amplifying are performed in different solutions.

Fragmenting in one embodiment, is performed before any type of amplification step. In some cases, fragmenting can be performed before a PCR step. In some cases, fragmenting can be performed before an MDA step. The fragments generated before an amplification step can be in any length disclosed herein. In some cases, fragments generated before an MDA step can be greater than 1000 bp length. For example, fragments generated before an MDA step in one embodiment, are ≥1000, ≥1500, ≥2000, ≥2500, ≥3000, ≥3500, ≥4000, ≥4500, ≥5000, ≥5500, ≥6000, ≥6500, ≥7000, ≥7500, ≥8000, ≥8500, ≥9000, ≥9500, or ≥10,000 bp length.

Fragmentation of polynucleotides after amplification of the polynucleotides in some embodiments, reduces amplification bias. Amplification bias can be reduced or prevented by dividing template polynucleotides into different reaction solutions, and then amplifying the polynucleotides in individual reaction solutions. In some embodiments, methods disclosed herein can comprise pre-amplifying at least one polynucleotide. Pre-amplifying can be performed using any amplification methods disclosed herein or known in the art. For example, pre-amplification can be performed by in vitro clonal expansion, MDA, PCR (e.g., randomly primed PCR). Pre-amplification can be performed in one or multiple rounds. In some embodiments, the methods can further comprise fragmenting the pre-amplified polynucleotides. In some embodiments, reagents for amplification can be added to the solution after fragmentation and then the resulting fragments can be distributed to a plurality of reaction solutions. In some other embodiments, the resulting fragments can be distributed to a plurality of reaction solutions and reagents for amplification can be added to multiple reaction solutions. The number of reaction solutions can be determined by the fragments sizes and number of fragments to be in one reaction solution. In some embodiments, the smaller the fragments, the more fragments there can be.

The resulting fragments can be distributed into at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 30, at least about 40, at least about 50, at least about 60, at least about 70, at least about 80, at least about 90, 100, at least about 200, 300, 400, 500, 600, 700, 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 3000, at least about 4000, at least about 5000, at least about 6000, at least about 7000, at least about 8000, at least about 9000, or at least about 10,000 reaction solutions. In some cases, the methods further comprise amplifying the fragments in the plurality of reaction solutions. The amplifying can be performed using any amplification methods disclosed herein or known in the art. For example, the amplification can be performed by in vitro clonal expansion, MDA, or PCR (e.g., randomly primed PCR). The amplification can be performed in one or multiple rounds. Any of the methods provided herein can be combined in any order to analyze a small number of cells. For example, polynucleotides from a small number of cells can be amplified with MDA. A sequencing library can then be generated using products from the MDA steps. In some cases, a fragmentation step can be performed before or after the amplification step. In some cases a fragmentation step can be performed after generating the sequencing library.

After the amplification step disclosed herein, the methods can further comprise pooling the amplified fragments into one solution for further analysis. In some cases, the methods can further comprise sequencing at least one of the polynucleotide fragments. The sequencing can be performed using any sequencing method disclosed herein or known in the art. The further analysis can include determining haplotype of the polynucleotide fragments. The determination of haplotype can be performed using any haplotyping method disclosed herein or known in the art. In one example, the methods can further include determining haplotype of a polynucleotide.

The method in one embodiment, comprises the following steps: (a) dividing the amplified polynucleotide fragments into multiple pools, whereby the concentration of fragments per pool is adjusted such that the number of overlapping fragments in each pool is minimized; (b) amplifying the polynucleotide fragments in the multiple pools; (c) fragmenting the amplified polynucleotide fragments in the multiple pools; (d), generating sequencing libraries in the multiple pools; (e) sequencing the sequencing library of step (d), thereby obtaining sequences of the polynucleotide fragments in the multiple pools; (f), assembling the sequences from b); and (g), comparing the assembled sequence to a reference sequence, thereby determining whether the assembled sequence is the same as the reference sequence. The reference sequence can be a genomic DNA sequence from a parent from which the polynucleotide is inherited. In some cases, the assembling is performed using fragments from the multiple pools having overlapping heterozygous single nucleotide variant (SNV) sites.

Methods described herein can be used, in one embodiment, for analyzing the genomic variation within a population of cells. The method can comprise, (a) distributing individual cells and/or individual nuclei from a cell suspension into a plurality of containers to obtain a plurality of distributed individual cells and/or individual nuclei; (b) creating indexed single cell sequencing libraries from the single cells and/or individual nuclei in one or more of the plurality of containers; (c) pooling a subset of the single cell sequencing libraries to make a pooled library comprising genomic information of a subset of the plurality of distributed cells and/or individual nuclei; (d) sequencing the pooled library to obtain incomplete genomic information of the subset of the plurality of distributed individual cells and/or individual nuclei; (e) aligning reads derived from one or more of the or more of the single cell sequencing libraries created from the distributed individual cells and/or individual nuclei to a reference genome in order to detect the presence or absence of genomic variation in the one or more of the distributed individual cells and/or individual nuclei; (f) analyzing the distribution of genomic variation(s) across the individual cells and/or individual nuclei to identify subpopulations of single cells that share common genomic features; and (g) analyzing the combined genomic information from identified subpopulations of cells and/or nuclei to identify genomic features that exist within the identified subpopulations.

The individual cells and/or individual nuclei, in one embodiment, are from a tumor sample. In a further embodiment, the tumor sample comprises a solid tumor, resected tissue or a fine needle aspirate.

The indexed single cell libraries are created in one embodiment, using a one-step transposase reaction. In another embodiment, the indexed single cell libraries are created using a transposase reaction followed by a PCR step with indexed primers.

The plurality of containers used in methods for analyzing the genomic variation within a population of cells, in one embodiment, have an average volume of from about 1 nL to about 1000 nL. In another embodiment, the average volume of the plurality of containers is from 0.1 nL to about 1 nL. In one embodiment, the plurality of containers comprises a plurality of chambers. In a further embodiment, the plurality of chambers is a plurality of microfluidic chambers. In another embodiment, the plurality of chambers is a plurality of microdroplets. In yet another embodiment, the plurality of chambers comprises a plurality of open microwells. The plurality of chambers in one embodiment, comprises from about 100 to about 10,000 chambers, from about 10,000 to about 100,000 chambers, or at least about 100,000 chambers. In one embodiment of a method for analyzing the genomic variation within a population of cells, from about 100 to about 1000 individual cells and/or nuclei are distributed into the plurality of containers which are a plurality of individual chambers. In one embodiment of a method for analyzing the genomic variation within a population of cells, there is an average of about 1 cell in each chamber. In another embodiment of a method for analyzing the genomic variation within a population of cells, there is an average of about 2 cells in each chamber.

In one embodiment of a method for analyzing the genomic variation within a population of cells, sequencing of the pooled indexed library is carried out to sufficient depth to obtain an average of between 0.01% and 0.1% coverage of the genome of each cell. In another embodiment of a method for analyzing the genomic variation within a population of cells, sequencing of the pooled indexed library is carried out to sufficient depth to obtain an average of between 0.1% and 1% coverage of the genome of each cell. In yet another embodiment of a method for analyzing the genomic variation within a population of cells, sequencing of the pooled indexed library is carried out to sufficient depth to obtain an average of between 1% and 5% coverage of the genome of each cell. In even another embodiment of a method for analyzing the genomic variation within a population of cells, sequencing of the pooled indexed library is carried out to sufficient depth to obtain an average of between 5% and 10% coverage of the genome of each cell. In even another embodiment of a method for analyzing the genomic variation within a population of cells, sequencing of the pooled indexed library is carried out to sufficient depth to obtain an average of between 10% and 25% coverage of the genome of each cell. In still another embodiment of a method for analyzing the genomic variation within a population of cells, sequencing of the pooled indexed library is carried out to sufficient depth to obtain an average of between 25% and 50% coverage of the genome of each cell. In one embodiment of the method for analyzing the genomic variation within a population of cells, the pooled indexed library is sequenced to sufficient depth to obtain between 10× and 100× coverage of the average bulk genome.

In one embodiment of the method for analyzing the genomic variation within a population of cells, the genomic variation is copy number variation, translocations, loss of heterozygosity, single nucleotide polymorphism or a combination thereof.

Methods of determining haplotype of a polynucleotide can include pre-amplifying the polynucleotide. The pre-amplifying can be performed using any amplification methods disclosed herein or known in the art. For example, the pre-amplification can be performed by in vitro clonal expansion, MDA, PCR (e.g., randomly primed PCR). The pre-amplification can be performed in one or multiple rounds. The methods of determining haplotype of a polynucleotide can further comprise fragmenting the pre-amplified polynucleotides. The resulting fragments can be distributed to a plurality of reaction solutions. In some embodiments, the resulting fragments can be distributed into at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 30, at least about 40, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 3000, at least about 4000, at least about 5000, at least about 6000, at least about 7000, at least about 8000, at least about 9000, or at least about 10,000 reaction solutions. In some cases, the methods can further comprise amplifying the fragments in the plurality of reaction solutions. The amplifying can be performed using any amplification methods disclosed herein or known in the art. For example, the amplification can be performed by in vitro clonal expansion, MDA, PCR (e.g., randomly primed PCR). The amplification can be performed in one or multiple rounds. In some cases, the methods of determining haplotype of a polynucleotide can further comprise sub-fragmenting the amplified polynucleotide fragments in the plurality of reaction solutions. The sub-fragmenting can be performed using any fragmentation method disclosed herein or known in the art. In some cases, the methods of determining haplotype of a polynucleotide can further comprise sequencing the sub-fragmented polynucleotides in the plurality of reaction solutions, thereby obtaining sequence reads of the sub-fragmented polynucleotides. The sequencing can be performed using any sequencing method disclosed herein or known in the art. In some cases, the methods of determining haplotype of a polynucleotide can further comprise assembling the sequence reads from more than one of the reaction solutions.

In some embodiments, the methods can comprise assembling the sequence reads from at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 30, at least about 40, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 3000, at least about 4000, at least about 5000, at least about 6000, at least about 7000, at least about 8000, at least about 9000, or at least about 10,000 of the reaction solutions. The assembling can be performed using any bioinformatic methods known in the art. In some cases, the assembling can be performed using overlapping heterozygous single nucleotide variant sites. The methods of determining haplotype of a polynucleotide disclosed herein can comprise determining haplotype of a region of length in a polynucleotide.

In some embodiments, methods are provided to select an embryo, e.g. for PGD. A small number of cells or nuclei (e.g., less than 10 cells or less than 10 nuclei) can be isolated from an embryo without preventing the embryo growth. Methods herein can allow for genetic analysis of such small number of cells with high fidelity amplification and sequencing library construction and combination thereof.

Methods herein can be used for selecting an embryo with a genetic characteristic. The methods can comprise transferring a cluster of cells from the embryo to a uniquely specified location on a surface. The methods can also comprise analyzing at least one polynucleotide from the cluster of cells, thereby determining whether the embryo has the genetic characteristic. In some cases, methods for selecting an embryo with a genetic characteristic can comprise: transferring a cluster of cells from the embryo to a uniquely specified location on a surface; and analyzing at least one polynucleotide from the cluster of cells, thereby determining whether the embryo has the genetic characteristic, wherein the cluster of cells is transferred in a solution of no more than 400 nL to the uniquely specified location. The analyzing can be performed by any methods and compositions disclosed herein. The methods for selecting an embryo with a genetic characteristic can be combined with any methods disclosed herein. The methods for selecting an embryo with a genetic characteristic can be used for selecting an embryo for preimplantation genetic diagnosis (PGD).

The cluster of cells disclosed herein can comprise any number of cells. In some cases, the cluster of cells can comprise no more than 1000 cells. For example, the cluster of cells comprise $\leq 50$, $\leq 49$, $\leq 48$, $\leq 47$, $\leq 46$, $\leq 45$, $\leq 44$, $\leq 43$, $\leq 42$, $\leq 41$, $\leq 40$, $\leq 39$, $\leq 38$, $\leq 37$, $\leq 36$, $\leq 35 \leq 34 \leq 33 \leq 32 \leq 31 \leq 30 \leq 29 \leq 28 \leq 27 \leq 26 \leq 25 \leq 24$, $\leq 23$, $\leq 22$, $\leq 21 \leq 20 \leq 19$, $\leq 18$, $\leq 17$, $\leq 16$, $\leq 15$, $\leq 14$, $\leq 13$, $\leq 12$, $\leq 11$, $\leq 10$, $\leq 9$, $\leq 8$, $\leq 7$, $\leq 6$, $\leq 5$, $\leq 4$, $\leq 3$, or $\leq 2$ cells, for example a single cell. In one embodiment, the cluster of cells comprises less than or equal to about 30 cells. In one case, the cluster of cells can comprise one cell or about one cell. The cluster of cells can split into a plurality of individual cells. In some cases, the cluster of cells can be split into a plurality of individual cells prior to the analyzing step. In some cases, the cluster of cells can be split into a plurality of individual cells after the analyzing step starts. In some cases, the cluster of cells can be split into a plurality of individual cells after the analyzing step finishes. The methods for selecting an embryo with a genetic characteristic can comprise analyzing at least one polynucleotide from each of the split cells. In some cases, methods for selecting an embryo with a genetic characteristic can comprise analyzing at least one polynucleotide from some, but not all of the split cells.

An embryo biopsy can be divided into multiple subsets and different analyses can be performed by the methods provided herein with the subsets, for example in different microwells or different microfluidic chambers (different vessels). Each of the subsets can contain one or more embryonic cells. In some cases, each of the subsets can contain one embryonic cell. If an embryo biopsy has 10 cells, the biopsy can be divided into 10 subsets. In one example, methods disclosed herein can be used to analyze the haplotype of the cell in one subset. And methods disclosed herein can also be used to detect a genetic variation in the cell in another subset. In another example, the methods can be used to detect a genetic variation in the cells in two subsets. The detected genetic variation can then be compared between the two cells to determine the genetic variability among different cells in embryo biopsy.

Although progress has been made in understanding the vast number of mutations in sequenced tumor samples and the processes generating them, another layer of variability has been discovered in the form of subclonal population structure (Cell Rep. 2014 Jun. 12; 7(5): 1740-1752, incorporated by reference in its entirety). Indeed, a sample of cells from a single tumor in many instances cannot be considered as an isogenic lineage of cancer cells with stromal contamination. The fraction of cancerous cells rather consists of a collection of subclones, with private and shared mutations, related by their joint evolutionary history going back to the most recent common ancestor.

Although clonal heterogeneity can be detected using next-generation DNA sequencing, the problems with analysis of single cells mentioned herein also plague this analysis. For example, current sample extraction strategies will lead to an underestimation of real tumor heterogeneity. Moreover, it has been reported that subclones can be resistant to a particular therapy. When these subclones are amplified, they are subjected to a process called competitive release, whereby the drug eradicates any susceptible competitors (Cell Rep. 2014 Jun. 12; 7(5): 1740-1752, incorporated by reference in its entirety). Rather than waiting for de novo resistance mutations to emerge, cancer likely escapes using existing subclonal variation. As a result, clonal dynamics and changes in clonal composition can inform therapy, highlighting the importance of monitoring cancer progression. The present invention addresses this need with the devices, systems and methods provided herein by providing a platform for analysis of heterogeneity within a tumor sample.

One embodiment provided herein is directed to a method for analyzing heterogeneity within a tumor sample. The method comprises isolating a plurality of cells and/or nuclei from the tumor sample. Isolating can also comprise a combination of cell(s) and nuclei. For example, one cell and one nucleus can be isolated by the methods described herein. Alternatively, the plurality of cells and/or nuclei can be obtained, i.e., the plurality of cells and/or nuclei can already have been isolated.

Isolating can be carried out e.g., with one of the transfer devices described herein, e.g., a microcapillary or a micropipette or a microdispenser Individual cell(s) and/or nuclei are deposited into individual containers. The individual chambers in some embodiments are individual microwells. In another embodiment, the individual chambers are individual microfluidic chambers. In yet another embodiment, the individual chambers are individual open microwells, droplets on a surface, or droplets in an emulsion. A cell and/or a nucleus in an individual chamber is also referred to herein as a tumor subpopulation.

Notably, preparation of sequencing libraries is carried out on nucleic acid from the plurality of individual cells and/or nuclei without prior amplification. In one embodiment, the library preparation method comprises a transposase reaction. In another embodiment, the library preparation comprises DNA fragmentation (e.g. enzymatically or mechanically), end-repair, A-tailing and adapter ligation.

In yet another embodiment, libraries can be prepared by targeted PCR. Libraries may also be enriched using capture or pull-down techniques. Methods for generating such libraries are described herein and can be used in the present method for analyzing heterogeneity within a tumor sample. Index sequences are added to the nucleic acid in each individual container such that a unique index sequence is associated with a unique container. Index sequences are added during the transposase reaction, during a ligation step, or during a PCR reaction (or other amplification reaction) or a combination thereof.

Individual libraries are then pooled and sequenced to provide sequence information of individual cells and/or nuclei. From this sequence information, the copy number profiles or other genomic structural abnormalities (e.g. translocations, deletions, amplifications, inversions, breakpoints, insertions) of individual cells and/or nuclei is determined. Based on the genomic alterations of each individual cell and/or nuclei, the clonal composition of the tumor is determined.

In a further embodiment, the method comprises analyzing the genomic features (i.e., genomic sequences) of two or more tumor subpopulations to determine the genomic features common to the cells within the two or more tumor subpopulations.

Methods disclosed herein can allow for the detection of genetic variation from a limited amount of genetic materials (e.g., genomic DNA from a single cell). Methods for analyzing at least one polynucleotide from a small number of cells can include determining whether the polynucleotide carries a genetic variation. A genetic variation can include a single nucleotide variation (SNV), an insertion, a deletion, an insertion/deletion, a rearrangement, a copy number variation (CNV), or a combination thereof. In some cases, methods for analyzing at least one polynucleotide from one or more cells can comprise determining whether the polynucleotide carries one or more polymorphisms, including one or more single nucleotide polymorphisms (SNPs). In some cases, a genetic variation can be a CNV. The polynucleotide fragments can be sequenced to a depth that allow to detect copy number variation of at least about 1 kb, at least about 2 kb, at least about 3 kb, at least about 4 kb, at least about 5 kb, at least about 6 kb, at least about 7 kb, at least about 8 kb, at least about 9 kb, at least about 10 kb, at least about 11 kb, at least about 12 kb, at least about 13 kb, at least about 14 kb, at least about 15 kb, at least about 16 kb, at least about 17 kb, at least about 18 kb, at least about 19 kb, at least about 20 kb, at least about 21 kb, at least about 22 kb, at least about 23 kb, at least about 24 kb, at least about 25 kb, at least about 26 kb, at least about 27 kb, at least about 28 kb, at least about 29 kb, at least about 30 kb, at least about 31 kb, at least about 32 kb, at least about 33 kb, at least about 34 kb, at least about 35 kb, at least about 36 kb, at least about 37 kb, at least about 38 kb, 39 kb, at least about 40 kb, at least about 41 kb, at least about 42 kb, at least about 43 kb, at least about 44 kb, at least about 45 kb, at least about 46 kb, at least about 47 kb, at least about 48 kb, 49 kb, at least about 50 kb, at least about 51 kb, at least about 52 kb, at least about 53 kb, at least about 54 kb, at least about 55 kb, at least about 56 kb, at least about 57 kb, at least about 58 kb, 59 kb, at least about 60 kb, at least about 61 kb, at least about 62 kb, at least about 63 kb, at least about 64 kb, at least about 65 kb, at least about 66 kb, at least about 67 kb, at least about 68 kb, 69 kb, at least about 70 kb, at least about 71 kb, at least about 72 kb, at least about 73 kb, at least about 74 kb, at least about 75 kb, at least about 76 kb, at least about 77 kb, at least about 78 kb, 79 kb, at least about 80 kb, at least about 81 kb, at least about 82 kb, at least about 83 kb, at least about 84 kb, at least about 85 kb, at least about 86 kb, at least about 87 kb, at least about 88 kb, at least about 89 kb, at least about 90 kb, at least about 91 kb, at least about 92 kb, 93 kb, at least about 94 kb, at least about 95 kb, at least about 96 kb, at least about 97 kb, at least about 98 kb, at least about 99 kb, or at least about 100 kb nucleotides in length. For example, the polynucleotide fragments can be sequenced to a depth that allows detection of a copy number variation of at least about 10 kb, at least about 20 kb, or at least about 50 kb nucleotides in length.

A genetic variation can be associated with a disease. In some cases, methods for analyzing at least one polynucleotide from one or more cells can comprise determining whether the polynucleotide carries a genetic variation associated with a disease, e.g., aneuploidy. In some cases, the disease can be a non-genetic disorder. In some cases, the disease can be a genetic disorder. For example, the genetic disorder can be 22q11.2 deletion syndrome, Angelman syndrome, Canavan disease, Charcot-Marie-Tooth disease, Color blindness, Cri du chat, Cystic fibrosis, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Tay-Sachs disease, or Turner syndrome.

Methods disclosed herein can include treating a disease by correcting a genetic variation associated with the disease. A genetic variation can be corrected by any methods disclosed herein or known in the art. In some cases, a genetic variation can be corrected using an enzyme. For example, the genetic variation can be corrected using a nuclease, including, but not limited to a Zinc Finger nuclease (ZFN), a Transcription Activator-Like Effector Nuclease (TALEN), a meganuclease, or a RNA-guided DNAase (e.g. a CRISPR associated protein 9, nuclease. In one case, the nuclease can be a CRISPR-associated protein (e.g., Cas9). In one case, the nuclease can be a Cas module-Repeat-Associated Mysterious Protein (Cmr).

Methods disclosed herein can include determining an epigenetic modification in a polynucleotide. An epigenetic modification can include acetylation, methylation, ubiquitylation, phosphorylation, sumoylation, ribosylation, citrullination of a polynucleotide. In some cases, an epigenetic modification can include histone modification, including acetylation, methylation, ubiquitylation, phosphorylation, sumoylation, ribosylation, or citrullination of a histone.

Methods disclosed herein can also include determining expression of a gene in the one or more cells. Expression of a gene can be determined by any methods known in the art. In some cases, expression of a gene can be determined using reverse-transcription PCR. In some cases, expression of a gene can be determined using whole transcriptome sequencing. In some cases, expression of a gene can be determined by reporter genes, Northern blotting, Western blotting, Fluorescent in situ hybridization (FISH), Serial Analysis of Gene Expression (SAGE), a microarray, RNA Seq, or a Tiling array.

EXAMPLES

The present invention is further illustrated by reference to the following Examples. However, it should be noted that these Examples, like the embodiments described above, are illustrative and are not to be construed as restricting the scope of the invention in any way.

Example 1—Direct Library Generation

The following example is further illustrated in FIGS. 18 and 19.

Pre-treatment before loading cells on a custom microfluidic device: Cells were washed and re-suspended in fresh PBS at a 1e6 cells/mL concentration and filtered using a 40 µm filter to remove cell debris and clumped cells. The filtered cells were stained using Syto 9 DNA stain. 10 µl of stained nuclei were mixed with 8 µl PBS, and 2 µl loading buffer [81.25 µl Percoll, 15 µl Superblock, 3 µl EDTA, 0.75 µl Tween 20 (10%)]. The ratio of PBS and loading buffer was optimized for neutral nuclei buoyancy.

Library preparation on custom microfluidic device: Prior to loading, cell sorting channels were primed with 1% BSA or 100% Superblock solution. The cell suspension was connected to the primed microfluidic device, where single cells were isolated from the suspension using mechanical cell traps. The trapped single cells were washed with PBS to remove untrapped cells, cell debris and extracellular DNA. Cell occupancy was determined by microscopy and recorded for analysis. The trapped and washed cells were then pushed into an inflatable reaction chamber, designed to hold variable nanolitre-scale volumes, where the cells were lysed in 1.2 nl final volume. The cell lysis buffer includes 25 µl Qiagen digestion buffer G2 (Guanidine HCl (800 mM), TrisCL (30 mM), EDTA (30 mM), Triton X-100 (0.5%), PCR water) and 2.5 µl Qiagen Protease. The nuclei were incubated at 50° C. for 1 hour to lyse the nuclei membrane and strip the genomic DNA from all bound proteins such as nucleases and histones, before inactivating the Protease at 70 C for 15 minutes.

Single-cell libraries were prepared using a modified NEXTERA protocol (Illumina). 10.8 nl of Tagmentation mix (TD Buffer (6 nl), TDE1 (1.6 nl), Buffer 1 (3.2 nl) [MgCl (1.22 mM) and Tween (0.3%)]) were added to each chamber and incubated at 55° C. for 5 minutes. The Tagmentation reaction was neutralized by adding 1 nl Qiagen Protease and 1 nl PCR water and incubated at 50° C. for 15 min. The Protease was then inactivated at 70° C. for 15 min. Following neutralization, 21 nl PCR master mix [NPM (10.5 nl), PPC (3.5 nl), Tween 20 (0.35 nl), PCR water (5.25 nl)] was added to each chamber. During the addition of the PCR mix, pre-spotted index primers ([20 µM*400 pl]) were added to the PCR reaction. 11 PCR cycles were performed to add flow-cell adapters and indices and amplify the fragmented DNA. The sequencing ready libraries were pooled and recovered from the chip. Ampure XP beads were used for size selection to remove excess primers and short fragments that do not contain genomic inserts of the desired length. Sequencing was performed on Illumina's HISEQ2000 Sequencing system.

Sequencing analysis to detect low-resolution sequence alterations at single-cell resolution: The obtained reads were trimmed to remove adapter contamination and aligned to the human reference genome. The software package HMMcopy was then used to correct for GC bias and mappability. Finally, reads were normalized and plotted using custom scripts.

Example 2—Genome-Wide Haplotyping Using Fragmentation Sites to Reconstruct Homologous Chromosomes Genomic DNA from a single cell is fragmented. The fragmented DNA comprises non-overlapping fragments of the maternal and paternal chromosome. The fragmented DNA is amplified to generate enough mass for DNA sequencing.

The amplified products are sequenced and the sequence reads of the fragments are obtained. The sequence reads are used to reconstruct maternal and paternal chromosomes by bioinformatically connecting contiguous fragments that share a unique fragmentation site on the same chromosome (FIG. 20). As detailed herein, these methods can be carried out in small volumes (e.g., 400 nL).

Example 3—Single-Cell Nanolitre-Volume MDA

Cells were resuspended in PBS supplemented with 5% glycerol, adjusted to a concentration of 1 cell/8 nL, and stained with SYTO9 DNA stain. The stained cells were identified later by fluorescent microscopy.

143 droplets, each composed of 8 nL of the cell suspension, were deposited onto a PDMS coated surface using a piezoelectric spotter. Thus, droplets containing single cells were obtained by limiting dilution. The substrate was then imaged using a fluorescent microscope to count the number of cells in each droplet. In general, observed single-cell occupancy was close to the theoretical maximum of 37% predicted by the Poisson distribution. 6 nL of alkaline buffer (KOH 400 nM, EDTA 10 mM, DTT 100 mM) was then deposited on each droplet using the spotter to lyse the cells and denature the double-stranded DNA (1001, FIG. 21).

All droplets were then covered with light mineral oil. The surface had a barrier composed of PDMS which kept the mineral oil on the droplet array (as described, for example, in FIG. 17). The substrate was then placed on a flatbed thermocycler, heated to 65° C. for 10 min, and then cooled to room temperature. The mineral oil was removed by pipette and 6 nL of neutralization buffer (Tris-HCl 1M pH 7.4) was deposited on each droplet to neutralize the alkaline buffer (1002, FIG. 21).

80 nL of MDA mix was then deposited on each droplet to perform MDA. The mix was composed of 58 nL Qiagen Repli-G Single Cell WGA Kit reaction buffer, 4 nL Qiagen Repli-G Single Cell WGA Kit phi 29 polymerase, 5% glycerol, and 0.1% Tween 20 surfactant (1003, FIG. 21).

The droplet array was again covered with light mineral oil, and the surface was incubated at 30° C. for 18 hours, 65° C. for 15 minutes, and then cooled to room temperature. Mineral oil was then removed, and 250 nL of BioRad Precision Blue™ Real-Time PCR Dye diluted to 12× was deposited on each reaction droplet that to be analyzed (1004, FIG. 21).

The droplets were manually extracted by pipette and diluted into 30 µL Qiagen Buffer EB. The addition of the blue dye added additional volume and a visual marker to the droplets, making it easier to extract by pipette. All of the above reagents except the Qiagen Repli-G Single Cell WGA Kit reagents and the BioRad Precision Blue™ Real-Time PCR Dye were decontaminated using a UV oven which delivers approximately 4 joules of UV energy prior to use (1005, FIG. 21).

For each single-cell MDA reaction sequenced, 5 ng of MDA product was used to prepare sequencing libraries using the Illumina TRUSEQ library preparation chemistry. Samples were sequenced on an Illumina MISEQ Sequencing instrument (paired end 2×75 bp reads).

Example 4—Comparison of Amplification Bias Among the Single-Cell MDA, Microfluidic MDA, and MALBAC Single-cell MDA sequencing data were generated from the methods described in Example 4. Microfluidic MDA data were from Wang et al., (J. Wang, H. C. Fan, B. Behr, Stephen R. Quake, Genome-wide Single-Cell Analysis of Recombination Activity and De Novo Mutation Rates in Human Sperm. Cell 150, 402-412 (2012), which is incorporated herein by reference in its entirety. MALBAC data from a single cancer cell line were from Zong et al., (C. Zong, S. Lu, A. R. Chapman, X. S. Xie, Genome-Wide Detection of Single-Nucleotide and Copy-Number Variations of a Single Human Cell. Science 338, 1622-1626 (2012)), which is incorporated herein by reference in its entirety.

The sequencing data were aligned to the human genome. The aligned data from all 3 samples were randomly down-sampled such that all 3 samples had the same amount of aligned data. The HMMcopy software tool (see: compbio.bccrc.ca/software/hmmcopy/) was used to correct for biases due to % GC content and mappability in all datasets. The human reference genome was then divided into non-overlapping 20 kbp bins and the number of sequencing reads in each bin was computed.

For the MALBAC sample, a cancer cell line with known CNVs was used. Since the purpose of this comparison was to compare variation in sequencing depth across the genome due to amplification, variation due to biological CNVs are confounding. CNV analysis was performed on the bulk DNA from the cancer cell line used and any chromosomes with significant CNVs were omitted from analysis. The sample from Wang et al. was a single sperm cell, which was haploid and thus has half of the genomic material as the other 2 samples.

FIG. 22 shows the reads per bin in log 2 scale for all bins in the reference genome. The MALBAC sample did not show chromosomes with biological CNVs. This figure gave a visual representation of amplification bias, as the variation in reads/bin can be seen across the genome. The single cell MDA sample compared favorably with the other two.

Another way of assessing bias was to examine the power spectra of reads/bin. This gave a measure of bias on multiple length scales in units of base pairs. A function in the programming language R, which performed a Fourier transform on the binned reads was shown in FIG. 23. The single cell MDA sample had lower variation on all length scales below $10^8$ bp.

The Lorenz curve shown in FIG. 24 is another way of assessing bias. It shows what fraction of the reference genome the reads are compressed into. For an ideally unbiased dataset in which all parts of the reference genome are equally represented, for any given fraction of the reference genome that is examined, one should find the same fraction of the sequencing data. Thus 0.1 of the reference (x-axis) should contain 0.1 of the reads (y-axis), 0.2 of the reference should contain 0.2 of the reads, etc. resulting in the diagonal (dotted line). The closer a dataset is to the diagonal, the less bias it has. For the inventor's sample (MDA), approximately 0.62 of the reference contains none of the reads (the x-intercept), meaning that all of the reads are compressed into the remaining 0.38 of the genome due to bias. That is, 0.38 of the reference is covered by at least one read. One must consider approximately 0.8 of the reference to see approximately 0.2 of the reads. However, this plot shows that the inventor's sample is less biased than either the sample from Zong et al. (MALBAC, dashed line) or Wang et al. (QUAKE, dotted line). Note, however, that it is specifically contemplated that if more sequencing data is used for any given sample, more coverage of the reference may result, shifting the x-intercept to the left in FIG. 24. Thus, when making comparisons between multiple samples in Lorenz curves, it is important to consider the same amount of aligned data for each sample.

Example 5—Fragmentation of Genomic DNA Followed by MDA in a Single Reaction Volume This Example is depicted in FIG. 25 via representative panels 1301 through 1306. Briefly, the steps are as follows: deposit cell(s) (1301); lyse cell(s) and free DNA (1302); fragment DNA (enzymatically, physically, or by other means) (1303); add MDA reaction mix (1304); incubate MDA reaction and amplify DNA (1305); and recover amplified DNA (1306).

Example 6—Initial Amplification by MDA Followed by Fragmentation, Isolation of Fragments into Individual Reaction Solutions, Amplification, and Pooling This Example is depicted in FIG. 26 via representative panels 1401 through 1409. Briefly, the steps are as follows: deposit cell(s) (1401); lyse cell(s) and free DNA (1402); add MDA reaction mix (1403); incubate MDA reaction and amplify DNA (1404); fragment DNA (enzymatically, physically, or by other means) (1405); recover amplified, fragmented DNA (1406); redeposit amplified, fragmented DNA combined with amplification mix (onto substrate or into an emulsion) (1407); incubate MDA reaction and amplify DNA (1408); and recover and pool amplified DNA (1409).

Example 7—Initial Amplification by Transposase-Based Fragmentation and Amplification, Followed by Isolation of Amplified Fragments into Individual Reaction Solutions, Amplification, and Pooling This Example is depicted in FIG. 27 via representative panels 1501 through 1510. Briefly, the steps are as follows: deposit cell(s) (1501); lyse cell(s) and free DNA (1502); add tagmentation reaction mix (1503); incubate reaction and fragment and tag DNA (1504); add PCR reaction mix (1505); incubate reaction and amplify fragmented, tagged DNA (1506); recover amplified, fragmented DNA (1507); redeposit amplified, fragmented DNA combined with amplification mix (onto substrate or into an emulsion) (1508); incubate reactions and amplify DNA (1509); and recover and pool amplified DNA (1510).

Example 8—Methods for Reducing Amplification Bias by Fragmenting the Template Polynucleotides Before Amplification, where the Fragmentation and Amplification are Performed in a Single Solution This example is depicted in FIG. 25 as described above and FIG. 28. With respect to FIG. 28, the method involves the steps of providing a polynucleotide in a nanoliter volume solution, fragmenting the polynucleotide in the solution, and amplifying the polynucleotide fragments in the same solution.

Example 9—Methods of Reducing Amplification Bias by Pre-Amplifying and Fragmenting a Template Polynucleotide Followed by Amplifying the Fragments in Multiple Reaction Solutions This Example is depicted in FIG. 29, and comprises: providing a polynucleotide in a nanoliter volume solution; amplifying the polynucleotide in the solution; fragmenting the amplified polynucleotides in the solution; dividing the solution having the fragments into multiple reaction solutions; amplifying the fragments in the multiple reaction solutions; and pooling the amplification products in the multiple reaction solutions.

Example 10—Methods of Long Range Haplotyping of a Polynucleotide

This Example is depicted in FIG. 30, and comprises: providing a solution comprising amplified polynucleotides; dividing the solution into multiple pools; amplifying polynucleotides in the multiple pools; fragmenting the amplified polynucleotides in the multiple pools; generating sequencing libraries in the multiple pools; sequencing the polynucleotides fragments in the multiple pools; assembling sequences from the multiple pools; and comparing the assembled sequence to a reference sequence.

Example 11—Robust, Low-Bias Microfabrication-Free Nanoliter-Volume Single-Cell MDA Genomic heterogeneity is appreciated for its functional significance across oncology, development, neuroscience, and biotechnology. Single-cell genome sequencing is a vital research tool in advancing these fields. Rapid advances in cell-handling, DNA amplification methods, and sequencing throughput have enabled genomic interrogation of human disease and physiology with single-cell resolution, with studies of heterogeneity in blood and solid tumors, circulating tumor cells, neurons, gametes, and embryos. However, despite intense interest in this method, it remains not widely accessible for at least two reasons: high cost and lack of robustness. As the cost of sequencing usefully large numbers of single-cell genomes continues to drop, equally scalable methods of preparing single-cell samples for sequencing have lagged far behind. More fundamentally, the robustness and reproducibility of single cell amplification methods, which is a requisite for routine analysis, is still elusive. In particular, a critical step in most single cell genome studies is performing whole genome amplification (WGA) to generate sufficient DNA mass for sequencing, a process that is prone to bias, contamination, and poor coverage. Preferential amplification of some genomic regions results in distorted representation of the original template and compromises the accuracy of downstream measurements. High variation in single-cell genomic coverage and bias, both within experiments and between users, remains a fundamental problem.

With an objective of assessing the robustness and performance of nanoliter-volume single-cell MDA, a commercially available non-contact liquid dispenser was adapted to systematically test amplification performance across large numbers of replicate reactions. The robustness and performance of a scalable nanoliter-volume single-cell MDA technology (referred to herein as droplet MDA) across a large dataset composed of 149 normal diploid cells was characterized. Using both low (0.02×) and higher (6.4×) depth whole genome sequencing (WGS), the performance of droplet MDA was compared to other recently reported state-of-the-art methods. This large single-cell dataset shows that the approach excels in one or more key performance metrics: amplification bias, robustness, scalability, and coverage breadth (fraction of genome covered by at least one sequencing read). The study further reveals that observed variability in droplet MDA performance is driven by biological difference in cell state. The copy number variation (CNV) measurement capabilities of droplet MDA and detected CNVs in single ovarian cancer cell line cells as small as 230 kb was then assessed. While it remains cost-prohibitive to perform whole genome sequencing (WGS) on large numbers of single cells to sufficient depth for single nucleotide variation (SNV) detection, targeted amplification and sequencing of single-cell WGA product can be used to infer clonal structure and evolutionary history at relatively low cost. To enable this strategy, PCR-targeted sequencing performance on single-cell droplet MDA product using known heterozygous loci was tested and a median allelic dropout (ADO) rate of 15% was observed. Finally, as a demonstration of the method on primary samples, single cells from two high-grade serous ovarian cancer samples were processed. Droplet MDA analysis was able to clearly distinguish between populations of cells with diploid and low aberration content, from those with multiple CNVs and chromosomal structure aberrations, and CNVs as small as 8 Mb were found using only 0.01× sequencing depth. Taken together, this dataset demonstrates that droplet MDA provides a scalable method of performing robust and accurate CNV and SNV measurements on large numbers of single cells.

Methods

Fabrication of Substrate:

Non-contact dispensing required removal of oil prior to deposition of additional reagents. The hydrophobicity of the substrate was thus adjusted such that deposited aqueous droplets did not excessively spread out but remained immobilized during addition and removal of oil. Glass slides (75 mm×50 mm) were spin coated with a 30 μm-layer of polydimethylsiloxane (PDMS) (Momentive). PDMS barriers, which keep the mineral oil on the reaction array, were fabricated using a polymethylmethacrylate mold. The PDMS base to curing agent ratio was 10:1 (by mass). The coated slides and barriers were baked for 24 hrs at 80° C., then stored for future use at room temperature. Immediately prior to an experiment, barriers were bonded to the slides by plasma oxidation, the assembled substrates were baked for 20 min at 80° C., then DNA was decontaminated by exposure to 4 J/cm$^2$ of UV radiation using a UV oven.

Cell Culture 184-hTERT cells were cultured at 37° C. in 5% CO2 in MEBM Mammary Epithelial Cell Basal Medium (Lonza) with 5 μg/mL transferrin (Sigma) and 2.5 μg/mL isoproterenol (Sigma). The media was further supplemented with MEGM Mammary Epithelial Cell Growth Medium Singlequots (Lonza) of 2 mL bovine pituitary extract, 0.5 mL hEGF, 0.5 mL insulin, and 0.5 mL hydrocortisone.

TOV2295 cells were cultured at 37° C. in 5% CO2 in a 1:1 mixture of MCDB 105/M199 (Sigma) supplemented with 10% fetal bovine serum.

Primary Sample Collection

The ovarian cancer samples were a subset of those used in a previous study. Briefly, tissue was obtained from tumor sites in women histologically diagnosed with high-grade serous ovarian cancer and undergoing debulking therapy. In both cases, tissue was collected prior to adjuvant therapy and frozen in cryovials.

Preparation of Cells

Cultured, frozen 184-hTERT and TOV2295 cells were thawed at room temperature. 150 μL of cells were washed with 1100 μL PBS in a 1.5 mL tube. The washed cells were pelleted by centrifugation at 2500 rpm and 4° C. for 5 min and the supernatant was discarded. After a second wash and spin, the cells were resuspended in PBS with 5% glycerol. Additional PBS with 5% glycerol was added as necessary to achieve a concentration of approximately 1 cell per 8 nL, which was confirmed by haemocytometer. SYTO9 nucleic acid stain (Life Technologies) was added to the suspension to a final concentration of 15 μM.

Preparation of Nuclei

Unsorted, 184-hTERT nuclei were prepared by thawing cultured, frozen 184-hTERT cells. 300 μL of cells was mixed with 300 μL of EZ lysis buffer (Sigma) in a 1.5 mL tube and incubated for 5 minutes on ice. 500 μL of PBS were added to the lysed cells and nuclei were pelleted by centrifugation at 2500 rpm and 4° C. for 5 min. The supernatant was discarded and the nuclei were resuspended in PBS with 5% glycerol. After filtering using a 70 μm filter, additional PBS with 5% glycerol was added as necessary to achieve a concentration of approximately 1 cell per 8 nL, which was confirmed by haemocytometer.

184-hTERT nuclei sorted by cell cycle were prepared as above but resuspended in 1 mL PBS. 2 μL of propidium iodide (PI) stain (Life Technologies) was added and nuclei were filtered through a second 70 μm filter prior to sorting. G1, S, and G2 populations were differentiated by DNA content, as determined by the relative fluorescence of PI stain, and sorted into separate 1.5 mL tubes using a FACSAria III instrument (BD Biosciences). After sorting, nuclei were diluted as necessary with PBS with 5% glycerol to achieve a concentration of approximately 1 nucleus per 8 nL.

For primary samples, three 40 μm wide cryosections were mechanically homogenized in a tube containing 1 mL EZ lysis buffer (Sigma) using a laboratory paddle-blender. The homogenized tissue was then filtered with a 70 μm filter and washed with PBS as described above. The washed nuclei were resuspended in 1 mL PBS and 2 μL of propidium iodide stain (Life Technologies) was added. Nuclei were filtered through a second 70 μm filter and sorted and diluted as described above.

The SYTO9 stain, PBS, and glycerol were all DNA decontaminated prior to use by exposure to 4 J/cm$^2$ of UV radiation using a UV oven.

Cell Deposition and Identification

Prepared cell/nuclei suspensions were aspirated and cells were deposited onto the substrate in 8 nL droplets using a non-contact piezoelectric spotter (S3, Scienion). The number of cells deposited at each position was determined by fluorescent/brightfield microscopy using a fluorescent microscope (Leica). The substrate was placed on a water-cooled chuck cooled to approximately 4° C. during all spotting steps.

Cell Lysis and Multiple Displacement Amplification

To lyse cells and nuclei and denature double-stranded genomic DNA, 6 nL of alkaline lysis buffer consisting of 400 mM KOH, 10 mM EDTA, and 100 mM DTT (pH~13) was added to each droplet. The droplet array was then covered with approximately 2 mL light mineral oil, and reactions were incubated at 65° C. for 10 min by placing the substrate onto a flatbed thermocycler (Bio-Rad). The oil was then removed by pipette and 6 nL of neutralization buffer consisting of 1 M TrisHCl (pH~4) was deposited on each droplet to neutralize the alkaline buffer. 80 nL of REPLI-g Single Cell Master mix (REPLI-g Single Cell Kit, Qiagen) supplemented with 0.1% Tween 20 surfactant was then added to each droplet and the array was again covered with light mineral oil. The MDA reactions (100 nL total volume) were then incubated at 30° C. for 18 hrs, after which amplification was discontinued by heating to 65° C. for 15 min. The mineral oil, alkaline lysis buffer, neutralization buffer, and water and Tween 20 used in the master mix were all DNA decontaminated prior to use by exposure to 4 J/cm$^2$ of UV radiation using a UV oven.

Extraction of Amplified DNA

After amplification, mineral oil was removed and approximately 250 nL of inert blue dye (Bio-Rad) was added to all reactions chosen for further processing in order to better visualize the droplets to make manual extraction by pipette easier. The array was then covered with light mineral oil and reaction droplets were extracted by pipette and transferred into 30 μL of 0.1 mM EDTA TE buffer (Teknova) in 96-well plates. Each 100 nL MDA reaction produced approximately 60 ng of double stranded DNA.

Whole Genome Library Preparation and Sequencing 5 ng of MDA product was used for sequencing library construction. DNA was fragmented by Covaris shearing, end-repaired, and A-tailed. Illumina adaptors were ligated to the fragments and the library was amplified by limited-cycle PCR, during which samples were barcoded. Samples were sequenced using a MISEQ Sequencing Instrument (Illumina), generating 75 bp paired-end reads. Samples chosen for high-depth sequencing were further sequenced on a HISEQ 2500 Sequencing System (Illumina), generating 125 bp paired-end reads.

Alignment and Analysis of Whole Genome Sequencing Data

Sequencing reads were trimmed of adaptor and barcode sequences by Illumina software on the sequencing instrument. Unaligned sequencing data (fastq files) from other published studies was downloaded from the NCBI online database. All sequencing data was aligned to the GRCh37-lite reference genome using Bowtie 2 (version 2.2.5). Aligned data was sorted and PCR duplicates were marked using Picard Tools (version 1.119). SAMtools (version 1.2) was used to index aligned, sorted data.

Statistics shown in Table 1 were calculated using Bedtools (version 2.23.0) after downsampling all samples to the same number of total sequenced bases. In samples for which bulk data was available, Control-FREEC was used to identify regions of the genome containing CNVs. These regions were omitted from subsequent analyses in the analysis of all single cell samples (Table 2).

TABLE 1

Alignment metrics for samples used in bias comparison

| Sample group | Sample | Number of reads | Number of bases | Percent duplicate reads | Percent mapped reads | Coverage breadth |
|---|---|---|---|---|---|---|
| bulk 184-hTERT gDNA | S47 | 311696 | 26332294 | 0.111968071 | 97.97976233 | 0.7368 |
| no cell/nucleus droplet | S24 | 311632 | 26324262 | 6.639882939 | 96.93901782 | 0.0359 |
| MDA | G4_S6 | 360200 | 26231462 | 23.86729595 | 97.02054414 | 0.0825 |
|  | G5_S7 | 368958 | 26337526 | 37.01695044 | 97.31134709 | 0.0765 |
| Droplet MDA on single | run10_11_S19 | 310802 | 26254854 | 0.17663979 | 98.0949286 | 0.7569 |
| unsorted 184-hTERT | run10_11_S20 | 310740 | 26250936 | 0.148033726 | 98.00090107 | 0.7676 |
| cells | run10_11_S21 | 310992 | 26270858 | 0.102896538 | 98.21281576 | 0.764 |
|  | run10_11_S22 | 311674 | 26329589 | 0.134114491 | 98.20806355 | 0.7653 |
|  | run10_11_S23 | 310762 | 26251138 | 0.176340737 | 97.90514928 | 0.7491 |
|  | run12_S10 | 311844 | 26339248 | 0.093957235 | 98.52522415 | 0.7504 |
|  | run12_S11 | 311390 | 26299992 | 0.143228749 | 98.30309258 | 0.4208 |
|  | run12_S12 | 311580 | 26315239 | 0.10494897 | 98.42223506 | 0.744 |
|  | run12_S13 | 311172 | 26281863 | 0.094802874 | 98.4214518 | 0.7548 |
|  | run12_S14 | 311878 | 26339842 | 0.120880601 | 98.363142 | 0.7421 |
|  | run12_S15 | 311226 | 26286641 | 0.094786425 | 98.44357477 | 0.7583 |
|  | run12_S16 | 312088 | 26359911 | 0.531260414 | 98.17359206 | 0.3204 |
|  | run12_S17 | 311586 | 26317081 | 0.080876548 | 98.32502102 | 0.7458 |
|  | run12_S18 | 310690 | 26242282 | 0.083040973 | 98.43187743 | 0.7487 |
|  | run12_S19 | 310866 | 26255905 | 0.092644419 | 98.50996893 | 0.7597 |
|  | run12_S1 | 311466 | 26306294 | 0.131314493 | 97.28573905 | 0.4824 |
|  | run12_S20 | 310636 | 26239410 | 0.758443967 | 98.35627551 | 0.0846 |
|  | run12_S21 | 311126 | 26279404 | 0.094174065 | 98.49450062 | 0.76 |
|  | run12_S22 | 310872 | 26257089 | 0.119341723 | 98.45145269 | 0.7625 |
|  | run12_S23 | 312038 | 26355373 | 0.110883931 | 98.50531025 | 0.761 |
|  | run12_S24 | 311354 | 26299132 | 0.123653462 | 98.50363252 | 0.7594 |
|  | run12_S25 | 311134 | 26280875 | 0.101885361 | 98.52475139 | 0.7563 |
|  | run12_S26 | 311944 | 26348394 | 0.086233427 | 98.52633806 | 0.7678 |
|  | run12_S27 | 311310 | 26293899 | 0.097330635 | 98.47226238 | 0.7568 |
|  | run12_S28 | 312078 | 26360058 | 0.099013708 | 98.61348765 | 0.7657 |
|  | run12_S29 | 311996 | 26350502 | 0.081731817 | 98.57402018 | 0.7606 |
|  | run12_S2 | 311340 | 26297755 | 0.086721912 | 97.62735273 | 0.6479 |
|  | run12_S30 | 310956 | 26265582 | 0.069463204 | 98.49946616 | 0.7653 |
|  | run12_S31 | 312046 | 26354819 | 0.094537344 | 98.64122597 | 0.7695 |
|  | run12_S32 | 311276 | 26291155 | 0.093486167 | 98.52446061 | 0.7597 |
|  | run12_S33 | 312410 | 26388532 | 0.062097884 | 98.67609872 | 0.7647 |
|  | run12_S34 | 311766 | 26332390 | 0.098150536 | 98.50560998 | 0.7614 |
|  | run12_S35 | 311222 | 26286827 | 0.103141809 | 98.62863165 | 0.7596 |
|  | run12_S36 | 311806 | 26337459 | 0.087875153 | 98.61484385 | 0.7644 |
|  | run12_S37 | 310594 | 26233830 | 0.146493493 | 97.76492785 | 0.7343 |
|  | run12_S38 | 311418 | 26303576 | 0.083167961 | 97.82960523 | 0.75 |
|  | run12_S39 | 311348 | 26297852 | 0.086398499 | 97.81209451 | 0.7112 |
|  | run12_S3 | 311048 | 26272038 | 0.195468224 | 97.99098531 | 0.4671 |
|  | run12_S40 | 310688 | 26243044 | 0.077891647 | 97.79714698 | 0.7247 |
|  | run12_S41 | 311298 | 26290050 | 0.103437863 | 97.74910215 | 0.7393 |
|  | run12_S42 | 312408 | 26387503 | 0.090266574 | 97.97060255 | 0.7526 |
|  | run12_S43 | 311906 | 26339446 | 0.100030137 | 97.38671266 | 0.7064 |

TABLE 1-continued

Alignment metrics for samples used in bias comparison

| Sample group | Sample | Number of reads | Number of bases | Percent duplicate reads | Percent mapped reads | Coverage breadth |
|---|---|---|---|---|---|---|
| | run12_S44 | 311896 | 26343110 | 0.086887937 | 97.9470721 | 0.7543 |
| | run12_S45 | 310848 | 26253533 | 0.101335701 | 97.91119776 | 0.7407 |
| | run12_S46 | 311054 | 26272825 | 0.113485118 | 97.81388441 | 0.7514 |
| | run12_S47 | 311066 | 26272806 | 0.089691577 | 97.91716227 | 0.7124 |
| | run12_S48 | 310958 | 26264741 | 0.096476051 | 97.92383537 | 0.7534 |
| | run12_S49 | 310850 | 26255142 | 0.091362393 | 98.00965096 | 0.7548 |
| | run12_S4 | 310802 | 26251475 | 0.132882028 | 98.18083539 | 0.6625 |
| | run12_S50 | 310920 | 26260694 | 0.101955487 | 97.77306059 | 0.7439 |
| | run12_S51 | 311472 | 26299921 | 0.156033287 | 95.68885807 | 0.642 |
| | run12_S52 | 312080 | 26337224 | 0.327480133 | 94.35176878 | 0.6015 |
| | run12_S53 | 310904 | 26258472 | 0.115469727 | 96.45967887 | 0.6833 |
| | run12_S54 | 311734 | 26328984 | 0.129276883 | 96.34111133 | 0.7057 |
| | run12_S55 | 311276 | 26281592 | 0.269856976 | 95.00764595 | 0.5627 |
| | run12_S56 | 311060 | 26266179 | 0.184208834 | 96.20459075 | 0.6536 |
| | run12_S57 | 310626 | 26237261 | 0.120723957 | 96.98190106 | 0.7223 |
| | run12_S58 | 311438 | 26296787 | 0.228295841 | 95.81136534 | 0.6422 |
| | run12_S59 | 310974 | 26256394 | 0.186510769 | 95.06582544 | 0.5349 |
| | run12_S5 | 311274 | 26293197 | 0.124649023 | 98.08785829 | 0.6123 |
| | run12_S60 | 311752 | 26330437 | 0.142100131 | 96.60242757 | 0.688 |
| | run12_S61 | 311826 | 26328967 | 0.193377076 | 95.9432504 | 0.6461 |
| | run12_S62 | 312492 | 26386499 | 0.186564776 | 96.11222047 | 0.6056 |
| | run12_S63 | 312652 | 26400728 | 0.148727659 | 95.88903957 | 0.6396 |
| | run12_S64 | 311452 | 26294724 | 0.119440556 | 95.38548476 | 0.5964 |
| | run12_S65 | 310894 | 26253423 | 0.182377273 | 96.50620469 | 0.6566 |
| | run12_S66 | 311794 | 26333315 | 0.15683432 | 96.80301738 | 0.7071 |
| | run12_S67 | 312054 | 26356243 | 0.098059951 | 96.50733527 | 0.7114 |
| | run12_S68 | 310722 | 26245334 | 0.126479618 | 96.51070732 | 0.7258 |
| | run12_S69 | 312308 | 26376369 | 0.146009708 | 95.91108777 | 0.7246 |
| | run12_S6 | 311598 | 26316612 | 0.112966065 | 98.0089731 | 0.5911 |
| | run12_S70 | 312200 | 26365290 | 0.198590647 | 95.6921845 | 0.6232 |
| | run12_S7 | 311450 | 26301852 | 0.084122652 | 97.88087976 | 0.5779 |
| | run12_S8 | 311220 | 26275580 | 0.077437183 | 98.37317653 | 0.7341 |
| | run12_S9 | 311144 | 26278443 | 0.809592986 | 98.17544288 | 0.076 |
| | run6_7_S10 | 311774 | 26323768 | 0.080827779 | 98.11465998 | 0.7007 |
| | run6_7_S11 | 311032 | 26261449 | 0.066874148 | 98.25677101 | 0.6874 |
| | run6_7_S12 | 311250 | 26273348 | 0.06875502 | 98.07036145 | 0.6741 |
| | run6_7_S13 | 311282 | 26283656 | 0.08513181 | 98.20259443 | 0.7027 |
| | run6_7_S14 | 310656 | 26234207 | 0.084659559 | 98.11624433 | 0.6334 |
| | run6_7_S15 | 311774 | 26328969 | 0.077620328 | 98.46298922 | 0.7183 |
| | run6_7_S16 | 311306 | 26292597 | 0.09315593 | 98.7266548 | 0.7245 |
| | run6_7_S17 | 312050 | 26355628 | 0.069219676 | 98.7226406 | 0.7321 |
| | run6_7_S18 | 311720 | 26325900 | 0.103618632 | 98.57981522 | 0.7205 |
| | run6_7_S19 | 311046 | 26270035 | 0.105129145 | 98.54362377 | 0.7183 |
| | run6_7_S20 | 310870 | 26258405 | 0.10132853 | 98.66182005 | 0.726 |
| | run6_7_S21 | 311970 | 26346214 | 0.063788185 | 98.49536814 | 0.7162 |
| | run6_7_S22 | 310580 | 26225153 | 0.08564621 | 98.59198918 | 0.6943 |
| | run6_7_S23 | 311390 | 26291859 | 0.072898937 | 98.57445647 | 0.7059 |
| | run6_7_S24 | 311834 | 26329342 | 0.077926076 | 98.58033441 | 0.7125 |
| | run6_7_S25 | 310916 | 26262206 | 0.075261485 | 98.71251399 | 0.7514 |
| | run6_7_S26 | 310802 | 26253259 | 0.085585035 | 98.48263525 | 0.7345 |
| | run6_7_S27 | 311092 | 26277977 | 0.10704229 | 98.65827472 | 0.7507 |
| | run6_7_S28 | 311590 | 26319163 | 0.092429154 | 98.62511634 | 0.746 |
| | run6_7_S29 | 310778 | 26251768 | 0.092027106 | 98.61798454 | 0.7513 |
| | run6_7_S30 | 311108 | 26279852 | 0.084215128 | 98.66734382 | 0.7537 |
| | run6_7_S31 | 310658 | 26240408 | 0.083693322 | 98.51219025 | 0.7429 |
| | run6_7_S32 | 311072 | 26277875 | 0.076831087 | 98.71315965 | 0.7519 |
| | run6_7_S33 | 310856 | 26259406 | 0.09136063 | 98.77210027 | 0.753 |
| | run6_7_S34 | 311528 | 26314314 | 0.138671323 | 97.75782594 | 0.4582 |
| | run6_7_S35 | 311140 | 26277034 | 0.064279745 | 98.06132288 | 0.6272 |
| | run6_7_S36 | 312022 | 26354477 | 0.093583145 | 97.95879778 | 0.6235 |
| | run6_7_S37 | 311412 | 26305971 | 0.083490681 | 98.6069901 | 0.7473 |
| | run6_7_S38 | 311592 | 26320383 | 0.069000488 | 98.61292973 | 0.7559 |
| | run6_7_S39 | 310902 | 26263034 | 0.081376125 | 98.54970377 | 0.7532 |
| | run6_7_S40 | 311616 | 26322816 | 0.091779626 | 98.57549035 | 0.7563 |
| | run6_7_S41 | 311354 | 26300904 | 0.098601592 | 98.75672065 | 0.747 |
| | run6_7_S42 | 311978 | 26351824 | 0.109302579 | 98.58131022 | 0.7489 |
| | run6_7_S43 | 311322 | 26298068 | 0.064884589 | 98.66729624 | 0.7548 |
| | run6_7_S44 | 311536 | 26316076 | 0.070938832 | 98.72952083 | 0.7535 |
| | run6_7_S45 | 311392 | 26303097 | 0.070650498 | 98.62038845 | 0.7471 |
| | run6_7_S46 | 312062 | 26358726 | 0.092609802 | 98.74031442 | 0.7491 |
| | run6_7_S7 | 311660 | 26321118 | 0.105563755 | 98.161458 | 0.71 |
| | run6_7_S8 | 311082 | 26268869 | 0.101259475 | 98.03363743 | 0.6688 |
| | run6_7_S9 | 311874 | 26335936 | 0.095551409 | 98.20568563 | 0.6812 |

TABLE 1-continued

Alignment metrics for samples used in bias comparison

| Sample group | Sample | Number of reads | Number of bases | Percent duplicate reads | Percent mapped reads | Coverage breadth |
|---|---|---|---|---|---|---|
| Droplet MDA on single 184-hTERT nuclei in G1 phase | S59 | 312000 | 26356323 | 0.065064103 | 97.56987179 | 0.7384 |
| | S60 | 311850 | 26341905 | 0.085297419 | 97.77392977 | 0.732 |
| | S62 | 311402 | 26304229 | 0.083814491 | 96.63907104 | 0.6918 |
| | S63 | 311554 | 26316930 | 0.082489713 | 97.71628674 | 0.7325 |
| | S64 | 311930 | 26350540 | 0.101945949 | 96.92911871 | 0.7125 |
| | S65 | 311114 | 26279703 | 0.067820799 | 97.49738038 | 0.7263 |
| | S66 | 311366 | 26300966 | 0.137137645 | 96.78802438 | 0.648 |
| | S67 | 311192 | 26287427 | 0.072623975 | 97.3855369 | 0.73 |
| | S68 | 311374 | 26301972 | 0.072260369 | 97.45579271 | 0.742 |
| | S69 | 311672 | 26327740 | 0.069945327 | 97.51469494 | 0.7389 |
| Droplet MDA on single 184-hTERT nuclei in S phase | S70 | 312348 | 26387255 | 0.069793948 | 97.14517141 | 0.7469 |
| | S71 | 311740 | 26335844 | 0.059985886 | 96.78353756 | 0.7415 |
| | S72 | 311818 | 26341793 | 0.059008781 | 97.2400567 | 0.7493 |
| | S74 | 311576 | 26319040 | 0.076385858 | 97.33130922 | 0.751 |
| | S75 | 310980 | 26270329 | 0.110618046 | 97.08727249 | 0.7456 |
| | S76 | 311194 | 26288317 | 0.062019191 | 97.17346735 | 0.7429 |
| | S77 | 310412 | 26221270 | 0.065396956 | 97.08999652 | 0.7334 |
| | S78 | 310770 | 26253784 | 0.089777006 | 96.8095376 | 0.7538 |
| | S79 | 310704 | 26244404 | 0.079818734 | 96.90380555 | 0.736 |
| | S80 | 310780 | 26253172 | 0.058562327 | 97.25111011 | 0.7568 |
| | S81 | 312016 | 26357343 | 0.080765089 | 97.20847649 | 0.7452 |
| Droplet MDA on single 184-hTERT nuclei in G2 phase | S82 | 311822 | 26338443 | 0.081136033 | 97.13618667 | 0.7428 |
| | S83 | 311468 | 26310462 | 0.07095432 | 97.19168582 | 0.7545 |
| | S84 | 311180 | 26285495 | 0.07326949 | 96.05598046 | 0.7215 |
| | S85 | 311938 | 26350291 | 0.064115305 | 97.54758959 | 0.7528 |
| | S86 | 310922 | 26264778 | 0.055962589 | 96.26851751 | 0.7485 |
| | S87 | 310728 | 26246833 | 0.095260163 | 97.19593986 | 0.7469 |
| | S88 | 311408 | 26305210 | 0.070646868 | 97.26949854 | 0.7529 |
| | S89 | 311678 | 26330701 | 0.088873774 | 97.22887082 | 0.7494 |
| | S90 | 311272 | 26292506 | 0.105374078 | 97.35536765 | 0.7537 |
| | S91 | 311234 | 26288674 | 0.077755001 | 97.11888804 | 0.7513 |
| | S92 | 311554 | 26317737 | 0.100785097 | 96.57170186 | 0.7518 |
| | S93 | 311352 | 26297965 | 0.073871374 | 96.75158663 | 0.7221 |
| | S94 | 311564 | 26317999 | 0.084733795 | 96.14043985 | 0.7305 |
| Nuc-seq single cell samples | SRX151835 | 262658 | 26265800 | 0.20559054 | 85.34748608 | 0.7095 |
| | SRX151836 | 263244 | 26324400 | 0.173223321 | 65.96693562 | 0.549 |
| MIDAS single-cell samples | SRX316149 | 527284 | 26364200 | 37.09006911 | 87.69543548 | 0.6972 |
| | SRX316150 | 525435 | 26271750 | 26.90703893 | 92.41028862 | 0.7503 |
| Microfluidic MDA single cell samples | SRX151616 | 264738 | 26209062 | 18.96478783 | 94.16706329 | 0.4818 |
| | SRX151727 | 264360 | 26171640 | 9.274852474 | 90.68278106 | 0.5194 |
| | SRX151728 | 265322 | 26266878 | 16.19541538 | 94.7897272 | 0.5267 |
| | SRX151729 | 265112 | 26246088 | 19.68752829 | 93.85957633 | 0.5264 |
| | SRX151846 | 253172 | 26299372 | 20.18785648 | 80.14906862 | 0.3839 |
| | SRX151850 | 254702 | 26300802 | 21.37910185 | 81.93418191 | 0.3942 |
| | SRX151852 | 251864 | 26233524 | 21.48778706 | 85.37464663 | 0.3935 |
| | SRX151853 | 253884 | 26224004 | 16.08648044 | 81.77199036 | 0.4361 |
| MALBAC single-cell samples | SRX202787 | 291290 | 26216100 | 6.813484843 | 84.80311717 | 0.6429 |
| | SRX202978 | 292504 | 26325360 | 6.779736345 | 85.26174001 | 0.6716 |
| | SRX204744 | 262628 | 26262800 | 19.3939717 | 93.17094902 | 0.7043 |
| | SRX204745 | 262786 | 26278600 | 21.81356693 | 91.96342271 | 0.6992 |
| | SRX205035 | 260934 | 26354334 | 7.946453893 | 58.96855143 | 0.4565 |

TABLE 2

Chromosomes considered in each cell type for bias analysis.

| Cell type | Chromosomes considered |
|---|---|
| 184-hTERT (droplet MDA) | 1, 2, 3, 4, 5, 6, 7, 8, 9, 10, 11, 12, 13, 14, 15, 16, 17, 18, 19, 21, 22, X |
| SW480 (MALBAC) | 1, 4, 10, 15, 16, 22, X |
| SK-BR-3 (nuc-seq) | 9, 11, 15, 21 |
| Sperm (microfluidic MDA) | 1, 2, 3, 4, 5, 6, 7, 8, 9, 10, 11, 12, 13, 14, 15, 16, 17, 18, 19, 20, 21, 22 |
| Neuron (MIDAS) | 1, 2, 3, 4, 5, 6, 7, 8, 9, 10, 11, 12, 13, 14, 15, 16, 17, 18, 19, 20, 21, 22, X |

Comparison of all samples using binned reads was performed as follows. The HMMcopy readcounter function was first used to determine the number of aligned reads falling within fixed-width bins across the genome for each sample. Duplicate reads were not included in these counts. The mean number of reads per bin of the sample with the fewest reads was then found, and a binomial distribution was then used to downsample the binned reads of all other samples to match this value to ensure that the same number of aligned reads was considered for all samples. HMMcopy functions in R were then used to correct downsampled binned reads for biases due to GC content and mappability.

Figures generated from binned read data were created using custom R scripts. The standard deviation (SD) of reads per bin was computed by considering log(base2) corrected reads per bin for bins considered "ideal" by HMMcopy (high mappability and no outliers). Power spectra plots were generated by concatenating the 1 kb binned read depths for each sample and considering only the number of bins of the sample with the smallest reference. Binned read depths were then entered into the R function periodogram in the "Genecycle" package, which estimates power spectral density by generating a smoothed periodogram using the command "periodogram(binned read depths, method="smooth")". To find the concordance between copy number state of bins of single cell samples and bulk DNA for the 184-hTERT cell line (FIG. 38), only bins with a mappability score above 0.85 were considered.

Lorenz curves were generated from the high depth sequencing data by downsampling all samples to the same number of aligned bases, where the reference for each sample consisted only of those chromosomes found to be free of CNVs as described above. To generate breadth vs. depth curves, each sample was downsampled to between 0.5× and 5× sequencing depth relative to its CNV-free reference at increments of 0.5× and Bedtools was used to calculated coverage breadth at each depth.

Targeted Library Preparation and Sequencing

A panel of 48 primer pairs were designed and synthesized and split into two pools of 24. Two 24-plex PCRs were assembled for each sample in 96-well plates and consisted of 50 nM forward primers, 50 nM reverse primers, approximately 5 ng MDA product, and 2× SsoFast EvaGreen PCR mix (Bio-Rad). Reactions were cycled on a Chromo 4 thermocycler (Bio-Rad) with cycling conditions of 98° C. for 3 min, followed by 18 cycles of [98° C. for 15 sec, 60° C. for 4 min, 72° C. for 30 sec] and the two 24-plexes were combined.

The multiplex product for each sample was used as template for 48 single-plex PCRs which were carried out using 48.48 Access Array integrated fluidic circuits according to the manufacturer's recommended protocol (Fluidigm). Amplicon sequencing libraries were generated and sequenced using a MISEQ Sequencing Instrument according to the manufacturer's protocol (Illumina).

Reads were trimmed of adaptor and barcode sequences by Illumina software and aligned to the GRCh37-lite reference genome using Bowtie 2. A binomial exact test was used to call the presence or absence of an allele at each locus covered by at least 50 reads. Allele dropout was calculated using the formula:

$$1 - \left( \frac{\text{homozygous calls} + 2 \times \text{heterozygous calls}}{\text{heterozygous calls in bulk}} \right)$$

Results

Nanoliter-Volume Single-Cell MDA Reaction Formulation

All cells and reagents were deposited onto a custom substrate using a commercially available piezoelectric non-contact liquid dispenser, which was used to dispense droplets with volumes ranging from 100-400 pL at a frequency of 500 Hz (FIGS. 4, 5). Droplets containing single cells were obtained by dispensing cells at limiting dilution, with observed single-cell occupancy closely approximating that predicted by the Poisson distribution. MDA reagents were then sequentially deposited onto each droplet. To minimize evaporation during heating of the substrate, the droplet array was covered with mineral oil prior to any thermocycling steps. A final MDA reaction volume of 100 nL was used for this study.

Assessment of Amplification Bias from Low Depth WGS

To evaluate the amplification bias of droplet MDA, cells from the 184-hTERT mammary epithelial cell line were analyzed. These cells have been previously well-characterized and have a chromosomally stable and nearly diploid karyotype. To make assessment of a large number of replicates practical, low depth (mean 0.02×) WGS of single-cell MDA reaction products was initially performed.

An analysis pipeline was developed, which allowed for the fair comparison of sample datasets with unequal sequencing depths. Briefly, raw reads for all samples were aligned, and unique aligned reads were binned into bins of equal size using the HMMcopy software package. Binned reads were then randomly downsampled using a binomial distribution, resulting in equal mean numbers of reads per bin across all samples, to ensure that the same quantity of aligned data, with duplicate reads removed, was compared for all samples. HMMcopy was then used to correct the binned read counts of each sample for GC and mappability biases.

The effect of amplification time on bias and coverage was first evaluated. Increasing bias with reduced MDA reaction time was observed, as determined by standard deviation (SD) of reads per 1 Mb bin (FIG. 31). This effect may be due to the lower yield of nanoliter volume reactions and losses in subsequent library preparation, as each genomic region must be amplified above a threshold to be represented in the library. Based on this result, all subsequent MDA reactions were performed for 18-20 hours. The typical yield of the 100 nL-volume MDA reactions was approximately 60 ng, representing roughly a 10,000 fold amplification of a normal diploid human genome. Low depth WGS was then performed on 149 single-cell and single-nuclei MDA products. Of these, FACS was used to obtain 10, 11, and 13 nuclei in G1, S, and G2 phases respectively (FIG. 32). The remaining 115 cells and nuclei were unsorted. Three reactions containing cell suspension fluid but no cells were also sequenced as stringent negative controls, in order to detect cell-free DNA in the suspension.

The bias of droplet MDA relative to other methods that achieve high coverage breadth were assessed: microfluidic MDA on single sperm cells, microwell MDA on single neurons (MIDAS), MDA of single cancer cell line cells in G2/M phase (Nuc-seq), and MALBAC on single cancer cell line cells, using all publicly available single-cell WGS data in each study. Sperm cells are haploid and thus are expected to have reduced coverage and increased bias over samples with higher ploidy, as is the case for all other methods that were compared. Conversely, the nuc-seq method, which selects single cells with at least 4 genome copies, is expected to benefit from increased ploidy. With this caveat, a comparison of each method using the pipeline described above to reanalyze all raw datasets using the same analysis tools and parameters and with equal quantities of aligned data was performed. To reduce the confounding of bias measurements by true biological variation in single cell genomes, CNV analysis on sequencing data from bulk DNA from cell lines where available was performed, and chromosomes with large-scale CNVs from the bias analysis were omitted (FIGS. 33A-C, Table 2). Chromosome X and Y were omitted for the sperm cells.

Basic alignment metrics using data from all samples randomly downsampled to the same number of total sequenced bases was first computed (Table 1). Single-cell droplet MDA libraries (N=149) had a mean duplicate rate of 0.12% (SD=0.025%), a mean alignment rate of 97.72% (SD=1.38%), and mean coverage breadth of 0.7% (SD=0.1%). This was the highest observed alignment rate and the lowest duplicate rate of all methods tested. Mean coverage breadth of droplet MDA samples was higher than all other datasets with the exception of those reported from MIDAS. Libraries generated from droplet MDA no-cell reactions had negligible coverage breadth (0.065%, SD=0.025%, N=3), showing that contamination, both from external sources and other reactions on the same substrate, do not contribute appreciably to sequencing data.

In order to include all sequenced single-cell droplet MDA samples, a comparison using a bin size of 1 Mb (mean reads per bin=100) was performed. Bias was then assessed by comparing the standard deviation (SD) in reads per bin (FIG. 34). When including all 149 droplet MDA samples, a median bias that is lower than both microfluidic MDA and nuc-seq was observed. When only the 8 droplet MDA samples (the highest number of samples available from any of the other methods compared) with the lowest SD were included, the droplet MDA method compares quite favorably to all other methods, with SD values of droplet MDA samples being significantly different from those of nuc-seq (two-sided Wilcoxon rank sum test p=0.044) and microfluidic MDA (p=0.00016), but not significantly different from those of MALBAC (p=0.13). These results are qualitatively reflected in the plots of read depth for the sample with the lowest SD from each method (FIG. 35). The MIDAS samples were found to exhibit SD that was below that of the unamplified bulk 184-hTERT DNA sample (0.152 versus 0.19).

Following examination of the distribution of SD values across the 149 droplet MDA samples, it was hypothesized that variability in sample state, including viability and cell cycle phase, is a major determinant of amplification performance. To test the effect of cell phase and ploidy on amplification bias, droplet MDA on single 184-hTERT cells sorted by G1, S, and G2 phases (1 Mb bins, mean reads per bin=102) was compared (FIG. 36). As previously observed, cells in G2 phase with higher ploidy yielded the lowest bias, exhibiting lower median SD than cells in other phases. These samples also exhibited lower SD than the nuc-seq samples (one-sided Wilcoxon rank sum test p=0.0095). Further, additional experiments using cryo-preserved cells generally showed increased variability and reduced performance relative to fresh samples. These results strongly support the notion that the main contributor to MDA variability is biological, and samples exhibiting the highest SD are likely cells with increased genomic variation due to the biological state of the cell, and not the result of variability in the performance of the method itself.

Assessment of Amplification Bias from High Depth WGS

Higher depth (mean 6.4×) WGS on the 15 184-hTERT single-cell droplet MDA samples with the highest coverage breadth and the 2 samples with the lowest coverage breadth as determined by low depth sequencing was next performed. A comparison was again performed to previously reported data sets by downsampling aligned reads from all datasets to a depth of 3.73× (as calculated relative to each sample's reference, taking into consideration omitted genomic regions). From this normalized data generated Lorenz curves were generated for each sample to analyse uniformity of coverage (FIG. 37A). MIDAS samples were not included in this analysis since available data was only to a depth of 0.2×. The droplet MDA samples were generally among the most uniform, with two samples having the best coverage of all datasets examined. The most biased of the droplet MDA samples was comparable to the microfluidic MDA samples. Reads were then binned using a bin size of 1 kb (mean reads per bin=30), samples from each method were ranked by SD in reads per bin, and coverage breadth was plotted as a function of sequencing depth (0.5 to 5×) for the sample with the lowest SD from each method (FIG. 37B). The droplet MDA sample achieved the highest coverage breadth of all samples at any given sequencing depth, covering approximately 80% of the reference genome when sequenced to 5× depth. Read depths from the 1 kb bins were then used to analyze the characteristic length scale of coverage bias by computing the power spectra of read density variations. Mean power spectra of all samples from each method, and the power spectrum of the sample with the lowest SD in reads per 1 kb bin from each method are presented in FIGS. 37C and 37D, respectively. As observed in other studies, the amplitudes of MDA samples generally exhibited a downward inflection point between $10^4$-$10^5$ bp, corresponding to the mean fragment length of MDA product. The mean power spectra of the droplet MDA samples dropped below that of MALBAC in this spatial frequency range as well. For the single lowest SD samples from each method, both droplet MDA and nuc-seq compared favorably with MALBAC.

CNV Calling

Since the 184-hTERT cell line is normal diploid and genomically stable, CNV-calling using droplet MDA was first assessed by comparing the concordance of copy number calls between single-cell samples and unamplified bulk DNA. The HMMcopy software package was again used, which takes in normalized binned read depth, groups contiguous bins into segments predicted to have equal copy number, and assigns an integer copy number to bins in each segment using a Hidden Markov Model. The high depth WGS data from the 15 samples and the unamplified bulk DNA was binned into bins of 1 Mb, 100 kb, and 10 kb (mean reads per bin=100), assigned an integer copy number to each bin using HMMcopy, and the bin-wise concordance between each single-cell sample and bulk was computed (FIG. 38). At 1 Mb, 100 kb, and 10 kb resolutions, the median concordance rate was 96.4% (2,487 bins), 93.1% (24,162 bins), and 83.4% (227,172 bins) respectively.

Droplet MDA was also applied to 30 single cells from the TOV2295 cell line, derived from an ovarian tumor, which is genomically unstable and has CNVs on multiple length scales. Low depth (mean 0.02×) WGS was performed on all 30 samples, and higher depth WGS (mean 6.4×) was performed on the 8 samples with the highest coverage breadth calculated from the low depth WGS data. Using the high depth data, reads were binned into 1 Mb, 100 kb, and 10 kb bins (mean reads per bin=100). Read depth plots from the 5 single-cell samples with the lowest SD in reads per bin (1 Mb bin size) qualitatively matched that of bulk DNA (FIG. 39) with many of the same large-scale variations discernible in both. HMMcopy was then used to find segments of contiguous bins with the same copy number. Since, unlike the 184-hTERT cell line, the TOV2295 cell line is genomically unstable, there is likely to be biological variation between the copy number profiles of individual single cells and the bulk sample. Nonetheless, segments with identical genomic location, length, and copy number in two or more of the single-cell and bulk samples were detected, as well as segments in two or more single-cell samples but not in the bulk (Table 2, Table 3). These segments may represent true CNV events and cell-to-cell heterogeneity. Using a 10 kb bin size, the smallest such segment with normal diploid copy number was 200 kb in length, while the smallest segment with abnormal copy number was 230 kb in length.

Table 3 shows the copy number segments identified in two or more TOV2295 single-cell and bulk DNA samples. "Reps" indicates the number of samples the segment appears in. Table A shows "State" values and their corresponding numeric copy numbers (for tables 3-5).

TABLE A

State values and corresponding copy number values for Tables 3-5.

| state | integer copy number |
|---|---|
| 1 | <=0 copies, homozygous deletion |
| 2 | 1 copy, heterozygous deletion |
| 3 | 2 copies, neutral |
| 4 | 3 copies, gain |
| 5 | 4 copies, amplification |
| 6 | >=5 copies, high level amplification |

TABLE 3

Copy number segments identified in two or more TOV2295 single-cell and bulk DNA samples.

| chr | start | end | state | size | reps |
|---|---|---|---|---|---|
| 1 | 1 | 690000 | 3 | 6.90E+05 | 3 |
| 1 | 1 | 7.00E+05 | 3 | 7.00E+05 | 2 |
| 1 | 1 | 780000 | 3 | 7.80E+05 | 2 |
| 1 | 143290001 | 143720000 | 2 | 4.30E+05 | 2 |
| 2 | 338760001 | 339660000 | 1 | 9.00E+05 | 2 |
| 3 | 531660001 | 532080000 | 2 | 4.20E+05 | 2 |
| 3 | 669360001 | 669730000 | 3 | 3.70E+05 | 2 |
| 4 | 881030001 | 881650000 | 2 | 6.20E+05 | 2 |
| 4 | 881030001 | 881650000 | 3 | 6.20E+05 | 3 |
| 4 | 881170001 | 881650000 | 2 | 4.80E+05 | 2 |
| 5 | 927530001 | 931200000 | 2 | 3.67E+06 | 2 |
| 5 | 927540001 | 931200000 | 1 | 3.66E+06 | 2 |
| 5 | 1006390001 | 1008170000 | 5 | 1.78E+06 | 2 |
| 6 | 1062570001 | 1062810000 | 3 | 2.40E+05 | 2 |
| 6 | 1120150001 | 1120710000 | 2 | 5.60E+05 | 2 |
| 6 | 1120710001 | 1121300000 | 4 | 5.90E+05 | 2 |
| 6 | 1121300001 | 1128310000 | 2 | 7.01E+06 | 2 |
| 7 | 1306130001 | 1309850000 | 2 | 3.72E+06 | 2 |
| 7 | 1391130001 | 1392830000 | 2 | 1.70E+06 | 2 |
| 8 | 1479380001 | 1479670000 | 6 | 2.90E+05 | 3 |
| 8 | 1538620001 | 1539200000 | 5 | 5.80E+05 | 3 |
| 9 | 1584050001 | 1607550000 | 2 | 2.35E+07 | 2 |
| 9 | 1679680001 | 1680420000 | 3 | 7.40E+05 | 2 |
| 9 | 1679720001 | 1680420000 | 3 | 7.00E+05 | 2 |
| 10 | 1814670001 | 1815960000 | 2 | 1.29E+06 | 2 |
| 11 | 1815960001 | 1816160000 | 3 | 2.00E+05 | 4 |
| 11 | 1878760001 | 1879260000 | 4 | 5.00E+05 | 2 |
| 12 | 2081430001 | 2084830000 | 2 | 3.40E+06 | 2 |
| 14 | 2200000001 | 2219190000 | 3 | 1.92E+07 | 3 |
| 15 | 2307350001 | 2327700000 | 3 | 2.03E+07 | 2 |
| 16 | 2430890001 | 2431300000 | 2 | 4.10E+05 | 2 |
| 17 | 2500250001 | 2503180000 | 3 | 2.93E+06 | 2 |
| 17 | 2564790001 | 2581450000 | 4 | 1.67E+07 | 2 |
| 18 | 2658900001 | 2659530000 | 3 | 6.30E+05 | 2 |
| 19 | 2659530001 | 2659760000 | 4 | 2.30E+05 | 2 |

TABLE 3-continued

Copy number segments identified in two or more TOV2295 single-cell and bulk DNA samples.

| chr | start | end | state | size | reps |
|---|---|---|---|---|---|
| 19 | 2659530001 | 2659770000 | 3 | 2.40E+05 | 2 |
| 20 | 2748240001 | 2748680000 | 5 | 4.40E+05 | 2 |
| 21 | 2781690001 | 2791680000 | 2 | 9.99E+06 | 2 |
| 21 | 2781690001 | 2791730000 | 3 | 1.00E+07 | 4 |
| 21 | 2791730001 | 2792870000 | 4 | 1.14E+06 | 3 |
| 21 | 2826700001 | 2829820000 | 1 | 3.12E+06 | 2 |
| 23 | 2887610001 | 2889230000 | 3 | 1.62E+06 | 2 |

Targeted Sequencing

To evaluate the effectiveness of droplet MDA for nucleotide-level measurements, targeted sequencing was performed on 29 of the 184-hTERT single cell droplet MDA samples that were whole genome sequenced. For each sample, a portion of the MDA product was used as template for a multiplex PCR reaction using 39 primer pairs targeting known heterozygous loci. The product was then inputted into singleplex PCR reactions targeting each locus using a commercial microfluidic device (Access Array™, Fluidigm Corp.). Products of all single-cell samples were then indexed, pooled and sequenced. For each sample, a binomial exact test was used to call the presence or absence of an allele at each locus covered by at least 50 reads (FIG. 40). The median allele dropout (ADO) across all samples was calculated to be 15%. As both targeted and whole genome sequencing on these samples was performed, it was determined whether there was any correlation between targeted sequencing performance and bias measured by WGS. Single-cell samples with lower SD in reads per 1 Mb bin generally also had lower ADO (FIG. 41). When including only the 25% of samples with lowest SD in reads per 1 MB, the median ADO is reduced to 8%.

Demonstration on Ovarian Cancers

As a demonstration of the applicability of droplet MDA to primary samples, the method was applied to 40 single nuclei isolated from two high-grade serous ovarian cancer tumor specimens that have been previously characterized in bulk using high-depth whole genome sequencing, low depth (0.01x) WGS was performed, and reads were binned using a bin size of 1 Mb. For each specimen, read depth plots of the 4 single nuclei samples with the lowest SD in reads per bin are shown (FIGS. 42A-B). In both cases, read depth profiles from 3 of the single nuclei closely matched that of bulk DNA while a fourth nucleus appeared to have a normal diploid genome, likely from non-cancerous tissue which was collected with the tumor. Using the binned read depths, copy number segments common to two or more samples (single nuclei and bulk) for each specimen was again found. 90 and 131 such segments ranging in length from 8 Mb to 250 Mb, and 11 Mb to 250 Mb for specimens 1 and 2, respectively were found (Table 4, Table 5).

TABLE 4

Copy number segments identified in two or more single-cell and bulk DNA samples from ovarian cancer specimen 1.

| chr | start | end | state | size | reps |
|---|---|---|---|---|---|
| 1 | 1 | 1.17E+08 | 3 | 1.17E+08 | 2 |
| 1 | 1 | 2.50E+08 | 3 | 2.50E+08 | 11 |
| 1 | 117000001 | 2.50E+08 | 4 | 1.33E+08 | 2 |
| 1 | 230000001 | 2.50E+08 | 4 | 2.00E+07 | 2 |

TABLE 4-continued

Copy number segments identified in two or more single-cell and bulk DNA samples from ovarian cancer specimen 1.

| chr | start | end | state | size | reps |
|---|---|---|---|---|---|
| 2 | 250000001 | 4.94E+08 | 3 | 2.44E+08 | 2 |
| 2 | 250000001 | 4.94E+08 | 4 | 2.44E+08 | 9 |
| 3 | 494000001 | 5.92E+08 | 3 | 9.80E+07 | 3 |
| 3 | 494000001 | 6.93E+08 | 2 | 1.99E+08 | 2 |
| 3 | 494000001 | 6.93E+08 | 3 | 1.99E+08 | 4 |
| 3 | 589000001 | 6.93E+08 | 4 | 1.04E+08 | 2 |
| 3 | 592000001 | 6.93E+08 | 4 | 1.01E+08 | 3 |
| 4 | 693000001 | 8.85E+08 | 2 | 1.92E+08 | 2 |
| 4 | 693000001 | 8.85E+08 | 3 | 1.92E+08 | 14 |
| 5 | 885000001 | 1.07E+09 | 3 | 1.81E+08 | 16 |
| 6 | 1066000001 | 1.11E+09 | 4 | 4.10E+07 | 2 |
| 6 | 1066000001 | 1.11E+09 | 4 | 4.40E+07 | 2 |
| 6 | 1066000001 | 1.11E+09 | 4 | 4.60E+07 | 2 |
| 6 | 1066000001 | 1.24E+09 | 3 | 1.72E+08 | 8 |
| 6 | 1110000001 | 1.24E+09 | 3 | 1.28E+08 | 2 |
| 6 | 1112000001 | 1.24E+09 | 3 | 1.26E+08 | 2 |
| 7 | 1238000001 | 1.40E+09 | 3 | 1.60E+08 | 3 |
| 7 | 1238000001 | 1.40E+09 | 4 | 1.60E+08 | 5 |
| 7 | 1238000001 | 1.40E+09 | 5 | 1.60E+08 | 10 |
| 8 | 1398000001 | 1.44E+09 | 1 | 4.10E+07 | 2 |
| 8 | 1398000001 | 1.45E+09 | 1 | 4.70E+07 | 3 |
| 8 | 1398000001 | 1.45E+09 | 2 | 4.70E+07 | 3 |
| 8 | 1398000001 | 1.45E+09 | 2 | 4.80E+07 | 4 |
| 8 | 1398000001 | 1.55E+09 | 3 | 1.47E+08 | 3 |
| 8 | 1445000001 | 1.55E+09 | 4 | 1.00E+08 | 6 |
| 8 | 1446000001 | 1.55E+09 | 4 | 9.90E+07 | 4 |
| 9 | 1545000001 | 1.62E+09 | 4 | 7.00E+07 | 2 |
| 9 | 1545000001 | 1.62E+09 | 5 | 7.10E+07 | 2 |
| 9 | 1545000001 | 1.69E+09 | 3 | 1.42E+08 | 10 |
| 9 | 1615000001 | 1.69E+09 | 3 | 7.20E+07 | 2 |
| 10 | 1687000001 | 1.73E+09 | 4 | 3.90E+07 | 4 |
| 10 | 1687000001 | 1.73E+09 | 5 | 3.90E+07 | 2 |
| 10 | 1687000001 | 1.73E+09 | 4 | 4.30E+07 | 2 |
| 10 | 1687000001 | 1.73E+09 | 5 | 4.30E+07 | 3 |
| 10 | 1687000001 | 1.73E+09 | 4 | 4.40E+07 | 2 |
| 10 | 1687000001 | 1.82E+09 | 3 | 1.36E+08 | 2 |
| 10 | 1726000001 | 1.82E+09 | 1 | 9.70E+07 | 7 |
| 10 | 1730000001 | 1.82E+09 | 2 | 9.30E+07 | 3 |
| 10 | 1731000001 | 1.82E+09 | 1 | 9.20E+07 | 3 |
| 11 | 1823000001 | 1.96E+09 | 3 | 1.36E+08 | 14 |
| 11 | 1823000001 | 1.96E+09 | 4 | 1.36E+08 | 2 |
| 12 | 1959000001 | 2.04E+09 | 4 | 7.60E+07 | 3 |
| 12 | 1959000001 | 2.04E+09 | 4 | 7.70E+07 | 3 |
| 12 | 1959000001 | 2.09E+09 | 3 | 1.34E+08 | 4 |
| 12 | 2035000001 | 2.09E+09 | 2 | 5.80E+07 | 3 |
| 12 | 2036000001 | 2.09E+09 | 2 | 5.70E+07 | 4 |
| 13 | 2093000001 | 2.21E+09 | 2 | 1.16E+08 | 4 |
| 13 | 2093000001 | 2.21E+09 | 3 | 1.16E+08 | 12 |
| 14 | 2209000001 | 2.32E+09 | 3 | 1.08E+08 | 12 |
| 14 | 2209000001 | 2.32E+09 | 4 | 1.08E+08 | 3 |
| 15 | 2317000001 | 2.42E+09 | 3 | 1.03E+08 | 18 |
| 16 | 2420000001 | 2.45E+09 | 3 | 3.40E+07 | 9 |
| 16 | 2420000001 | 2.51E+09 | 1 | 9.10E+07 | 2 |
| 16 | 2420000001 | 2.51E+09 | 2 | 9.10E+07 | 2 |
| 16 | 2420000001 | 2.51E+09 | 3 | 9.10E+07 | 4 |
| 16 | 2454000001 | 2.51E+09 | 1 | 5.70E+07 | 11 |
| 17 | 2511000001 | 2.55E+09 | 1 | 4.10E+07 | 3 |
| 17 | 2511000001 | 2.59E+09 | 2 | 8.20E+07 | 7 |
| 17 | 2511000001 | 2.59E+09 | 3 | 8.20E+07 | 5 |
| 17 | 2552000001 | 2.59E+09 | 3 | 4.10E+07 | 2 |
| 18 | 2593000001 | 2.67E+09 | 1 | 7.90E+07 | 10 |
| 18 | 2593000001 | 2.67E+09 | 2 | 7.90E+07 | 5 |
| 18 | 2593000001 | 2.67E+09 | 3 | 7.90E+07 | 2 |
| 18 | 2626000001 | 2.67E+09 | 1 | 4.60E+07 | 2 |
| 19 | 2672000001 | 2.68E+09 | 1 | 8.00E+06 | 2 |
| 19 | 2672000001 | 2.68E+09 | 2 | 8.00E+06 | 2 |
| 19 | 2672000001 | 2.72E+09 | 6 | 4.70E+07 | 3 |
| 19 | 2672000001 | 2.73E+09 | 3 | 6.00E+07 | 4 |
| 19 | 2672000001 | 2.73E+09 | 4 | 6.00E+07 | 3 |
| 19 | 2672000001 | 2.73E+09 | 5 | 6.00E+07 | 2 |
| 19 | 2680000001 | 2.72E+09 | 6 | 3.90E+07 | 4 |
| 19 | 2719000001 | 2.73E+09 | 1 | 1.30E+07 | 2 |
| 19 | 2719000001 | 2.73E+09 | 2 | 1.30E+07 | 4 |
| 19 | 2719000001 | 2.73E+09 | 3 | 1.30E+07 | 3 |
| 20 | 2732000001 | 2.80E+09 | 2 | 6.40E+07 | 3 |
| 20 | 2732000001 | 2.80E+09 | 3 | 6.40E+07 | 16 |
| 21 | 2796000001 | 2.85E+09 | 1 | 4.90E+07 | 2 |
| 21 | 2796000001 | 2.85E+09 | 2 | 4.90E+07 | 3 |
| 21 | 2796000001 | 2.85E+09 | 3 | 4.90E+07 | 12 |
| 21 | 2796000001 | 2.85E+09 | 4 | 4.90E+07 | 2 |
| 22 | 2845000001 | 2.90E+09 | 1 | 5.20E+07 | 10 |
| 22 | 2845000001 | 2.90E+09 | 2 | 5.20E+07 | 6 |
| 22 | 2845000001 | 2.90E+09 | 3 | 5.20E+07 | 3 |
| X | 2898000001 | 3.05E+09 | 1 | 1.56E+08 | 2 |
| X | 2898000001 | 3.05E+09 | 2 | 1.56E+08 | 11 |
| X | 2898000001 | 3.05E+09 | 3 | 1.56E+08 | 3 |

"Reps" indicates the number of samples the segment appears in.

TABLE 5

Copy number segments identified in two or more single-cell and bulk DNA samples from ovarian cancer specimen 2

| chr | start | end | state | size | reps |
|---|---|---|---|---|---|
| 1 | 1 | 3.70E+07 | 2 | 3.70E+07 | 2 |
| 1 | 1 | 3.80E+07 | 1 | 3.80E+07 | 4 |
| 1 | 1 | 3.80E+07 | 2 | 3.80E+07 | 4 |
| 1 | 1 | 2.50E+08 | 3 | 2.50E+08 | 4 |
| 1 | 36000001 | 2.50E+08 | 3 | 2.14E+08 | 2 |
| 1 | 37000001 | 2.50E+08 | 4 | 2.13E+08 | 2 |
| 1 | 38000001 | 2.50E+08 | 3 | 2.12E+08 | 4 |
| 2 | 250000001 | 2.78E+08 | 1 | 2.80E+07 | 6 |
| 2 | 250000001 | 2.78E+08 | 2 | 2.80E+07 | 2 |
| 2 | 250000001 | 4.94E+08 | 3 | 2.44E+08 | 4 |
| 2 | 277000001 | 4.94E+08 | 3 | 2.17E+08 | 2 |
| 2 | 278000001 | 4.94E+08 | 3 | 2.16E+08 | 3 |
| 3 | 494000001 | 6.82E+08 | 3 | 1.88E+08 | 3 |
| 3 | 494000001 | 6.93E+08 | 3 | 1.99E+08 | 10 |
| 3 | 494000001 | 6.93E+08 | 4 | 1.99E+08 | 2 |
| 3 | 682000001 | 6.93E+08 | 1 | 1.10E+07 | 3 |
| 4 | 693000001 | 7.43E+08 | 3 | 5.00E+07 | 2 |
| 4 | 693000001 | 7.50E+08 | 3 | 5.70E+07 | 6 |
| 4 | 693000001 | 7.50E+08 | 4 | 5.70E+07 | 4 |
| 4 | 693000001 | 7.53E+08 | 4 | 6.00E+07 | 2 |
| 4 | 693000001 | 8.85E+08 | 3 | 1.92E+08 | 2 |
| 4 | 750000001 | 8.25E+08 | 1 | 7.50E+07 | 2 |
| 4 | 750000001 | 8.85E+08 | 2 | 1.35E+08 | 5 |
| 4 | 750000001 | 8.85E+08 | 3 | 1.35E+08 | 2 |
| 4 | 825000001 | 8.51E+08 | 3 | 2.60E+07 | 3 |
| 4 | 851000001 | 8.85E+08 | 1 | 3.40E+07 | 4 |
| 5 | 885000001 | 9.39E+08 | 4 | 5.40E+07 | 2 |
| 5 | 885000001 | 9.51E+08 | 4 | 6.60E+07 | 5 |
| 5 | 885000001 | 1.07E+09 | 3 | 1.81E+08 | 2 |
| 5 | 939000001 | 1.07E+09 | 2 | 1.27E+08 | 2 |
| 5 | 951000001 | 1.07E+09 | 2 | 1.15E+08 | 3 |
| 6 | 1066000001 | 1.08E+09 | 1 | 1.30E+07 | 5 |
| 6 | 1066000001 | 1.08E+09 | 2 | 1.40E+07 | 3 |
| 6 | 1066000001 | 1.14E+09 | 3 | 7.50E+07 | 3 |
| 6 | 1066000001 | 1.24E+09 | 3 | 1.72E+08 | 2 |
| 6 | 1079000001 | 1.14E+09 | 4 | 6.20E+07 | 3 |
| 6 | 1080000001 | 1.14E+09 | 4 | 6.00E+07 | 2 |
| 6 | 1141000001 | 1.24E+09 | 2 | 9.70E+07 | 2 |
| 6 | 1191000001 | 1.24E+09 | 1 | 4.70E+07 | 3 |
| 6 | 1192000001 | 1.24E+09 | 1 | 4.60E+07 | 3 |
| 7 | 1238000001 | 1.30E+09 | 3 | 6.30E+07 | 2 |
| 7 | 1238000001 | 1.30E+09 | 3 | 6.50E+07 | 5 |
| 7 | 1238000001 | 1.30E+09 | 3 | 6.60E+07 | 4 |
| 7 | 1238000001 | 1.40E+09 | 3 | 1.60E+08 | 2 |
| 7 | 1303000001 | 1.40E+09 | 5 | 9.50E+07 | 4 |
| 7 | 1304000001 | 1.40E+09 | 5 | 9.40E+07 | 2 |
| 7 | 1377000001 | 1.40E+09 | 6 | 2.10E+07 | 4 |
| 8 | 1398000001 | 1.49E+09 | 3 | 8.90E+07 | 2 |
| 8 | 1398000001 | 1.49E+09 | 3 | 9.10E+07 | 2 |

TABLE 5-continued

Copy number segments identified in two or more single-cell and bulk DNA samples from ovarian cancer specimen 2

| chr | start | end | state | size | reps |
|---|---|---|---|---|---|
| 8 | 1398000001 | 1.49E+09 | 3 | 9.30E+07 | 7 |
| 8 | 1398000001 | 1.49E+09 | 4 | 9.40E+07 | 2 |
| 8 | 1487000001 | 1.55E+09 | 5 | 5.80E+07 | 2 |
| 8 | 1489000001 | 1.55E+09 | 5 | 5.60E+07 | 2 |
| 8 | 1491000001 | 1.55E+09 | 5 | 5.40E+07 | 7 |
| 8 | 1529000001 | 1.55E+09 | 5 | 1.60E+07 | 2 |
| 9 | 1545000001 | 1.59E+09 | 2 | 4.00E+07 | 2 |
| 9 | 1545000001 | 1.59E+09 | 2 | 4.20E+07 | 2 |
| 9 | 1545000001 | 1.61E+09 | 2 | 6.60E+07 | 5 |
| 9 | 1545000001 | 1.69E+09 | 3 | 1.42E+08 | 5 |
| 9 | 1585000001 | 1.69E+09 | 3 | 1.02E+08 | 3 |
| 9 | 1587000001 | 1.69E+09 | 3 | 1.00E+08 | 3 |
| 9 | 1611000001 | 1.69E+09 | 3 | 7.60E+07 | 4 |
| 9 | 1611000001 | 1.69E+09 | 4 | 7.60E+07 | 2 |
| 10 | 1687000001 | 1.78E+09 | 3 | 8.80E+07 | 5 |
| 10 | 1687000001 | 1.78E+09 | 3 | 8.90E+07 | 2 |
| 10 | 1687000001 | 1.79E+09 | 3 | 1.03E+08 | 2 |
| 10 | 1687000001 | 1.79E+09 | 3 | 1.06E+08 | 2 |
| 10 | 1687000001 | 1.79E+09 | 3 | 1.07E+08 | 2 |
| 10 | 1687000001 | 1.82E+09 | 2 | 1.36E+08 | 3 |
| 10 | 1687000001 | 1.82E+09 | 3 | 1.36E+08 | 2 |
| 10 | 1775000001 | 1.82E+09 | 1 | 4.80E+07 | 4 |
| 10 | 1776000001 | 1.82E+09 | 2 | 4.70E+07 | 2 |
| 10 | 1793000001 | 1.82E+09 | 1 | 3.00E+07 | 2 |
| 10 | 1794000001 | 1.82E+09 | 1 | 2.90E+07 | 2 |
| 11 | 1823000001 | 1.89E+09 | 3 | 6.80E+07 | 2 |
| 11 | 1823000001 | 1.89E+09 | 3 | 7.10E+07 | 5 |
| 11 | 1823000001 | 1.96E+09 | 3 | 1.36E+08 | 2 |
| 11 | 1891000001 | 1.96E+09 | 2 | 6.80E+07 | 3 |
| 11 | 1894000001 | 1.96E+09 | 1 | 6.50E+07 | 3 |
| 11 | 1894000001 | 1.96E+09 | 2 | 6.50E+07 | 3 |
| 12 | 1959000001 | 1.99E+09 | 5 | 3.00E+07 | 2 |
| 12 | 1959000001 | 1.99E+09 | 5 | 3.40E+07 | 2 |
| 12 | 1959000001 | 1.99E+09 | 4 | 3.50E+07 | 4 |
| 12 | 1959000001 | 2.00E+09 | 5 | 3.70E+07 | 7 |
| 12 | 1959000001 | 2.09E+09 | 3 | 1.34E+08 | 2 |
| 12 | 1959000001 | 2.09E+09 | 4 | 1.34E+08 | 2 |
| 12 | 1989000001 | 2.09E+09 | 3 | 1.04E+08 | 2 |
| 12 | 1996000001 | 2.01E+09 | 1 | 1.30E+07 | 2 |
| 12 | 1996000001 | 2.09E+09 | 3 | 9.70E+07 | 6 |
| 12 | 2009000001 | 2.09E+09 | 3 | 8.40E+07 | 2 |
| 13 | 2093000001 | 2.16E+09 | 3 | 6.30E+07 | 8 |
| 13 | 2093000001 | 2.16E+09 | 4 | 6.30E+07 | 5 |
| 13 | 2093000001 | 2.21E+09 | 3 | 1.16E+08 | 4 |
| 13 | 2156000001 | 2.21E+09 | 1 | 5.30E+07 | 5 |
| 13 | 2156000001 | 2.21E+09 | 2 | 5.30E+07 | 9 |
| 14 | 2209000001 | 2.30E+09 | 1 | 9.30E+07 | 2 |
| 14 | 2209000001 | 2.30E+09 | 2 | 9.30E+07 | 2 |
| 14 | 2209000001 | 2.30E+09 | 1 | 9.40E+07 | 2 |
| 14 | 2209000001 | 2.32E+09 | 1 | 1.08E+08 | 3 |
| 14 | 2209000001 | 2.32E+09 | 2 | 1.08E+08 | 9 |
| 14 | 2302000001 | 2.32E+09 | 4 | 1.50E+07 | 4 |
| 14 | 2303000001 | 2.32E+09 | 4 | 1.40E+07 | 3 |
| 15 | 2317000001 | 2.42E+09 | 3 | 1.03E+08 | 18 |
| 15 | 2317000001 | 2.42E+09 | 4 | 1.03E+08 | 3 |
| 16 | 2420000001 | 2.51E+09 | 3 | 9.10E+07 | 6 |
| 16 | 2420000001 | 2.51E+09 | 4 | 9.10E+07 | 11 |
| 17 | 2511000001 | 2.52E+09 | 3 | 1.10E+07 | 4 |
| 17 | 2511000001 | 2.59E+09 | 2 | 8.20E+07 | 12 |
| 17 | 2522000001 | 2.59E+09 | 1 | 7.10E+07 | 5 |
| 18 | 2593000001 | 2.67E+09 | 3 | 7.90E+07 | 14 |
| 18 | 2593000001 | 2.67E+09 | 4 | 7.90E+07 | 3 |
| 19 | 2672000001 | 2.71E+09 | 3 | 4.00E+07 | 2 |
| 19 | 2672000001 | 2.71E+09 | 3 | 4.20E+07 | 2 |
| 19 | 2672000001 | 2.73E+09 | 2 | 6.00E+07 | 2 |
| 19 | 2672000001 | 2.73E+09 | 3 | 6.00E+07 | 10 |
| 19 | 2712000001 | 2.73E+09 | 1 | 2.00E+07 | 3 |
| 19 | 2714000001 | 2.73E+09 | 1 | 1.80E+07 | 2 |
| 20 | 2732000001 | 2.80E+09 | 3 | 6.40E+07 | 17 |
| 20 | 2732000001 | 2.80E+09 | 4 | 6.40E+07 | 3 |
| 21 | 2796000001 | 2.85E+09 | 1 | 4.90E+07 | 6 |
| 21 | 2796000001 | 2.85E+09 | 2 | 4.90E+07 | 11 |
| 21 | 2796000001 | 2.85E+09 | 3 | 4.90E+07 | 3 |
| 22 | 2845000001 | 2.90E+09 | 2 | 5.20E+07 | 11 |
| 22 | 2845000001 | 2.90E+09 | 3 | 5.20E+07 | 6 |
| X | 2898000001 | 3.02E+09 | 3 | 1.20E+08 | 3 |
| X | 2898000001 | 3.02E+09 | 4 | 1.20E+08 | 3 |
| X | 2898000001 | 3.02E+09 | 4 | 1.21E+08 | 3 |
| X | 3018000001 | 3.05E+09 | 5 | 3.60E+07 | 4 |
| X | 3018000001 | 3.05E+09 | 6 | 3.60E+07 | 2 |
| X | 3019000001 | 3.05E+09 | 6 | 3.50E+07 | 5 |

"Reps" indicates the number of samples the segment appears in.

This example demonstrates a single-cell MDA method that exploits the improved reaction kinetics and reduced reagent consumption of nanoliter-scale volumes using a commercially available liquid dispensing system has been developed. This approach preserves the programmable and multistep nanoliter-volume processing of microfluidic droplet-based devices, but without the need for specialized microfabrication. Unlike systems that formulate nanoliter-volume single-cell reactions on an open array, this method avoids the possibility of cross-contamination between reactions by using non-contact dispensing to place reactions in spatially distinct locations separated by oil. This approach is also rapid and highly scalable, providing a straightforward path to assembling over 1000 reactions on a 1 square inch substrate. In this study, 154 100 nL-reactions were formulated per substrate in approximately 4 minutes, and this number could be increased significantly by simply reducing the pitch of the droplet array and/or increasing the substrate area. In combination with a micromanipulation system that could deposit a single cell onto a predetermined substrate location, the open-array format also enables applications in which the improved reaction kinetics from nanoliter-volume processing are desired but only a few single cells are available and each cell must be tracked from sample collection to reaction formulation, an application that is not currently possible with existing microfluidic devices.

Using this system, for the first time, robust low-bias single-cell nanoliter-volume MDA on a large dataset composed of 149 normal diploid single cells has been demonstrated, while previous studies have presented data from less than 10 replicates. In total, 219 single-cell droplet MDA samples were analyzed for this study. Such large replicate sets are essential to establish reproducibility that is needed in applications such as single-cell tumor sequencing where biological insight depends on a method that is consistent across large numbers of cells. The low depth WGS data indicate that, overall, the bias of droplet MDA compares favorably to that of other methods considered, with the least biased samples being on par with other methods. The bias comparisons of cells sorted by cell state suggest that the poor uniformity of coverage of the most biased samples is not technical, but rather represents true genomic variation of the cells, potentially being the result of cell cycle, necrosis or apoptosis. The high depth WGS data shows that the least biased samples have comparably low bias on multiple length scales. This highly uniform coverage allows for a high fraction of the genome to be recovered with relatively low sequencing effort and also enables accurate CNV calling. Copy number segments as small as 200 kb in length were identified using 6.4×WGS in a cancer cell line, and as small as 8 Mb in primary tumor specimens using only 0.02× WGS. In both primary specimens, low depth WGS was also used to distinguish likely non-cancerous cells from the tumor. A significant advantage of MDA is that its high coverage breadth and large mean fragment length allow for both whole genome sequencing and targeted sequencing to be applied to the same single cell. This was demonstrated by performing both on 29 single cells, achieving excellent SNV measurement performance as quantified by low ADO.

Ultimately, this method provides an accessible way for researchers to exploit the benefits of nanoliter-volume processing for robust and cost-effective interrogation of single-cell genomic variation at both the copy number and single-nucleotide level.

Example 12—Transposase-Based Haplotyping in Nanoliter-Scale Reaction Volumes Nanolitre-Volume CPT-Seq In CPT-seq, high-molecular weight DNA is aliquoted into separate reactions, each of which contains a Tn5 transposase-DNA adaptor complex (transposome) with a unique adaptor sequence. Tn5 transposase has the beneficial property of remaining bound to a DNA template molecule, without fragmenting it, until a protein denaturation treatment is applied. This allows each DNA template molecule to be indexed by the transposome multiple times for short-read sequencing library preparation while keeping the template molecule structurally intact, allowing the original template molecule to be bioinformatically reconstructed using the index. Thus, the contiguity between alleles that co-occur on the same molecule is physically preserved, and the length over which this contiguity is preserved (haplotype block length) is limited only by the length of the template molecule. After the transposition reaction, all aliquots are pooled and then re-aliquoted into a new set of reaction containers. The transposase is denatured, causing the template molecules to be fragmented into adaptor-tagged fragments 100-300 bp in length, and these fragments are then PCR-amplified, with each reaction having a unique DNA index sequence. The binding property of the transposome to the original template molecule allows contiguity to be preserved while the template is pooled and re-aliquoted. Without this property, the template would be fragmented by the transposase, and contiguity between alleles on the same molecule would be lost. The PCR product is then sequenced.

These two levels of indexing—one for transposition and one for PCR—allow for the original template to be "virtually" partitioned into N×M partitions where N is the number of transposition reactions and M is the number of PCR reactions. This partitioning is important in order to prevent maternal and paternal copies of the same genomic region from being present in the same partition, as this would prevent proper haplotyping of this region. The two-level indexing strategy allows for this high number of partitions while having to use only N and M physical containers. It also allows for the template concentration in each PCR reaction to be much higher than it would be without this strategy.

Transposition and PCR amplification efficiencies are improved by reducing reaction volumes to the nanoliter-scale. This is evidenced by the ability to obtain breadth of coverage comparable to that of bulk genomic DNA when combining sequencing data from nanoliter-volume transposase-based sequencing library preparation on 10 individual single cells. Thus, performing CPT-seq with all reactions in nanoliter-scale volumes may improve coverage and allow the method to be used on much smaller input DNA amounts. This may allow application of this method to the haplotyping of DNA-limited samples such as on embryo biopsies for preimplantation genetic diagnosis.

This method can be implemented using a nanoliter-volume dispenser such as a spotter and methods that partition a solution into droplets on a slide or into an array of microwells. Alternatively, partitioning can be accomplished using an array of microfluidic chambers.

This method has advantages over prior haplotyping methods that use either multiple displacement amplification (MDA) or PCR to amplify diluted DNA molecules. MDA has been shown to introduce biases that result in the requirement of extremely high sequencing depth for complete genome phasing, and PCR-based techniques limit the haplotype block length due to the difficulty in amplifying long DNA fragments by PCR. The use of a transposase allows for much longer DNA fragments to be tagged by the same index, enabling the construction of much longer haplotype blocks. An example of a workflow that applies this method to a sample is shown in FIG. 43.

Nanoliter-Volume Transposase-Based Haplotyping

Another way to perform haplotyping by transposition is to perform the required partitioning for avoidance of co-partitioned paternal and maternal copies, but using purely physical partitioning and only a single indexing step to bioinformatically group the products of each physical reaction. In this strategy, DNA template molecules are aliquoted into multiple reactions, transposition without the need for indexing is performed, followed by addition of PCR reagents and amplification with a unique index for each reaction. In this case the binding property of Tn5 is not necessary as there is no need to keep template molecules intact for physical transport. The use of nanoliter-volumes in this strategy serves two purposes: to make the implementation of the thousands of physical reactions required for partitioning feasible, and to improve reaction efficiencies in order to obtain high coverage of the femtogram-scale quantities of DNA that are in each reaction. This method can be implemented using previously described technology. An example of a workflow that applies this method to a sample composed of a few cells is shown in FIG. 44.

Examples 13-15

Microfluidic Chip Fabrication

Devices were entirely made out of PDMS (RTV615, General Electric). The flow, control, and membrane layers were assembled using multilayer soft lithography techniques (Unger, M. A. et al. Science 288, 113-116 (2000); and Thorsen, T. et al. Science 298, 580-584 (2002), each incorporated by reference herein in their entireties) while the iso-osmotic bath and cover layers were integrated by PDMS stamping (Satyanarayana, S. et al. J. Microelectromech. Syst. 1414, 392-399 (2005), incorporated by reference herein in its entirety). Chips were covalently bound to glass slides by oxygen plasma treatment. Detailed protocols for mold and device fabrication are as follows.

Wafer Fabrication Protocol

Each new microfluidic design is created with a drawing software such as AutoCAD. Multiplexers, isolation valves, osmolarity regulator, hydration lines etc. can be added when necessary to offer a better control of the microenvironment. Designs are printed at 20,000 dpi on transparent masks. The fabrication of molds on a silicone substrate is performed using common photolithography techniques as described below.

Flow Wafer
Flow Channels Low
1. Dehydrate a wafer for 10-15 minutes at 150° C.
2. Treat the wafer with vapor phase HMDS for at least 5 minutes.
3. Pour SPR220-7.0 resist on half the diameter of the wafer. Ramp at 500 rpm for 10 seconds, then spin at 5,200 rpm for 45 seconds.
5. Pre-bake the wafer at 115° C. for 120 seconds.
6. Expose using a 1050 mJ/cm$^2$ energy dose.
7. Develop in MF319 bath for around 2.5 minutes.
8. Rinse with DI water and dry the wafer with compressed nitrogen.
9. Ramp from 115 to 190° C. and leave for 1 hour for hard bake.
Aim: 7.5 µm after reflow
Cell Traps
1. Pour SU8-2010 resist on half the diameter of the wafer.
2. Ramp at 500 rpm for 30 seconds, then spin at 2,400 rpm for 45 seconds.
3. Soft bake the wafer for 2 minutes at 65° C., 6 minutes at 95° C., and 1 minute at 65° C.
4. Expose using a long pass filter and a 210 mJ/cm$^2$ energy dose.
5. Perform a post-exposure bake for 1 minute at 65° C., 4 minutes at 95° C., and 1 minute at 65° C.
6. Develop in an SU8 developer primary bath for around 1.5 minutes, then rinse in a SU8 developer secondary bath
7. Rinse with IPA and dry the wafer with compressed nitrogen
Aim: 12µ
Flow Channels High
1. Treat the wafer with vapor phase HMDS for at least 2 minutes.
2. Pour AZ50XT resist on half the diameter of the wafer.
3. Ramp at 500 rpm for 30 seconds, then spin at 3,500 rpm for 45 seconds.
4. Pre-bake the wafer at 85° C. for 2 minutes, and 115° C. for 10 minutes.
5. Wait overnight to rehydrate the resist.
6. Expose using a 840 mJ/cm$^2$ energy dose
7. Develop in diluted 400XT developer bath for around 4 minutes.
8. Rinse with DI water and dry the wafer with compressed nitrogen.
9. Ramp from 65° C. to 190° C. and leave overnight for hard bake.
Aim: 15 µm after reflow
Chambers
1. Pour SU8-100 resist on half the diameter of the wafer.
2. Ramp at 500 rpm for 30 seconds, then spin at 2,700 rpm for 50 seconds.
3. Soft bake the wafer for 20 minutes at 65° C., 50 minutes at 95° C., and 5 minutes at 65° C.
4. Expose using a 875 mJ/cm$^2$ energy dose.
5. Perform a post-exposure bake for 2 minutes at 65° C., 17 minutes at 95° C., and 2 minutes at 65° C.
6. Develop in an SU8 developer primary bath for around 7 minutes, then rinse in a SU8 developer secondary bath.
7. Rinse with IPA and dry the wafer with compressed nitrogen.
8. Ramp up and down from room temperature to 150° C. for 10 minutes.
Aim: 100 µm
TMCS treat wafer for 30 min.
Control Wafer
Control Channels
1. Dehydrate a wafer for 10-15 minutes at 150° C.
2. Pour SU8-2025 resist on half the diameter of the wafer.
3. Ramp at 500 rpm for 30 seconds, then spin at 2,700 rpm for 30 seconds.
4. Soft bake the wafer for 3 minutes at 65° C., 6 minutes at 95° C., and 2 minutes at 65° C.
5. Expose using a 315 mJ/cm$^2$ energy dose.
6. Perform a post-exposure bake for 2 minutes at 65° C., 5 minutes at 95° C., and 1 minutes at 65° C.
7. Develop in an SU8 developer primary bath for around 1 minutes, then rinse in a SU8 developer second bath
8. Rinse with IPA and dry the wafer with compressed nitrogen.
9. Ramp up and down from room temperature to 150° C. for 10 minutes.
Aim: 30 µm
Displacement Chambers
1. Pour SU8-100 resist on half the diameter of the wafer.
2. Ramp at 500 rpm for 30 seconds, then spin at 1,200 rpm for 70 seconds.
3. Soft bake the wafer for 35 minutes at 65° C., 95 minutes at 95° C., and 5 minutes at 65° C.
4. Expose using a 770 mJ/cm$^2$ energy dose.
5. Perform a post-exposure bake for 2 minutes at 65° C., 20 minutes at 95° C., and 2 minutes at 65° C.
6. Develop in an SU8 developer primary bath for around 15 minutes, then rinse in a SU8 developer secondary bath
7. Rinse with IPA and dry the wafer with compressed nitrogen
8. Ramp up and down from room temperature to 150° C. for 10 minutes.
Aim: 210 µm
9. Parylene coat control wafer.
Device Fabrication Protocol
Flow Layer
1. Plasma oxidize 100*100 mm glass slide for 10 sec.
2. Pour ~10 g of 10:1 PDMS in the center of the flow wafer.
3. Degas until all air bubbles are gone.
4. Sandwich PDMS between flow wafer and oxidized glass slide.
5. Add 200 g weight on top of glass slide and cure PDMS for 30 min at 80° C.
6. Use a scalpel and tweezers to carefully lift flow wafer off.
Control/Displacement Layer
1. Pour 55 g of 10:1 PDMS on the control/displacement wafer.
2. Degas until most air bubbles are gone (~40 min).
3. Cure PDMS for 60 min at 80° C.
4. Cut around the edge of the control/flow wafer with a surgical knife, then peel off PDMS layer from silicon wafer.
Membrane:
1. Pour ~10 g of 10:1 PDMS in the center of the blank parylene coated wafer.
2. Spin wafer at 6000 rpm for 60 sec, then cure PDMS for 30 min at 80° C.
Chip Assembly:
1. Plasma oxidize PDMS for 20 sec and bond the control layer to the blank.
2. Bake assembly for 5 min at 80° C.

3. Lift bonded layers off blank wafer, punch holes, and ablate vias.
4. Plasma oxidize PDMS for 20 sec and bond the control layer assembly to the flow layer.
5. Bake assembly for 5 min at 80° C.
6. Peal PDMS, cut chips to size and bond to glass slide (25 sec plasma).

Alternatively, there is an optional spotting step that may be carried out prior to step 4 of the chip assembly protocol, as follows:
1. Perform image recognition to adjust for position and rotation.
2. Spot desired content directly into wells.
3. Optional wash steps can be performed to prevent cross-contamination between different depositions (FIGS. 10 E/F).

In Example 15 below, the method described spotting index sequences, but the process may be adjusted to spot protein covered beads or any oligonucleotide (FIGS. 10 C/D shows equal resuspension of dispensed RNAseP template).

Example 13—Library Construction

The amount of DNA template recovered from single cells requires the optimization of current library preparation chemistries to accommodate the reduced input amounts and increased sensitivity. A typical library preparation protocol includes DNA fragmentation (shearing, sonication, or nebulization), followed by DNA end-repair (A tailing or blunt ends), and platform specific adaptor ligation. This workflow can result in significant losses of template DNA.

The NEXTERA chemistry (Illumina™) provides an alternative workflow that uses a modified transposition reaction for rapidly generating genomic libraries for NGS. During the reaction, an engineered transposome complex creates staggered double-stranded breaks randomly spread over the entire genome and simultaneously ligates the end of the transferred transposon strand to the 5' end of the target fragment (for example, see US Patent application publication no. 2010/0120098, incorporated by reference herein in its entirety for all purposes). This "tagmentation" reaction produces a mixed population of tagged DNA fragments that contain different (AB tagged) as well as similar (AA or BB tagged) adaptor sequences on both ends. PCR is used to enrich for the desired AB-tagged sequences and to add platform specific flow-cell binding sites as well as reaction specific indices (enrichment is shown in p; this figure is adapted from Syed, F., Grunenwald, H. & Caruccio, N. Next-generation sequencing library preparation: simultaneous fragmentation and tagging using in vitro transposition. Nat. Methods|Appl. Notes (2009). doi:10.1038/nmeth.f.272, incorporated by reference herein in its entirety for all purposes).

A microfluidic device integrating the inflatable chamber was designed by the inventors, manufactured and spotted with index primers. Furthermore, a system for single-cell trapping (White, A. K. et al. High-throughput microfluidic single-cell RT-qPCR. Proc. Natl. Acad. Sci. U.S.A. 108, 13999-4004 (2011), incorporated by reference herein in its entirety) to rabidly prepare dual-indexed genomic libraries from single-cells. FIG. 4A and FIG. 5 show a schematic of an embodiment of the device, featuring two semi-independent arrays of 24 single-cell processing units. The core of each processing unit is the 40 nL inflatable reaction chamber (IV), which is connected to (1) a cell trap (II) optimized for single-cell capture and an adjacent lysis chamber (III), (2) a reagent inlet (V), and 3) an chamber holding the spotted index primers (VI).

Reactions are assembled in parallel by metering out precisely defined volumes. A mutual bus channel (VII) supplies the reagents to all chambers. Integrated peristaltic pumps or precise pressures gradients across the membrane can be used to control reagent addition or extraction from the chamber. The supply channel (VII) can then be flushed and replaced with a new reagent. All reaction chambers are connected in serial to enable the pooled recovery for downstream analysis.

While the lysis chamber can be a potential source of template losses, the chamber was included in the initial design to create a combined lysis volume with the adjacent cell trap, in case cells or nuclei adhere to the cell trap and cannot be moved after capture. Interlayer connections (vias) (Huft, J., Da Costa, D. J., Walker, D. & Hansen, C. L. Three-dimensional large-scale microfluidic integration by laser ablation of interlayer connections. Lab Chip 10, 2358-65 (2010), incorporated by reference herein in its entirety for all purposes) are used to facilitate three-dimensional fluid routing in order to further reduce device complexity and maintain scalability.

Nuclei suspensions were prepared from cell lines, using the following protocol:
1) On ice, add 50 µl Sigma EZ lysis buffer to 50 µl of cells (1e6 cells/ml).
2) On ice, incubate cells for 5 min.
3) Spin nuclei at 1500 rpm for 10 min at 4 C.
4) Discard supernatant without disrupting the nuclei pellet and resuspend nuclei in 100 µl ice cold PBS
5) Use a 40 µm filter to remove cell debris and clumped nuclei.
6) On ice, add 0.15 µl Syto 9 DNA stain to 49.85 µl filtered nuclei.
7) Prepare loading buffer:
   Percoll: 81.25 µl
   Superblock: 15 µl
   EDTA: 3 µl
   Tween 20 (10%): 0.75 µl
8) One ice, mix 10 µl of stained nuclei, 6 µl PBS, and 4 µl loading buffer.

(The Ratio of PBS and Loading Buffer has to be Optimized for Neutral Nuclei Buoyancy)

Prior of loading, cell sorting channels were primed with 1% BSA or 100% Superblock solution. The nuclei suspension was connected to the primed microfluidic device, where single nuclei were isolated from the suspension using mechanical cell traps (FIG. 11). The trapped nuclei were washed with PBS to remove untrapped nuclei, cell debris and extracellular DNA. The trapped and washed single nucleic are then pushed into the inflatable reaction chamber, where the cells were lysed in 1.2 nl final volume. The cell lysis buffer includes 25 µl Qiagen digestion buffer G2 (Guanidine HCl (800 mM), TrisCL (30 mM), EDTA (30 mM), Triton X-100 (0.5%), PCR water) and 2.5 µL Qiagen Protease. The nuclei were incubated at 50 C for 1 hour to lyse the nuclei membrane and strip the genomic DNA from all bound proteins such as nucleases and histones, before inactivating the Protease at 70 C for 15 minutes.

Single-cell libraries were prepared using a modified NEXTERA protocol (Illumina). 10.8 nl of Tagmentation mix (TD Buffer (6 nl), TDE1 (1.6 nl), Buffer 1 (3.2 nl) [MgCl (1.22 mM) and Tween (0.3%)]) were added to each chamber and incubated at 55 C for 5 minutes. The Tagmentation reaction was neutralized by adding 1 nl Qiagen Protease and 1 nl PCR water and incubated at 50 C for 15 min. The Protease was then inactivated at 70 C for 15 min. Following neutralization, 21 nl PCR master mix {NPM (10.5 nl), PPC (3.5 nl), Tween 20 (0.35 nl), PCR water (5.25 nl)} was added to each chamber. During the addition of the PCR mix, pre-spotted index primers (160 nmol [400 nM*400 pl]) were resolved and added to the PCR reaction. 9-15 PCR cycles were performed to add flow-cell adapters and indices and amplify the fragmented DNA. The final libraries had the following structure: [flow-cell adapter 1][index 1][transposon adapter A][insert][transposon adapter B][index 2][flow-cell adapter 2].

The sequencing ready libraries were pooled and recovered from the chip. Ampure XP™ beads were used for size selection to remove excess primers and short fragments that do not contain genomic inserts of the desired length. Sequencing analysis was then performed to detect low-resolution sequence alterations at single-cell resolution.

Example 14—Bead Purification and Selection on Chip

Many analytical applications, such as PCR, sequencing, and genotyping, require high quality DNA template inputs. Excess primers, primer dimers, nucleotides, enzymes and salt can distort results or inhibit reactions and therefore a reliable purification system is required to essentially remove all contaminates from the template.

Agencourt™ solid-phase paramagnetic bead technology is a highly efficient purification system that utilizes magnetic separation and simple washing procedures. The system also allows for the selective binding of fragments that are longer than a cut-off length, a characteristic that is ideally suited for library size selection. The cut-off can be simply adjusted by changing the binding buffer to sample ratio to remove short fragments from the population.

The Agencourt™ solid-phase paramagnetic bead system was deployed on the described library preparation device to demonstrate the applicability of the inflatable chamber architecture. 9.6 nl of a 100 bp ladder (TrackIt™ ladder, Life) was mixed with AMPure XP™ beads under binding conditions at a bead to sample ratio of 0.6×, 0.8×, 2.0× and 2.5×. The beads were separated to the side of the chamber using a magnetic field gradient. The supernatant was removed from the chambers by reducing the chamber volume without removing the beads. Subsequently, the chamber was flushed with Ethanol twice to remove unbound molecules and contaminants, before eluting the DNA back into solution phase using an elution buffer (10 mM Tris-HCL ph 8.5, 0.1% Tween). The purified product was recovered from the microfluidic device and the size cut-off was determined. It was shown that the tatrazine maker was completely removed in all experiments (FIG. 12A and FIG. 12B) and the expected size selections were achieved (Table B).

The light line shows the bead purified reaction and the dark line shows the on-chip control.

TABLE B

Bead calibration for size cutoff

| Bead to sample ratio | Cutoff size |
|---|---|
| 0.6× | ≥500 bp |
| 0.8× | ≥300 bp |
| 2.0× | ≥200 bp |
| 2.5× | ≥100 bp |

Example 15—Targeted PCR

While whole genome sequencing generates the most comprehensive datasets for a sample, the sheer scale of sequencing effort can be cost prohibitive for large sets of samples and substantial investments in bioinformatics is necessary to achieve an effective translation of these information. A targeted sequencing workflow focuses on a selected set of gene regions that are chosen based on prior knowledge. This provides a more cost-efficient and systematic approach to identify variations in biological systems, such as mutations relevant to cancer or aberrations in other genetic disorders, compared to a whole genome sequencing approach.

The flexibility of the described library preparation device facilitates the adaption of a single-cell targeted sequencing workflow. After isolating single-cells and lysing them in the reaction chamber (described earlier), multiplex PCR can be performed to amplify the regions of interest and to add adapters to the 5' and 3' end of the amplicons. A second round of PCR, using spotted index primers that are unique for each chamber, is used to add platform specific flow-cell binding sites as well as reaction specific indices. Purification steps after the first and second PCR can be used to select for the desired product. This, combined with NGS, is a powerful and economic tool for comprehensive genotyping, including SNV detection, across hundreds to thousands of single cells.

Example 16—Determination of Tumor Heterogeneity Through Single Cell Sequencing

Methods

Device Fabrication Process

Microfluidic devices were fabricated using a modified multilayer soft lithography workflow (Unger, M. A. et al. Science 288, 113-116 (2000); and Thorsen, T. et al. Science 298, 580-584 (2002), each incorporated by reference herein in their entireties). First, 4-inch silicon wafers (SILICON QUEST) were patterned by photolithography. Photomasks were designed in AutoCAD (Autodesk Inc.) and either printed on transparency films at a 20,000 dpi resolution (CAD/ART SERVICES INC.) or written directly onto chrome masks using a laser writer system (LW405 Laser Mask Writer, Microtech). Chrome masks were developed and etched following manufacturer's directions. The patterns were transferred to the "flow" substrate in four lithographic steps. First, SPR220-7.0 photoresist (Microchem) was used to define 6.5 micrometer high pumps, valves, and channels connecting reaction chambers. A rounded channel geometry to facilitate the fabrication of valves was achieved by reflowing the resist at 115° C., immediately followed by a hard bake at 190° C. for 1 hour. Second, the cell traps, cell inlet filters, as well as the chambers holding the indexing primers, were fabricated in 12 micrometer high SU-8 2010 photoresist (Microchem) and hard baked at 150° C. for 30 min. Next, a 15 µm thick AZ50XT (AZ Electronic) layer was deposited to define the channels connecting the cell traps as well as the inlet valves. To obtain rounded channel walls, the resist was again reflowed and hard-baked by ramping the temperature from 65° C. to 190° C. and then holding the temperature overnight. The hard bake protected the AZ photoresist from SU-8 developer erosion. Finally, the 100 µm high bus channels and reaction chambers were manufactured in SU-8 100 photoresist (Microchem).

The "control" mold comprises two layers. First, the control channels were fabricated in 30 micrometer SU-8 2025 photoresist (Microchem). A short 15 min hard-bake at 150° C. protected the resist from further development during the subsequent manufacturing step. Second, the displacement chambers were defined in a 210 micrometer thick SU-8 100 photoresist layer. To prevent PDMS from sticking to the photoresist structures and substrate, the "flow" mold was treated with tri-methyl-chloro-silane (TMCS, Aldrich) vapour overnight and the "control" mold and a blank silicon wafer were parylene coated.

The microfluidic devices were fabricated using QSil 216 (Quantum Silicones), a two-part, clear, liquid elastomer. The two components were mixed (ARE-310 Mixer, Thinky) in a 10:1 base to catalyst ratio by weight. Oxygen-plasma bonding (PDC-32G & PDC-FMG, Harrick Plasma) was used to assemble the devices using the following settings: RF power settings, high; Oxygen gas pressure, 600 mTorr; Treatment time, 25 sec. The devices were assembled from three layers. The top "control" layer was cast from 55 g PDMS mixture, degassed and cured at 80° C. for 60 min. The middle layer, a thin blank membrane, was made by spin coating the blank wafer with PDMS at 5,500 rpm (G3 Spin Coater, Specialty Coating Systems, Inc.) and cured for 30 min at 80° C. After baking, the cured PDMS was removed from the control mold and bonded to the blank membrane. The two-layer structure was then incubated for 5 min at 80° C., before removing it from the blank wafer in order to punch 0.71 mm access ports and laser ablate interlayer (Huft, J., Da Costa, D. J., Walker, D. & Hansen, C. L. Three-dimensional large-scale microfluidic integration by laser ablation of interlayer connections. Lab on a Chip 10, 2358-2365 (2010) incorporated by reference herein in its entirety). The bottom "flow" layer was fabricated using an imprinting workflow to facilitate the deposition of indexing primers into open microfluidic structures with minimal distortion of the array. PDMS in its liquid state was sandwiched between the "flow" mold and a plasma-oxidized glass slide (100×100 mm$^2$ Schott D263 Borosilicate Glass, S.I. Howard Glass Co.) and baked for 30 min at 80° C. The stronger adhesion of the cured PDMS towards the glass slide allowed the "flow" mold to be lifted off, while the cast membrane remained attached to the glass slide. Fiducial markers were used to accurately interface the imprinted PDMS membrane with a contact-less micro-dispenser (sciFLEXARRAYER S3, Scienion AG). To avoid primer cross-contamination, a rigorous wash routine was implemented between subsequent dispensing steps. During the automated spotting routine, 700 pL of each sequencing primer was deposited into the microfluidic chambers using a PDC-70 Type 1 nozzle. Droplet volumes before and after each deposition step were recorded for quality control. After primer deposition, the two-layer structure was aligned and bonded to the flow layer. The assembled device was removed from the glass slide used for imprinting and boded to a new glass slide. The final devices were incubated at 80° C. for 2 hours.

Device operation was semi-automated. Custom LabView software (National Instruments) was used to control on-chip valves through an output card (PCI-6512, SCB-100, National Instruments) and solenoids (MH1 Miniature valve, FESTO). Tygon tubing (Cole-Parmer) and 20-gauge stainless steel pins were used to connect the control ports of the microfluidic device to the solenoids. Compressed air (25-30 psi) and Krytox (DuPont) oil in the control channels was used to operate the device.

Library Preparation Protocol and Device Operation

The tissue was finely minced with scalpels then mechanically disaggregated for one minute using a Stomacher 80 Biomaster (Seward Limited, Worthing) in 1-2 mL cold DMEM-F12 medium (DMEM/F12, STEMCELL Technologies). Aliquots from the resulting suspension of cells and organoids were cryopreserved in viable freezing medium (47:47:6 DMEM:FBS:DMSO) and stored at −196° C. until further processing. Thawed tissue suspensions were enzymatically dissociated to single cells by sequential incubation in warm (37 degree C.) 300 U/mL collagenase (STEMCELL Technologies) plus 100 U/mL hyaluronidase (STEMCELL Technologies) for 2.5 hours, 0.25 trypsin/EDTA (Corning) while triturating with a pipette for 4 minutes, then 5 U/mL dispase (STEMCELL Technologies) plus 0.1 m-g/mL DNAse I (STEMCELL Technologies) while triturating with a pipette for 4 minutes, before passing through a 50 micron filter (Eirew, P. et al. Dynamics of genomic clones in breast cancer patient xenografts at single-cell resolution. Nature 518, 422-426 (2015) incorporated by reference herein in its entirety).

Dissociated cells were then centrifuged for 10 min at 1500×g and re-suspended in fresh PBS (Life Technologies) to a final concentration of 1e6 cells/mL. Cells were again filtered using a 40 micrometer filter to remove cell debris and clumped cells. A 0.15 microliter SYTO 9 Green Fluorescent Nucleic Acid Stain (Life Technologies) was added to 49.85 microliter filtered cells. 10 microliter of stained cells were then mixed with 8 microliter PBS, and 2 microliter loading buffer (81.25 microliter Percoll, Sigma-Aldrich; 15 microliter SuperBlock PBS Blocking Buffer, Fisher Scientific; 3 microliter UltraPure 0.5M EDTA, Life Technologies; 0.75 microliter 10% Tween 20, Sigma-Aldrich). The ratio of PBS and loading buffer was optimized for neutral cell buoyancy and can be adjusted for different cell types.

Prior to cell loading, cell sorting channels and inlet ports were primed with a Pluronic solution (10% Pluronic F-127, Sigma-Aldrich; 0.3% Syto9 stain in UltraPure DNase/RNase-Free Distilled water, ThermoFisher). Priming helped to prevent cells from adhering to the PDMS. The prepared single-cell suspension was connected to the sample inlets using microcapillary pipette tips and 5-6 psi of pressure was applied to inject the cell suspension into the device and to push out any trapped air against an inlet valve. Pressure was then reduced to 1.5-2.5 psi and cell loading and separation valves were opened to allow flow through the cell-sorting channels. The trapped cells were washed with PBS to remove untrapped cells, cell debris, and extracellular DNA. After washing, the trapped cells were isolated into single chambers by closing the cell separation valves. Cell occupancy was determined by microscopy and recorded for analysis. Using the on-chip peristaltic pump, 1.2 nanoliter lysis buffer was used to push the trapped and washed cells into the inflatable reaction chamber. The cell lysis buffer was prepared with 25 µl lysis buffer G2 (QIAGEN) and 2.5 microliter QIAGEN Protease (Protease was resuspend in 7 mL UltraPure water). The cells were lysed at 50° C. for 1 hour on a flatbed thermocycler (Bio-Rad PTC-200), before inactivating the protease at 70 degree C. for 15 minutes (and finally cooled to 10 degree C.). The displacement chamber was pressurized at 7-8 psi during the heating step.

Next, single-cell libraries were prepared using a modified NEXTERA protocol (NEXTERA DNA Library Preparation Kit, Illumina). 10.8 nanoliter of Tagmentation mix (6 nanoliter TD Buffer, 1.6 nanoliter TDE1, 3.2 nanoliter Buffer 1 [1.22 mM Magnesium chloride solution (Sigma-Aldrich) and 0.3% Tween 20 in water]) were added through the reagent inlet to each chamber and incubated on a flatbed thermocycler at 55° C. for 10 minutes. Bus channels were flushed with 20 microliter UltraPure water and tried with compressed air, before adding the next reagent. The tagmentation reaction was neutralized by adding 1 nanoliter Qiagen Protease and 1 nanoliter PCR water, and incubated at 50° C. for 15 min. The Protease was then inactivated at 70° C. for 15 min. Following neutralization, 21 nanoliter PCR master mix (10.5 nanoliter NPM, 3.5 nanoliter PPC, 0.35 nanoliter 10% Tween 20, 6.65 nanoliter PCR water) was added to each chamber. During PCR master mix addition, pre-spotted index primers (20 micro Molar×700 picoliter per primer) were resolved and added to the PCR reaction. PCR was performed using the following conditions: 72° C. for 3 min; 95° C. for 30 sec; 11 cycles of 95° C. for 10 sec, 55° C. for 30 sec and 72° C. for 30 sec; 72° C. for 5 min; and finally 10° C. The final libraries were pooled and recovered from the microfluidic device by flushing 12 microliter EBT through the inflatable reaction chamber array (FIGURE Operation—F). Finally, size selection was performed using a 1.8×Ampure XP bead (Beckman Coulter) to sample ratio. Libraries insert size and quantity were determined using a Bioanalyzer High Sensitivity DNA kit (Agilent) and the QUBIT dsDNA HS Assay Kit (Thermo Fisher Scientific) respectively, and were sequenced on a HISEQ 2500 Sequencing System using paired-end 125 bp reads.

Bulk Library Preparation

Flash frozen xenograft tissues were thawed and immediately homogenized in lysis buffer using a rotor-stator homogenizer (Polytron PT1000). DNA was prepared from the lysate using the Qiagen AllPrep DNA/RNA Mini kit (Qiagen). 184-hTert cells were thawed and DNA was extracted with the QIAmp DNA mini kit (Qiagen) following the protocol for cultured cells. DNA was quantified using the QUBIT dsDNA HS Assay Kit (ThermoFisher Scientific) and bulk libraries were constructed following the NEXTERA DNA Sample Preparation Guide (Illumina) with the following alteration: after tagmentation, the DNA was purified from the transposome using the NUCLEOSPIN PCR clean-up kit (Clontech). Libraries were assessed for correct insert size using a Bioanalyzer (Agilent) and quantified using QUBIT, and were sequenced on a HISEQ 2500 Sequencing System using paired-end 125 bp reads.

Results

An alternative to both bulk and single-cell WGA approaches is provided, whereby indexed libraries are prepared directly on single-cell template DNA without pre-amplification (Adey, A. et al. Rapid, low-input, low-bias construction of shotgun fragment libraries by high-density in vitro transposition. Genome Biology 11, R119 (2010) incorporated by reference herein in its entirety) (FIG. 45A). Libraries are pooled for highly multiplexed sequencing at low depth, producing highly uniform coverage amenable to integer copy number inference, and minimizing the risk of introduced copy number artefacts and polymerase errors. Following sequencing, single-cell copy number profiles are clustered to infer sub-populations clonal in copy number space (FIG. 45B). Sequencing reads from all cells may be pooled to produce a high-depth "bulk-equivalent genome" amenable to SNV, LOH, and breakpoint inference; alternatively, all cells within each copy number clone can be pooled to produce a set of high-depth "clonal genomes" (FIG. 45B).

The approach provided herein overcomes some of the principle challenges of bulk tumor sequencing, permitting removal of contaminating normal cells and identification of sub-clonal copy number alterations at high resolution. The method is carried out to analyze 64 diploid cells from an immortalized breast epithelium cell line. Through direct comparison to past studies employing multiplexed low-coverage single-cell sequencing, it is demonstrated that lack of pre-amplification results in more uniform coverage than DOP-PCR based methods, both in terms of dispersion in reads per bin, and in the fraction of the genome recovered as more cells are pooled. Through comparison to a bulk sample, we demonstrate that the coverage uniformity of our pooled single-cell genomes is equivalent to a bulk genome when sequenced at the same coverage depth. Due to low dispersion, we are able to multiplex more cells per sequencing lane than previously published single-cell studies (192 cells per lane), resulting in substantially reduced costs for single-cell copy number analysis. Finally, we apply our method to sequence 595 single cells from two passages of a patient-derived triple negative breast cancer xenograft line, yielding a detailed map of this tumor's copy number architecture, while also inferring SNVs, LOH, and breakpoints on the high-depth, low-bias pooled "bulk-equivalent genome".

The direct library preparation protocol (FIGS. 45A-B) was applied to generate 659 multiplexed low-coverage single-cell whole genome sequencing libraries without pre-amplification using a microfluidic device (FIGS. 46A-H).

Microfluidic Device Performance

Figure 46A:
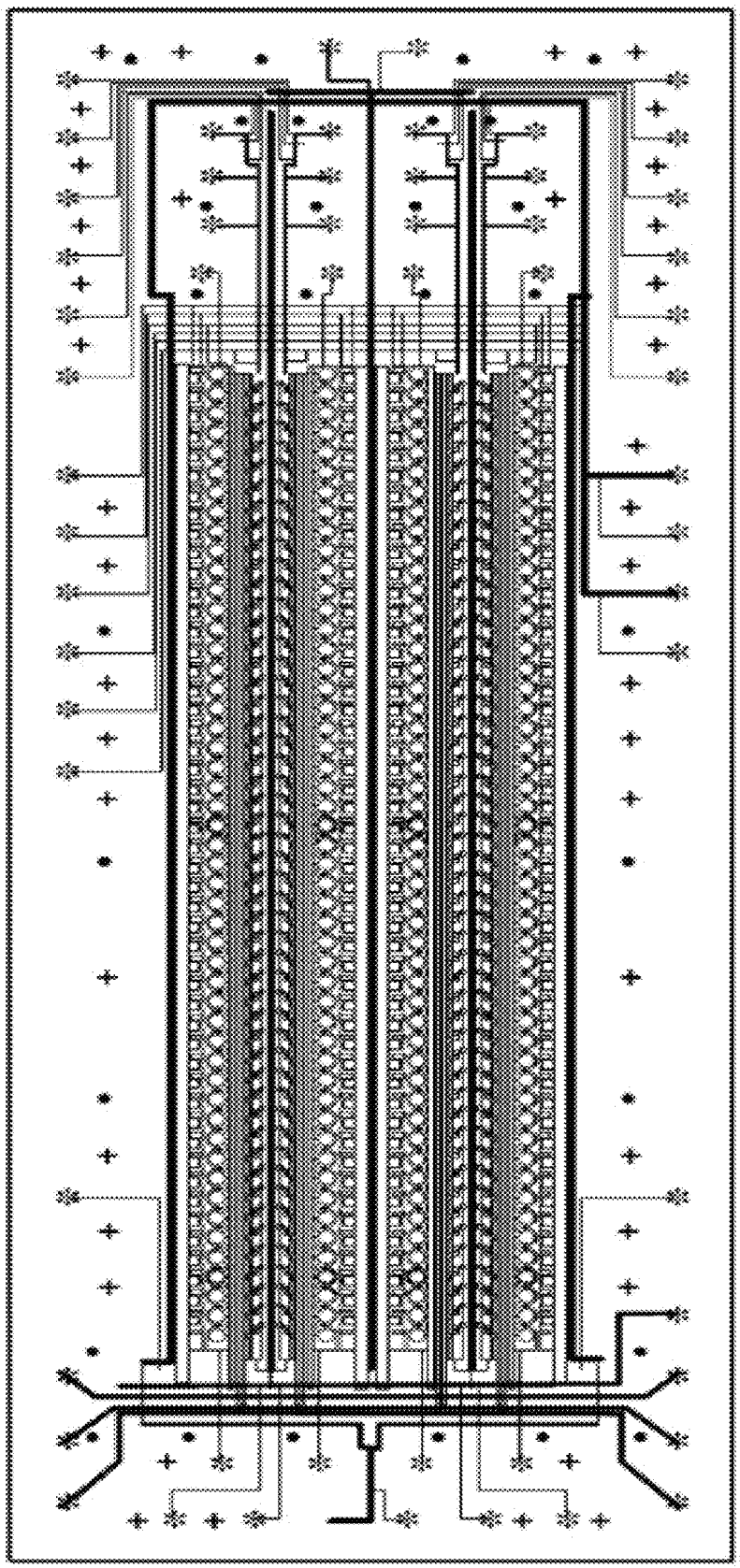
Figure 46B:
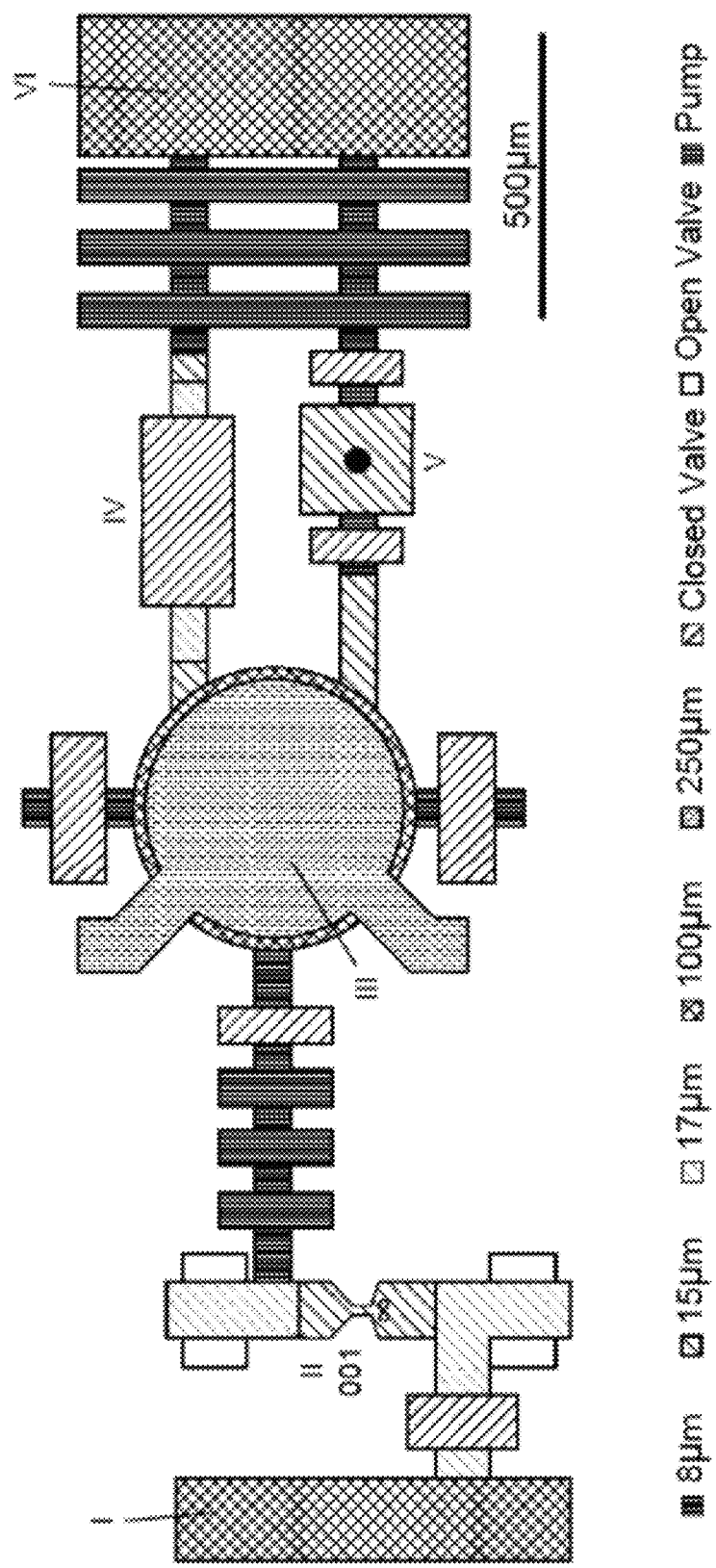

The microfluidic device integrates the entire single-cell library preparation workflow, including: cell isolation, imaging, lysis, DNA fragmentation, barcoding, and sequencing adaptor incorporation. It features 192 cell processing units arrayed in four columns of 48 (FIGS. 46A, 46B). Each cell processing unit includes an inflatable reaction chamber (FIG. 46C), as well as a chamber containing a unique set of index barcodes which were pre-spotted during device fabrication and integrated into the chip (FIGS. 46D, 46E).

During an experiment, a cell suspension was injected into each of four cell-loading inlets; single cells were sequentially caught in cell traps and washed with PBS to remove contamination and untrapped cells. Integrated valves above and below each cell trap were closed to isolate trapped cells into individual cell processing units, and high-magnification fluorescent microscopy was used to unambiguously identify true single cells and flag chambers with multiple cells and contaminating debris (FIGS. 46F, 46G, 46H). Four no-template control (NTC) chambers without cell traps were included to assess contamination for each chip run. Next, each trapped cell was transferred into its inflatable reaction chamber through actuation of a peristaltic pump. Cells were lysed, and single-cell libraries prepared by employing a "one-pot" fragmentation library preparation protocol (NEXTERA, Illumina) directly on unamplified genomic DNA released from the single cells. Index barcodes were re-suspended and pushed into the reaction chamber, and 11 PCR cycles were applied on-chip to incorporate both the barcodes and Illumina sequencing adaptors onto the tagmented DNA. Following this, valves separating the reaction chambers were opened, permitting the pooled recovery of indexed single-cell libraries for multiplexed sequencing, while maintaining the identity of sequencing reads. Using this streamlined workflow a single operator can construct 192 single cell libraries in 2.5 hours hands-on time and at a cost of less than $0.5 per cell (including dead volumes and consumables). Analysis of NTC reactions indicates that control chambers had very low levels of contamination. We subsequently carried out highly multiplexed low-coverage sequencing of 192 libraries per Illumina HISEQ Sequencing System lane. This approach permits the economical profiling of thousands of single cells.

Uniformity of Coverage and Sequencing Metrics

Figure 47B:
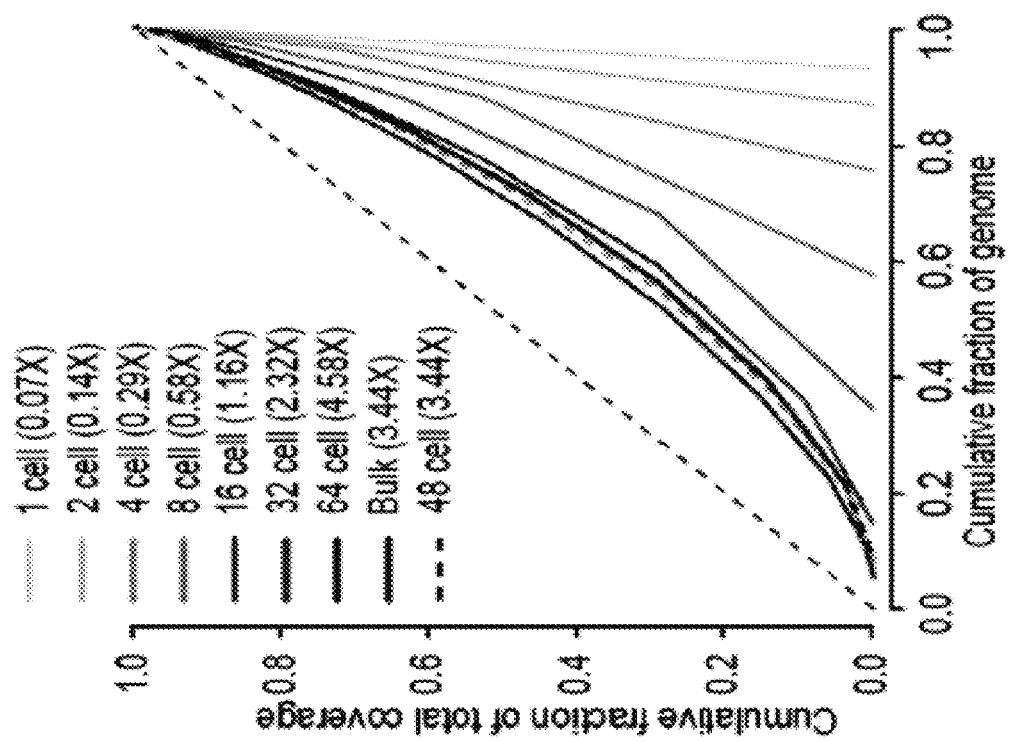
Figure 47A:
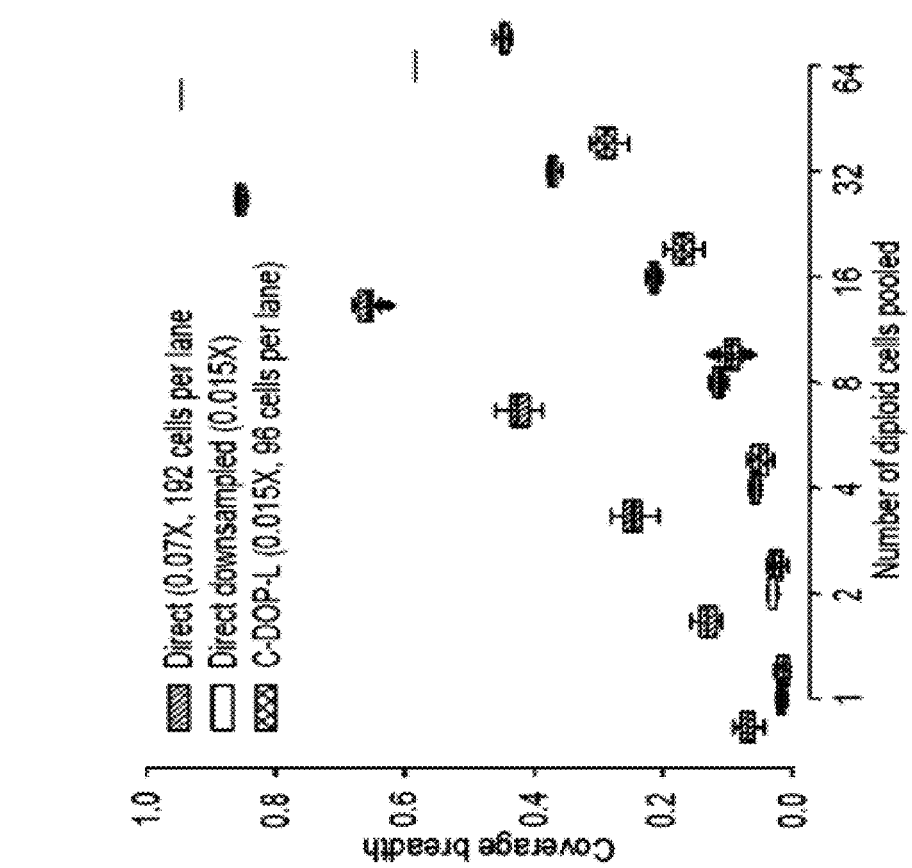

To evaluate the uniformity of coverage obtained by direct single cell library construction, 192 indexed samples from 184-hTERT-L2 an immortalized normal breast epithelial cell line were sequenced (152 single cells identified with fluorescence microscopy, 8 no-template controls). This cell line is primarily diploid, but is known to acquire some copy number alterations with serial passaging (Burleigh, A. et al. A co-culture genome-wide RNAi screen with mammary epithelial cells reveals transmembrane signals required for growth and differentiation. Breast Cancer Research 17, 4 (2015) incorporated by reference herein in its entirety). Using a hidden Markov model (Ha, G. et al. Integrative analysis of genome-wide loss of heterozygosity and monoallelic expression at nucleotide resolution reveals disrupted pathways in triple-negative breast cancer. Genome Research 22, 1995-2007 (2012) incorporated by reference herein in its entirety), we inferred copy number profiles and identified 64 fully diploid cells (mean 3.09+−0.58 million reads, 0.07+−0.01× coverage depth per cell). To examine how coverage breadth (defined as the fraction of the genome covered by at least one sequencing read) increases with the number of diploid single-cell genomes pooled, we carried out bootstrap sampling (n=30 draws per condition) and pooling of these cells, and compared our results to diploid cells sequenced using the C-DOP-L protocol (Baslan, T. et al. Optimizing sparse sequencing of single cells for highly multiplex copy number profiling. Genome Research 1-11 (2015) incorporated by reference herein in its entirety), a variant of DOP-PCR (FIG. 47A). This was the only published dataset we identified which featured a comparable number of diploid cells sequenced in multiplex at 96 cells per Illumina HISEQ Sequencing System lane (Baslan, T. et al. Optimizing sparse sequencing of single cells for highly multiplex copy number profiling. Genome Research 1-11 (2015) incorporated by reference herein in its entirety).

Analysis indicates that pooling the genomes of 64 diploid cells prepared without pre-amplification results in 94.65% genome coverage. While multiplexing half as many samples per sequencing lane (96 vs. 192), pooling of 64 diploid genomes prepared with C-DOP-L results in a median of 44.70% coverage breadth (Baslan, T. et al. Optimizing sparse sequencing of single cells for highly multiplex copy number profiling. Genome Research 1-11 (2015) incorporated by reference herein in its entirety), comparable to pooling 8 cells sequenced using direct library preparation (median 42.57% coverage breadth). To determine how coverage uniformity for our pooled samples compares to a bulk genome, one Lorenz curve for each condition was plotted in FIG. 47A, using the pooled genome with median coverage breadth for that condition (FIG. 47B, solid grey curves). A bulk genome for the same diploid cell line prepared using the standard NEXTERA protocol was sequenced at 3.44× (FIG. 47B, solid black curve), and it was shown that pooled genome corresponding to 48 single cells with the same coverage depth (3.44×) achieves equivalent coverage breadth and uniformity (FIG. 47B, dashed grey curve).

Figure 47C:
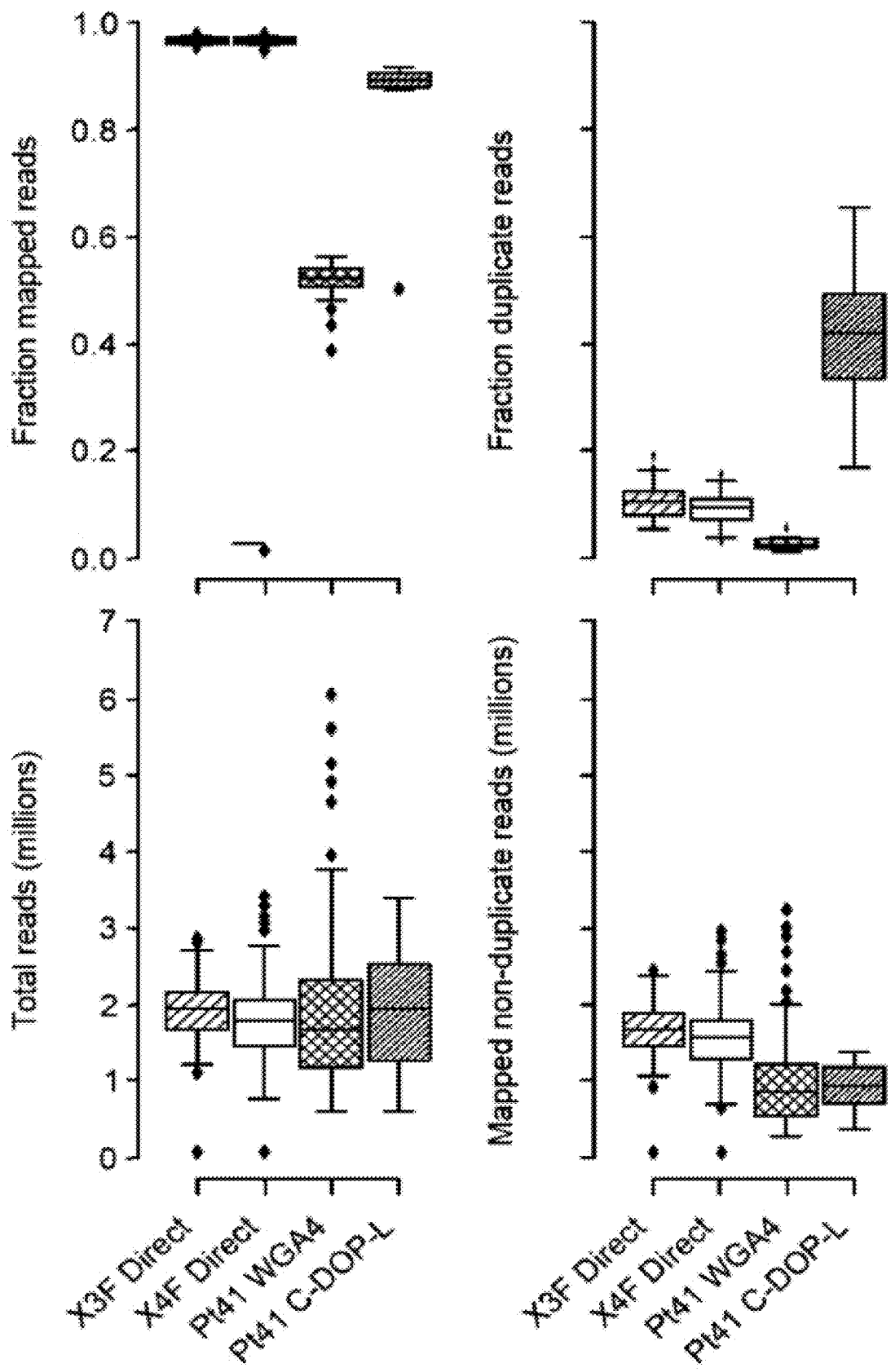

Multiplexed sequencing of 384 samples was carried out from a third-passage patient-derived primary triple-negative breast cancer xenograft tumor (SA501X3F; 296 single cells identified with fluorescence microscopy, 32 no-template controls), as well as 384 samples from a fourth-passage xenograft tumor derived from X3F (SA501X4F; 299 single cells identified with fluorescence microscopy, 22 no-template controls). FIG. 47C shows sequencing metrics for breast cancer tumor cells which underwent sequencing using our direct library preparation method (SA501X3F, X3F Direct; SA501X4F, X4F Direct), WGA4 whole genome amplification (Navin, N. et al. Tumour evolution inferred by single-cell sequencing. Nature 472, 90-94 (2011); Baslan, T. et al. Optimizing sparse sequencing of single cells for highly multiplex copy number profiling. Genome Research 1-11 (2015), each incorporated by reference herein in their entireties) (Pt41 ER-positive breast cancer cells, P541 WGA4, n=74), and C-DOP-L (Baslan, T. et al. Optimizing sparse sequencing of single cells for highly multiplex copy number profiling. Genome Research 1-11 (2015) incorporated by reference herein in its entirety) (same patient, Pt41 C-DOP-L, n=64). While all libraries featured a median of approximately 2 million reads per cell, WGA4 libraries suffered from low mappability due to WGA adaptor contamination, while C-DOP-L libraries had high duplicate rates. This results in a substantially reduced number of usable reads per cell for these methods relative to direct library preparation without pre-amplification.

Figure 47D:
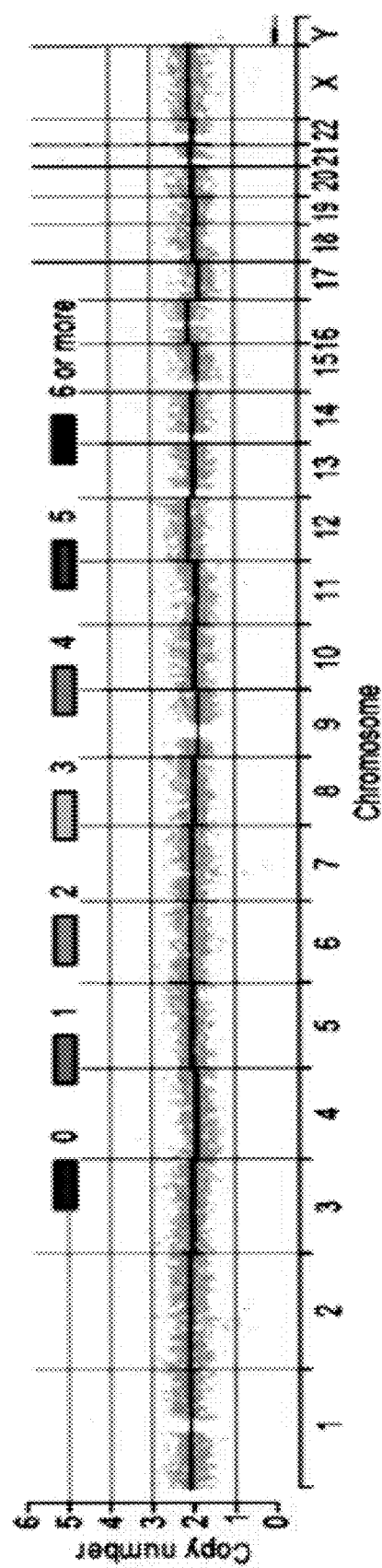

Finally, FIG. 47D shows a copy number profile for a sample diploid cell from cell line 184-hTERT-L2, and a fourth-passage xenograft tumor cell from sample SA501X4F, inferred using a hidden Markov model (Ha, G. et al. Integrative analysis of genome-wide loss of heterozygosity and monoallelic expression at nucleotide resolution reveals disrupted pathways in triple-negative breast cancer. Genome Research 22, 1995-2007 (2012) incorporated by reference herein in its entirety).

Copy Number Heterogeneity in a Breast Cancer Xenograft Tumor

We next sought to examine Copy number heterogeneity in the low-coverage single-cell breast cancer xenograft samples was examined. Sub-populations with shared copy number profiles were identified.

For each low-coverage single-cell genome, binned read counts (200 Kb bins) were extracted, GC-content correction applied, and low-mappability regions removed from the analysis. Profiles were segmented and hidden copy number states derived using a hidden Markov model with seven states and Student's-t emissions (Ha, G. et al. Integrative analysis of genome-wide loss of heterozygosity and monoallelic expression at nucleotide resolution reveals disrupted pathways in triple-negative breast cancer. Genome Research 22, 1995-2007 (2012) incorporated by reference herein in its entirety). Following hidden state inference, profiles were converted to integer copy number scale by dividing all bin counts by half the median value of bins assigned to the "neutral" (2-copy) state. Integer copy number values were assigned to all segments by rounding the segment median to the nearest integer. The median absolute deviation (MAD) of all bins assigned to the "neutral" (2-copy) state was computed, and all samples identified as single cells by fluorescence imaging with MAD<0.15 were retained for downstream analysis.

FIG. 48A displays a heatmap of integer copy number states for 259 single cells from xenograft sample SA501X3F. Three distinct sub-populations were apparent: a major clonal group with one copy of chromosome X (Clone A), a minor population with two copies of chromosome X and numerous smaller alterations relative to the dominant population (Clone B; see chromosomes 1, 2, 3, 6, 8, 14, 15, 18, and 20), and a third sub-population which shares the profile of Clone B but features additional alterations in chromosome 11 (Clone C).

Representative single-cell copy number profiles from each of the three clones are presented in FIG. 48B. Dimensionality reduction and hierarchical clustering of the integer copy number profiles was used to derive the clone assignments (FIG. 48C). It should be noted that while cells within a clone share most major copy number alterations, numerous cells with unique amplifications and deletions are evident, especially within the dominant clonal group. The lack of contamination in the no-template control samples and the clear placement of segment medians along integer copy number values, suggests that these events represent genuine copy number diversity in this highly-rearranged triple negative tumor A similar copy number heatmap for the subsequent xenograft passage SA501X4F indicates that by the fourth passage, the two minor clones are no longer detectable, and the population is dominated by one major clonal group.

Pooling of Single-Cell Genomes Yields High-Depth, Low-Bias Clonal and Bulk-Equivalent Genomes As demonstrated in FIGS. 48A-C, multiplexed sequencing of unamplified single-cells yields highly uniform low-coverage genomes suitable for integer copy number inference. These may be used to provide insight into the copy number heterogeneity and clonal architecture of tumors. However, while other approaches to single-cell sequencing may permit such insights, the strength of our method lies in the ability to subsequently pool information from multiple cells to yield high-depth clonal or bulk-equivalent genomes with coverage breadth and uniformity equal to that of a bulk genome prepared using standard protocols. In FIGS. 49A-E, copy number profiles, loss of heterozygosity (LOH), single nucleotide variants (SNVs), and breakpoints on a merged genome for xenograft tumor SA501X3F were inferred. These variants were compared to those inferred on a standard genome for the same sample with equal coverage depth.

Figure 49A:
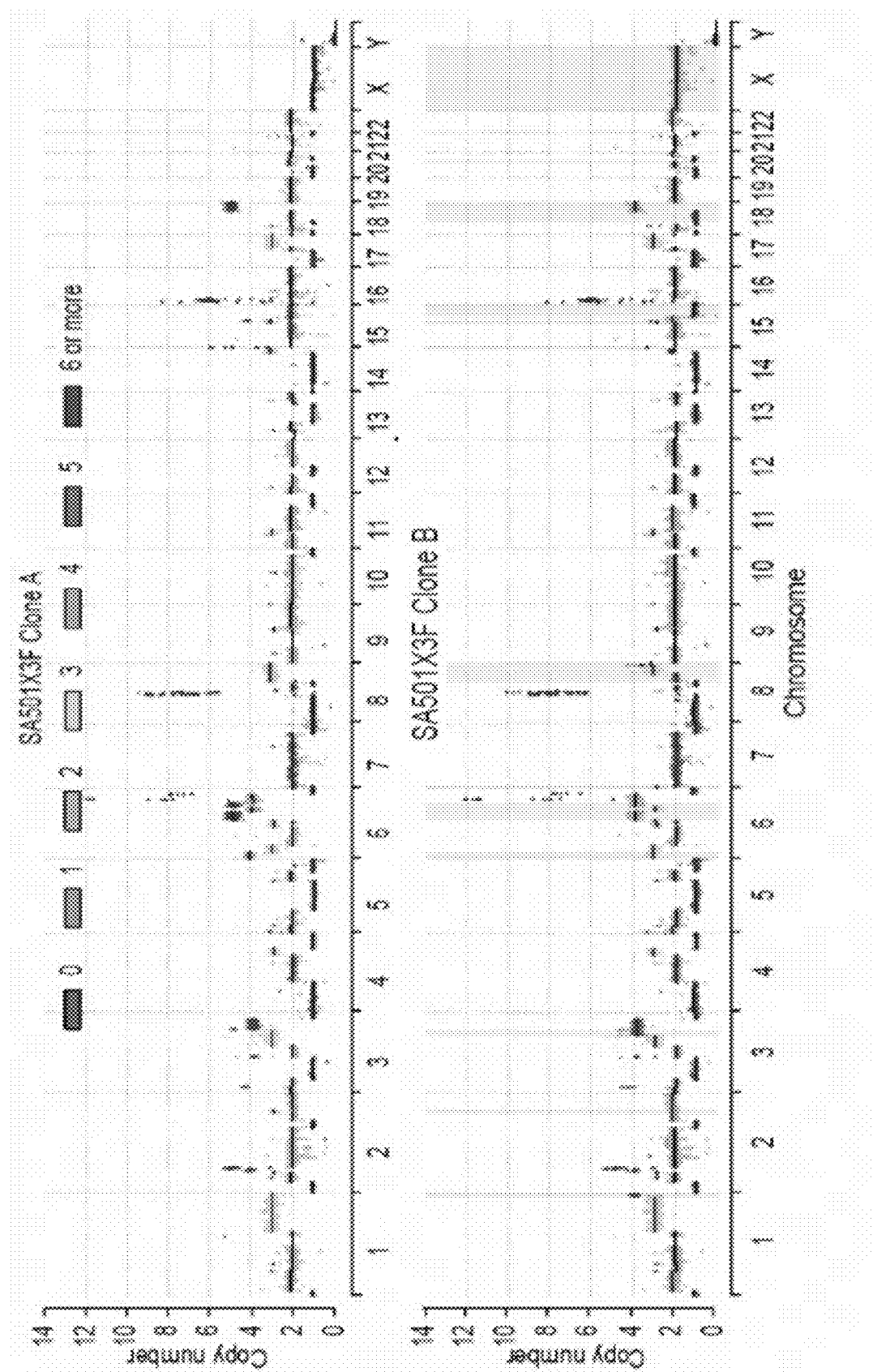
Figure 49A:
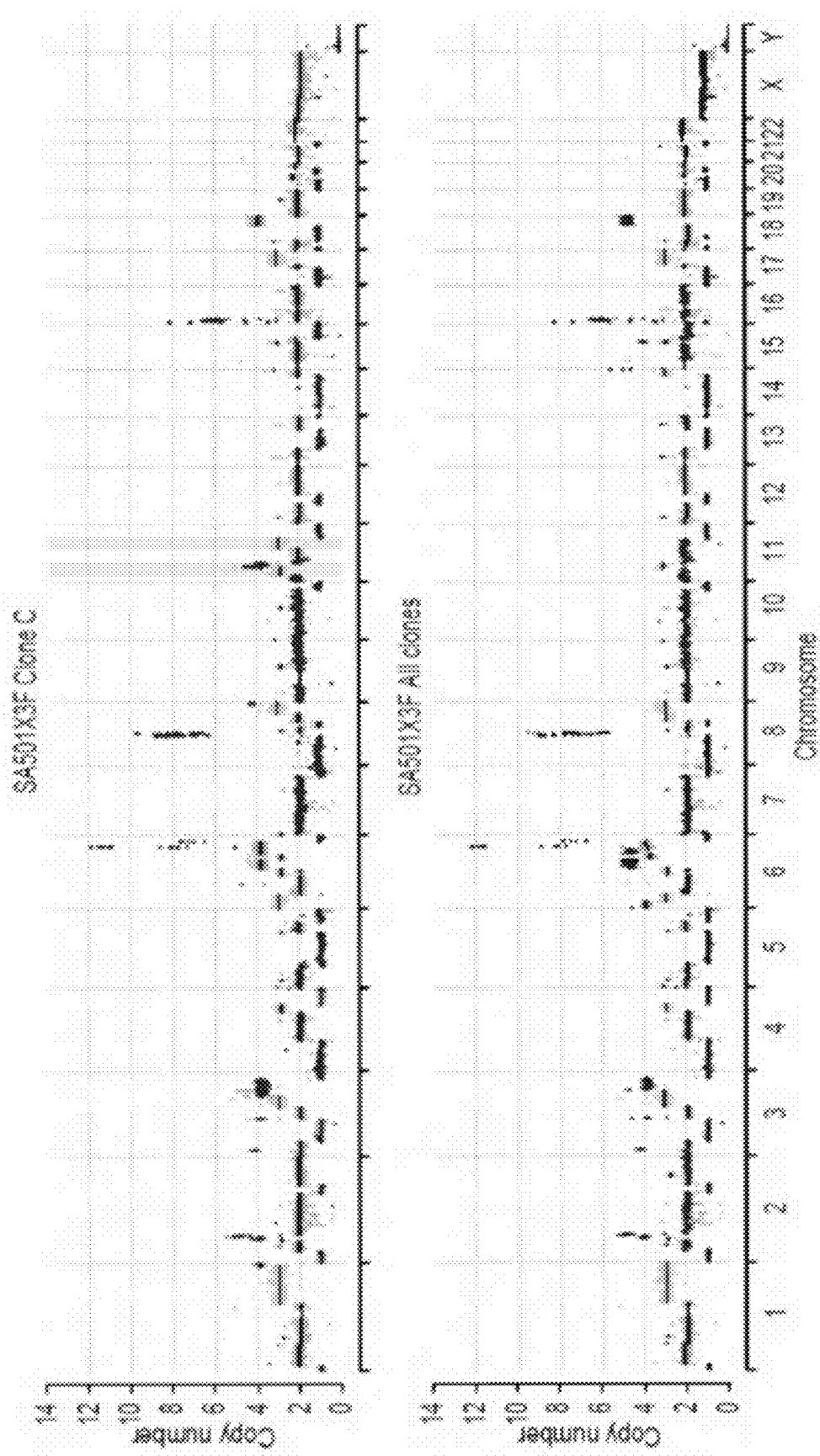
Figure 49B:
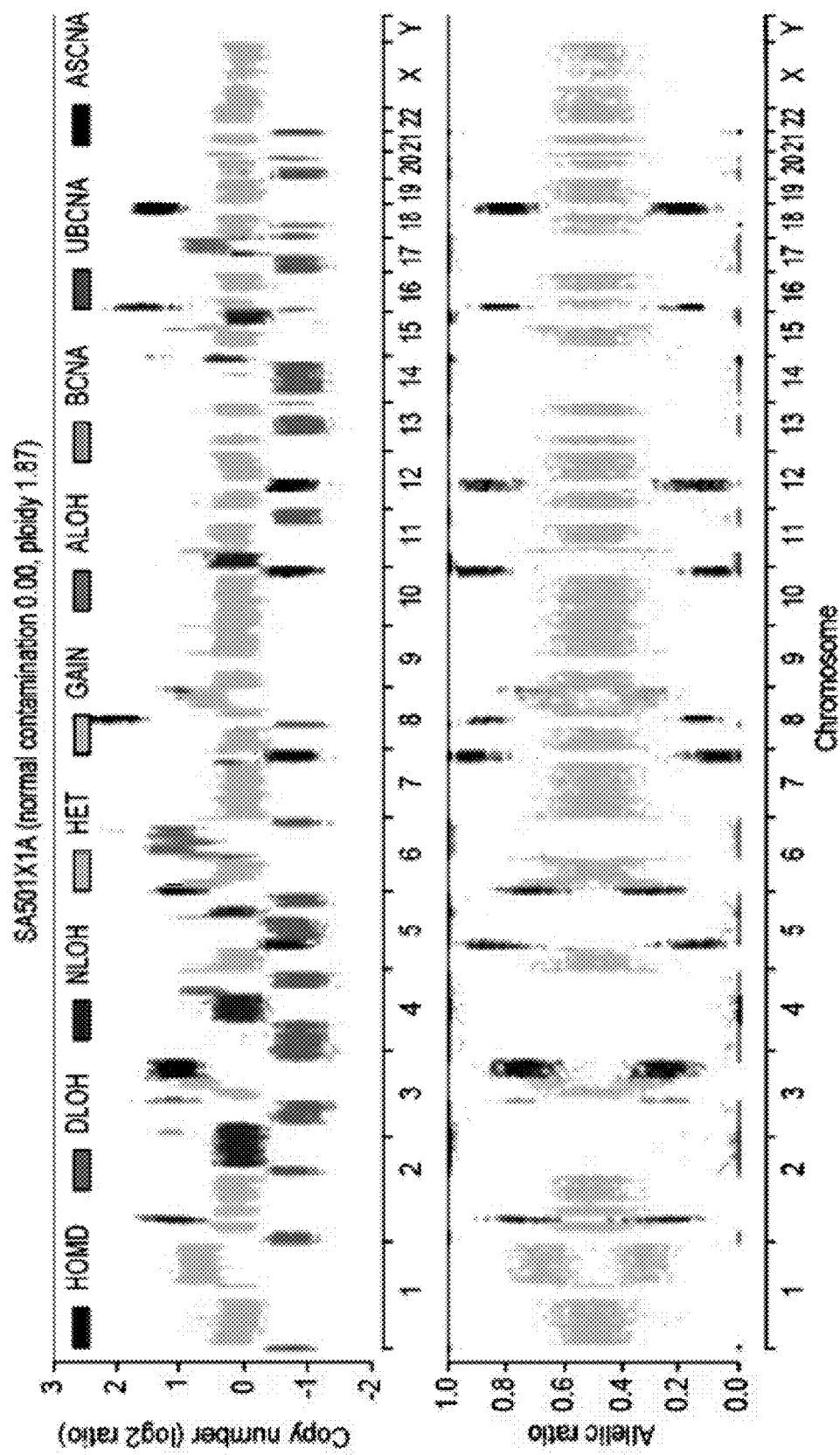
Figure 49C:
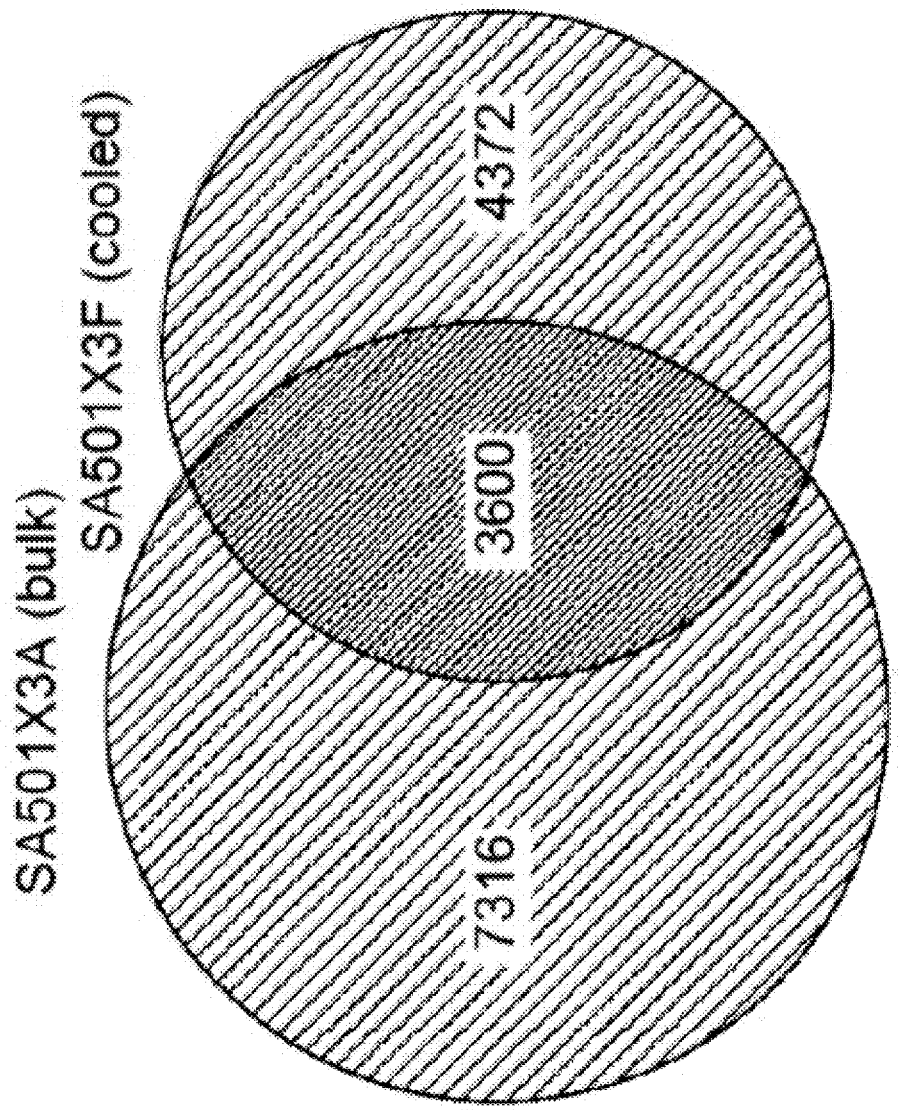
Figure 49E:
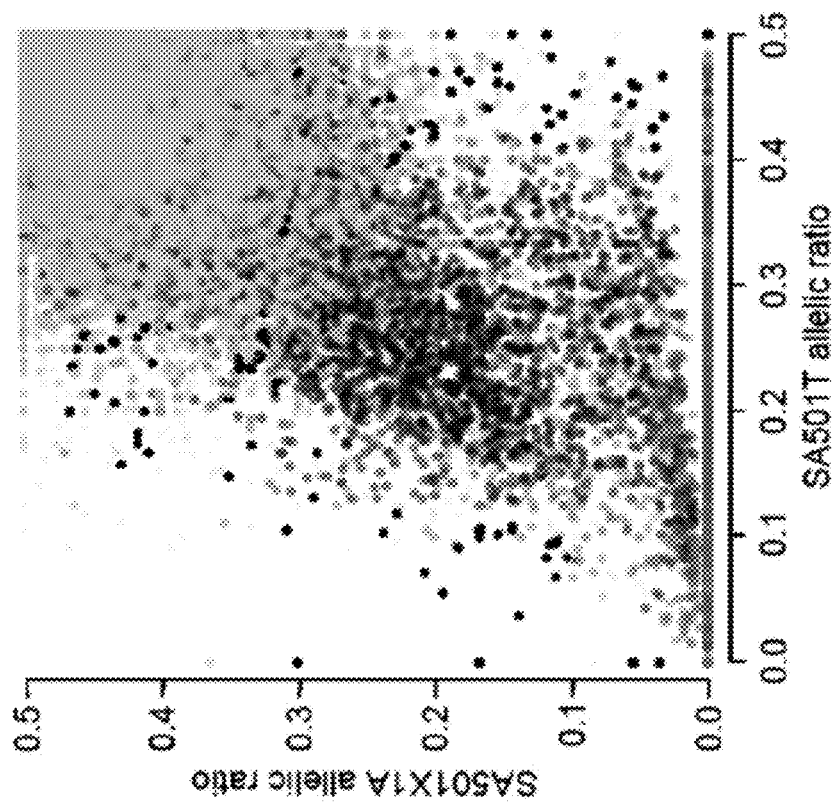
Figure 49D:
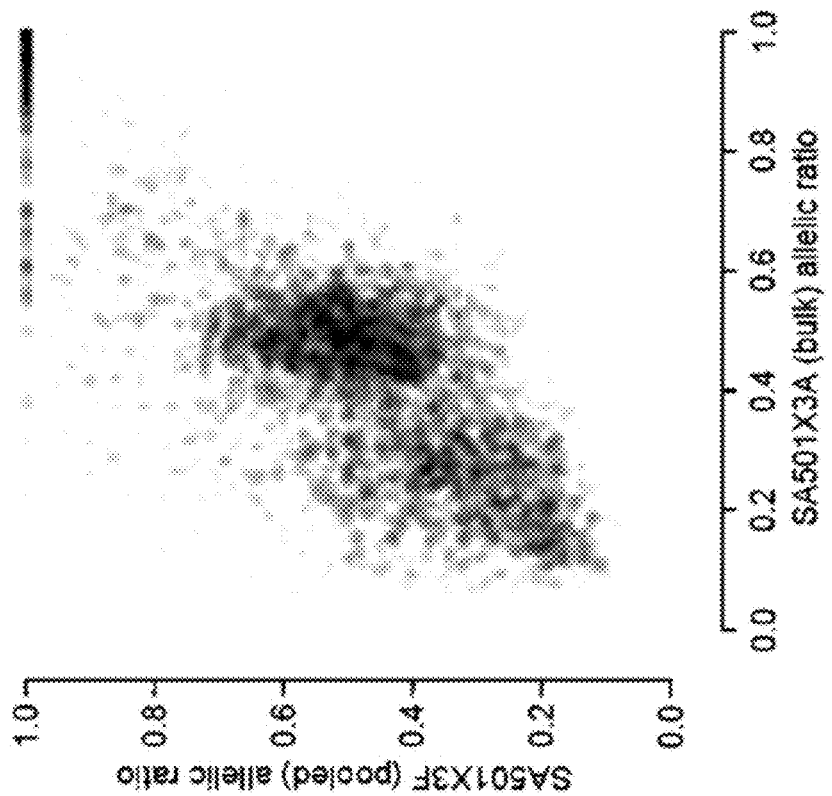

A pooled genome for each clonal sub-population identified in FIGS. 48A-C, as well as a genome for all three populations combined, and inferred copy number profiles using the same model parameters applied to the single-cell samples (FIG. 49A). Despite numerous differences in copy number, little evidence of minor Clones B and C is evident (as shifts in median segment values) in the combined copy number profile, underscoring the challenge of identifying sub-clonal copy number changes from bulk genomes. FIG. 49B shows the output of a hidden Markov model for simultaneous inference of copy number and LOH (Ha, G. et al. TITAN: Inference of copy number architectures in clonal cell populations from tumor whole-genome sequence data. Genome Research 24, 1881-1893 (2014) incorporated by reference herein in its entirety), applied to a merged "bulk-equivalent" genome of all SA501X3F sequencing reads prepared with the microfluidic device (including those samples identified as single-cells, multiple cells, and cells with contaminating debris). In FIG. 49C, a Venn diagram illustrates the overlap in high-confidence SNV calls between the bulk-equivalent and standard SA501X3F genomes (Ding2011), while the scatter plot in FIG. 49D shows that allele ratios for these SNVs are highly correlated between the two genomes. Similarly, FIG. 49E shows the correlation in allelic ratios for heterozygous germline variants, colored by their inferred LOH state (Ha, G. et al. TITAN: Inference of copy number architectures in clonal cell populations from tumor whole-genome sequence data. Genome Research 24, 1881-1893 (2014) incorporated by reference herein in its entirety), between the SA501X3F bulk-equivalent and standard bulk genome.

Analysis showed that compared to existing methods for single cell copy number analyses, direct library preparation produced more usable reads per cell, permitted more cells to be multiplexed per sequencing lane, and generated genomes with lower dispersion in reads per bin. Pooling multiple cells produced a bulk-equivalent genome with equivalent coverage breadth and uniformity as a standard bulk genome with the same coverage depth.

Example 17—Transposase-Based Sequencing Library Construction from Sub-Haploid Amounts of DNA Whole genome sequencing of genomic DNA (gDNA) isolated from 1-10 cells, with higher fidelity than current methods, and with the sequencing data segregated into parental haplotypes is provided herein. To the inventors' knowledge, this capability does not currently exist.

Previous haplotype-resolved WGS methods have either suffered from high amplification bias (B. A. Peters et al., Accurate whole-genome sequencing and haplotyping from 10 to 20 human cells. *Nature* 487, 190-195 (2012), incorporated by reference herein in its entirety for all purposes) or required large quantities of template DNA (S. Amini et al., Haplotype-resolved whole-genome sequencing by contiguity-preserving transposition and combinatorial indexing. *Nat Genet* 46, 1343-1349 (2014), incorporated by reference herein in its entirety for all purposes).

In the present method, a whole genome amplification step is omitted and therefore, the amplification bias associated with whole genome amplification is also omitted. Additionally, the present method only requires a small amount of template. Accordingly, the methods and devices provided herein find utility where only a limited amount of DNA is available for analysis such as preimplantation genetic diagnosis of embryo biopsies or the genetic analysis of circulating tumor cells.

Method:

As a preliminary demonstration of this method, the following steps were performed using reagents from the NEXTERA library preparation kit (Illumina).

In separate experiments, 10 human haploid cell equivalents of high molecular weight gDNA were distributed across different numbers (10, 68, 96, 220) of microwells of a Wafergen SmartChip using a piezoelectric spotter (S3, Scienion) using a PDC70 type 4 nozzle capable of dispensing 100-400 pL droplets. This spotter was used to deposit reagents in microwells in all subsequent steps. For each number of microwells used, the gDNA concentration was adjusted such that the total amount of DNA in all wells was 10 haploid cells' worth (approx. 33 pg). The gDNA was deposited in a 2 nL volume.

16.5 nL of tagmentation mix, containing the transposome, was deposited into each microwell. The array was sealed and incubated at 55° C. for 10 min in order to simultaneously fragment and tag the DNA with a common adapter sequence.

8 nL of a neutralization mix composed of protease and 0.1% tween 20 surfactant was deposited in each microwell. The array was sealed and incubated at 50 C for 15 min and 70 C for 15 min. to deactivate the transposase and strip it from the DNA fragments.

2.6 nL of a unique pair of DNA indices were then spotted into each microwell, followed by 60.9 nL of PCR mix containing reagents required for amplification of library fragments. The array was sealed and thermocycled for 16 PCR cycles using the recommended cycling protocol.

The product of all microwells were then extracted from the array, pooled, and sequenced on a MISEQ DNA sequencer (Illumina).

For the experiment in which 96 wells were used (~32.3 MBp of gDNA per reaction), the indexed and pooled libraries were sequenced to approximately 0.01× sequencing depth (base pairs of aligned data/base pairs of starting template per reaction). If sequencing libraries were successfully generated from such small amounts of input template in each indexed reaction, "islands" of sequencing reads corresponding to the gDNA fragments originally dispensed into each well are expected to be uncovered, where the coverage of each fragment depends on the sequencing depth used. Even at the low sequencing depth used in this experiment, such islands of reads were observed, with coverage similar to that previously observed in transposition reactions using 10,000 times more DNA template.

This example also demonstrates that the fidelity of sequencing library preparation can be improved by increasing the number of reactions the template was partitioned into. For the experiments using 10, 68, and 220 reactions, the representational bias of each library was assessed by dividing the reference genome into bins of 1 MBp length, binning aligned reads (with duplicates removed) into these bins and finding the standard deviation (SD) in reads per bin. It was found that SD decreases with increasing numbers of reactions (FIG. 50). This data suggests that further increasing the number of reactions should lower the representational bias to a level comparable with that of a sequencing library generated from much larger quantities of gDNA, which will enable analysis such as the detection of copy number variants with high resolution.

While embodiments have been shown and described herein, it is noted that such embodiments are provided by way of example only. Numerous variations, changes, and substitutions will now occur to those skilled in the art without departing from the provided disclosure. It should be understood that various alternatives to the embodiments described herein may be employed in practicing the disclosure. It is intended that the following claims define the scope of the invention and that methods and structures within the scope of these claims and their equivalents be covered thereby.

All publications, patents, and patent applications mentioned in this specification are herein incorporated by reference to the same extent as if each individual publication, patent, or patent application was specifically and individually indicated to be incorporated by reference.

The invention claimed is:

1. A method for generating indexed single cell sequencing libraries from a cell population, comprising,
    distributing individual cells and/or individual nuclei from a cell suspension into a plurality of containers; and
    creating indexed single cell sequencing libraries from the individual cells and/or the individual nuclei in one or more of the plurality of containers, wherein creating the indexed single cell libraries comprises
    subjecting unamplified DNA from the individual cells and/or individual nuclei to a transposase reaction, wherein the transposase reaction comprises fragmenting and tagging the unamplified DNA with a tagging sequence to generate tagmented DNA;
    subjecting the tagmented DNA to 9 to 15 polymerase chain reaction (PCR) cycles to add unique single cell indices and sequencing adaptors to the tagmented DNA, thereby generating indexed single cell sequencing libraries.

2. The method of claim 1, wherein the cell population is from a tumor sample.

3. The method of claim 2, wherein the tumor sample comprises a solid tumor, resected tissue or a fine needle aspirate.

4. The method of claim 2, wherein the tumor is a breast tumor.

5. The method of claim 1, wherein the containers have an average volume of from 1 nL to 1000 nL.

6. The method of claim 1, wherein the containers have an average volume of from 0.1 nL to 1 nL.

7. The method of claim 1, wherein the plurality of containers comprises a plurality of chambers, a plurality of open microwells, or a plurality of microdroplets.

8. The method of claim 7, wherein the plurality of containers is a plurality of chambers.

9. The method of claim 8, wherein the plurality of chambers comprises from 100 to 10,000 chambers.

10. The method of claim 8, wherein the plurality of chambers comprises from 10,000 to 100,000 chambers.

11. The method of claim 1, wherein from about 100 to about 1000 individual cells and/or nuclei are each distributed into individual containers.

12. The method of claim 1, wherein the transposase comprises Tn5 transposase.

13. The method of claim 1, wherein the transposase reaction is a one-step transposase reaction.

14. The method of claim 1, further comprising analyzing genomic variation from the cell population, comprising,
    pooling a subset of the indexed single cell sequencing libraries to make a pooled library comprising genomic information of a subset of a plurality of the individual cells and/or the individual nuclei;
    sequencing the pooled library to obtain incomplete genomic information of the subset of the plurality of the individual cells and/or the individual nuclei;
    aligning sequence reads derived from one or more of the indexed single cell sequencing libraries to a reference genome in order to detect the presence or absence of genomic variation in the one or more of the individual cells and/or the individual nuclei;
    analyzing a distribution of genomic variation(s) across the individual cells and/or the individual nuclei to provide identified subpopulations of single cells that share common genomic features; and
    analyzing combined genomic information from the identified subpopulations of single cells to identify genomic features that exist within the identified subpopulations.

15. The method of claim 14, wherein sequencing the pooled library comprises sequencing to sufficient depth to obtain an average of between 0.01% and 0.1% coverage of the genome of each cell.

16. The method of claim 14, wherein sequencing the pooled library comprises sequencing to sufficient depth to obtain an average of between 0.1% and 1% coverage of the genome of each cell.

17. The method of claim 14, wherein sequencing the pooled library comprises sequencing to sufficient depth to obtain an average of between 1% and 5% coverage of the genome of each cell.

18. The method of claim 14, wherein sequencing the pooled library comprises sequencing to sufficient depth to obtain an average of between 5% and 10% coverage of the genome of each cell.

19. The method of claim 14, wherein sequencing the pooled library comprises sequencing to sufficient depth to obtain an average of between 10% and 25% coverage of the genome of each cell.

20. The method of claim 14, wherein sequencing the pooled library comprises sequencing to sufficient depth to obtain an average of between 25% and 50% coverage of the genome of each cell.

21. The method of claim 14, wherein the pooled library is sequenced to sufficient depth to obtain between 10× and 100× coverage of the average bulk genome of the population of cells.

22. The method of claim 14, wherein the genomic variation is copy number variation, translocations, loss of heterozygosity, single nucleotide polymorphism or a combination thereof.

23. The method of claim 22, wherein the genomic variation is copy number variation.

24. The method of claim 14, further comprising determining the phylogenic lineage of the identified subpopulations.

* * * * *